US012668777B2

(12) United States Patent
Zhou

(10) Patent No.: US 12,668,777 B2
(45) Date of Patent: Jun. 30, 2026

(54) CHIMERIC ANTIGEN RECEPTOR T CELLS AND METHODS OF USE THEREOF

(71) Applicant: Augusta University Research Institute, Inc., Augusta, GA (US)

(72) Inventor: Gang Zhou, Martinez, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 46 days.

(21) Appl. No.: 17/395,184

(22) Filed: Aug. 5, 2021

(65) Prior Publication Data

US 2022/0054546 A1      Feb. 24, 2022

Related U.S. Application Data

(60) Provisional application No. 63/061,339, filed on Aug. 5, 2020.

(51) Int. Cl.

| | |
|---|---|
| *C12N 5/0783* | (2010.01) |
| *A61K 40/11* | (2025.01) |
| *A61K 40/31* | (2025.01) |
| *A61K 40/42* | (2025.01) |
| *A61P 35/00* | (2006.01) |

(52) U.S. Cl.
CPC ............ *C12N 5/0636* (2013.01); *A61K 40/11* (2025.01); *A61K 40/31* (2025.01); *A61K 40/4211* (2025.01); *A61K 40/4242* (2025.01); *A61P 35/00* (2018.01); *A61K 2239/48* (2023.05); *A61K 2239/50* (2023.05)

(58) Field of Classification Search
CPC ........ A61K 35/17; A61K 40/11; A61K 40/31; A61K 40/4211; A61K 40/4242; A61K 2239/48; A61K 2239/50; C12N 5/0636; C12N 2510/00; C12N 2501/515; A61P 35/00; C07K 14/7051
See application file for complete search history.

(56) References Cited

U.S. PATENT DOCUMENTS

| | | | |
|---|---|---|---|
| 5,190,929 | A | 3/1993 | Borch et al. |
| 5,359,046 | A | 10/1994 | Capon et al. |
| 5,686,281 | A | 11/1997 | Roberts |
| 6,103,521 | A | 8/2000 | Capon et al. |
| 7,052,694 | B2 | 5/2006 | Pease et al. |
| 7,332,582 | B2 | 2/2008 | Hardy et al. |
| 7,390,888 | B2 | 6/2008 | Pease et al. |
| 7,411,051 | B2 | 8/2008 | Rosen et al. |
| 7,446,190 | B2 | 11/2008 | Sadelain et al. |
| 7,488,802 | B2 | 2/2009 | Collins et al. |
| 7,521,051 | B2 | 4/2009 | Collins et al. |
| 7,524,498 | B2 | 4/2009 | Hardy et al. |
| 7,563,869 | B2 | 7/2009 | Honjo et al. |
| 7,741,465 | B1 | 6/2010 | Eshhar et al. |
| 7,981,416 | B2 | 7/2011 | Hardy et al. |
| 8,088,905 | B2 | 1/2012 | Collins et al. |

| | | | |
|---|---|---|---|
| 8,114,845 | B2 | 2/2012 | Langermann et al. |
| 8,188,238 | B2 | 5/2012 | Pease et al. |
| 8,287,856 | B2 | 10/2012 | Li et al. |
| 8,383,796 | B2 | 2/2013 | Korman et al. |
| 8,580,247 | B2 | 11/2013 | Li et al. |
| 8,609,089 | B2 | 12/2013 | Langermann et al. |
| 8,709,416 | B2 | 4/2014 | Langermann et al. |
| 8,728,474 | B2 | 5/2014 | Honjo et al. |
| 8,779,105 | B2 | 7/2014 | Korman et al. |
| 9,067,999 | B1 | 6/2015 | Honjo et al. |
| 9,073,994 | B2 | 7/2015 | Honjo et al. |
| 9,084,776 | B2 | 7/2015 | Korman et al. |
| 9,102,725 | B2 | 8/2015 | Korman et al. |
| 9,181,527 | B2 | 11/2015 | Sentman |
| 9,205,148 | B2 | 12/2015 | Langermann et al. |
| 9,255,147 | B2 | 2/2016 | Pease et al. |
| 9,273,135 | B2 | 3/2016 | Korman et al. |
| 9,358,289 | B2 | 6/2016 | Korman et al. |
| 9,387,247 | B2 | 7/2016 | Korman et al. |
| 9,393,301 | B2 | 7/2016 | Honjo et al. |
| 9,492,539 | B2 | 11/2016 | Korman et al. |
| 9,492,540 | B2 | 11/2016 | Korman et al. |

(Continued)

FOREIGN PATENT DOCUMENTS

| | | |
|---|---|---|
| WO | 2007/056539 A2 | 5/2007 |
| WO | 2017/218850 A1 | 12/2017 |
| WO | 2018/038945 A1 | 3/2018 |

OTHER PUBLICATIONS

Onishi M. et al. Identification and characterization of a constitutively active STAT5 mutant that promotes cell proliferation. Mol Cell Biol. Jul. 1998; 18(7):3871-9. doi: 10.1128/MCB.18.7.3871. PMID: 9632771; PMCID: PMC108971. (Year: 1998).*

Zhao L, Cao YJ. Engineered T Cell Therapy for Cancer in the Clinic. Front Immunol. Oct. 11, 2019;10:2250. doi: 10.3389/fimmu.2019.02250. PMID: 31681259; PMCID: PMC6798078. (Year: 2019).*

Ding ZC et al. IL-7 signaling imparts polyfunctionality and stemness potential to CD4(+) T cells. Oncoimmunology. Apr. 25, 2016;5(6):e1171445. doi: 10.1080/2162402X.2016.1171445. PMID: 27471650; PMCID: PMC4938319 (Year: 2016).*

Ding et al. Persistent STAT5 activation reprograms the epigenetic landscape in CD4+ T cells to drive polyfunctionality and antitumor immunity. Sci Immunol. Oct. 30, 2020;5(52):eaba5962. PMID: 33127608; PMCID: PMC8265158.). (Year: 2020).*

(Continued)

*Primary Examiner* — Alexander W Nicol
(74) *Attorney, Agent, or Firm* — Pabst Patent Group LLP

(57) ABSTRACT

Disclosed herein are engineered polyfunctional CD4$^+$ T cells/CAR T cells and methods of their use for the treatment of cancers. One embodiment provides a method of producing polyfunctional CD4$^+$ T cells by constitutively activating STAT5A in the cells to induce a polyfunctional phenotype. Also provided is a method of reversing exhaustion in tumor-specific CD4$^+$ T cells by engineering the cells to express Fos, Jun, Nr4a1, or combinations thereof but not express Tox, Pdcd1, Ctla4, Haver2, Lag3, Tigit, Slam6, Nrf4a2, and administering the engineered cells to a subject.

6 Claims, 103 Drawing Sheets

Specification includes a Sequence Listing.

(56) References Cited

U.S. PATENT DOCUMENTS

| | | |
|---|---|---|
| 9,580,507 B2 | 2/2017 | Korman et al. |
| 9,629,877 B2 | 4/2017 | Cooper et al. |
| 2006/0177932 A1* | 8/2006 | Nakauchi .............. C12N 5/0647 |
| | | 435/456 |
| 2007/0202077 A1 | 8/2007 | Brodsky et al. |

OTHER PUBLICATIONS

Adachi, K., et al., "IL-7 and CCL 19 expression in CAR-T cells improves immune cell infiltration and CAR-T cell survival in the tumor", Nat. Biotechnol, 36: 346-351 (2018).

Alfei, F., et al., "TOX reinforces the phenotype and longevity of exhausted T cells in chronic viral infection", Nature, 571: 265-269 (2019).

Aubert, R.D., et al., "Antigen-specific CD4 T-cell help rescues exhausted CD8 T cells during chronic viral infection", Proc. Natl. Acad. Sci. USA, 108: 21182-21187 (2011).

Bajgain, P., et al., "CAR T cell therapy for breast cancer: harnessing the tumor milieu to drive T cell activation", J. Immunother Cancer, 6: 34 (2018).

Bandapalli, O.R., et al., "The activating STAT5B N642H mutation is a common abnormality in pediatric T-cell acute lymphoblastic leukemia and confers a higher risk of relapse", Haematologica, 99(10): e188-e192 (2014).

Bass, K.K., et al., "Immunopotentiation with low-dose cyclophosphamide in the active specific immunotherapy of cancer", Cancer Immunol., Immunother, 47: 1-12 (1998).

Berger, R., et al., "Phase I Safety and Pharmacokinetic Study of CT-011, a Humanized Antibody Interacting with PD-1, in Patients with Advanced Hematologic Malignancies", Clin. Cancer Res., 14: 3044-3051 (2008).

Bernstein, B.E., et al., "A Bivalent Chromatin Structure Marks Key Developmental Genes in Embryonic Stem Cells", Cell, 125: 315-326 (2006).

Bevan, M.J., "Helping the CD8+ T-cell response", Nat. Rev. Immunol., 4: 595-602 (2004).

Birkenkamp, K.U., et al., "Regulation of constitutive STAT5 phosphorylation in acute myeloid leukemia blasts", Leukemia, 15: 1923-1931 (2001).

Borst, J., et al., "CD4+ T cell help in cancer immunology and immunotherapy", Nat. Rev. Immunol., 18: 635-647 (2018).

Brode, S., et al., "Immune-potentiating effects of the chemotherapeutic drug cyclophosphamide", Crit. Rev., Immunol., 28: 109-126 (2008).

Butler, A., et al., "Integrating single-cell transcriptomic data across different conditions, technologies, and species", Nat Biotechnol, 36: 411-420 (2018).

Butte, M.J., et al., "Programmed Death-1 Ligand 1 Interacts Specifically with the B7-1 Costimulatory Molecule to Inhibit T Cell Responses", Immunity, 27: 111-122 (2007).

Chai, S.K., et al., "Constitutive activation of JAKs and STATs in BCR-Abl-expressing cell lines and peripheral blood cells derived from leukemic patients", J. Immunol., 159: 4720-4728 (1997).

Chen, J., et al., "NR4A transcription factors limit CAR T cell function in solid tumours", Nature, 567: 530-534 (2019).

Choudhary, C., et al., "Activation mechanisms of STAT5 by oncogenic Flt3-ITD", Blood, 110: 370-374 (2007).

Crawford, A., et al., "Molecular and Transcriptional Basis of CD4+ T Cell Dysfunction during Chronic Infection", Immunity, 40: 289-302 (2014).

Cubillos-Ruiz, J.R., et al., "Polyethylenimine-based siRNA nanocomplexes reprogram tumor-associated dendritic cells via TLR5 to elicit therapeutic antitumor immunity", J. Clin. Invest., 119(8): 2231-2244 (2009).

D'Aloia, M.M., et al., "CAR-T cells: the long and winding road to solid tumors", Cell Death Dis., 9: 282 (2018).

Davila, M.L., "CAR T cells find strength in polyfunction", Blood, 132: 769-770 (2018).

Ding, Z.C., et al., "Cytotoxic Chemotherapy and CD4+ Effector T Cells: An Emerging Alliance for Durable Antitumor Effects", Clin. Dev. Immunol., 890178 (2012).

Ding, Z.C., et al., "IL-7 signaling imparts polyfunctionality and stemness potential to CD4+ T cell", Oncoimmunology, 5: e1171445 (2016).

Ding, Z.C., et al., "Polyfunctional CD4+ T cells are essential for eradicating advanced B-cell lymphoma after chemotherapy", Blood, 120: 2229-2239 (2012).

Erbe, D.V., et al., "Small Molecule Ligands Define a Binding Site on the Immune Regulatory Protein", J. Biol. Chem., 277: 7363-7368 (2002).

Fesnak, A.D., et al., "Engineered T cells: the promise and challenges of cancer immunotherapy", Nat. Rev. Cancer, 16: 566-581 (2016).

Freeman, G.J., "Structures of PD-1 with its ligands: Sideways and dancing cheek to cheek", Proc. Natl. Acad. Sci. U. S. A, 105: 10275-10276 (2008).

Fujiwara, H., et al., "Antileukemia multifunctionality of CD4+ T cells genetically engineered by HLA class I-restricted and WT1-specific T-cell receptor gene transfer", Leukemia, 29: 2393-2401 (2015).

Gacerez, A.T., et al., "T-bet promotes potent antitumor activity of CD4+ CAR T cells", Cancer Gene Ther., 25: 117-128 (2018).

Garcon, L., et al., "Constitutive activation of STAT5 and Bcl-xL overexpression can induce endogenous erythroid colony formation in human primary cells", Blood, 108: 1551-1554 (2006).

Gilham, D.E., et al., "CAR-T cells and solid tumors: tuning T cells to challenge an inveterate foe", Trends Mol. Med., 18: 377-384 (2012).

Grant, C.E., et al., "Article Navigation FIMO: scanning for occurrences of a given motif", Bioinformatics, 27: 1017-1018 (2011).

Habtetsion, T., et al., "Alteration of Tumor Metabolism by CD4+ T Cells Leads to TNF-a-Dependent Intensification of Oxidative Stress and Tumor Cell Death", Cell Metab., 28: 228-242 (2018).

Hengst, J.C.D, et al., "Cooperation between Cyclophosphamide Tumoricidal Activity and Host Antitumor Immunity in the Cure of Mice Bearing Large MOPC-315 Tumors", Cancer Res., 41: 2163-2167 (1981).

Hengst, J.C.D., et al., "Importance of Timing in Cyclophosphamide Therapy of MOPC-315 Tumor-bearing Mice", Cancer Res., 40: 2135-2141 (1980).

Hildner, K., et al., "Batf3 Deficiency Reveals a Critical Role for CD8a+ Dendritic Cells in Cytotoxic T Cell Immunity", Science, 322: 1097-1100 (2008).

Hirschhorn-Cymermann, D., et al., "Induction of tumoricidal function in CD4+ T cells is associated with concomitant memory and terminally differentiated phenotype", J. Exp. Med., 209: 2113-2126 (2012).

Hoyos, V., et al., "Engineering CD19-specific T lymphocytes with interleukin-15 and a suicide gene to enhance their anti-lymphoma/leukemia effects and safety", Leukemia, 24: 1160-1170 (2010).

Hunder, N.N., et al., "Treatment of Metastatic Melanoma with Autologous CD4+ T Cells against NY-ESO-1", N. Engl. J. Med., 358: 2698-2703 (2008).

Hwang, S.J., et al., "Blimp-1-mediated CD4 T cell exhaustion causes CD8 T cell dysfunction during chronic toxoplasmosis", J. Exp. Med., 213: 1799-1818 (2016).

June C.H., et al., "Chimeric Antigen Receptor Therapy", N. Engl. J. Med., 379: 64-73 (2018).

Khan, O., et al., "TOX transcriptionally and epigenetically programs CD8+ T cell exhaustion", Nature, 571: 211-218 (2019).

Kollman, S., et al., "Twins with different personalities: STAT5B—but not STAT5A—has a key role in BCR/ABL-induced leukemia", Leukemia, 33: 1583-1597 (2019).

Kontro, M., et al., "Novel activating STAT5B mutations as putative drivers of T-cell acute lymphoblastic leukemia", Leukemia, 28: 1738-1742 (2014).

Kralovics, R., et al., "A Gain-of-Function Mutation of JAK2 in Myeloproliferative Disorders", N. Engl. J. Med., 352: 1779-1790 (2005).

Kuczma, M.P., et al., "The impact of antibiotic usage on the efficacy of chemoimmunotherapy is contingent on the source of tumor-reactive T cells", Oncotarget, 8: 111931-111942 (2017).

(56)         References Cited

OTHER PUBLICATIONS

Li, B., et al., "Vascular Endothelial Growth Factor Blockade Reduces Intratumoral Regulatory T Cells and Enhances the Efficacy of a GM-CSF-Secreting Cancer Immunotherapy", Clin. Cancer Res., 12(22): 6808-6816 (2006).

Li, Z., et al., "Identification of transcription factor binding sites using ATAC-seq", Genome Biol., 20: 45 (2019).

Liang J, et al., "Design of New Oxazaphosphorine Anticancer Drugs", Curr. Pharm. Des., 13(9): 963-78 (2007).

Liu, X., et al., "Genome-wide analysis identifies NR4A1 as a key mediator of T cell dysfunction", Nature, 567: 525-529 (2019).

Ding Z.-C. et al., IL-7 signaling imparts polyfunctionality and stemness potential to CD4+ T cells. OncoImmunology, vol. 5, Issue No. 6, p. e1171445 (13 pages) (Apr. 2016).

Lu, Y.C., et al., "Treatment of Patients With Metastatic Cancer Using a Major Histocompatibility Complex Class II-Restricted T-Cell Receptor Targeting the Cancer Germline Antigen MAGE-A3", J. Clin. Oncol., 35: 3322-3329 (2017).

Machiels, J.P.H., et al., "Cyclophosphamide, Doxorubicin, and Paclitaxel Enhance the Antitumor Immune Response of Granulocyte/Macrophage-Colony Stimulating Factor-secreting Whole-Cell Vaccines in HER-2/neu Tolerized Mice", Cancer Res., 61: 3689-3697 (2001).

Mann, T.H., et al., "Tick-TOX, it's time for T cell exhaustion", Nat. Immunol., 20: 1092-1094 (2019).

Martinez, G.J., et al., "The Transcription Factor NFAT Promotes Exhaustion of Activated CD8+ T Cells", Immunity, 42: 265-278 (2015).

Miller, B.C., et al., "Subsets of exhausted CD8+ T cells differentially mediate tumor control and respond to checkpoint blockade", Nat. Immunol., 20: 326-336 (2019).

Molnar, E.L., et al., "Crystal structure of the complex between programmed death-1 (PD-1) and its ligand PD-L2", PNAS, 105: 10483-10488 (2008).

Nanou, A., et al., "The dual role of LSD1 and HDAC3 in STAT5-dependent transcription is determined by protein interactions, binding affinities, motifs and genomic position", Nucleic Acid Res., 45: 142-145 (2017).

Newick, K., et al., "CAR T Cell Therapy for Solid Tumors", Annu. Rev. Med., 68: 139-152 (2017).

Onishi, M., et al., "Identification and Characterization of a Constitutively Active STAT5 Mutant That Promotes Cell Proliferation", Mol. Cell. Biol., 18: 3871-3879 (1998).

Owen, D.L., et al., "STAT5 and CD4 + T Cell Immunity", F1000Res, 6: 32 (2017).

Paley, M.A., et al., "Progenitor and Terminal Subsets of CD8+ T Cells Cooperate to Contain Chronic Viral Infection", Science, 338: 1220-1225 (2012).

Pardoll, D.M., et al., "The role of CD4+ T cell responses in antitumor immunity", Curr. Opin. Immunol., 10: 588-594 (1998).

Pauken, K.E., et al., "Overcoming T cell exhaustion in infection and cancer", Trends Immunol., 36: 265-276 (2015).

Pereira, R.M., et al., "Transcriptional and epigenetic regulation of T cell hyporesponsiveness", J. Leukoc. Biol., 102: 601-615 (2017).

Perna, S.K., et al., "Interleukin-7 Mediates Selective Expansion of Tumor-redirected Cytotoxic T Lymphocytes (CTLs) without Enhancement of Regulatory T-cell Inhibition", Clin. Cancer Res., 20: 131-139 (2014).

Pham, H.T.T., et al., "STAT5BN642H is a driver mutation for T cell neoplasia", J. Clin. Invest., 128: 387-401 (2018).

Quezada, S.A., et al., "Tumor-reactive CD4+ T cells develop cytotoxic activity and eradicate large established melanoma after transfer into lymphopenic hosts", J. Exp. Med., 207: 637-650 (2010).

Ribiero, D., et al., "STAT5 is essential for IL-7-mediated viability, growth, and proliferation of T-cell acute lymphoblastic leukemia cells", Blood Adv., 2: 2199-2213 (2018).

Riedel, S.S. et al., "Non-Invasive Imaging Provides Spatiotemporal Information on Disease Progression and Response to Therapy in a Murine Model of Multiple Myeloma", PLoS One, 7: e52398 (2012).

Rossi, J., et al., "Preinfusion polyfunctional anti-CD19 chimeric antigen receptor T cells are associated with clinical outcomes in NHL", Blood, 132: 804-814 (2018).

Sadelain, M., "CAR therapy: the CD19 paradigm", J. Clin. Invest., 125: 3392-3400 (2015).

Sammartino, C., et al., "Anti-GBM disease following CTLA4 blockade in a patient with metastatic melanoma", Clinical Kidney Journal, 3(2): 135-137 (2010).

Schietinger, A., et al., "Tolerance and exhaustion: defining mechanisms of T cell dysfunction", Trends Immunol., 35: 51-60 (2014).

Schmidl, C., et al., "Epigenetic mechanisms regulating T-cell responses", J. Allergy Clin. Immunol., 142: 728-743 (2018).

Schuringa, J.J., et al., "Constitutive Activation of STAT5A Promotes Human Hematopoietic Stem Cell Self-Renewal and Erythroid Differentiation", J. Exp. Med., 200: 623-635 (2004).

Schuringa, J.J., et al., "Enforced Activation of STAT5A Facilitates the Generation of Embryonic Stem-Derived Hematopoietic Stem Cells That Contribute to Hematopoiesis In Vivo", Stem Cells, 22: 1191-1204 (2004).

Scott, A.C., et al., "TOX is a critical regulator of tumour-specific T cell differentiation", Nature, 571: 270-274 (2019).

Seo, H., et al., "TOX and TOX2 transcription factors cooperate with NR4A transcription factors to impose CD8+ T cell exhaustion", Proc. Natl. Acad. Sci. USA, 116: 12410-12415 (2019).

Shuai, K., et al., "Constitutive activation of STAT5 by the BCR-ABL oncogene in chronic myelogenous leukemia", Oncogene, 13: 247-254 (1996).

Shum, T., et al., "Constitutive Signaling from an Engineered IL7 Receptor Promotes Durable Tumor Elimination by Tumor-Redirected T Cells", Cancer Discov., 7: 1238-1247 (2017).

Sillaber, C., et al., "STAT5 activation contributes to growth and viability in Bcr/Abl-transformed cells", Blood, 95: 2118-2125 (2000).

Sommermeyer, D., et al., "Chimeric antigen receptor-modified T cells derived from defined CD8+ and CD4+ subsets confer superior antitumor reactivity in vivo", Leukemia, 30:492-500 (2015).

Spiekermann, K., et al., "Overexpression and Constitutive Activation of FLT3 Induces STAT5 Activation in Primary Acute Myeloid Leukemia Blast Cells", Clin. Cancer Res., 9: 2140-2150 (2003).

Spranger, S., et al., "Tumor-Residing Batf3 Dendritic Cells Are Required for Effector T Cell Trafficking and Adoptive T Cell Therapy", Cancer Cell., 31: 711-712 (2017).

Taieb, J., "Chemoimmunotherapy of Tumors: Cyclophosphamide Synergizes with Exosome Based Vaccines", J. Immunol., 176: 2722-2729 (2006).

Tirosh, I., et al., "Dissecting the multicellular ecosystem of metastatic melanoma by single-cell RNA-seq", Science, 352: 189-196 (2016).

Tran, E., et al., "Cancer Immunotherapy Based on Mutation-Specific CD4+ T Cells in a Patient with Epithelial Cancer", Science, 344: 641-645 (2014).

Trapnell, C., et al., "The dynamics and regulators of cell fate decisions are revealed by pseudotemporal ordering of single cells", Nat. Biotechnol., 32: 381-386 (2014).

Tripathi, S.K., et al., "Transcriptional and epigenetic regulation of T-helper lineage specification", Immunol. Rev., 261: 62-83 (2014).

Turtle, C.J., et al., "CD19 CAR-T cells of defined CD4+:CD8+ composition in adult B cell ALL patients", J. Clin. Invest., 126(6): 2123-2138 (2016).

Van der Most, R.G., et al., "Tumor eradication after cyclophosphamide depends on concurrent depletion of regulatory T cells: a role for cycling TNFR2-expressing eVector-suppressor T cells in limiting eVective chemotherapy", Cancer Immunol. Immunother, 58: 1219-1228 (2009).

Wang, D., et al., "Tumor-specific MHC-II expression drives a unique pattern of resistance to immunotherapy via LAG-3/FCRL6 engagement", JCI Insight, 3(24): e120360 (2018).

Wei, G., et al., "Global Mapping of H3K4me3 and H3K27me3 Reveals Specificity and Plasticity in Lineage Fate Determination of Differentiating CD4+ T Cells", Immunity, 30: 155-167 (2009).

Wherry, E.J., et al., "Molecular and cellular insights into T cell exhaustion", Nat. Rev. Immunol., 15: 486-499 (2015).

(56)          References Cited

OTHER PUBLICATIONS

Wingelhofer, B., et al., "Implications of STAT3 and STAT5 signaling on gene regulation and chromatin remodeling in hematopoietic cancer", Leukemia, 32: 1713-1726 (2018).

Wu, T., et al., "The TCF1-Bcl6 axis counteracts type I interferon to repress exhaustion and maintain T cell stemness" , Sci. Immunol., 1(6): eaai8593 (2016).

Xie, Y., et al., "Naive tumor-specific CD4+ T cells differentiated in vivo eradicate established melanoma", J. Exp. Med., 207: 651-667 (2010).

Yao, C., et al., "Single-cell RNA-seq reveals TOX as a key regulator of CD8+ T cell persistence in chronic infection", Nat. Immunol., 20: 890-901 (2019).

Yu, G., et al., "clusterProfiler: an R Package for Comparing Biological Themes Among Gene Clusters", OMICS, 16: 284-287 (2012).

Zhang, Y., et al., "Model-based Analysis of ChIP-Seq (MACS)", Genome Biol, 9: R137 (2008).

Kaur and Dufour, "Cell lines: Valuable tools or useless artifacts", Spermatogenesis. Jan. 1, 2012;2(1):1-5. doi: 10.4161/spmg.19885.

Zhao, E., et al., "Cancer mediates effector T cell dysfunction by targeting microRNAs and EZH2 via glycolysis restriction", Nat. Immunol., 17: 95-103 (2016).

* cited by examiner

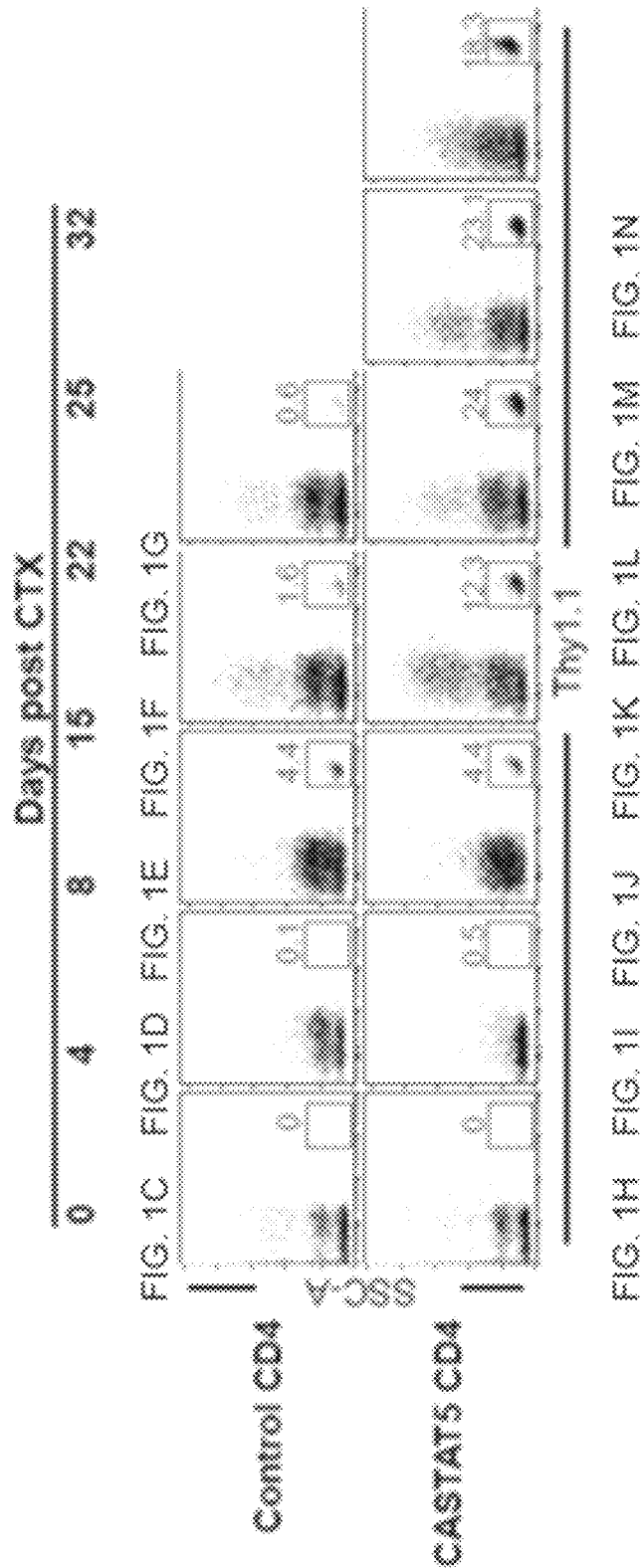

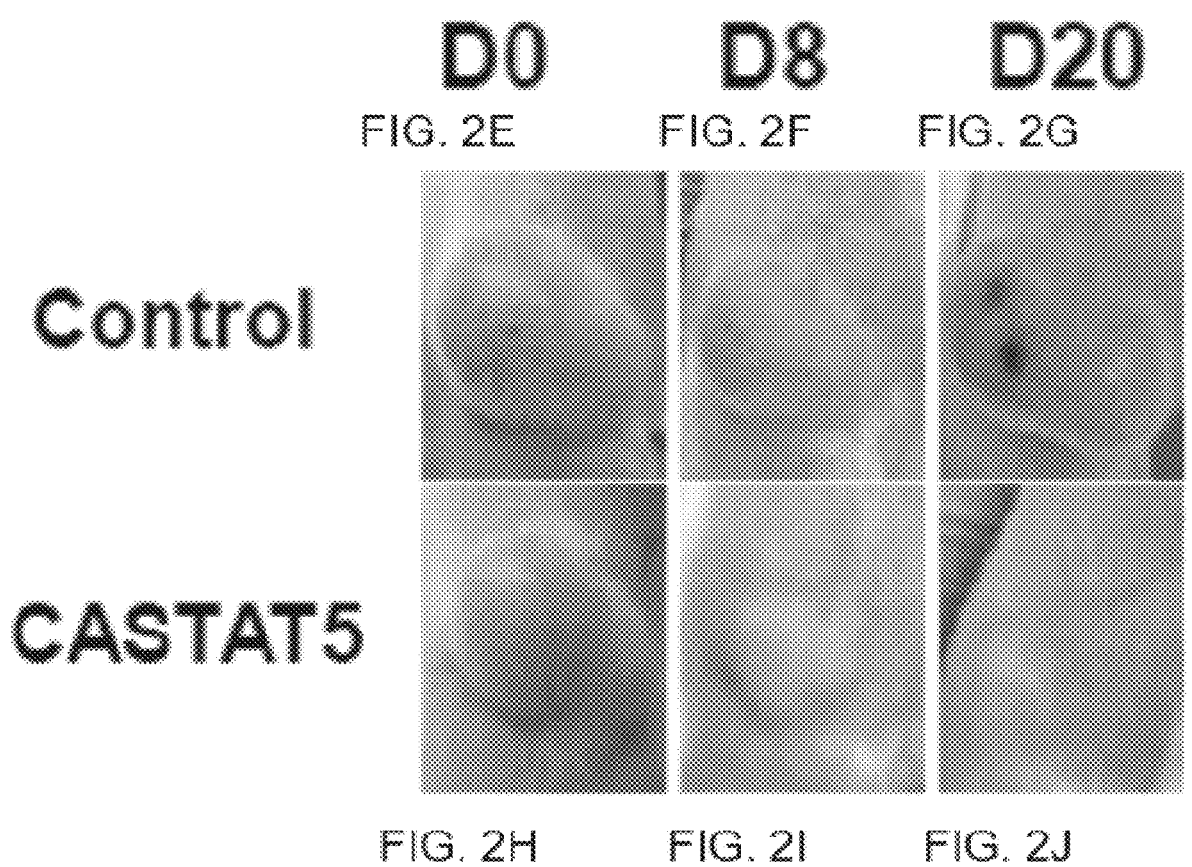
FIG. 2K
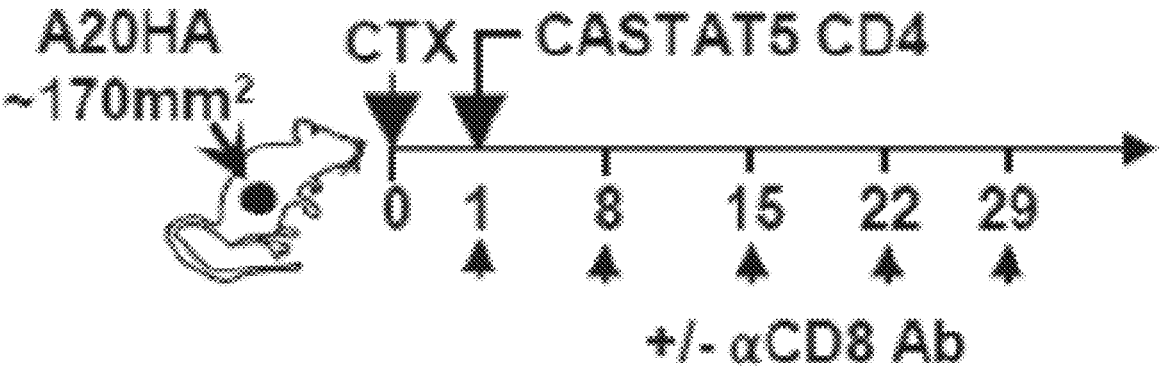

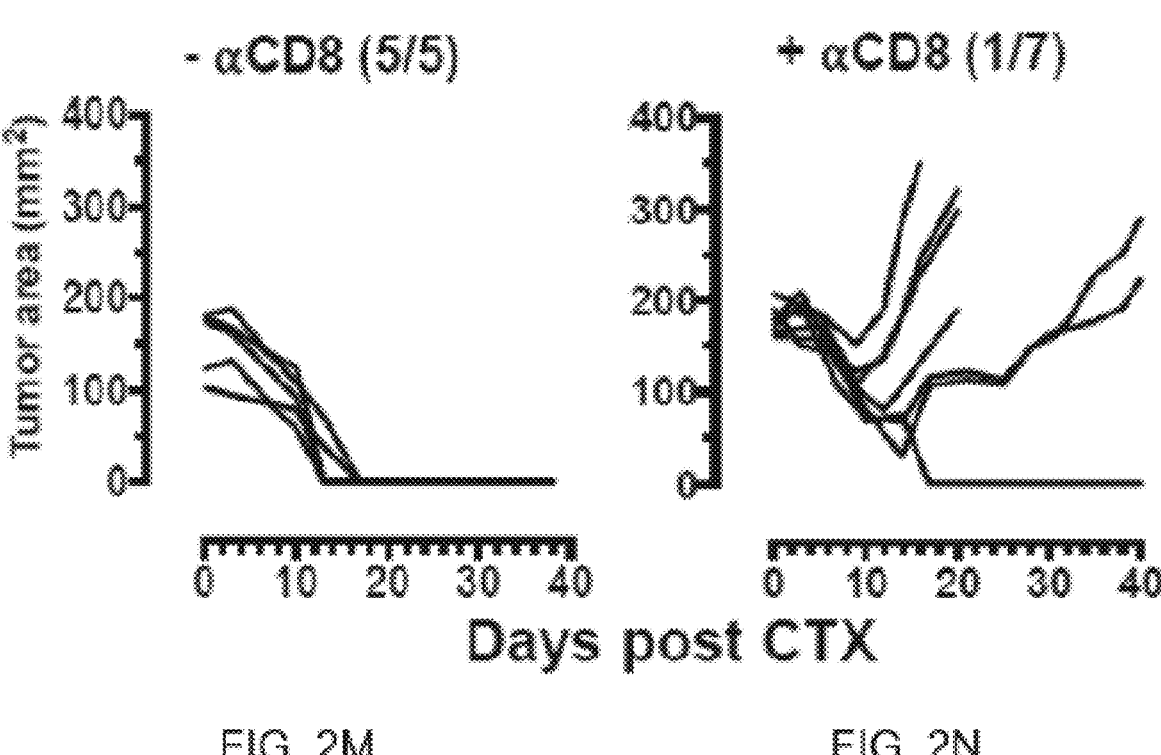
FIG. 2M                                        FIG. 2N
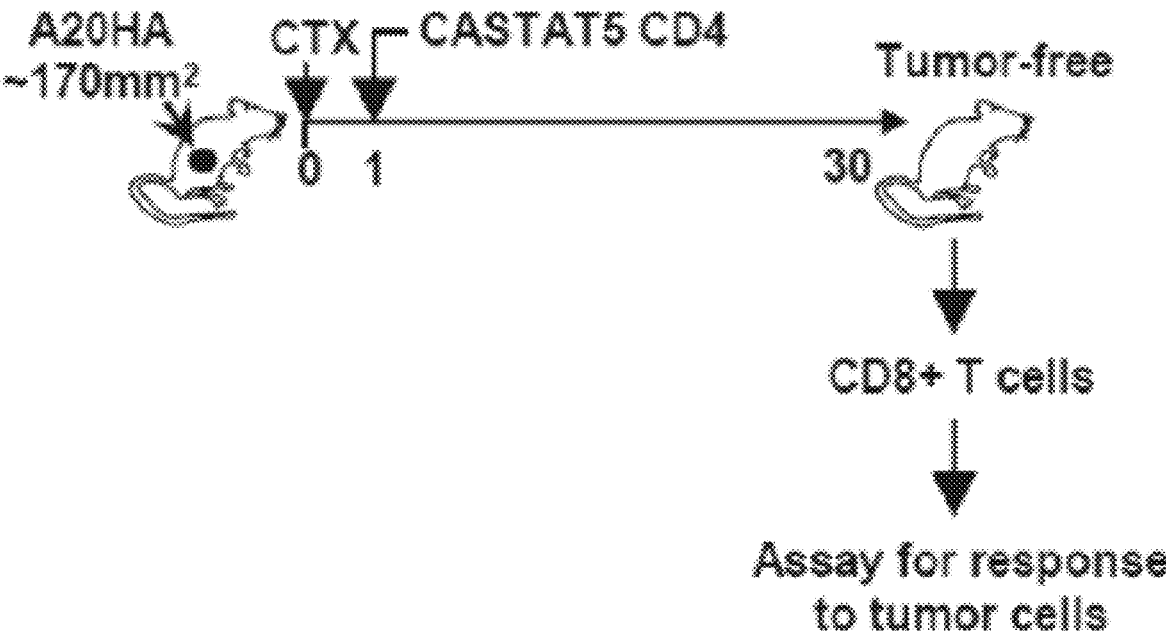
FIG. 2O CD8⁺ T cells co-cultured with

MOPC315 — FIG. 2P
A20HA — FIG. 2Q
A20WT — FIG. 2R

FIG. 2S    FIG. 2T    FIG. 2U

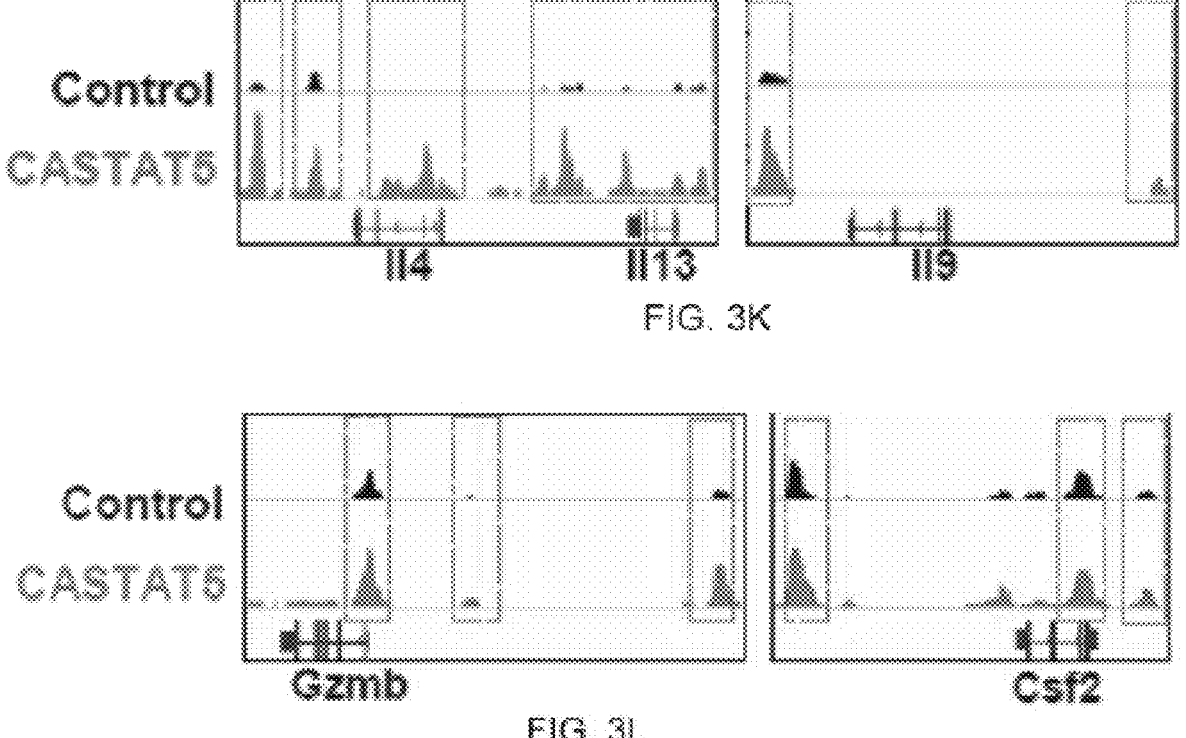
FIG. 3K
FIG. 3L
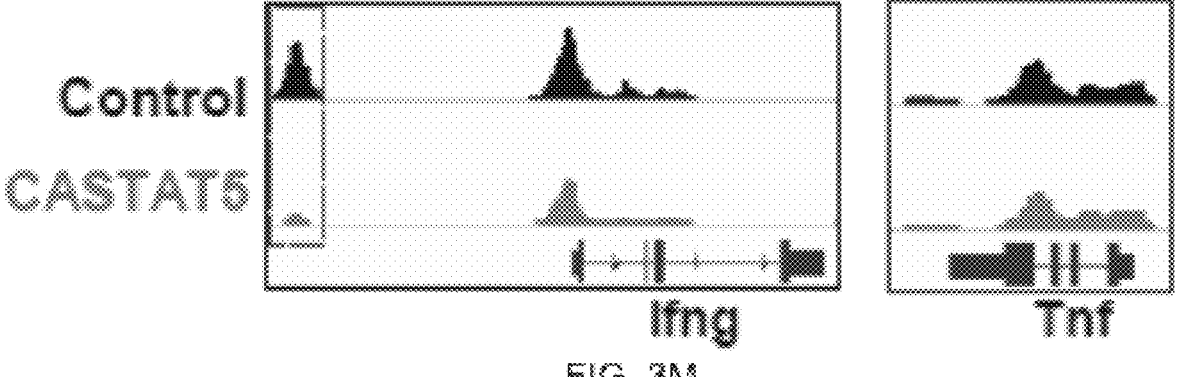
FIG. 3M

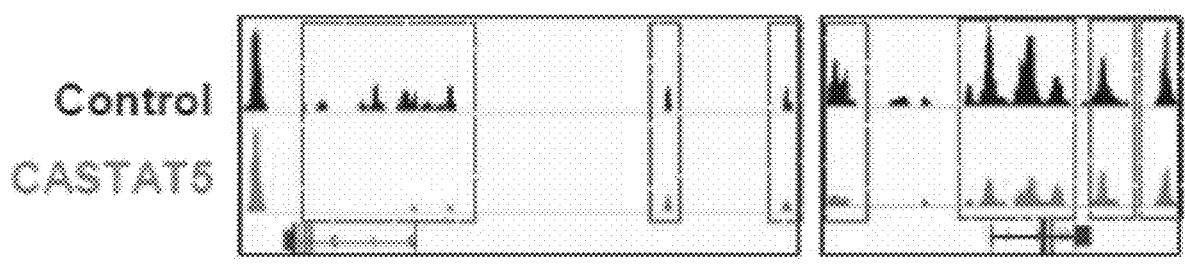
FIG. 3N
CASTAT5 > Control (Top1000)
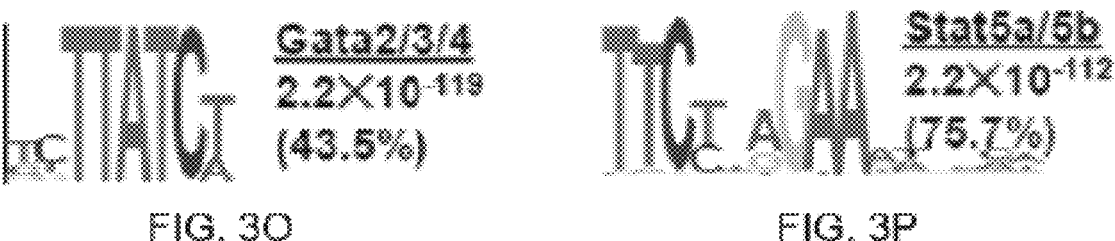
FIG. 3O                   FIG. 3P
Control > CASTAT5 (Top500)
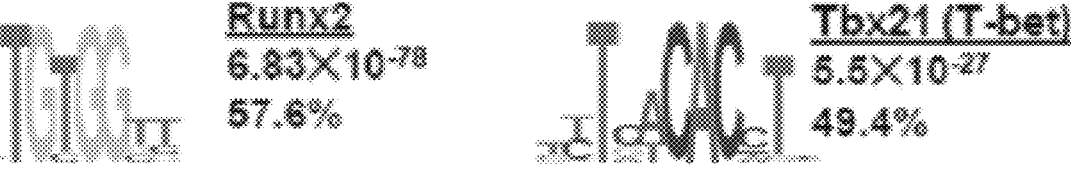
FIG. 3Q                   FIG. 3R

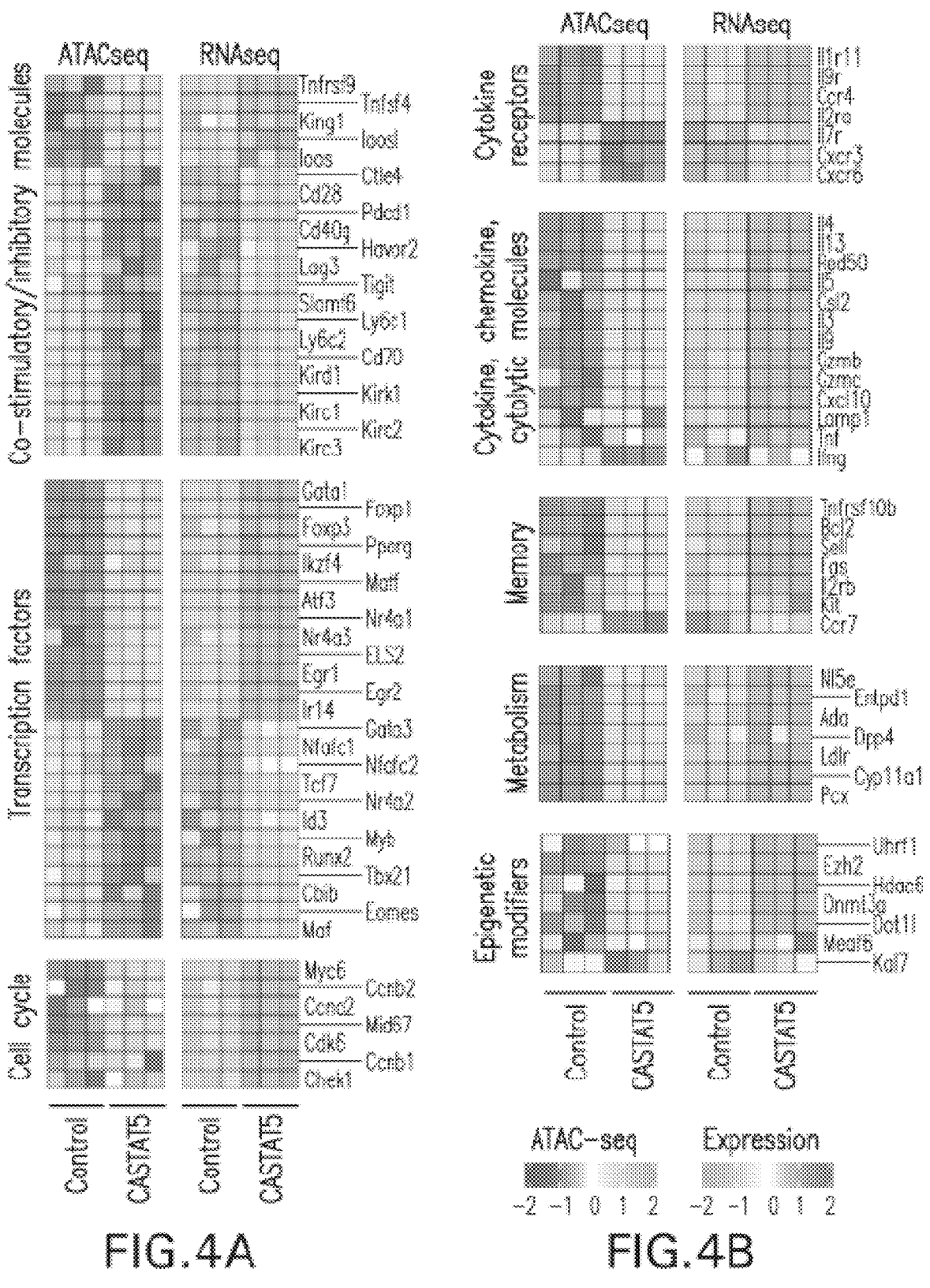
FIG.4A                    FIG.4B

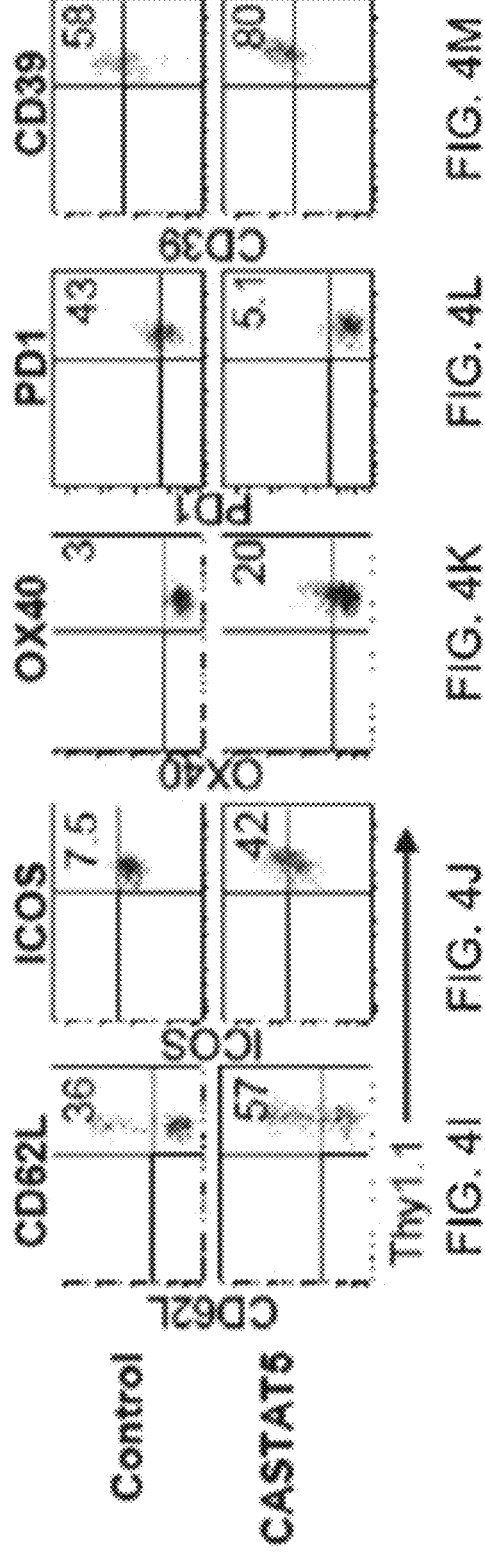

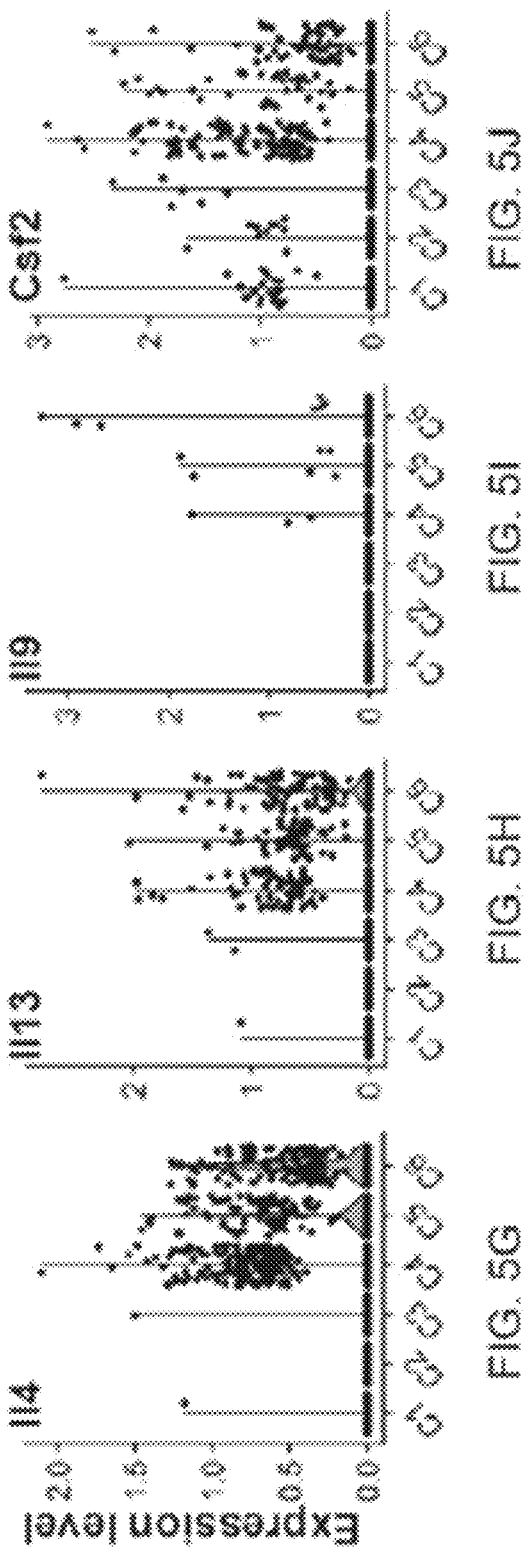

| Group | CD4+ CD19CAR | | CD8+ CD19CAR | |
|---|---|---|---|---|
| | Control CD4 | CASTAT5 CD4 | Control CD8 | CASTAT5 CD8 |
| I | / | / | + | / |
| II | + | / | + | / |
| III | / | + | + | / |
| IV | / | / | / | + |
| V | + | / | / | + |
| VI | / | + | / | + |

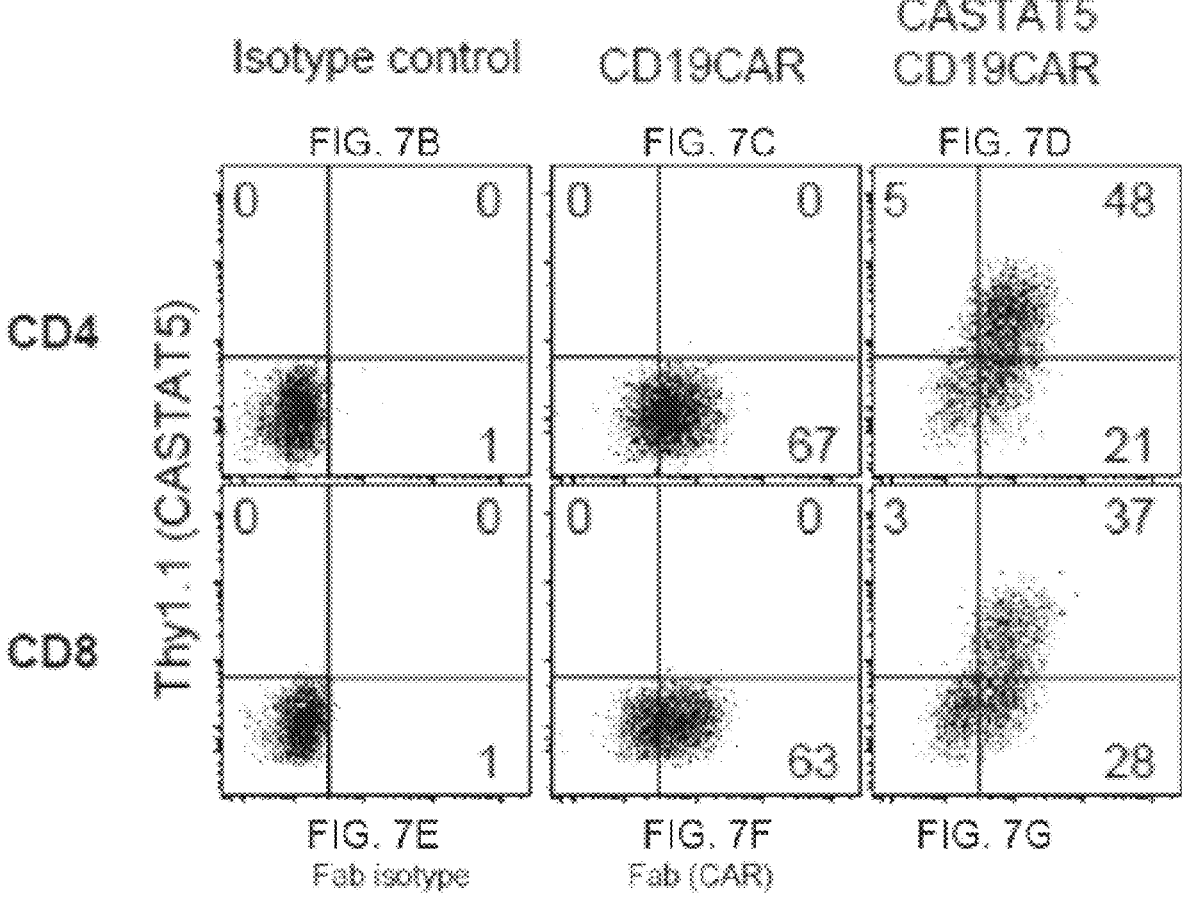

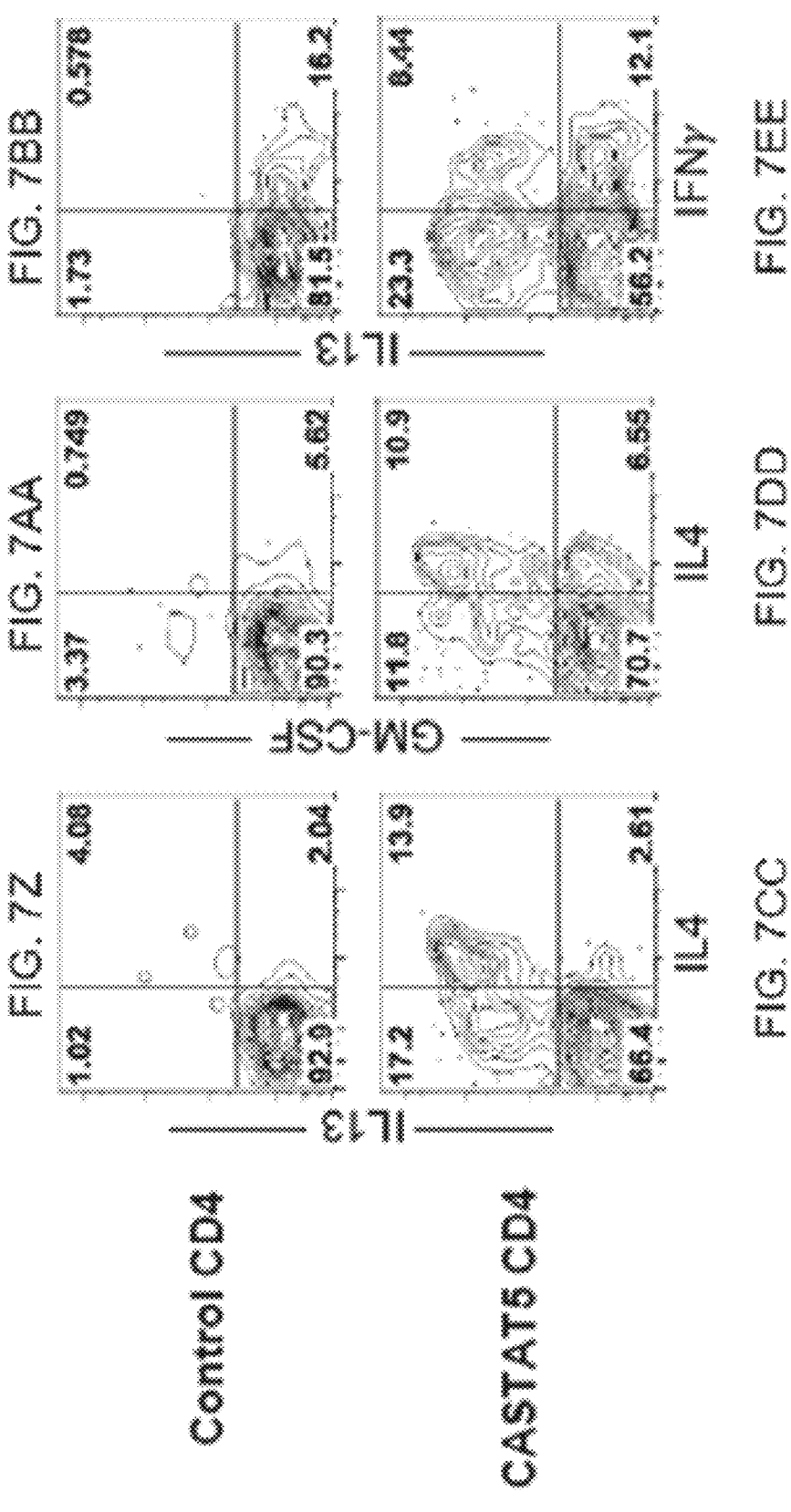

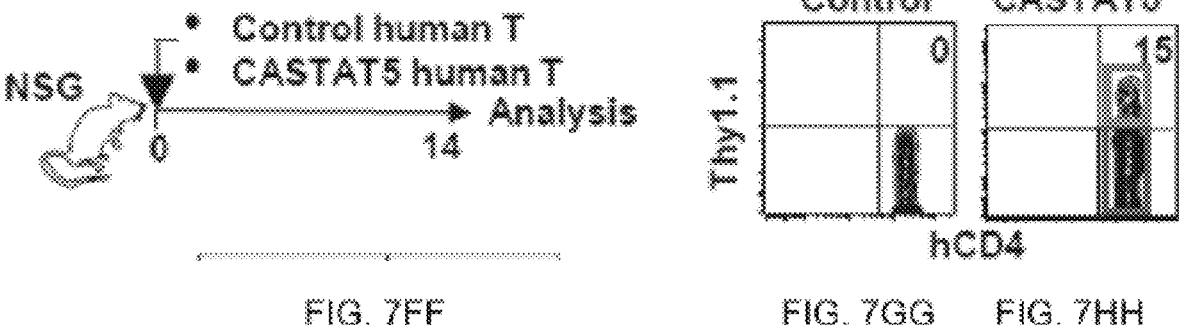
FIG. 7FF          FIG. 7GG     FIG. 7HH
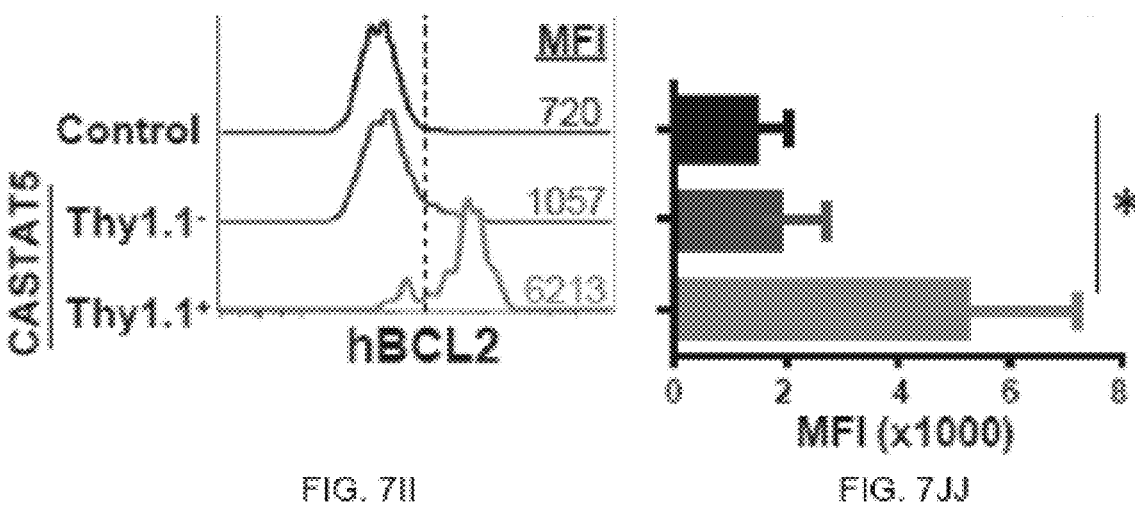
FIG. 7II                 FIG. 7JJ

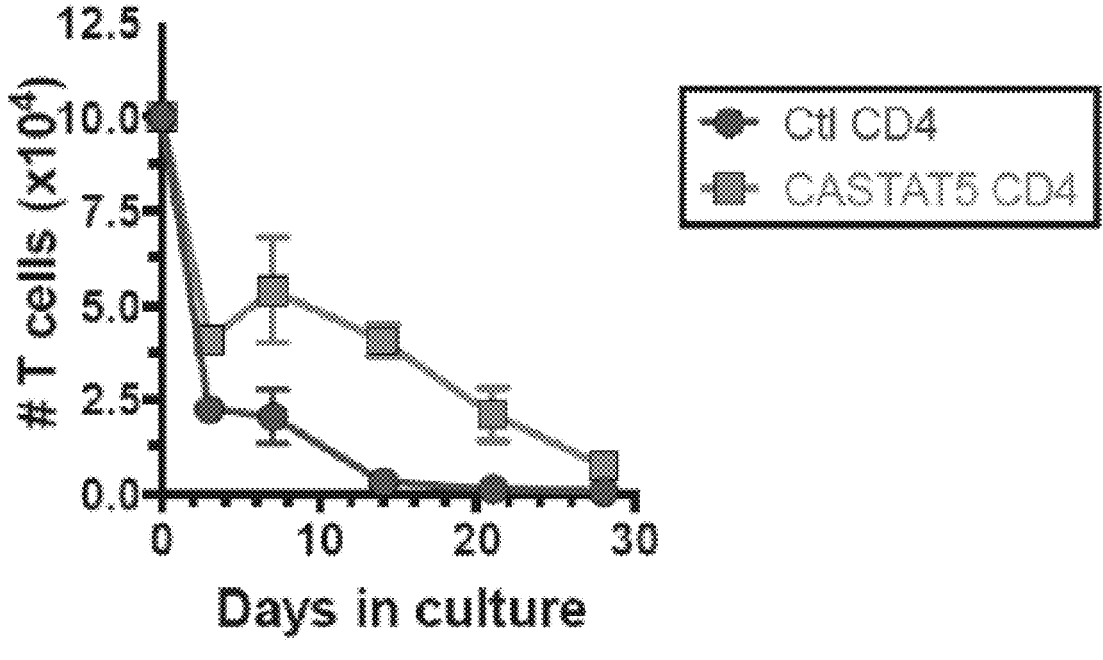
FIG. 8D
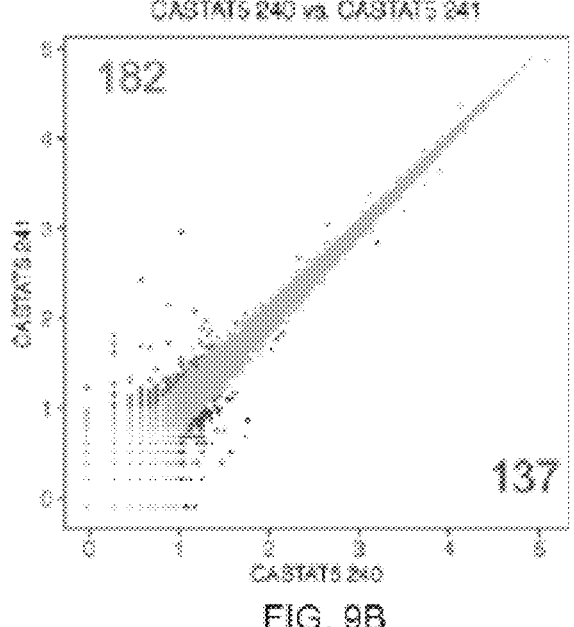
FIG. 9A                    FIG. 9B

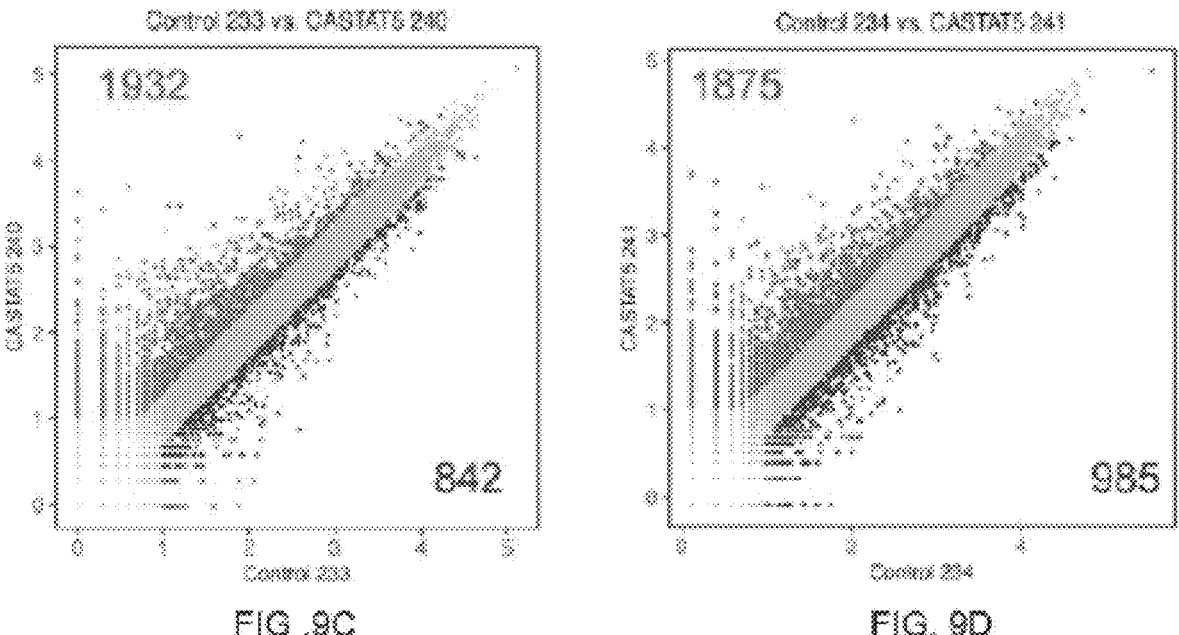
FIG .9C                 FIG. 9D
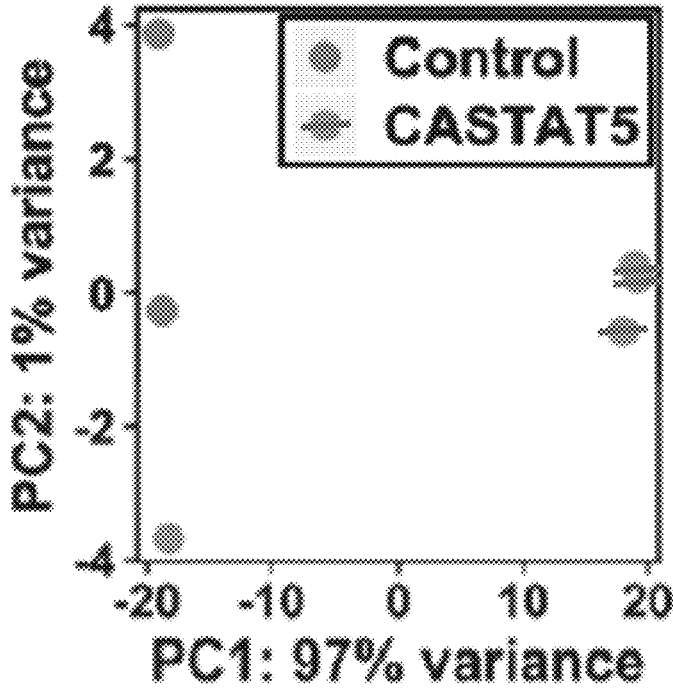
FIG. 9E

CASTAT5 CD4 ATAC-seq

CASTAT5 OCR   CASTAT5 CCR

Stat5a ChIP-seq peaks

STAT5a Chip-seq (GSE79518)

CASTAT5 > Control (Top1000)

FIG. 12A

Control > CASTAT5 (Top500)

Cluster 4 network

Cluster 5 network

Cytokine/chemokines receptors

Cell cycle regulators

Transcription factors

SEQUENCE LISTING

<160> NUMBER OF SEQ ID NOS: 4

<210> SEQ ID NO 1
<211> LENGTH: 4414
<212> TYPE: DNA
<213> ORGANISM: Homo sapiens

<400> SEQUENCE: 1

```
agatggccgg agtaaaagaa ggagggaggt gctgcggtgg tgggggtgat cttggcttca      60
ctagaatccc cagttcttcc cctctctaca gttttgtctc tgaggtcaca aaacctgtgg     120
cccccaagac acacatgcgc acacacgcgc gtgcacacac acaccccaca catttatttt     180
ttaatctagg ggctcaaaag atgacacgcg ccagagctgg aaggcgtcgc caattggtcc     240
acttttccct cctccctttt tgcggatgag aaaactgagg cccaggtttg ggatttccag     300
agcccgggat ttcccggcaa cgcccgacaa ccacattccc ccggctattc tgacccgccc     360
```

-continued

```
cggttccggg acgctccctg ggagccgccg ccgagggcct gctgggactc ccgggggacc    420
ccgccgtcgg ggcagccccc acgcccgcg ccgcccgccg ggaacggccg ccgctgttgc    480
gcacttgcag gggagccggc gactgagggc gaggcaggga gggagcaagc ggggctggga    540
gggctgctgg cgcgggctcg cgcgctgtgt atggtctatc gcaggcagct gacctttgag    600
gaggaaatcg ctgctctccg ctccttcctg tagtaacagc cgccgctgcc gccgccgcca    660
ggaaccccgg ccgggagcga gagccgcggg gcgcagagcc ggcccggctg ccggacggtg    720 cggcccccacc aggtgaacgg ccatggcggg ctggatccag gcccagcagc tgcagggaga    780
cgcgctgcgc cagatgcagg tgctgtacgg ccagcacttc cccatcgagg tccggcacta    840
cttggcccag tggattgaga gccagccatg ggatgccatt gacttggaca atccccagga    900
cagagcccaa gccacccagc tcctggaggg cctggtgcag gagctgcaga agaaggcgga    960
gcaccaggtg ggggaagatg ggttttttact gaagatcaag ctggggcact acgccacgca   1020
gctccagaaa acatatgacc gctgccccct ggagctggtc cgctgcatcc ggcacattct   1080
gtacaatgaa cagaggctgg tccgagaagc caacaattgc agctctccgg ctgggatcct   1140
ggttgacgcc atgtcccaga agcaccttca gatcaaccag acatttgagg agctgcgact   1200
ggtcacgcag gacacagaga atgagctgaa gaaactgcag cagactcagg agtacttcat   1260
catccagtac caggagagcc tgaggatcca agctcagttt gcccagctgg cccagctgag   1320
cccccaggag cgtctgagcc gggagacggc cctccagcag aagcaggtgt ctctggaggc   1380
ctggttgcag cgtgaggcac agacactgca gcagtaccgc gtggagctgg ccgagaagca   1440
ccagaagacc ctgcagctgc tgcggaagca gcagaccatc atcctggatg acgagctgat   1500
ccagtggaag cggcggcagc agctggccgg gaacggcggg cccccgagg gcagcctgga   1560 cgtgctacag tcctggtgtg agaagttggc cgagatcatc tggcagaacc ggcagcagat   1620
ccgcagggct gagcacctct gccagcagct gcccatcccc ggcccagtgg aggagatgct   1680
ggccgaggtc aacgccacca tcacggacat tatctcagcc ctggtgacca gcacattcat   1740
cattgagaag cagcctcctc aggtcctgaa gacccagacc aagtttgcag ccaccgtacg   1800
cctgctggtg ggcgggaagc tgaacgtgca catgaatccc ccccaggtga aggccaccat   1860
catcagtgag cagcaggcca agtctctgct taaaaatgag aacacccgca acgagtgcag   1920
tggtgagatc ctgaacaact gctgcgtgat ggagtaccac caagccacgg gcaccctcag   1980
tgcccacttc aggaacatgt cactgaagag gatcaagcgt gctgaccggc ggggtgcaga   2040
gtccgtgaca gaggagaagt tcacagtcct gtttgagtct cagttcagtg ttggcagcaa   2100
tgagcttgtg ttccaggtga agactctgtc cctacctgtg gttgtcatcg tccacggcag   2160
ccaggaccac aatgccacgg ctactgtgct gtgggacaat gcctttgctg agccgggcag   2220
ggtgccattt gccgtgcctg acaaagtgct gtggccgcag ctgtgtgagg cgctcaacat   2280
gaaattcaag gccgaagtgc agagcaaccg gggcctgacc aaggagaacc tcgtgttcct   2340
ggcgcagaaa ctgttcaaca cagcagcag ccacctggag gactacagtg gcctgtccgt   2400
gtcctggtcc cagttcaaca gggagaactt gccgggctgg aactacacct tctggcagtg   2460
gtttgacggg gtgatggagg tgttgaagaa gcaccacaag ccccactgga atgatggggc   2520
catcctaggt tttgtgaata agcaacaggc ccacgacctg ctcatcaaca agcccgacgg   2580
gaccttcttg ttgcgcttta gtgactcaga aatcggggc atcaccatcg cctggaagtt   2640
tgactccccg gaacgcaacc tgtggaacct gaaaccattc accacgcggg atttctccat   2700
```

-continued

```
caggtccctg gctgaccggc tggggggacct gagctatctc atctatgtgt ttcctgaccg      2760
ccccaaggat gaggtcttct ccaagtacta cactcctgtg ctggctaaag ctgttgatgg      2820
atatgtgaaa ccacagatca agcaagtggt ccctgagttt gtgaatgcat ctgcagatgc      2880 tggggggcagc agcgccacgt acatggacca ggccccctcc ccagctgtgt gcccccaggc      2940
tccctataac atgtacccac agaaccctga ccatgtactc gatcaggatg gagaattcga      3000
cctggatgag accatggatg tggccaggca cgtggaggaa ctcttacgcc gaccaatgga      3060
cagtcttgac tcccgcctct cgccccctgc cggtctttc acctctgcca gaggctccct      3120
ctcatgaatg tttgaatccc acgcttctct ttggaaacaa tatgcaatgt gaagcggtcg      3180
tgttgtgagt ttagtaaggc tgtgtacact gacacctttg caggcatgca tgtgcttgtg      3240
tgtgtgtgtg tgtgtgtgtc cttgtgcatg agctacgcct gcctcccctg tgcagtcctg      3300
ggatgtggct gcagcagcgg tggcctcttt tcagatcatg gcatccaaga gtgcgccgag      3360
tctgtctctg tcatggtaga gaccgagcct ctgtcactgc aggcactcaa tgcagccaga      3420
cctattcctc ctgggcccct catctgctca gcagctattt gaatgagatg attcagaagg      3480
ggaggggaga caggtaacgt ctgtaagctg aagtttcact ccggagtgag aagctttgcc      3540
ctcctaagag agagagacag agagacagag agagagaaag agagagtgtg tgggtctatg      3600
taaatgcatc tgtcctcatg tgttgatgta accgattcat ctctcagaag ggaggctggg      3660
gttcattttc gagtagtatt ttatacttta gtgaacgtgg actccagact ctctgtgaac      3720
cctatgagag cgcgtctggg cccggccatg tccttagcac aggggggccg ccggtttgag      3780
tgagggtttc tgagctgctc tgaattagtc cttgcttggc tgcttggcct tgggcttcat      3840
tcaagtctat gatgctgttg cccacgtttc ccgggatata tattctctcc cctccgttgg      3900
gccccagcct tctttgcttg cctctctgtt tgtaaccttg tcgacaaaga ggtagaaaag      3960
attgggtcta ggatatggtg ggtggacagg ggccccggga cttggagggt tggtcctctt      4020
gcctcctgga aaaacaaaa acaaaaaaact gcagtgaaag acaagctgca aatcagccat      4080
gtgctgcgtg cctgtggaat ctggagtgag gggtaaaagc tgatctggtt tgactccgct      4140
ggaggtgggg cctggagcag gccttgcgct gttgcgtaac tggctgtgtt ctggtgaggc      4200
cttgctccca accccacacg ctcctccctc tgaggctgta ggactcgcag tcaggggcag      4260
ctgaccatgg aagattgaga gcccaaggtt taaacttctc tgaagggagg tggggatgag      4320 aagagggggtt tttttgtact ttgtacaaag accacacatt tgtgtaaaca gtgtttttgga      4380 ataaaatatt tttttcataa aaaaaaaaaa aaaa      4414
```

\<210\> SEQ ID NO 2
\<211\> LENGTH: 2379
\<212\> TYPE: DNA
\<213\> ORGANISM: Artificial Sequence
\<220\> FEATURE:
\<223\> OTHER INFORMATION: Description of Artificial Sequence: Synthetic
      polynucleotide

\<400\> SEQUENCE: 2

```
atggcgggct ggattcaggc ccagcagctt caggggagatg ccctgcgcca gatgcaagtg        60
ttgtatgggc agcatttccc catcgaggtc cggcactacc tggcccagtg gatcgagagc       120
cagccgtggg atgctattga cttggataat ccccaggacc gaggtcaggc cacccaactc       180 ctggaggggcc tggtgcagga gctgcagaag aaggcggagc accaggtggg ggaagatggg       240
tttttgctga agatcaagct ggggcactat gccacacagc tccagaacac gtatgaccgc       300
```

```
tgtcccatgg agctggttcg ctgtatccgt cacattctgt acaacgaaca gaggctggtt      360
cgcgaagcca acaattgcag ctcccctgct ggtgtcctgg ttgacgccat gtcccagaag      420
caccttcaga tcaaccaaag gtttgaggag ctgcgcctga tcacacagga cacggagaac      480
gagctgaaga agctgcagca gacccaagag tacttcatca tccagtacca ggagagcctg      540
cggatccaag ctcagtttgc ccagctgggc cagctgaacc cccaggagcg catgagcagg      600
gagacggccc tccagcagaa gcaagtgtcc ctggagacct ggctgcagcg agaggcacag      660
acactgcagc agtaccgagt ggagctggct gagaagcacc agaagaccct gcagctgctg      720
cggaagcagc agaccatcat cctggacgac gagctgatcc agtggaagcg gagacagcag      780
ctggccggga acgggggtcc ccccgagggc agcctggacg tgctgcagtc ctggtgtgag      840
aagctggccg agatcatctg gcagaaccgg cagcagatcc gcagggctga gcgcctgtgc      900
cagcagctgc ccatcccagg ccccgtggag gagatgctgg ctgaggtcaa cgccaccatc      960
acggacatca tctcagctct ggtcaccagc acgttcatca tcgagaagca gcctcctcag     1020
gtcctgaaga cccagaccaa gtttgcggcc accgtgcgcc tgctggtggg gggaaagctg     1080
aatgtgcaca tgaacccccc gcaggtgaag gcgaccatca tcagcgagca gcaggccaag     1140
tccctgctca agaatgagaa cacccgcaat gagtgcagcg gcgagatcct gaacaactgt     1200
tgcgtcatgg agtaccacca ggccactggc acgctcagcg cccacttcag aaacatgtca     1260
ctgaaaagaa tcaagcgcgc cgacaggcgt ggtgcagagt cggtgacgga ggagaagttc     1320
acagtcctgt ttgagtctca gttcagcgtt ggcagcaacg agctggtgtt ccaggtgaag     1380
accctgtccc tccctgtggt cgttatcgtc catggcagcc aggaccacaa tgctactgcc     1440
accgtgctgt gggacaatgc ctttgctgag ccgggcaggg tgccatttgc tgtgcctgac     1500
aaggtgctgt ggccgcagct gtgtgaagcg ctcaacatga aattcaaggc tgaagtacag     1560
agcaaccggg gcttgaccaa agagaacctc gtgttcctgg cacagaaact gttcaacatc     1620
agcagcaacc acctcgagga ctacaacagc atgtctgtgt cctggtccca gttcaaccgg     1680
gagaacttgc ccggctggaa ctacaccttc tggcagtggt tcgacggggt gatggaggtg     1740
ctgaagaagc accataagcc ccattggaat gatgggggcta tcctgggttt cgtgaacaag     1800
caacaggccc acgacctgct catcaacaag ccggacggga ccttcctgct gcgcttcagt     1860
gactcggaaa tcgggggcat caccattgct tggaagtttg actctccgga ccgaaacctc     1920
tggaatctga gccattcac gacgcgagat ttctccattc ggtccctggc cgaccggctg     1980
ggggacctga actaccttat ctacgtgttc ccagaccgac ccaaggacga ggtctttgcc     2040
aagtattaca ctcctgtact tgcgaaagca gttgacggat acgtgaagcc acagatcaag     2100
caagtggtcc ctgagttcgt caatgcattc acagatgccg gagccagcgc cacctacatg     2160
gaccaggctc cttccccagt cgtgtgccct caacctcact acaacatgta cccacccaac     2220
cctgaccctg tccttgacca agatggcgag tttgacctgg atgagagcat ggatgttgcc     2280
aggcacgtgg aagaactttt acgccggccc atggacagtc tcgacgcccg cctctcccca     2340
cctgctggtc tcttcacctc cgctagaagc tccctgtcc                            2379
```

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
    primer -continued

```
<400> SEQUENCE: 3
atccatggag atctatgaag tggcc                                              25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atgtcgacgt taactcatct gggg                                              24
```

CHIMERIC ANTIGEN RECEPTOR T CELLS AND METHODS OF USE THEREOF

STATEMENT REGARDING FEDERALLY SPONSORED RESEARCH

This invention was made with government support under CA215523 awarded by the National Institutes of Health. The government has certain rights in the invention.

TECHNICAL FIELD OF THE INVENTION

This invention is generally related to the field of immunotherapy, more specifically adoptive cell therapy and related therapies.

SEQUENCE LISTING

The instant application contains a Sequence Listing which has been submitted electronically in ASCII format and is hereby incorporated by reference in its entirety. Said ASCII copy, created on Sep. 9, 2021, is named 064466_126_SL.txt and is 9,878 bytes in size.

BACKGROUND OF THE INVENTION

Recent advances in adoptive T-cell therapy (ACT), especially CD19-targeting chimeric antigen receptor (CAR) T-cell therapy (CD19CART), have highlighted the potential of immunotherapy to achieve durable and curative patient outcomes (Sadelain, M., *J Clin Invest*, 125:3392-3400 (2015); June C. H. and M. Sadelain, *N Engl J Med*, 379: 64-73 (2018)). However, even for the well-developed CD19CART, many patients failed to respond to the treatment, or succumbed to late relapse after initial response (Fesnak, A. D., *Nat Rev Cancer*, 16:566-581 (2016)). Moreover, by far ACT in general has not been effective in treating most solid tumors. The major barriers to effective ACT include deficiencies in donor T cell expansion, persistence and tumor-infiltration, as well as loss of effector functions in the immunosuppressive tumor microenvironment (TME) (Gilham, D. E., et al., *Trends Mol Med*, 18:377-384 (2012); Newick, K., et al., *Annu Rev Med*, 68:139-152 (2017); D'Aloia, M. M., et al., *Cell Death Dis*, 9:282 (2018)). There is increasing demand for novel strategies that can overcome these barriers so as to improve the efficacy of ACT.

The infusion products of ACT usually contain both CD8$^+$ and CD4$^+$ T lymphocytes, and CD8$^+$ T cells are considered as the major effector population that mediates the tumor-killing effects. Recent studies demonstrate that tumor-specific CD8$^+$ T cells are susceptible to functional exhaustion in the TME, a process characterized by progressive loss of effector functions, which may contribute to failed tumor growth control (Schietinger, A., et al., *Trends Immunol*, 35:51-60 (2014); Pauken, K. E. and E. J. Wherry, *Trends Immunol*, 36:265-276 (2015)). CD4$^+$ T cells are regarded as helper cells that act to potentiate CD8$^+$ T cell responses (Pardoll, D. M., et al., *Curr Opin Immunol*, 10:588-594 (1998); Bevan, M. J., *Nat Rev Immunol*, 4:595-602 (2004); Ding, Z. C., and G. Zhou, *CLin Dev Immunol*, 890178 (2012); Borst, J., et al., *Nat Rev Immunol*, 18:635-647 (2018)). With relevance to CD19CAR T cell therapy, the co-presence of CD4$^+$ and CD8$^+$ T cells in the infusion products was found to correlate with favorable patient outcomes (Turtle, C. J., et al *J Clin Invest*, (2016)), although the mechanism of CD4$^+$-CD8$^+$ T cell cooperation awaits to be elucidated. A likely possibility is that CD4$^+$ helper T cells can prevent CD8$^+$ T cell exhaustion in the TME, as it has been demonstrated in the setting of chronic viral infection (Aubert, R. D., et al., *Proc Natl Acad Sci USA*, 108:21182-21187 (2011)). Apart from their role as helpers, CD4$^+$ T cells can act as the driver of antitumor immune responses in ACT. Case report studies showed that adoptive transfer of ex vivo expanded tumor-specific CD4$^+$ T cell clones can lead to tumor regression in patients with metastatic tumors (Hunder, N. N. et al., *N Engl J Med*, 358:2698-2703 (2008); Tran, E., *Science*, 344:641-645 (2014)). A recent clinical study demonstrated the safety and efficacy of administering CD4$^+$ T cells genetically engineered to express tumor-specific T cell receptors (TCRs) (Lu, Y. C., et al., *J Clin Oncol*, 35:3322-3329 (2017)). CD4$^+$ T cell-based CAR T cell therapy also showed robust antitumor effects in some preclinical models (Gacerez, A. T., et al., *Cancer Gene Ther*, 25:117-128 (2018); Wang, D., ct al., *JCI Insight*, 3 (2018)). Whether CD4$^+$ T cells are used as helpers or "stand-alone" effectors in ACT, their functional status appears to be a key determinant of the therapy outcome. The presence of CD4$^+$ T cells with a polyfunctional phenotype, characterized by concomitant production of multiple inflammatory cytokines, has been associated with favorable immunological events, including dendritic cell activation, antigen epitope spreading, immunostimulatory cytokine milieu, CD8$^+$ T cell activation, and ultimately, improved antitumor effects in tumor-bearing mice or cancer patients (Hunder, N. N. et al., *N Engl J Med*, 358:2698-2703 (2008); Tran, E., *Science*, 344:641-645 (2014); Quezada, S. A., et al., *J Exp Med*, 207:637-650 (2010); Xic, Y., et al., *J Exp Med*, 207:651-667 (2010); Ding. Z. C., et al., *Blood*, 120:2229-2239 (2010); Hirschhorn-Cymermann, D., et al., *J Exp Med*, 209:2113-2126 (2012); Fujiwara, H., et al., *Leukemia*, 29:2393-2401 (2015); Rossi, J., et al., *Blood*, 132:804-814 (2018)). However, CD4$^+$ T cells are not immune to tumor-induced dysfunction or exhaustion (Crawford, A., et al., *Immunity*, 40:289-302 (2014)), and exhausted CD4$^+$ T cells may exacerbate CD8$^+$ T cell dysfunction (Hwang, S., et al., *J Exp Med*, 213:1799-1818 (2016)). Thus, finding ways to generate exhaustion-resistant, polyfunctional CD4$^+$ T cells may have important implications for ACT.

It is an object of the invention to provide polyfunctional CD4$^+$ T cells and CAR T cells, and methods of making and using the same.

SUMMARY OF THE INVENTION

Disclosed herein are engineered polyfunctional CD4$^+$ T cells/CAR T cells and methods of their use for the treatment of cancers. One embodiment provides a method of producing polyfunctional CD4$^+$ T cells by constitutively activating STAT5A in the cells to induce a polyfunctional phenotype. Also provided is a method of reversing exhaustion in tumor-specific CD4$^+$ T cells by engineering the cells to express Fos, Jun, Nr4a1, or combinations thereof but not express Tox, Pdcd1, Ctla4, Haver2, Lag3, Tigit, Slam6, Nrf4a2, and administering the engineered cells to a subject.

One embodiment provides a method of adoptive cell transfer including administering a population of modified CD4$^+$ T cells genetically engineered to express one or more of genes selected from the group consisting of Fos, Jun, Nr4a1, and combinations thereof and not express one or more genes selected from the group consisting of Tox, Pdcd1, Ctla4, Haver2, Lag3, Tigit, Slam6, Nrf4a2, and combinations thereof to a subject in need thereof in an amount effective to induce an immune response. The T cells can be autologous or allogenic. The T cells can be tumor-specific T cells. The T cells can be further engineered to express a tumor antigen receptor. In one embodiment, the tumor antigen receptor is CD19 receptor.

Also provided is a method of adoptive transfer including isolating CD4$^+$ T cells from a subject, genetically engineering the CD4$^+$ T cell to constitutively express Stat5a activity, wherein the constitutive STAT5a activity induces expression of one or more of Fos, Jun, Nr4a1, or combinations thereof and silences expression of one or more of Tox, Pdcd1, Ctla4, Haver2, Lag3, Tigit, Slam6, Nrf4a2, or combinations thereof, and administering the genetically engineered CD4$^+$ T cells to the subject in an amount effective to induce an immune response.

One embodiment provides a method of improving the efficacy of CD19 chimeric antigen receptor (CAR) therapy in a subject in need thereof by engineering CD19 chimeric antigen receptor cells to constitutively express STAT5a, wherein STAT5a expression induces polyfunctionality in the cells; and administering the cells to the subject in an amount effective to induce an immune response and reduce tumor burden in the subject.

The disclosed methods are useful for treating subjects with cancer. In one embodiment the cancer is hematologic cancer such as B cell lymphoma. In another embodiment, the cancer is solid cancer such as colorectal, renal, lung breast, kidney, bladder, uterine, or prostate.

Also provided is a method of producing polyfunctional T cells by inducing the expression of Fos, Jun, Nr4a1, or combinations thereof in a population of T cells in an amount effective to induce polyfunctionality, and silencing the expression of Tox, Pdcd1, Ctla4, Haver2, Lag3, Tigit, Slam6, Nrf4a2, or a combination thereof in the population of T cells, wherein the gene expression phenotype induces polyfunctionality in the population of T cells. The gene expression is increased and decreased by constitutively activating Stat5a. The gene expression is induced by retroviral or lentiviral transduction. The gene expression is silenced by siRNA, RNAi, or CRISPR/Cas.

Another embodiment provides a method of reversing T cell exhaustion in a population of tumor-specific CD4$^+$ T cells in a patient in need thereof, by increasing the expression of one or more genes selected from the group consisting of Fos, Jun, Nr4a1, and combinations thereof in a population of T cells in an amount effective to induce polyfunctionality, decreasing the expression one or more genes selected from the group consisting of Tox, Pdcd1, Ctla4, Haver2, Lag3, Tigit, Slam6, Nrf4a2, and combinations thereof in the population of T cells in an amount effective to induce polyfunctionality, wherein the gene expression phenotype reverses exhaustion and induces polyfunctionality in the population of CD4$^+$ T cells, and administering the population of CD4$^+$ T cells to the subject in need thereof, wherein the administered CD4$^+$ T cells induce an immune response in the tumor. The gene expression phenotype is induced by constitutive STAT5a expression.

BRIEF DESCRIPTION OF THE DRAWINGS

FIGS. 2E-2J are representative images of tumors in mice before treatment and at different time points after treatment. FIG. 2K is a schematic illustration of the timeline of experimental procedures. Briefly, A20HA-bearing mice were treated with CTX followed by adoptive transfer of CASTAT5-transduced HA-specific CD4+ T cells. At the indicated time points, a cohort of mice were injected with anti-CD8a mAb (200 μg per injection). FIGS. 2M-2N are graphs showing tumor growth over time for mice with and without anti-CD8a mAb treatment. FIG. 2O is a schematic illustration of the timeline of experimental procedures. Briefly, 30 days after receiving CASTAT5-transduced HA-specific CD4+ T cells, host CD8+ T cells were purified, labeled with violet dye and incubated with equal number of irradiated A20HA, A20WT or MOPC315 cells. 7 days later, CD8+ T cells were harvested and evaluated for cell proliferation (violet dye dilution) and activation (CD25 and CD44) by FACS. FIGS. 2P-2U are representative dot plots showing CD25 and CD44 expression in CD8+ T cells incubated with irradiated A20HA, A20WT or MOPC315 cells.

FIGS. 3K-3N are graphs showing the chromatin accessibility tracks of some representative genes. The bottom peaks correspond to CASTAT5 and the top peaks correspond to control CD4+ T cells. The rectangles in FIGS. 3K-3L mark ATAC peaks showing increased signal intensity in CASTAT5 CD4+ T cells compared to control CD4+ T cells, while the rectangles in FIGS. 3M-3N_mark ATAC peaks that disappeared or reduced in intensity in CASTAT5 CD4+ T cells. FIGS. 3O-3R are schematics showing the results from MEME-Chip motif analysis identified transcription factor consensus binding sites significantly enriched in the top 1000 and top 500 ATAC peaks with gain or loss of chromatin accessibility in CASTAT5 CD4+ T cells, respectively.

FIGS. 4A-4B are small panel heatmaps showing matched ATACseq and RNAseq data. Columns represent samples and rows represent genes. Three biological replicates are shown for both CASTAT5 and control CD4+ T cells. Genes are grouped into several functional categories.

FIGS. 5C-5J are violin plots showing differential expression of 8 selected effector molecules among the six clusters of single CD4+ T cells.

FIG. 6I is a graph showing the frequencies of host B cells in blood. At the indicated time points, tail blood was collected from each mouse and the presence of host B cells in blood was evaluated by CD19 and B220 co-stain.

FIGS. 7B-7G are flow cytometry plots showing CD19CAR and CASTAT5 expression in transduced T cells. The numbers in plots indicate the percentage of cells in the corresponding quadrant. FIGS. 7Z-7EE are cytokine profiles of donor CD4+CD19CAR T cells. Ten days after T cell transfer, splenocytes from a cohort of mice from group V and VI were prepared and stimulated with PMA/ionomycin in the presence of GolgiStop for 4 hr before intracellular cytokine staining (ICS) for the indicated cytokines. Numbers in representative dot plots indicate percentage of cells in corresponding quadrant. FIG. 7FF is a schematic illustration showing experimental procedures followed for FIGS. 7GG-7MM. Briefly, human total T cells purified from the PBMC of a healthy donor were mock-transduced (control) or transduced with CASTAT5 retrovirus. Transduced T cells were adoptively transferred to NSG mice (5×10⁶ cells/mouse). Two weeks after T-cell transfer, the donor CD4+ T cells in mice spleens were assayed for the presence of CASTAT5 as measured by the expression of Thy1.1. h (FIGS. 7GG-7HH). FIG. 7II is a line graph showing results of FACS analysis of the expression profiles of hBCL2 in CASTAT5-transduced human T cells that were either positive (Thy1.1⁺) or negative (Thy1.1⁻) for CASTAT5, distinguished by the presence of absence of Thy1.1, respectively. hBCL2 in mock-transduced CD4+ T cells (control) were included as a control. Numbers indicate the mean fluorescence intensity (MFI) of hBCL2⁺ cells. FIG. 7JJ is a bar graph showing the results of hBCL2 MFI. FIGS. 7KK-7MM are cytokine profiles of CASTAT5-transduced human CD4+ T cells. T cells recovered from NSG mice were stimulated with PMA/ionomycin in the presence of GolgiStop for 4 hr before intracellular cytokine staining (ICS) for the indicated cytokines. Numbers in representative dot plots indicate percentage of cells in corresponding quadrant.

FIG. 8D is a graph showing live cells counts over time for control and CASTAT5 CD4+ T cells in medium containing no cognate antigen or growth factors.

FIGS. 9A-9D are scatter plots showing pair-wise comparison between the biological replicates of the specified T cell samples as well as between CASTAT5 and control CD4+ T cell samples. The x and y-axis represent normalized and log 10 transformed RNAseq read counts for each sample. FIG. 9E is a PCA plot of RNAseq data. The circles indicate the sample groups.

FIG. 12A-12B show HOMER analysis results using the libraries of 400 bp sequences in FASTA format derived from top 1000 and top 500 ATAC peaks with gain or loss of chromatin accessibility in CASTAT5 CD4+ T cells as inputs. The top ranked motifs with significant p values are shown.

FIG. 15B is a chart showing correlation of gene module with cell cluster identity as defined in FIGS. 5A-5B and the expression status of CASTAT5. Each row corresponds to a module eigengene and the columns are clusters 1-6 and CASTAT5 status. The values in the cells are presented as "Pearson r (p value)", and gradient-coded by direction and degree of the correlation. 14 modules of co-expressed transcripts are presented with their respective correlation parameters to clusters and CASTAT5 expression status.

DETAILED DESCRIPTION OF THE INVENTION

Figure 1A:
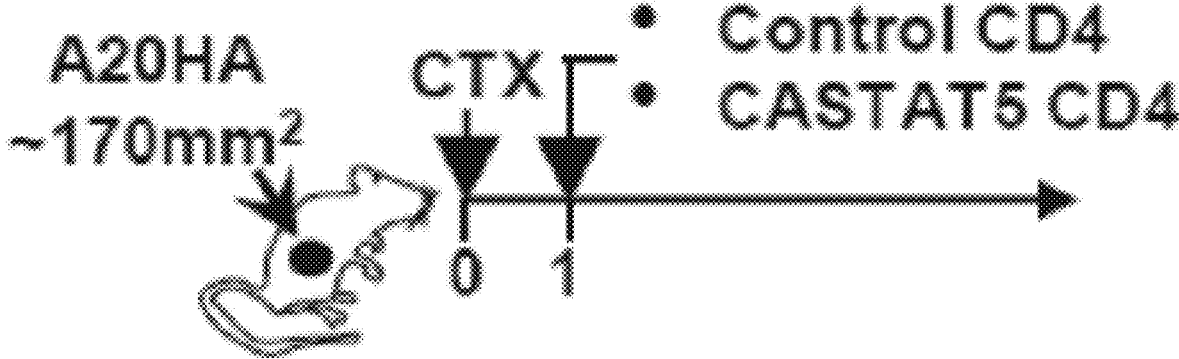
FIG. 1A is a schematic illustration showing the time line of experimental procedures in which mice with established A20HA tumor were conditioned with CTX (150 mg/kg) when tumor sizes reached about 170 mm$^2$. Mock-transduced (control CD4) or constitutively active STAT5A (CASTAT5)-transduced (CASTAT5 CD4) HA-specific CD4+ T cells (10$^5$ cells/mouse) were adoptively transferred to mice the next day.

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a." "an." "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "adoptive cell transfer" or ACT is a type of immunotherapy in which a patient's own T cells are collected, expanded ex vivo, and re-infused into the patient. Two types of ACT are chimeric antigen receptor (CAR) and T cell receptor (TCR) T cell therapy. Both techniques improve the ability of T cell receptors to recognize and attack specific antigens. In CAR T-cell therapy, T cells are engineered to produce receptors on their surface called chimeric antigen receptors. The receptors allow the T cells to recognize and attach to antigens on tumor cells. In TCR-T cell therapy, T cells are collected from a patient, modified to express a TCR specific to a tumor antigen, expanded ex vivo, and re-infused into the patient.

As used herein "chimeric antigen receptor" or "CAR" refers to synthetic constructs that are designed to be expressed in host T cells or NK cells and to induce an immune response against a specific target antigen and cells expressing that antigen.

As used herein, "T cell receptor" or "TCR" refers to a protein complex found on the surface of T cells, or T lymphocytes, that is responsible for recognizing fragments of antigen as peptides bound to major histocompatibility complex molecules.

As used herein, "chimeric antigen receptor T cells" or "CAR-T cells" are T cells that have been genetically engineered to express and produce a chimeric T cell receptor. This gives the engineered T cells the ability to target a specific protein. The basis of CAR-T immunotherapy is to modify T cells to recognize cancer cells in order to more effectively target and destroy them. T cells are harvested from a subject by leukapheresis, followed by elutriation to remove myeloid cells. T lymphocyte enrichment, transgene delivery, and ex vivo expansion. The resulting CAR-T cells are infused into subjects to attack their tumors. CAR-T cells can be either derived from T cells in a subject's own blood (autologous) or derived from the T cells of another healthy donor (allogeneic). Once isolated from a subject, these T cells are genetically engineered to express a specific CAR, which programs them to target an antigen that is present on the surface of tumors. For safety, CAR-T cells are engineered to be specific to an antigen expressed on a tumor that is not expressed on healthy cells.

As used herein, the term "endogenous concentration" refers to the level at which a molecule is natively expressed (i.e., in the absence of expression vectors or recombinant promoters) by a cell (which cell can be a normal cell, a cancer cell or an infected cell).

As used herein, the terms "treat," "treating." "treatment" and "therapeutic use" refer to the elimination, reduction or amelioration of one or more symptoms of a disease or disorder.

As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "cancer" refers to a neoplasm or tumor resulting from abnormal uncontrolled growth of cells. As used herein, cancer explicitly includes leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations.

As used herein, an "immune cell" refers to any cell from the hemopoietic origin including, but not limited to, T cells, B cells, monocytes, dendritic cells, and macrophages.

As used herein, the terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

As used herein, the term "CD19" refers to the Cluster of Differentiation 19 protein, which is an antigenic determinant detectable on leukemia precursor cells.

As used herein, a "polyfunctional T cell" refers to a T cell that can produce multiple cytokines. Similarly, "polyfunctionality" refers to the ability to produce multiple cytokines.

As used herein, "STAT5" refers to Signal transducer and activator of transcription 5.

As used herein, "Fos" and "Jun" refers to members of a family of related transcription factors that dimerize via a leucine zipper structure and interact with DNA through a bipartite domain formed between regions of each protein that are rich in basic amino acids. "Fos" refers to Fos Proto-Oncogene, AP-1 Transcription Factor Subunit and "Jun" refers to Jun Proto-Oncogene, AP-1 Transcription Factor Subunit.

As used herein, "nuclear receptor 4A1" or "NR4A1" refers to nuclear receptor subfamily 4 group A member 1").

As used herein, "nuclear receptor 4A2" or "NR4A 2" refers to nuclear receptor subfamily 4 group A member 2").

As used herein, "Tox" refers to thymocyte selection-associated high-mobility group box As used herein. "Pdcd1" refers to programmed cell death 1.

As used herein, "CTLA-4" or "CTLA4" refers to cytotoxic T-lymphocyte-associated protein 4.

As used herein, "HAVCR2" refers to Hepatitis A virus cellular receptor 2.

As used herein, "LAG3" refers to Lymphocyte-activation gene 3.

As used herein, "SLAMF6" refers to the Self-ligand receptor of the signaling lymphocytic activation molecule (SLAM) family member-6.

As used herein, "Tigit" refers to T-cell immunoreceptor with Ig and ITIM domains.

II. Methods of Engineering Polyfunctional T Cells/CAR T Cells

Disclosed herein are engineered polyfunctional T cells/CAR T cells and methods of making and using the same. It was previously reported that CD4+ T cells exposed to interleukin 7 (IL7) during antigenic stimulation in vitro can acquire polyfunctionality in a STAT5-dependent manner. However, inducing CD4 polyfunctionality with IL7 may encounter some limitations in clinical settings. For instance, patient-derived T cells, which presumably contain exhausted CD4+ T cells, may not respond to IL7 and become polyfunctional. Moreover, it is uncertain whether IL7-induced CD4 polyfunctionality, acquired during in vitro stimulation, can sustain in the TME after T cell infusion. At the time of the invention there was an unmet need for effective methods of generating exhaustion-resistant, polyfunctional CD4+ T cells for use in ACT.

The disclosed engineered polyfunctional CD4+ T cells/CAR T cells overcome the limitations restricting the efficiency of IL7 induction of CD4 polyfunctionality by allowing cell-intrinsic, continuous engagement of the IL7 signaling pathway through STAT5 activation. It has been discovered that persistent activation of signal transducer and activator of transcription 5 (STAT5) in tumor-specific CD4+ T cells drives the development of polyfunctional T cells with superior antitumor activities. In one embodiment, expression of a constitutively active STAT5A in tumor-specific CD4+ T cells establishes a distinct epigenetic and transcriptional landscape, endowing CD4+ T cells polyfunctionality, exhaustion-resistance and tumor-infiltrating capability. In another embodiment, T cells engineered to co-express specific cell-targeting chimeric antigen receptors (CAR) and CASTAT5 give rise to polyfunctional CD4[+] CAR T cells capable of providing optimal help to CD8[+] T cells to achieve durable and curative outcomes in cancer and other diseases.

A. STAT5

In one embodiment, T cells and CAR T cells are engineered to constitutively express STAT5. Signal transducer and activator of transcription 5 (STAT5) refers to two highly related proteins, STAT5A and STAT5B, which are part of the seven-membered STAT family of proteins. Though STAT5A and STAT5B are encoded by separate genes, the proteins are 90% identical at the amino acid level. STAT5 proteins are involved in cytosolic signaling and in mediating the expression of specific genes. Aberrant STAT5 activity has been shown to be closely connected to a wide range of human cancers, and silencing this aberrant activity is an area of active research in medicinal chemistry.

Nucleic acid sequences for STAT5A are known in the art. The consensus sequence for human STAT5A is as follows:

```
   1 agatggccgg agtaaaagaa ggagggaggt gctgcggtgg tgggggtgat cttggcttca 61 ctagaatccc cagttcttcc cctctctaca gttttgtctc tgaggtcaca aaacctgtgg 121 cccccaagac acacatgcgc acacacgcgc gtgcacacac acaccccaca catttatttt 181 ttaatctagg ggctcaaaag atgacacgcg ccagagctgg aaggcgtcgc caattggtcc 241 acttttccct cctccctttt tgcggatgag aaaactgagg cccaggtttg ggatttccag 301 agcccgggat ttcccggcaa cgcccgacaa ccacattccc ccggctattc tgacccgccc 361 cggttccggg acgctccctg ggagccgccg ccgagggcct gctgggactc ccggggggacc 421 ccgccgtcgg ggcagccccc acgcccggcg ccgcccgccg ggaacggccg ccgctgttgc 481 gcacttgcag gggagccggc gactgagggc gaggcaggga gggagcaagc ggggctggga 541 gggctgctgg cgcgggctcg cgcgctgtgt atggtctatc gcaggcagct gaccttttgag 601 gaggaaatcg ctgctctccg ctccttcctg tagtaacagc cgccgctgcc gccgccgcca 661 ggaaccccgg ccgggagcga gagccgcggg gcgcagagcc ggcccggctg ccggacggtg 721 cggccccacc aggtgaacgg ccatggcggg ctggatccag gcccagcagc tgcagggaga
```

```
 781 cgcgctgcgc cagatgcagg tgctgtacgg ccagcacttc cccatcgagg tccggcacta 841 cttggcccag tggattgaga gccagccatg ggatgccatt gacttggaca atccccagga 901 cagagcccaa gccacccagc tcctggaggg cctggtgcag gagctgcaga agaaggcgga 961 gcaccaggtg ggggaagatg ggttttttact gaagatcaag ctggggcact acgccacgca 1021 gctccagaaa acatatgacc gctgcccccct ggagctggtc cgctgcatcc ggcacattct 1081 gtacaatgaa cagaggctgg tccgagaagc caacaattgc agctctccgg ctgggatcct 1141 ggttgacgcc atgtcccaga agcaccttca gatcaaccag acatttgagg agctgcgact 1201 ggtcacgcag gacacagaga atgagctgaa gaaactgcag cagactcagg agtacttcat 1261 catccagtac caggagagcc tgaggatcca agctcagttt gcccagctgg cccagctgag 1321 cccccaggag cgtctgagcc gggagacggc cctccagcag aagcaggtgt ctctggaggc 1381 ctggttgcag cgtgaggcac agacactgca gcagtaccgc gtggagctgg ccgagaagca 1441 ccagaagacc ctgcagctgc tgcggaagca gcagaccatc atcctggatg acgagctgat 1501 ccagtggaag cggcggcagc agctggccgg gaacggcggg ccccccgagg gcagcctgga 1561 cgtgctacag tcctggtgtg agaagttggc cgagatcatc tggcagaacc ggcagcagat 1621 ccgcagggct gagcacctct gccagcagct gcccatcccc ggcccagtgg aggagatgct 1681 ggccgaggtc aacgccacca tcacggacat tatctcagcc ctggtgacca gcacattcat 1741 cattgagaag cagcctcctc aggtcctgaa gacccagacc aagtttgcag ccaccgtacg 1801 cctgctggtg ggcgggaagc tgaacgtgca catgaatccc ccccaggtga aggccaccat 1861 catcagtgag cagcaggcca agtctctgct taaaaatgag aacacccgca acgagtgcag 1921 tggtgagatc ctgaacaact gctgcgtgat ggagtaccac caagccacgg gcaccctcag
```

-continued

```
1981 tgcccacttc aggaacatgt cactgaagag gatcaagcgt gctgaccggc ggggtgcaga 2041 gtccgtgaca gaggagaagt tcacagtcct gtttgagtct cagttcagtg ttggcagcaa 2101 tgagcttgtg ttccaggtga agactctgtc cctacctgtg gttgtcatcg tccacggcag 2161 ccaggaccac aatgccacgg ctactgtgct gtgggacaat gcctttgctg agccgggcag 2221 ggtgccattt gccgtgcctg acaaagtgct gtggccgcag ctgtgtgagg cgctcaacat 2281 gaaattcaag gccgaagtgc agagcaaccg gggcctgacc aaggagaacc tcgtgttcct 2341 ggcgcagaaa ctgttcaaca acagcagcag ccacctggag gactacagtg gcctgtccgt 2401 gtcctggtcc cagttcaaca gggagaactt gccgggctgg aactacacct tctggcagtg 2461 gtttgacggg gtgatggagg tgttgaagaa gcaccacaag ccccactgga atgatggggc 2521 catcctaggt tttgtgaata agcaacaggc ccacgacctg ctcatcaaca agcccgacgg 2581 gaccttcttg ttgcgcttta gtgactcaga aatcggggc atcaccatcg cctggaagtt 2641 tgactccccg gaacgcaacc tgtggaacct gaaaccattc accacgcggg atttctccat 2701 caggtccctg gctgaccggc tgggggacct gagctatctc atctatgtgt ttcctgaccg 2761 ccccaaggat gaggtcttct ccaagtacta cactcctgtg ctggctaaag ctgttgatgg 2821 atatgtgaaa ccacagatca agcaagtggt ccctgagttt gtgaatgcat ctgcagatgc 2881 tggggggcagc agcgccacgt acatggacca ggcccctcc ccagctgtgt gcccccaggc 2941 tccctataac atgtacccac agaaccctga ccatgtactc gatcaggatg gagaattcga 3001 cctggatgag accatggatg tggccaggca cgtggaggaa ctcttacgcc gaccaatgga 3061 cagtcttgac tccgcctct cgcccctgc cggtctttc acctctgcca gaggctccct 3121 ctcatgaatg tttgaatccc acgcttctct ttggaaacaa tatgcaatgt gaagcggtcg
```

-continued

```
3181 tgttgtgagt ttagtaaggc tgtgtacact gacacctttg caggcatgca tgtgcttgtg 3241 tgtgtgtgtg tgtgtgtgtc cttgtgcatg agctacgcct gcctcccctg tgcagtcctg 3301 ggatgtggct gcagcagcgg tggcctcttt tcagatcatg gcatccaaga gtgcgccgag 3361 tctgtctctg tcatggtaga gaccgagcct ctgtcactgc aggcactcaa tgcagccaga 3421 cctattcctc ctgggcccct catctgctca gcagctattt gaatgagatg attcagaagg 3481 ggaggggaga caggtaacgt ctgtaagctg aagtttcact ccggagtgag aagctttgcc 3541 ctcctaagag agagagacag agagacagag agagagaaag agagagtgtg tgggtctatg 3601 taaatgcatc tgtcctcatg tgttgatgta accgattcat ctctcagaag ggaggctggg 3661 gttcattttc gagtagtatt ttatacttta gtgaacgtgg actccagact ctctgtgaac 3721 cctatgagag cgcgtctggg cccggccatg tccttagcac aggggggccg ccggtttgag 3781 tgagggtttc tgagctgctc tgaattagtc cttgcttggc tgcttggcct tgggcttcat 3841 tcaagtctat gatgctgttg cccacgtttc ccgggatata tattctctcc cctccgttgg 3901 gccccagcct tctttgcttg cctctctgtt tgtaaccttg tcgacaaaga ggtagaaaag 3961 attgggtcta ggatatggtg ggtggacagg ggccccggga cttggagggt tggtcctctt 4021 gcctcctgga aaaaacaaaa acaaaaaaact gcagtgaaag acaagctgca aatcagccat 4081 gtgctgcgtg cctgtggaat ctggagtgag gggtaaaagc tgatctggtt tgactccgct 4141 ggaggtgggg cctggagcag gccttgcgct gttgcgtaac tggctgtgtt ctggtgaggc 4201 cttgctccca accccacacg ctcctccctc tgaggctgta ggactcgcag tcaggggcag 4261 ctgaccatgg aagattgaga gcccaaggtt taaacttctc tgaaggaggg tggggatgag 4321 aagagggggtt tttttgtact ttgtacaaag accacacatt tgtgtaaaca gtgtttggga
```

-continued

```
    4381 ataaaatatt tttttcataa aaaaaaaaaa aaaa
```
(SEQ ID NO: 1, NCBI Reference Sequence:
NM_001288718.1 which is incorporated by
reference in its entirety).

In one embodiment, CD4+ T cells are engineered to
constitutively express STATA by being transduced with the
sequence according to SEQ ID NO:1, or a functional fragment thereof. In another embodiment, random mutagenesis
is performed to introduce constitutively activating mutations
into human STATSA.

The consensus sequence for murine CASTAT5A is as
follows:

```
                                                     (SEQ ID NO: 2)
    1 atggcgggct ggattcaggc ccagcagctt cagggagatg ccctgcgcca gatgcaagtg 61 ttgtatgggc agcatttccc catcgaggtc cggcactacc tggcccagtg gatcgagagc 121 cagccgtggg atgctattga cttggataat ccccaggacc gaggtcaggc cacccaactc 181 ctggagggcc tggtgcagga gctgcagaag aaggcggagc accaggtggg ggaagatggg 241 tttttgctga agatcaagct ggggcactat gccacacagc tccagaacac gtatgaccgc 301 tgtcccatgg agctggttcg ctgtatccgt cacattctgt acaacgaaca gaggctggtt 361 cgcgaagcca acaattgcag ctcccctgct ggtgtcctgg ttgacgccat gtcccagaag 421 caccttcaga tcaaccaaag gtttgaggag ctgcgcctga tcacacagga cacggagaac 481 gagctgaaga agctgcagca gacccaagag tacttcatca tccagtacca ggagagcctg 541 cggatccaag ctcagtttgc ccagctgggc cagctgaacc cccaggagcg catgagcagg 601 gagacggccc tccagcagaa gcaagtgtcc ctggagacct ggctgcagcg agaggcacag 661 acactgcagc agtaccgagt gggagctggc gagaagcacc agaagaccct gcagctgctg 721 cggaagcagc agaccatcat cctggacgac gagctgatcc agtggaagcg gagacagcag 781 ctggccggga acgggggtcc ccccgagggc agcctggacg tgctgcagtc ctggtgtgag 841 aagctggccg agatcatctg gcagaaccgg cagcagatcc gcaggctga gcgcctgtgc 901 cagcagctgc ccatcccagg ccccgtggag gagatgctgg ctgaggtcaa cgccaccatc 961 acggacatca tctcagctct ggtcaccagc acgttcatca tcgagaagca gcctcctcag 1021 gtcctgaaga cccagaccaa gtttgcggcc accgtgcgcc tgctggtggg gggaaagctg 1081 aatgtgcaca tgaacccccc gcaggtgaag gcgaccatca tcagcgagca gcaggccaag 1141 tccctgctca agaatgagaa cacccgcaat gagtgcagcg gcgagatcct gaacaactgt 1201 tgcgtcatgg agtaccacca ggccactggc acgctcagcg cccacttcag aaacatgtca 1261 ctgaaaagaa tcaagcgcgc cgacaggcgt ggtgcagagt cggtgacgga ggagaagttc 1321 acagtcctgt ttgagtctca gttcagcgtt ggcagcaacg agctggtgtt ccaggtgaag 1381 accctgtccc tccctgtggt cgttatcgtc catggcagcc aggaccacaa tgctactgcc 1441 accgtgctgt gggacaatgc ctttgctgag ccgggcaggg tgccatttgc tgtgcctgac 1501 aaggtgctgt ggccgcagct gtgtgaagcg ctcaacatga aattcaaggc tgaagtacag 1561 agcaaccggg gcttgaccaa agagaacctc gtgttcctgg cacagaaact gttcaacatc 1621 agcagcaacc acctcgagga ctacaacagc atgtctgtgt cctggtccca gttcaaccgg 1681 gagaacttgc ccggctggaa ctacaccttc tggcagtggt tcgacggggt gatggaggtg 1741 ctgaagaagc accataagcc ccattggaat gatggggcta tcctgggttt cgtgaacaag
```

```
                        -continued
1801 caacaggccc acgacctgct catcaacaag ccggacggga ccttcctgct gcgcttcagt 1861 gactcggaaa tcgggggcat caccattgct tggaagtttg actctccgga ccgaaacctc 1921 tggaatctga agccattcac gacgcgagat ttctccattc ggtccctggc cgaccggctg 1981 ggggacctga actaccttat ctacgtgttc ccagaccgac ccaaggacga ggtctttgcc 2041 aagtattaca ctcctgtact tgcgaaagca gttgacggat acgtgaagcc acagatcaag 2101 caagtggtcc ctgagttcgt caatgcattc acagatgccg gagccagcgc cacctacatg 2161 gaccaggctc cttccccagt cgtgtgccct caacctcact acaacatgta cccacccaac 2221 cctgaccctg tccttgacca agatggcgag tttgacctgg atgagagcat ggatgttgcc 2281 aggcacgtgg aagaactttt acgccggccc atggacagtc tcgacgcccg cctctcccca 2341 cctgctggtc tcttcacctc cgctagaagc tccctgtcc
```

In one embodiment, CD4+ T cells are engineered to constitutively express STAT5A by being transduced with the sequence according to SEQ ID NO:2, or a functional fragment thereof. In one embodiment, specific STAT5A mutations (H299R and S711F) are introduced into SEQ ID NO: 2 to create CASTAT5.

In one embodiment, STAT5A is transduced into the T cells using retroviral vectors. Retroviral vectors are easy to manipulate in the laboratory and provide stable, long-term gene expression in the infected cells and their progeny because they stably integrate into the genome. Methods of using retroviral vectors to introduce DNA into T cells is well known in the art, for example in Simmons, *Methods Mol Biol.* 1323:99-108 (2016).

B. Reversing Exhaustive Phenotype

The molecular mechanisms governing CD8$^+$ T cell exhaustion have been extensively studied in recent years (Wherry, E. J., et al., *Nat Rev Immunol,* 15:486-499 (2015); Pereira, R. M., et al., *J Leukoc Biol,* 102:601-615 (2017)). These studies provide a plethora of information on the transcriptional and epigenetic programs controlling the phenotype and function of exhausted murine and human CD8$^+$ T cells induced in the setting of chronic viral infections or cancer. A number of transcription factors, including NFAT, TOX and NR4A1, are found to play critical roles in inducing and maintaining CD8$^+$ T cell exhaustion (Seo, H., et al., *Proc Natl Acad Sci USA,* 116:12410-12415 (2019); Chen, J., et al., *Nature,* 567:530-534 (2019); Yao, C., et al., *Nat Immunol,* 20:890-901 (2019); Khan, O., et al., *Nature,* 571:211-218 (2019); Scott, A. C., et al., *Nature,* 571:270-274 (2019); Alfei, F., et al., *Nature,* 571:265-269 (2019); Liu, X., et al., *Nature,* 567:525-529 (2019); Martinez, G. J., et al., *Immunity,* 42:265-278 (2015)). The overarching consensus is that the exhaustion initiation transcription factor NFAT1, in the absence of it partner AP-1 (Fos/Jun), induces and interacts with NR4A1 and TOX to drive a transcriptional program leading to exhaustion (Seo, H., et al., *Proc Natl Acad Sci USA,* 116:12410-12415 (2019); Martinez, G. J., et al., *Immunity,* 42:265-278 (2015); Mann, T. H., et al., *Nat Immunol,* 20:1092-1094 (2019)). Exhausted CD8$^+$ T cells are a heterogeneous population containing subsets of progenitor exhausted and terminally exhausted cells that can be distinguished by varied expression levels of a panel of genes including Tcf7, Tbx21, Eomes and Slamf6 (Paley, M. A., et al., *Science,* 338:1220-1225 (2012); Wu, T., et al., *Sci Immunol,* 1 (2016); Miller, B. C., et al., *Nat Immunol,* 20:326-336 (2019)). As the knowledge on exhausted CD8$^+$ T cells rapidly accumulates, the understanding of exhaustion in CD4$^+$ T cells is relatively limited. Transcriptomic profiling of virus-specific CD4$^+$ T cells during chronic viral infections revealed that exhausted CD4$^+$ T cells exhibit a molecular profile distinct from exhausted CD8$^+$ T cells, though some common features of CD4$^+$ and CD8$^+$ T cell exhaustion exist (Crawford, A., et al., *Immunity,* 40:289-302 (2014)).

Without being bound by any one theory, it is believed that STAT5 is involved in regulation of CD4$^+$ T cell exhaustion i.e. whether a CD4$^+$ T cells become polyfunctional or exhausted. In the absence of CASTAT5, tumor-specific CD4$^+$ T cells have limited cytokine production, reduced proliferative capacity, high levels of Pdcd1 and Ctla4, and failed to eradicate tumors in mice. In addition, these CD4$^+$ T cells express both Nfatc1 and Nfatc2, but are in paucity of Fos and Jun. These CD4$^+$ T cells also express Tox and Slamf6, molecules associated with CD8$^+$ T cell exhaustion. These features implicate a population of CD4$^+$ T cells destined to exhaustion. It has been discovered that CASTAT5-induced transcriptional reprogramming can divert the fate of CD4$^+$ T cells from exhaustion to polyfunctionality. Notably, CASTAT5 upregulates the levels of Fos and Jun but represses the expression of Tox, Pdcd1, Ctla4, Haver2 (Tim3), Lag3, Tigit and Slamf6, suggesting that CASTAT5 enables T cells to acquire resistance to exhaustion. Prominent levels of Nr4a1, a key regulator of exhaustion in CD8$^+$ T cells, are not detected in exhausted tumor-specific CD4$^+$ T cells; instead, CASTAT5 markedly upregulates Nr4a1 but reduces Nr4a2 in polyfunctional CD4$^+$ T cells.

One embodiment provides a method of reducing exhaustive phenotype in CD4$^+$ T cells by engineering T cells to express a specific gene set to induce polyfunctionality, without the use of CASTAT5. In such an embodiment, T cells are engineered to express Fos, Jun, Nr4a1, or a combination thereof, and to reduce or eliminate expression of Tox, Pdcd1, Ctla4, Haver2 (Tim3), Lag3, Tigit, Slam6, Nr4a2, or a combination thereof. In such an embodiment, the CD4$^+$ T cells will exhibit polyfunctionality, not exhaustion. Cells can be engineered to express specific genes through the use of genetic engineering or molecular biology techniques, which was discussed in detail above. In order to eliminate expression of genes in a cell, genes can be silenced using methods known in the art such as but not limited to antisense oligonucleotides, siRNA, RNAi, and Crispr/cas9.

In one embodiment, expression of 1, 2, or all 3 genes of Fos, Jun, Nr4al in the polyfunctionality phenotype are induced or increased. In another embodiment, expression of 1, 2, 3, 4, 5, 6, 7, or all 8 of the genes of Tox, Pdcd1, Ctla4, Haver2 (Tim3), Lag3, Tigit, Slam6, and Nr4a2 is silenced or reduced. In some embodiments, 1, 2, or 3 of the genes Fos, Jun, Nr4al are overexpressed alongside the silencing of 1, 2, 3, 4, 5, 6, 7, or all 8 of the genes of Tox, Pdcd1, Ctla4, Haver2 (Tim3), Lag3, Tigit, Slam6, and Nr4a2.

C. Engineered T Cells/CAR T Cells

Chimeric antigen receptor T cell (CAR T cells, CARTs) compositions and methods of their use are provided. CARs are synthetic constructs that are designed to be expressed in host T cells or NK cells and to induce an immune response against a specific target antigen and cells expressing that antigen. The CAR typically comprises an antibody fragment, such as a scFv or Fab fragment, incorporated in a fusion protein that also comprises additional components, such as a CD3- or CD28 transmembrane domain and selective T-cell activating moieties, including the endodomains of CD3-CD28, OX40, 4-1 BB, Lck and/or ICOS. Generally, the constructs may comprise a leader sequence linked to a scFv, Fab or other antibody moiety, generally with a hinge or other linker between the scEv and a transmembrane domain. The transmembrane domain will be attached to an intracellular signaling domain, such as CD28 or CD3-, and typically will include one or more co-stimulatory domains as dis cussed below. CARs are designed with an activation domain, costimulatory domain, transmembrane domain and antigen-binding domain. The activation domain is an intracellular domain, such as CD3. The costimulatory domain can increase the activity of the CAR T cell, like proliferation and persistence. The transmembrane domain plays a role of the structural anchor. The antigen-binding domain which can combine with the target antigen is an important component of CARS and usually includes a single chain variable fragment (scFvs).

As described in U.S. Pat. Nos. 5,359,046, 5,686,281 and 6,103,521, the extracellular domain may be obtained from any of the wide variety of extracellular domains or secreted proteins associated with ligand binding and/or signal transduction. The extracellular domain may be part of a protein which is monomeric, homodimeric, heterodimeric, or associated with a larger number of proteins in a non-covalent complex. In particular, the extracellular domain may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed or all or part of the hinge region may be removed.

CAR-T cells are T cells that have been genetically engineered to express and produce a chimeric T cell receptor. This gives the engineered T cells the ability to target a specific protein. The basis of CAR-T immunotherapy is to modify T cells to recognize cancer cells in order to more effectively target and destroy them. T cells are harvested from a subject by leukapheresis, followed by elutriation to remove myeloid cells. T lymphocyte enrichment, transgene delivery, and ex vivo expansion. The resulting CARTs are infused into subjects to attack their tumors. CARTs can be either derived from T cells in a subject's own blood (autologous) or derived from the T cells of another healthy donor (allogeneic). Once isolated from a subject, these T cells are genetically engineered to express a specific CAR, which programs them to target an antigen that is present on the surface of tumors. For safety, CARTs are engineered to be specific to an antigen expressed on a tumor that is not expressed on healthy cells.

Methods of producing CARTs are known in the art and is described in U.S. Pat. Nos. 7,446,190, 7,741,465, 9,181,527, and 9,629,877.

Genetic modification for introduction of the CAR construct into T cells can be accomplished by transducing (or otherwise delivering) a T cell composition with a recombinant DNA or RNA construct, such as for example, a vector. A vector may be any agent capable of delivering or maintaining nucleic acid in a host cell, and includes viral vectors (e.g. retroviral vectors, lentiviral vectors, adenoviral vectors, or adeno-associated viral vectors), plasmids, naked nucleic acids, nucleic acids complexed with polypeptide or other molecules and nucleic acids immobilized onto solid phase particles. The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art. To achieve durable clinical responses to cell-based gene therapies, permanent transgene expression is often required. Murine gammaretroviruses and lentiviruses are two available clinical gene therapy vector systems that afford long-term CAR transgene expression. Considerable clinical evidence shows that retroviral vectors are safe when expressed in human T cells.

Selection of promoter and other regulatory sequences for protein expression are well known to those of skill in the art. Cell specific promoters for expression in T-cells include, but are not limited to, human CD2, distal Lck, and proximal Lck. In other embodiments, non-tissue specific promoters such as non-tissue specific promoters including viral promoters such as cytomegalovirus (CMV) promoter, β-actin promoter phosphoglycerate kinase (PGK) promoter, ubiquitin promoter, and EF-1a promoter can be used. This list is not meant to be limiting. An expression construction preferably also includes sequences to allow for the replication of the expression construct. Transcription of the DNA encoding the polypeptides of the present invention by higher eukaryotes may be increased by inserting an enhancer sequence into the vector. Enhancers are cis-acting elements of DNA, usually about from 10 to 300 by that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers. Preferably, a retroviral vector (either gamma-retroviral or lentiviral) is employed for the introduction of the CAR nucleic acid construct into the cell. For example, a polynucleotide encoding a co-stimulatory ligand protein (e.g., tumor necrosis factor (TNF) ligand, such as 4-1BBL, OX40L, CD70, LIGHT, and CD30L, or an Ig superfamily ligand, such as CD80 and CD86), or a receptor that binds an antigen, or a variant, or a fragment thereof, can be cloned into a retroviral vector and expression can be driven from its endogenous promoter, from the retroviral long terminal repeat, or from a promoter specific for a target cell type of interest. Non-viral vectors may be used as well.

One embodiment provides a CART composition including CD19 chimeric antigen receptor T cells constitutively expressing STAT5A. In one embodiment, the CART is a CD4$^+$ T cell. In another embodiment, the CART is a CD8$^+$ T cell.

In another embodiment, the CART composition comprises CD4$^+$ T cells engineered to show expression of a panel of genes selected from the group consisting of Fos, Jun, and Nr4al but show no expression of genes selected from the group consisting of Tox, Pdcd1, Ctla4, Haver2 (Tim3), Lag3, Tigit, Slam6, and Nr4a2. In such an embodiment, the CD4$^+$ T cells can be tumor-specific T cells that show exhaustive phenotype. By expressing Fos, Jun, and Nr4al (or combination thereof) but silencing Tox, Pdcd1, Ctla4, Haver2 (Tim3), Lag3, Tigit, Slam6, and Nr4a2 (or a combination thereof) the CD4$^+$ T cells can be rescued from the exhaustive phenotype and become polyfunctional T cells.

C. Pharmaceutical Compositions

The engineered polyfunctional T cells/CARTs described herein can be formulated into pharmaceutical compositions. Pharmaceutical compositions containing the engineered polyfunctional T cells/CARTs can be formulated for parenteral administration including by not limited to intramuscular, intraperitoneal, intravenous (IV) or subcutaneous injection.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed engineered polyfunctional T cells/CARTs, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally, for intravenous injection or infusion, dosage may be lower.

The dosage administered to a patient is typically $1 \times 10^5$ to $1 \times 10^9$ cells per administration. In another embodiment, the dosage administered to a patient is $1 \times 106$ to $1 \times 10^7$ cells per administration. In yet another embodiment, the dosage administered to the subject is $1 \times 10^6$ to $3 \times 10^6$ cells per administration.

In certain embodiments, the engineered polyfunctional T cells/CARTs are administered locally, for example by injection directly into a site to be treated.

In some embodiments, compositions disclosed herein, are administered in an aqueous solution, by parenteral injection or infusion. The formulation may also be in the form of a suspension or emulsion. In general, pharmaceutical compositions are provided including effective amounts of engineered polyfunctional T cells/CARTs, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN® 20 (polysorbate-20), TWEEN® 80

(polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

III. Methods of Use

In some embodiments, the disclosed engineered polyfunctional T cells/CARTs are used for adoptive cell therapy, and related therapies.

A. Adoptive Transfer

In one embodiment, the disclosed engineered polyfunctional T cells/CARTs are used for adoptive cell therapy. In such an embodiment, T cells are engineered to constitutively express STAT5A. The T cells are preferably human T cells. The cells can be autologous or heterologous. The cells are typically transduced in vitro. The transduced cells can optionally be expanded in vitro to obtain a large population of transduced cells that can be administered to a subject in need thereof. Such subjects typically have or are believed to have a cancer or tumor. The T cells can be CD8$^+$ or CD4$^+$. The transduced cells can be administered in one or more doses to the subject.

In another embodiment, CD4$^+$ T cells are engineered to express a CAR and to constitutively express STAT5A. In such an embodiment, the CAR targets the T cell to a tumor or tumor cell by binding to a tumor antigen. A tumor antigen may include a cell surface molecule. Tumor antigens of known structure and having a known or described function, include the following cell surface receptors: HER1, HER2, HER3, HER4, epidermal growth factor receptor (EGFR), vascular endothelial cell growth factor, vascular endothelial cell growth factor receptor, insulin-like growth factor-I, insulin-like growth factor-II, transferrin receptor, estrogen receptor, progesterone receptor, follicle stimulating hormone receptor (FSH-R), retinoic acid receptor, MUC-1, NY-ESO-1, NA 17-A, Melan-A/MART-1, tyrosinase, Gp-100, MAGE, BAGE, GAGE, any of the CTA class of receptors including in particular HOM-MEL-40 antigen encoded by the SSX2 gene, carcinoembryonic antigen, and PyLT; p97 (melanotransferrin), Additional tumor associated antigens include prostate surface antigen (PSA); β-human chorionic gonadotropin (β-HCG); glycosyltransferase β-1,4-N-acetylgalactosaminyltransferases (GalNAc); NUC18; melanoma antigen gp75; human cytokeratin 8; high molecular weight melanoma antigen.

Tumor antigens of interest include antigens regarded in the art as "cancer/testis" (CT) antigens that are immunogenic in subjects having a malignant condition. CT antigens include at least 19 different families of antigens that contain one or more members and that are capable of inducing an immune response, including but not limited to MAGEA (CT1); BAGE (CT2); MAGEB (CT3); GAGE (CT4); SSX (CT5); NY-ESO-1 (CT6); MAGEC (CT7); SYCP1 (C8); SPANXB1 (CT11.2); NA88 (CT18); CTAGE (CT21); SPA17 (CT22); OY-TES-1 (CT23); CAGE (CT26); HOM-TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARa fusion protein, PTPRK, K-ras, N-ras, Triosephosphate isomeras, Bage-1, Gage 3,4, 5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15 (58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein/cyclophilin C-associated protein), TAAL6, TAG72, TLP, and TPS. Other tumor-associated and tumor-specific antigens are known to those of skill in the art and are suitable for targeting by the disclosed fusion proteins.

In another embodiment, the CAR targets the T cell to a tumor or tumor cell via an oncogene. Exemplary oncogenes that can be targeted to direct the disclosed T cells to tumors, tumor cells, or tumor microenvironments include, but are not limited to ABL1, ABL2, AKT1, AKT2, ATF1, BCL11A, BCL2, BCL3, BCL6, BCR, BRAF, CARD11, CBLB, CBLC, CCND1, CCND2, CCND3, CDX2, CTNNB1, DDB2, DDIT3, DDX6, DEK, EGFR, ELK4, ERBB2, ETV4, ETV6, EVI1, EWSR1, FEV, FGFR1, FGFRIOP, FGFR2, FUS, GOLGA5, GOPC, HMGA1, HMGA2, HRAS, IRF4, JUN, KIT, KRAS, LCK, LMO2, MAF, MAFB, MAML2, MDM2, MET, MITF, MPL, MYB, MYC, MYCLI, MYCN, NCOA4, NFKB2, NRAS, NTRK1, NUP214, PAX8, PDGFB, PIK3CA, PIM1, PLAG1, PPARG, PTPN11, RAF1, REL, RET, ROS1, SMO, SS18, TCLIA, TET2, TFG, MLL, TLX1, TPR, and USP6.

The adoptive transfer can be combined with other therapies for the treatment of cancer. Such additional therapies include chemotherapy, radiation therapy, and surgery or a combination thereof. The adoptive transfer of TCR-T can be combined with cancer vaccines so that the TCR-T will be further expanded in vivo to reduce the number of transferred TCR-T cells and the associated toxicity.

One embodiment provides a method for reducing tumor burden in a subject in need thereof by administering engineered T cells that constitutively overexpress Stat5a, wherein the engineered cells inhibit or reduce tumors that express CD19. The subject can optionally be treated with a cotherapy for cancer.

In another embodiment, the disclosed methods can be used to reverse exhaustion in tumor-specific CD4+ T cells. In such an embodiment, CD4+ T cells are harvested from the tumor or tumor-microenvironment of the subject. The cells are then engineered to express a polyfunctional gene phenotype instead of an exhaustive gene phenotype. In such an embodiment, the expression of Fos, Jun, Nr4a1, or combinations thereof are increased in the population of T cells and the expression of Tox, Pdcd1, Ctla4, Haver2, Lag3, Tigit, Slam6, Nrf4a2, or a combination thereof is silenced in the population of T cells. This gene expression phenotype reverses exhaustion and induces polyfunctionality in the population of CD4+ T cells. The renewed population of CD4+ T cells can be administered back to the subject to induce an immune response in the tumor. In some embodiments, the polyfunctional gene phenotype is induced by constitutively expressing STAT5A in the cells.

B. Subjects to be Treated

1. Treatment of Cancer

The disclosed engineered polyfunctional T cells/CARTs and methods can be used to treat cancer. Generally, the methods include stimulating or enhancing an immune response to cancer, reducing or preventing tumor growth or progression, or a combination thereof in the subject by administering to the subject an amount of engineered polyfunctional T cells/CARTs constitutively expressing STAT5a. The method can reduce or more symptoms of the cancer.

Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless explicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

The methods and engineered polyfunctional T cells/CARTs disclosed herein are useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoictic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma.

Cancers caused by aberrations in apoptosis can also be treated by the disclosed methods and compositions. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions in the ovary, bladder, breast, colon, lung, skin, pancreas, or uterus. In other specific embodiments, sarcoma, melanoma, or leukemia is treated or prevented by the methods and compositions.

Specific cancers and related disorders that can be treated or prevented by methods and engineered polyfunctional T cells/CARTs disclosed herein include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pincocytoma, pincoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

IV. Combination Therapies

The disclosed engineered polyfunctional T cells/CARTs can be administered to a subject in need thereof alone or in combination with one or more additional therapeutic agents. In some embodiments, the additional therapeutic agents are administered separately, but simultaneously. The additional therapeutic agent can also be administered as part of the same composition. In other embodiments, the engineered polyfunctional T cells/CARTs and the second therapeutic agent are administered separately and at different times, but as part of the same treatment regime.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. The engineered polyfunctional T cells/CARTs can be the first or the second therapeutic agent. In some embodiments, the engineered polyfunctional T cells/CARTs are administered in combination with a second therapeutic agent.

The engineered polyfunctional T cells/CARTs and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary additional therapeutic agents include, but are not limited to, cytokines, chemotherapeutic agents, radionuclides, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatoires, ligands that bind to Toll-Like Receptors (including but not limited to polyinosinic: polycytidylic acid (polyI:C) and CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the engineered polyfunctional T cells/CARTs can be co-administered with one or more additional agents that function to enhance or promote an immune response or reduce or inhibit an immune response.

A. Chemotherapeutic Agents

The disclosed engineered polyfunctional T cells/CARTs can be combined with one or more chemotherapeutic agents and pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ (2) and combinations thereof.

B. Other Immunomodulators

1. PD-1 antagonists

In some embodiments, the engineered polyfunctional T cells/CARTs are co-administered with a PD-1 antagonist. Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, Proc Natl Acad Sci U. S. A, 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor. Other PD-1 antagonists contemplated by the methods of this invention include antibodies that bind to PD-1 or ligands of PD-1, and other antibodies.

Suitable anti-PD-1 antibodies include, but are not limited to, those described in the following U.S. Pat. Nos. 7,332, 582, 7,488,802, 7,521,051, 7,524,498, 7,563,869, 7,981,416, 8,088,905, 8,287,856, 8,580,247, 8,728,474, 8,779,105, 9,067,999, 9,073,994, 9,084,776, 9,205,148, 9,358,289, 9,387,247, 9,492,539, 9,492,540, all of which are incorporated by reference in their entireties. See also Berger et al., Clin Cancer Res, 14:3044-3051 (2008).

Exemplary anti-B7-H1 (also referred to as anti-PD-L1) antibodies include, but are not limited to, those described in the following U.S. Pat. Nos. 8,383,796, 9,102,725, 9,273, 135, 9,393,301, and 9,580,507 all of which are specifically incorporated by reference herein in their entirety.

For anti-B7-DC (also referred to as anti-PD-L2) antibodies see U.S. Pat. Nos. 7,411,051, 7,052,694, 7,390,888, 8,188,238, and 9,255,147 all of which are specifically incorporated by reference herein in their entirety.

Other exemplary PD-1 receptor antagonists include, but are not limited to B7-DC polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., Immunity, Vol. 27, pp. 111-122, (2007)). Such fragments also include the soluble ECD portion of the PD-1 protein that includes mutations, such as the A99L mutation, that increases binding to the natural ligands (Molnar et al., PNAS, 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119 (8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

2. CTLA4 Antagonists

In some embodiments, the second therapeutic agent is an antagonist of CTLA4, for example an antagonistic anti-CTLA4 antibody. An example of an anti-CTLA4 antibody contemplated for use in the methods of the invention includes an antibody as described in PCT/US2006/043690 (Fischkoff et al., WO/2007/056539).

Dosages for anti-PD-1, anti-B7-H1, and anti-CTLA4 antibody, are known in the art and can be in the range of, for example, 0.1 to 100 mg/kg, or with shorter ranges of 1 to 50 mg/kg, or 10 to 20 mg/kg. An appropriate dose for a human subject can be between 5 and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., Clinical Kidney Journal, 3(2):135-137 (2010), published online December 2009.

In other embodiments, the antagonist is a small molecule. A series of small organic compounds have been shown to bind to the B7-1 ligand to prevent binding to CTLA4 (see Erbe et al., J Biol Chem, 277:7363-7368 (2002). Such small organics could be administered alone or together with an anti-CTLA4 antibody to reduce inhibitory signal transduction of T cells.

3. Potentiating Agents

In some embodiments, additional therapeutic agents include a potentiating agent. The potentiating agent acts to increase efficacy the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (U.S. patent application No. 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, et al., "Design of New Oxazaphosphorine Anticancer Drugs", Curr Pharm Des, 13(9):963-78 Review 2007). These include mafosfamide (NSC 345842), glufosfamide (D19575, beta-D-glucosylisophosphoramide mustard), S-(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

Low doses of CTX (<200 mg/kg) can have immune stimulatory effects, including stimulation of anti-tumor immune responses in humans and mouse models of cancer (Brode & Cooke Crit Rev, Immunol, 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+ MDSC. These primary effects have numerous secondary effects; for example following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al., Cancer Immunol. Immunother, 58:1219-1228 (2009). A similar result was observed in the HHD2 tumor model: adoptive transfer of CD4+

CD25+ Treg after CTX pretreatment eliminated therapeutic response to vaccine (Taieb, J., J Immunol, 176:2722-2729 (2006)).

Numerous human clinical trials have demonstrated that low dose CTX is a safe, well-tolerated, and effective agent for promoting anti-tumor immune responses (Bas, & Mastrangelo Cancer Immunol, Immunother, 47:1-12 (1998)).

The optimal dose for CTX to potentiate an anti-tumor immune response, is one that lowers overall T cell counts by lowering Treg levels below the normal range but is sub-therapeutic (see Machiels et al., Cancer Res, 61:3689-3697 (2001)).

In human clinical trials where CTX has been used as an immunopotentiating agent, a dose of 300 mg/m2 has usually been used. For an average male (6 ft., 170 pound (78 kg) with a body surface area of 1.98 m2), 300 mg/m2 is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al., Cancer Res, 61:3689-3697 (2001), Hengst et al., Cancer Res, 41:2163-2167 (1981), Hengst, Cancer Res, 40:2135-2141 (1980)).

For larger mammals, such as a primate, such as a human, patient, such mg/m2 doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib (SUTENT®), anti-TGFβ or Imatinib (GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g., Avastin, VEGF-Trap) (see, for example, Li et al., Clin Cancer Res, November 15; 12 (22): 6808-16 (2006)), anthracyclines, oxaliplatin, doxorubicin, TLR4 antagonists, and IL-18 antagonists.

EXAMPLES

Example 1. CASTAT5-Transduced CD4⁺ T Cells Undergo Robust Expansion and Acquire a Polyfunctional Phenotype Upon Adoptive Transfer Materials and Methods Cell lines: B-cell lymphoma cell line A20 and murine colorectal cancer cell line CT26 were obtained from American Type Culture Collection (ATCC). HA-expression A20 tumor cell line (A20HA) was generated as described previously (Ding, Z. C., et al., Blood, 120:2229-2239 (2010)). CD26-CD19 cells were generated by transfecting cells with a vector encoding murine CD19 (pCMV3-mCD19, Sino-Biological Inc.) using Lipofectamine 2000. CD19⁺ tumor cells were FACS-sorted, expanded and cryopreserved. Plasmacytoma cell line MOPC315.GFP was described previously (Riedel, S. S. et al., PLoS One, 7: e52398 2012)). Tumor cells were cultured in RPMI 1640 (HyClone Laboratories) supplemented with 10% fetal bovine serum albumin (FBS), 1% penicillin/streptomycin (HyClone Laboratories), 1% non-essential amino acids and 1% glutamine (Corning) at 37° C. in a 5% $CO^2$ incubator.

Mice: BALB/c mice (Thy1.2⁺/⁺) of 4 to 6 weeks of age were purchased from Charles River. 6.5 TCR-Tg mice on a BALB/c (Thy1.1⁺/⁺) background expressing an αβTCR specific for amino acids 110-120 from influenza HA presented by MHC class II molecule IEd were described previously (Ding, Z. C., et al., Blood, 120:2229-2239 (2010)). The CD45.1⁺/⁺ mice on a Balb/c ground and immunocompromised NOD-Scid IL2Ry-null mice (NSG) mice were purchased from Jackson Laboratory. All mice were housed under specific pathogen-free (SPF) conditions by Laboratory Animal Services of the Augusta University. All animal experiments were approved by the Institutional Animal Care and Use Committee (IACUC) of Augusta University.

Tumor challenge and in vivo treatment: Tumor cells were subcutaneously injected to the right flank of mice ($5 \times 10^6$ tumor cells/mouse in 100 µl PBS). The tumor size was monitored by caliper every other day, and expressed as the product of two perpendicular diameters in square millimeters. When tumor sizes reached desired size (170 mm² for A20WT and A20HA, 100 mm² for CT26-CD19), mice were randomly assigned into groups to receive the specified treatments. CTX was dissolved in PBS and i.p. injected to mice at a dose of 150 mg/kg. For adoptive T-cell transfer, in vitro cultured T cells were harvested, wash twice with PBS and injected into each recipient via tail vein. To deplete host CD8⁺ T cells, CD8a depletion antibodies were given by weekly i.p. injection (200 µg per injection) for 5 weeks with the first injection right after T cell transfer.

Results

It was previously shown that IL7 conditioning during in vitro antigenic stimulation imparts polyfunctionality to CD4⁺ T cells, and the IL7-conditioned polyfunctional CD4⁺ T cells can mediate robust antitumor effects upon adoptive transfer to tumor-bearing mice (Ding, Z. C., et al., Oncoimmunology, 5, e1171445 (2016)). Although it was shown that ectopic expression of a constitutively active form of STAT5A (CASTAT5) can recapitulate IL7 in inducing CD4⁺ T cell polyfunctionality in vitro, the in vivo behavior of CASTAT5-transduced CD4⁺ T cells remained to be examined.

Figure 1B:
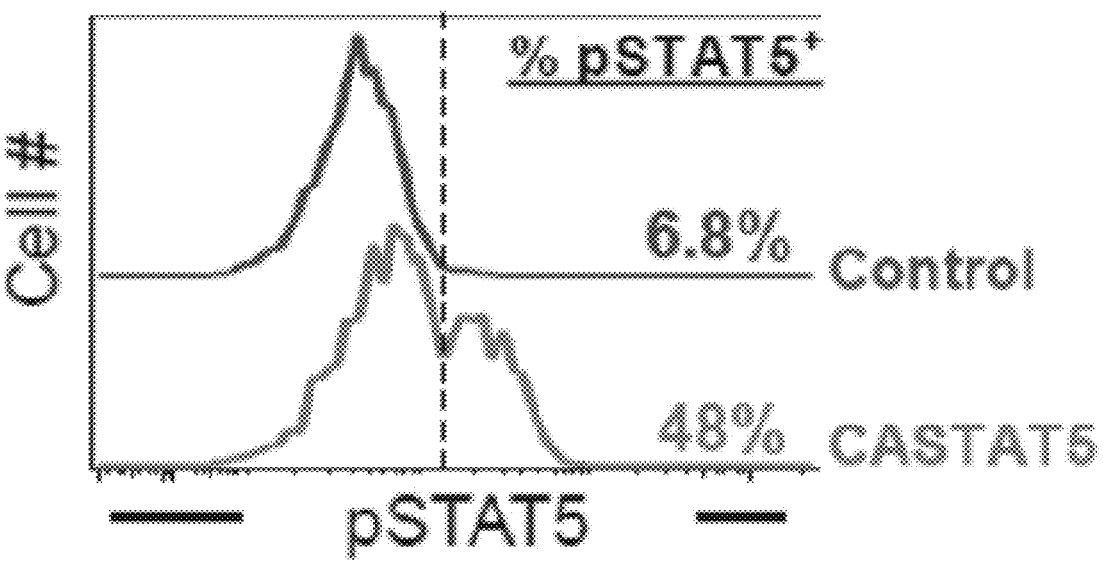
FIG. 1B is a flow cytometry graph showing the level of phosphorylated STAT5 (pSTAT5) in donor CD4+ T cells before adoptive transfer, mock-transduced HA-specific CD4+ T cells (Control) or CASTAT5 retrovirus (CASTAT5) transduced CD4+ T cells. Numbers indicate the percent of pSTAT5+ cells in total CD4+ T cells.
Figures 7K, 7L, 7M, 8A:
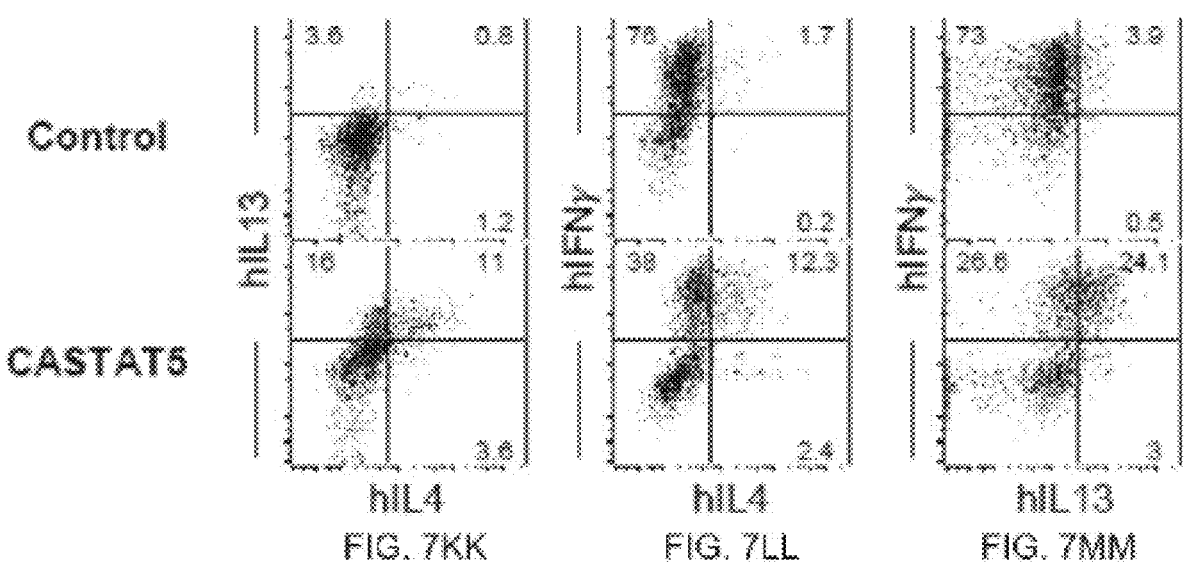
FIG. 8A is a schematic illustrations depicting the experimental procedures of in vitro serial antigenic stimulation. Briefly, mock-transduced (control) and CASTAT5-transduced HA-specific CD4+ T cells were labeled with violet dye and co-cultured in triplicate wells with A20HA tumor cells at 2:1 ratio. T cells were harvested and re-plated in new culture with fresh A20HA tumor cells every four days. At each harvest, CD4+ T cells were enumerated.
Figure 8B:
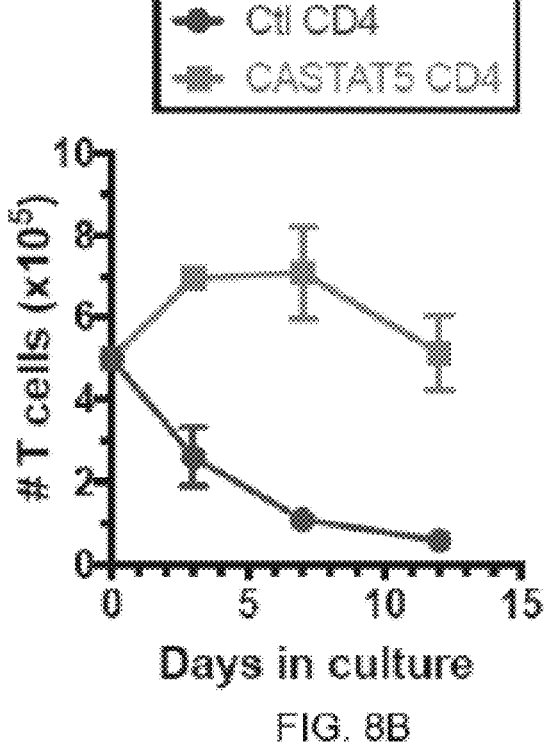
FIG. 8B is a graph showing T cell numbers plotted against time.
Figure 8C:
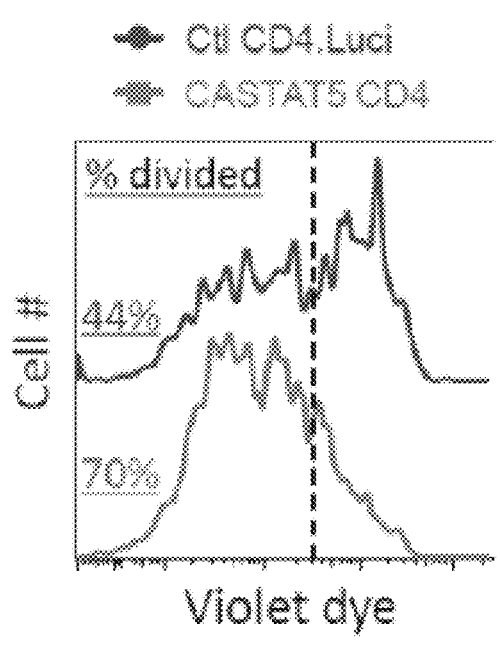
FIG. 8C is a flow cytometry histogram showing cell division status of T cells after 3 rounds of stimulation. Numbers indicate the percentage of divided CD4+ T cells.

The impact of persistent STAT5 activation, transmitted by CASTAT5, on T cell expansion, functional status and migration in vivo was examined in a mouse model of ACT. Mice with large established HA-expressing B-cell lymphoma A20 tumors (A20HA) received lymphodepleting chemotherapy (CTX) followed by adoptive transfer of either CASTAT5-transduced (CASTAT5 CD4) or mock-transduced (control CD4) HA-specific CD4⁺ T cells derived from 6.5 TCR Tg mice one day later (FIG. 1A). To evaluate donor T cell expansion in vivo, tail blood from each mouse was collected weekly for FACS analysis. CASTAT5 CD4 T cells, which exhibited increased levels of phosphorylated STAT5 (pSTAT5) (FIG. 1B), underwent robust and sustained expansion, reaching a plateau (19±4.6%) about 3 weeks after transfer, whereas control CD4⁺ T cells only had transient and modest expansion (FIGS. 1C-1N). The proliferative advantage of CASTAT5 CD4⁺ T cells over the control CD4⁺ T cells was also confirmed in vitro. Upon serial repeated stimulations, CASTAT5 CD4⁺ T cells had more robust proliferation and accumulation than control CD4⁺ T cells (FIGS. 8A-8C), suggesting enhanced survival capability.

Figure 1O:
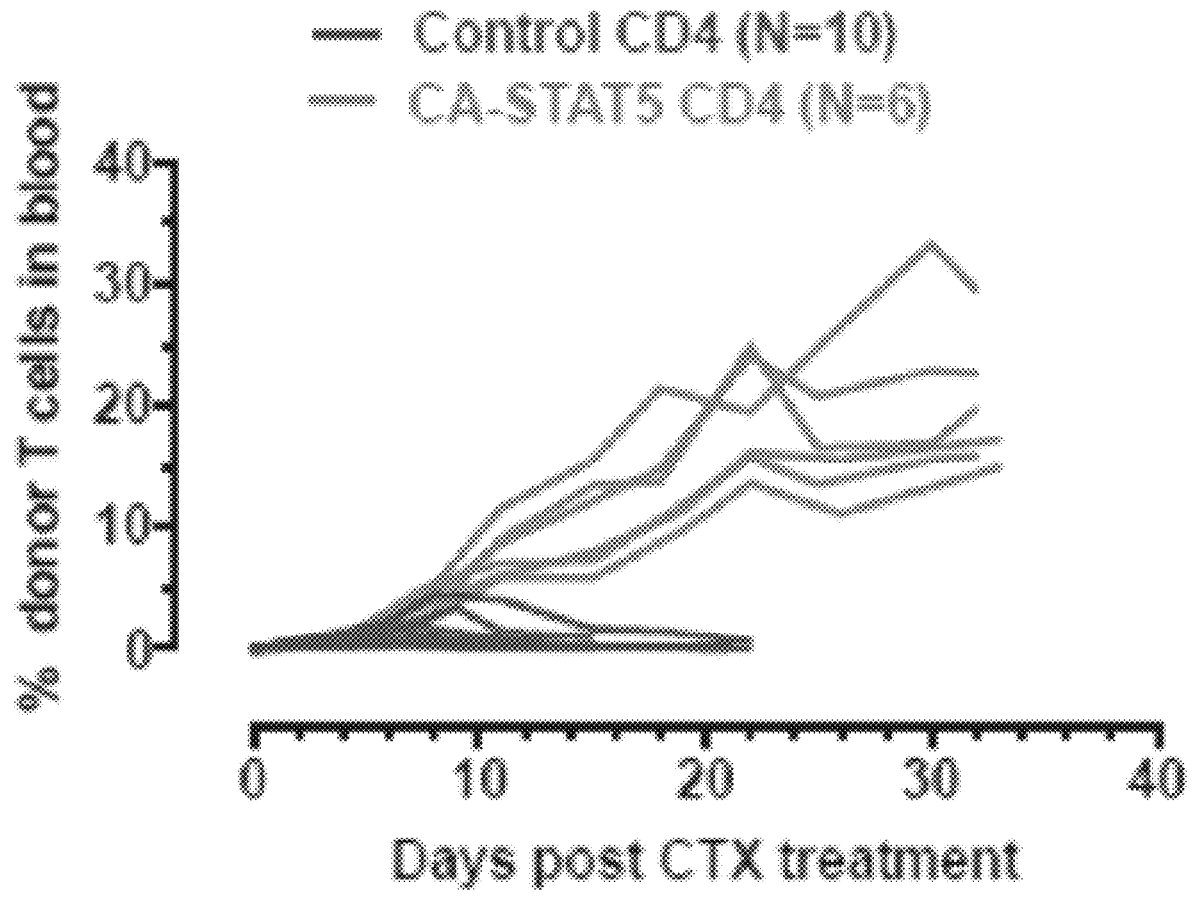
FIG. 1O is a graph showing the average frequencies of donor T cells against time.
Figure 1P:
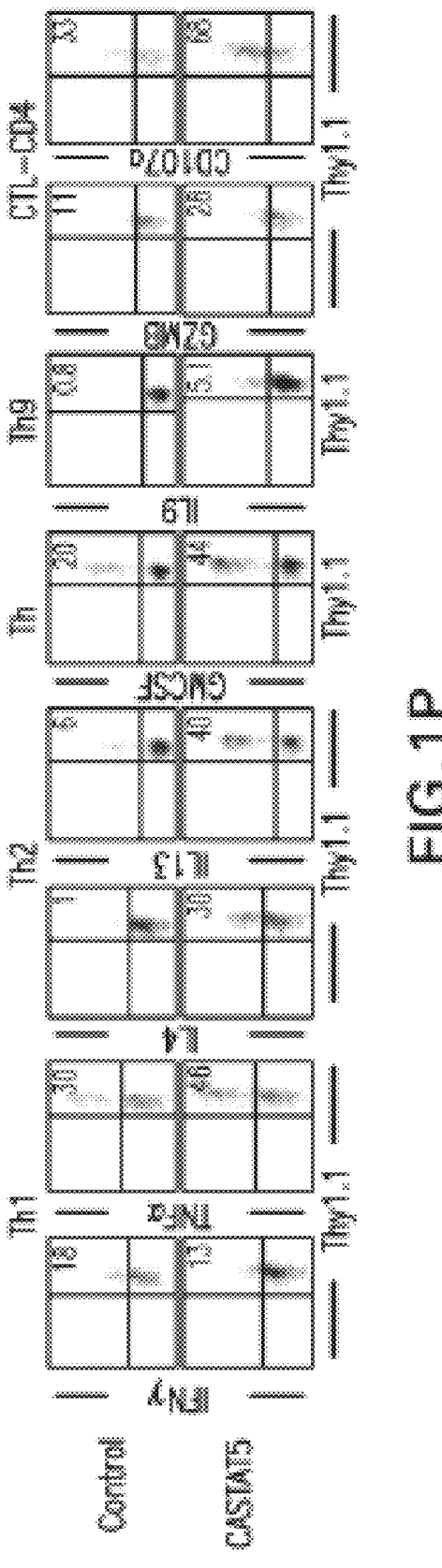
FIG. 1P shows representative dot plots depicting the cytokine profiles of the donor CD4+ T cells. Numbers indicate the percentages of cytokine-producing cells in total donor CD4+ T cells.
Figure 1Q:
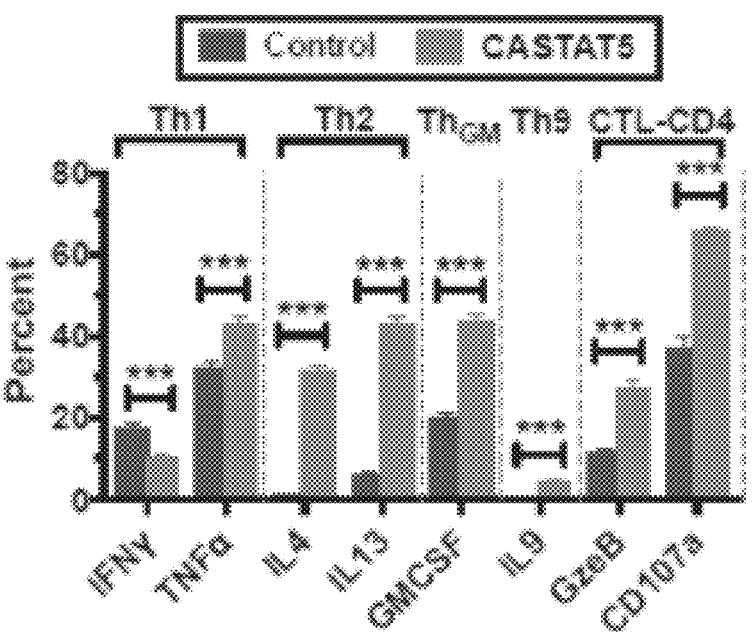
FIG. 1Q is a bar graph showing the pooled date from FIG. 1P.
Figure 1R:
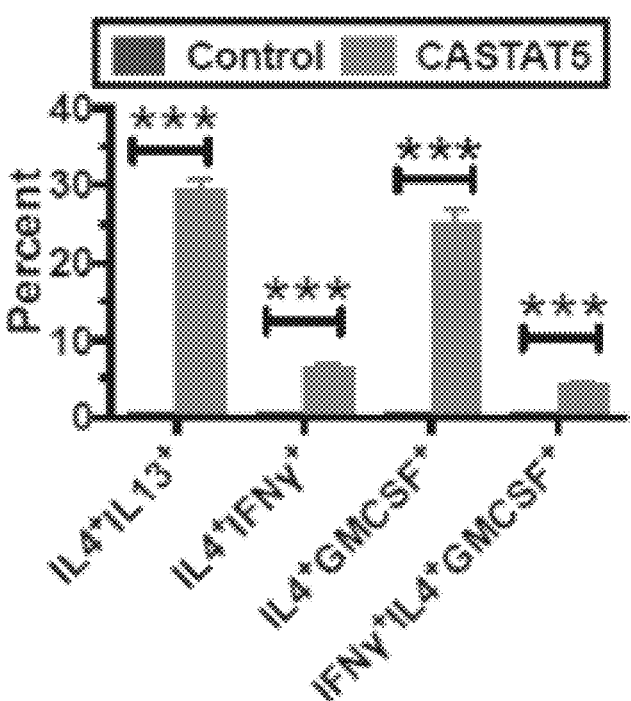
FIG. 1R is a bar graph showing the percent of donor CD4+ T cells co-expressing the indicated effector molecules.

A cohort of mice were sacrificed 10 days after T cell transfer and donor T cells in spleens were assessed for cytokine production by intracellular cytokine staining (ICS). FIGS. 1P-1Q show that CASTAT5 CD4⁺ T cells had some mixed changes in Th1 cytokine productions compared to the control CD4⁺ T cells, for example, slight reduction in IFNγ but modest gain in TNFα; notably. CASTAT5 CD4⁺ T cells had markedly elevated productions of cytokines characteristic of the Th2 (IL4, IL13), Th9 (IL9) and ThGM (GMCSF aka CSF2) lineages, in addition to cytolytic molecule granzyme B (GZMB) and degranulation marker CD107a (LAMP1), which are hallmarks of cytolytic CD4⁺ T cells (CTL-CD4). Th17 cytokines, including IL17A, IL21 and IL22, were not detected in CASTAT5 or control CD4⁺ T cells (data not shown). Cytokine co-staining analysis revealed at the single cell level that CASTAT5 enabled CD4⁺ T cells to concurrently express 2 or 3 cytokines characteristic of different Th lineages, exhibiting a unique polyfunctional phenotype (FIG. 1R).

Example 2. CASTAT5 Enhances CD4⁺ T Cell Tumor Infiltration and Retention

Materials and Methods

Bioluminescent imaging (BLI): BLI was performed on a Spectral Advanced Molecular Imaging X (Ami X) system (Spectral Instruments Imaging). Luciferase-transduced T cells were seeded in a 96-well plate ($1\times10^5$ cells/well in 200 μl medium), and luciferase expression was immediately examined upon addition of D-luciferin substrate (150 g/ml final concentration). To track T cell migration in vivo, each mouse received an intraperitoneal injection of 150 mg/kg D-luciferin and anesthetized by inhalation of 2.5% isoflurane. Mice were then placed into the camera chamber on a left lateral decubitus position, where a controlled flow of 2% isofluane was administered via a nose cone. The photographic images were acquired and overlaid with pseudocolor luminescent images. All BLI data were analyzed with AMI View (Spectral Instruments Imaging) software. The luminescence was quantified as photon/see as an indicator of tumor burden.

Results

Figure 1S:
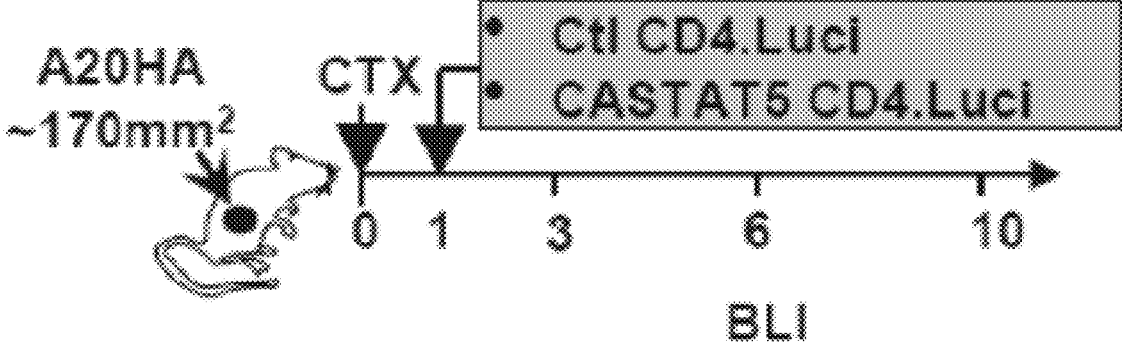
FIG. 1S is a schematic showing the experimental procedures that were followed for Figures IT-1U. Briefly, HA-specific CD4$^+$ T cells were transduced with luci-carrying retrovirus alone (Ctl CD4.Luci) or co-transduced with luci- and CASTAT5-carrying retrovirus (CASTAT5 CD4.Luci). The transduction efficiency of luciferase gene was evaluated by BLI before T cell transfer with numbers represent the luciferase signal intensity in T cells quantified as photon/see (FIG. 1T). 0.1×106 virus-transduced T cells were transferred into CTX-conditioned tumor-bearing mice. BLI was conducted periodically to visualize luciferase-expressing donor CD4$^+$ T cells in vivo. Representative images of mice in each group at specific time points are shown (FIG. 1T).
Figure 1T:
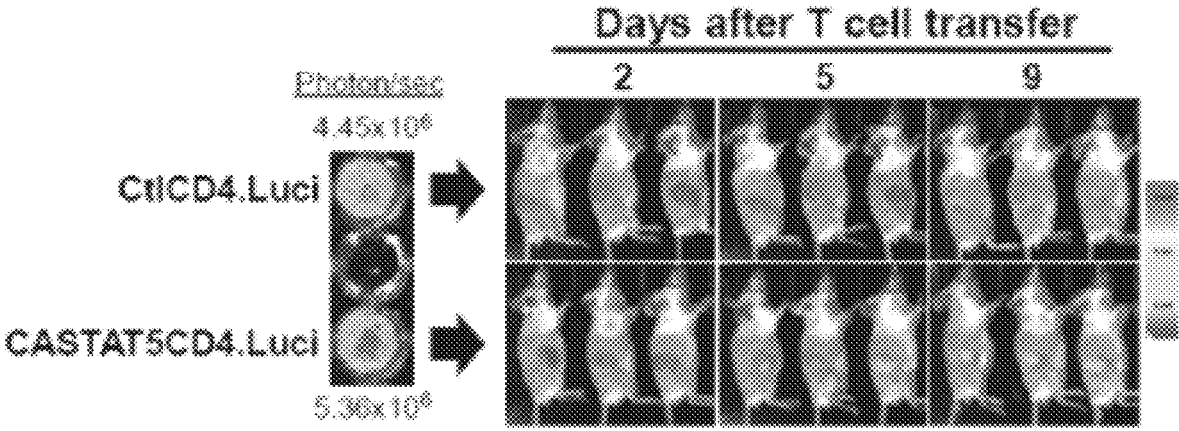
FIGS. 1C-1N are flow cytometry plots showing the kinetics of donor CD4+ T cell expansion in peripheral blood. Representative dot plots at specific time points are shown, and the numbers represent the percentages of donor CD4+ T cells.
FIG. 1U shows the results of in vivo T cell luciferase signal intensity quantified as mean+/−s.d.*p<0.05. p<0.01, *p<0.001.
Figure 1U:
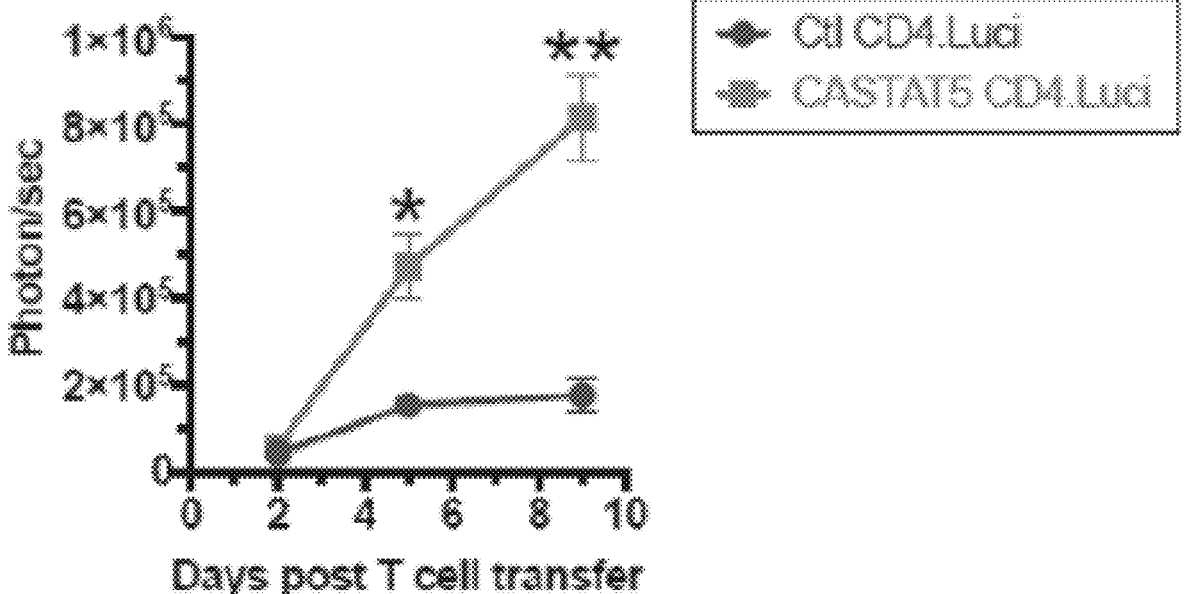

The effect of CASTAT5 on the tumor-infiltrating capacity of tumor-specific CD4⁺ T cells was examined next. To track and quantify tumor-infiltrating donor T cells. T cells were engineered to express luciferase (luci) so that they can be visualized by bioluminescence imaging (BLI). As shown in FIG. 1S schema, tumor-specific CD4⁺ T cells, transduced with the luci-carrying viral vector alone (control CD4.luci) or co-transduced with luci and CASTAT5-carrying viral vectors (CASTAT5 CD4.luci), were transferred into CTX-conditioned tumor-bearing mice. The control and CASTAT5 CD4⁺ T cells showed comparable photon intensities before transfer, indicating similar transduction efficiency of the luciferase gene (FIG. 1T). Notably, CASTAT5 CD4⁺ T cells were readily detectable in tumors on day 5, and remained within the tumors at least by day 9 (FIG. 1T); in contrast, the intra-tumoral presence of control CD4⁺ T cells was modest on day 5, and became barely detectable on day 9 (FIG. 1T). It should be noted that during the 10-day timespan of imaging the frequencies of the control and CASTAT5 CD4⁺ donor T cells were still comparable (FIG. 1O). The results suggest that the improved presence of CASTAT5 CD4⁺ T cells in tumors was not simply due to stronger donor T cell expansion, but rather the result of enhanced tumor infiltration and retention.

Example 3. CASTAT5 CD4⁺ T Cells Eradicate Advanced Tumors Through Eliciting Antitumor CD8⁺ T Cell Responses

Materials and Methods

Cell preparation, flow cytometry analysis: Peripheral blood was collected via tail vein bleeding. Spleen and tumor samples were digested and gently dissociated into single-cell suspension. Red blood cells were lysed by ACK lysing buffer. For surface molecule detection, cells were stained with fluorochrome-conjugated antibodies for 10 minutes at room temperature in the dark. To detect intranuclear molecules (Foxp3, EZH2, Tbet, GATA3, etc), transcription factor staining buffer set was used following manufacturer's instruction. For intracellular cytokine staining, spleen cells were stimulated with 10 μg/ml cognate HA peptide or PMA/ionomycin in the presence of GolgiStop for 4 hours at 37° C. Cells were harvested and surface stained, followed by cytokine staining with intracellular fixation and permeabilization kit from BD Biosciences. For detection of CD19-CAR expression in transduced T cells, FITC-conjugated polyclonal mouse anti-rat-F (ab) 2 antibodies were used to detect the 1D3 scFv; FITC-conjugated normal polyclonal mouse IgG antibodies were used as an isotype control. To detect phosphorylated STAT5 (pSTAT5) in T cells, cells were fixed in 2% formaldehyde in PBS for 20 minutes at room temperature. Cells were then pelleted and permeabilized by ice-cold methanol at –20° C. for 30 min. After wash twice with PBS, 5 μl pSTAT5-PE was added into each sample and incubated at room temperature for 20 minutes in the dark. Cells were washed twice with PBS and subjected to FACS analysis. All FACS data were acquired on a LSRII instrument (BD Biosciences) and analyzed using Flowjo software (Tree Star).

Results

Figures 2A, 2B, 2C, 2D:
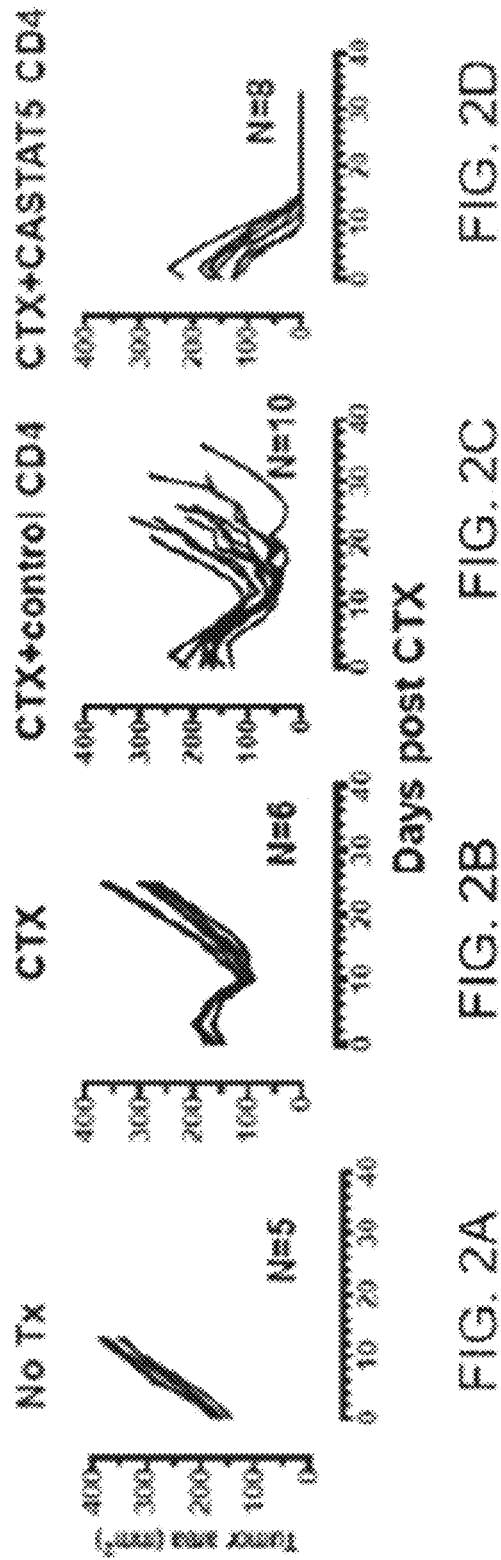
FIGS. 2A-2D are graphs showing tumor growth over time in mice with established A20HA tumors either untreated or treated with CTX along, CTX+control CD4 T cells, or CTX+CASTAT5 CD4 T cells.
Figure 2L:
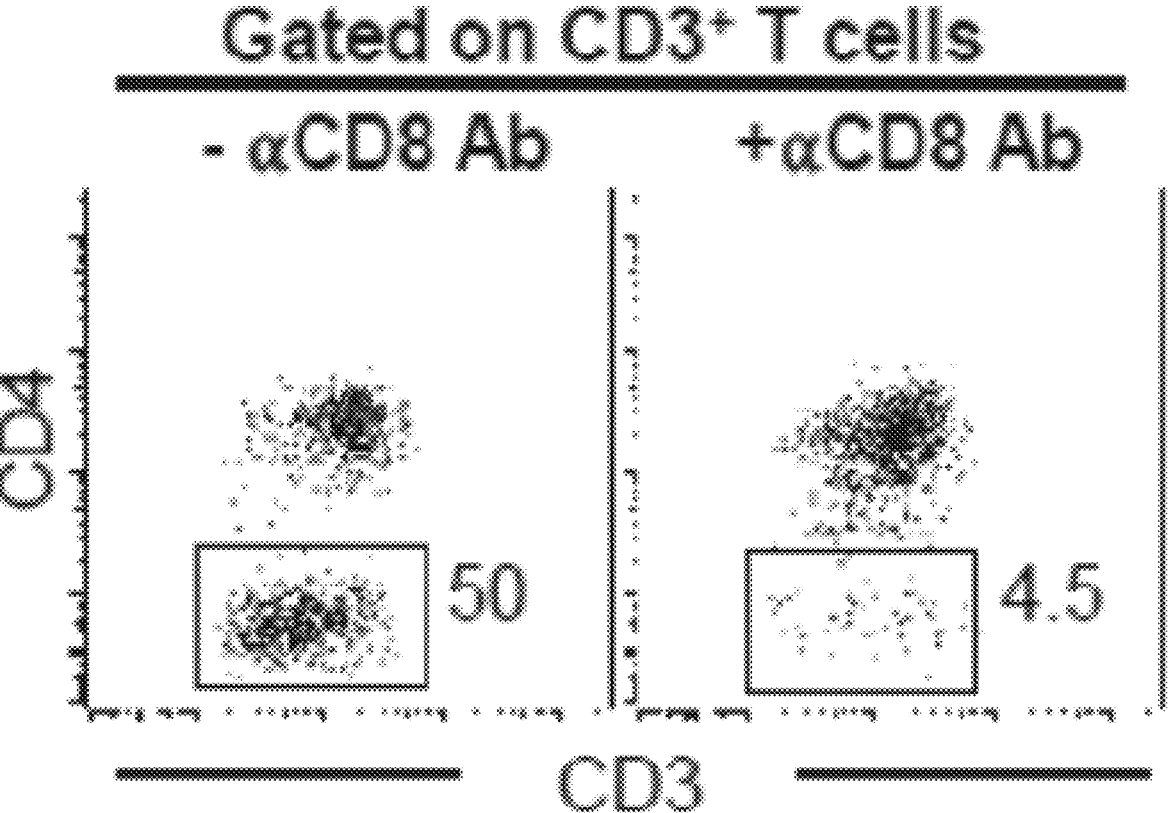
FIG. 2L is a flow cytometry plot showing CD8+ cells in mice with or without anti-CD8a mAb treatment.
Figures 2S, 2T, 2U:
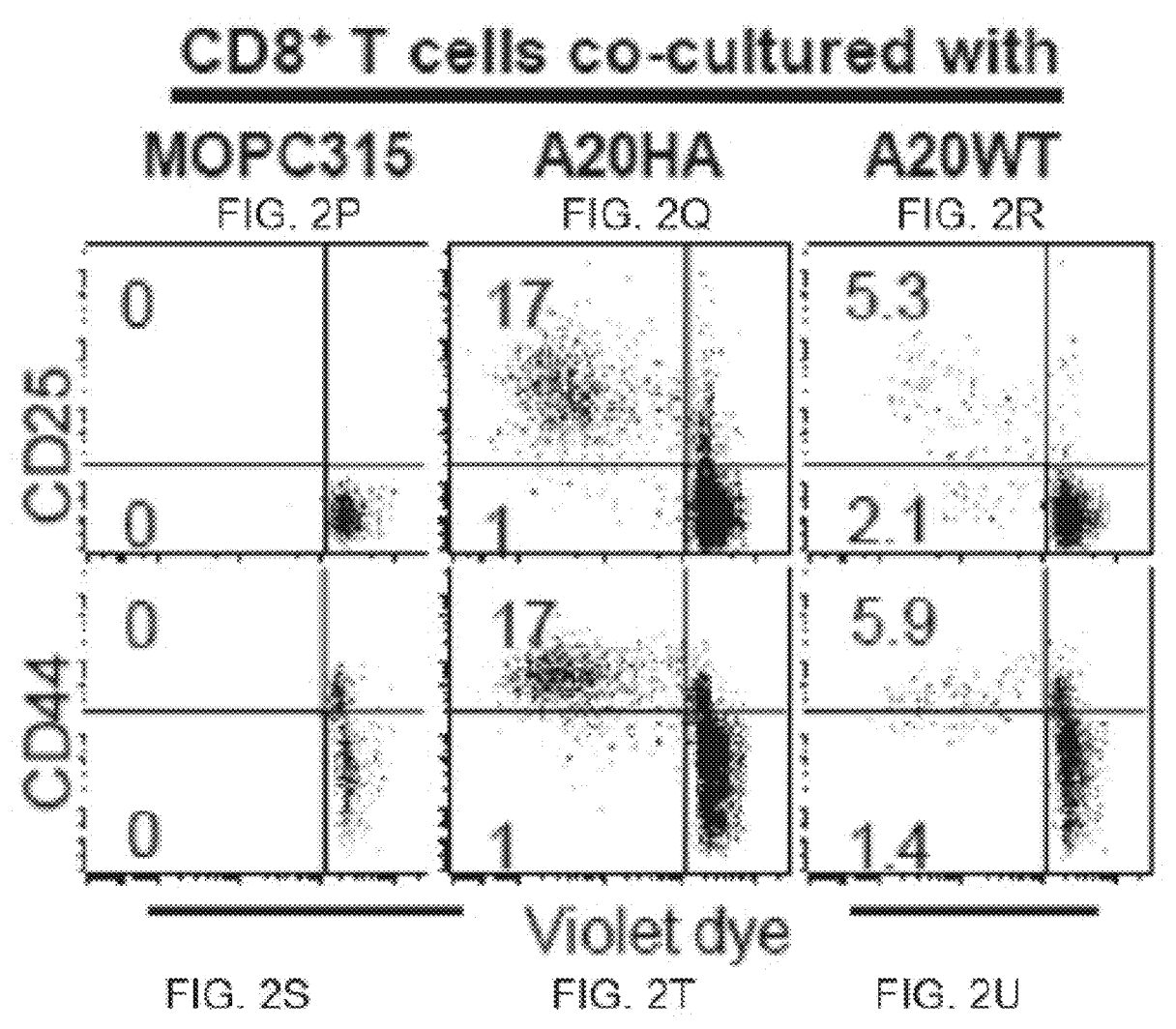
Figure 2V:
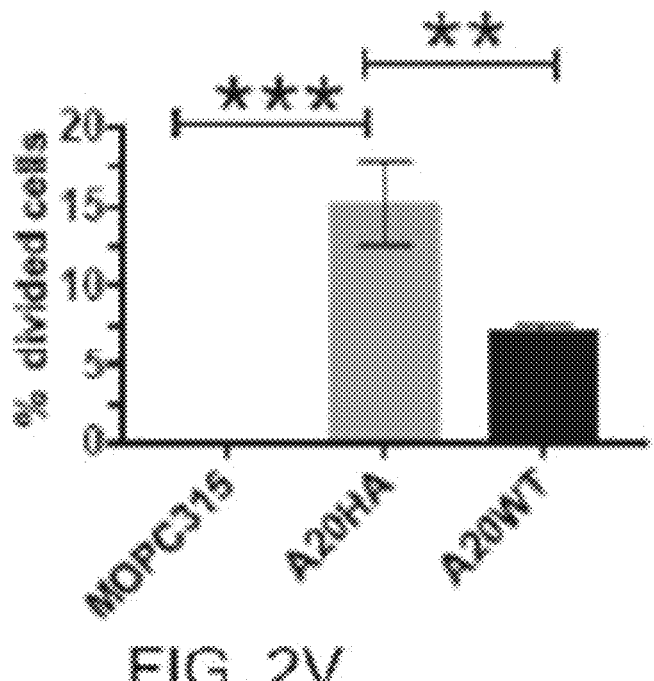
FIG. 2V is a graph summarizing the frequencies of divided CD8+ T cells under each culture condition.
Figures 2W, 2X:
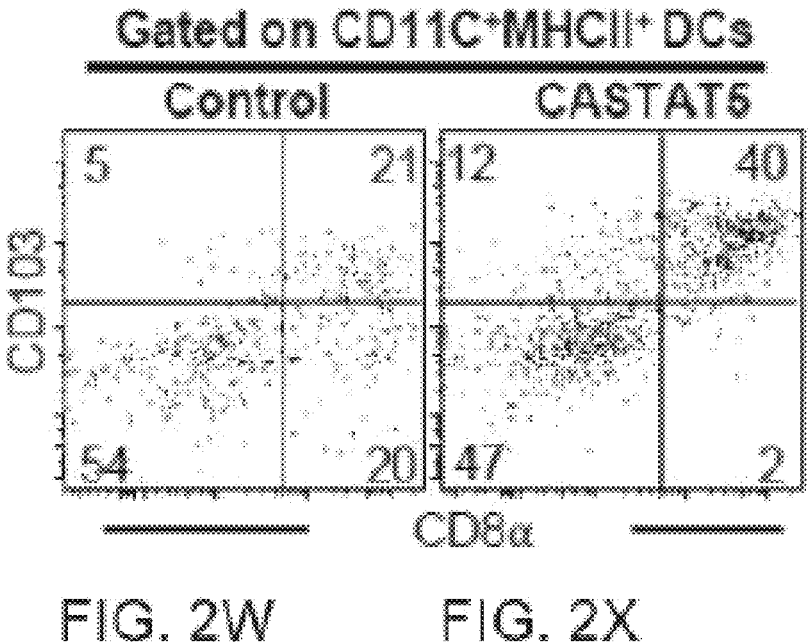
FIGS. 2W-2X are representative dot plots showing the frequencies of CD8a+CD103+CD11c+ dendritic cells in mice after treatment. Tumor-bearing mice were treated as described in FIG. 1A. 10 days after T cell transfer, mice were sacrificed to collect spleens for FACS analysis.
Figure 2Y:
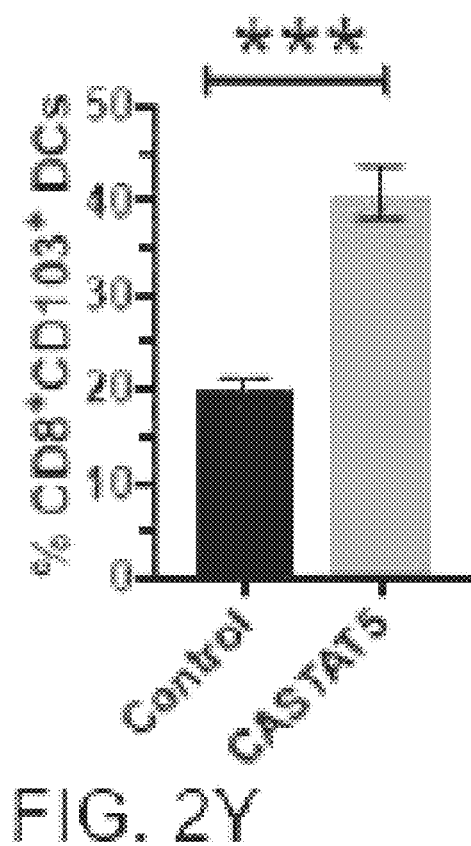
FIG. 2Y is a bar graph showing the results of the FACS analysis.

The antitumor efficacy of ACT was evaluated by monitoring tumor growth. FIGS. 2A-2D show that CTX conditioning alone transiently delayed tumor growth compared to untreated mice. Although adoptive transfer of control CD4⁺ T cells after CTX resulted in further delay in tumor growth, all mice later succumbed to tumor relapses. In sharp contrast, adoptive transfer of CASTAT5 CD4 T cells after CTX led to complete regression of large well-vascularized tumors in all treated mice (FIGS. 2A-2J). CD4⁺ T cells can activate a multitude of immune cells, especially cytotoxic CD8⁺ T cells, to mediate tumor rejection (Borst, et al., *Nat Rev Immunol,* 18:635-647 (2018)). To investigate the role of endogenous CD8⁺ T cells in the curative effect of CASTAT5 CD4⁺ T cells, mice were injected with depleting antibody to remove CD8⁺ T cells after receiving CASTAT5 CD4⁺ T cell infusion (FIGS. 2K-2M). FIG. 2N-2O show that CD8⁺ T cell depletion abolished the curative effect of CASTAT5 CD4⁺ T cells, indicating that host CD8⁺ T cells were a critical component of CASTAT5 CD4⁺ T cell-induced antitumor immunity. The result implied that the endogenous CD8⁺ T cells might be primed against tumor-associated antigens. To examine CD8⁺ T cell reactivity toward tumors, host CD8⁺ T cells were isolated from mice 30 days after receiving CASTAT5 CD4⁺ T cell infusion, at which time mice already had complete tumor regression. Purified CD8⁺ T cells were labeled with violet dye and co-cultured with irradiated tumor cells (FIG. 2P). 7 days after culture, CD8⁺ T cells were evaluated for cell proliferation (violet dye dilution) and activation markers (CD25 and CD44). FIGS. 2P-2V show that a significant fraction (15.3±2.7%) of CD8⁺ T cells underwent multiple rounds of cell division and expressed high levels of CD25 and CD44 in response to A20HA cells, the initial tumor inoculants. Interestingly, a smaller fraction of CD8 T cells (7.3±0.2%) responded to wild-type A20 cells (A20WT) cells which do not express HA but were unresponsive to MOPC315, a plasmacytoma cell line unrelated to A20 cells. The results suggest that the endogenous CD8[+] T cells were primed against not only HA, the antigen targeted by CASTAT5 CD4[+] T cells, but also other A20-derived tumor-associated antigens, indicating the occurrence of epitope spread in the presence of CASTAT5 CD4[+] T cells. It has been well-established that CD8a[+] CD11c[+]CD103[+] dendritic cells can effectively activate CD8[+] T cells through cross-priming (Hildner, et al., *Science*, 322:1097-1100 (2008); Spranger, et al., *Cancer Cell*, 31:711-712 e714 (2017)). Indeed, there was significantly increased presence of this DC subset in mice receiving CASTAT5 CD4 T cells (FIGS. 2W-2Y), suggesting the involvement of DCs in bridging the crosstalk between donor CD4[+] T cells and host CD8[+] T cells.

Aberrant activation of STAT5 has been associated with leukemic transformation (Chai, S. K., et al., *J Immunol*, 159:4720-4728 (1997); Spickermann, K., et al., *Clin Cancer Res*, 9:2140-2150 (2003); Birkenkamp, K. U., et al., *Leukemia*, 15:1923-1931 (2001); Shuai, K., et al., *Oncogene*, 13:247-254 (1996); Ribicro, D., et al., *Blood Adv*, 2:2199-2213 (2018); Pham, H. T. T., et al., *J Clin Invest*, 128:387-401 (2018)), raising the question whether CASTAT5-transduced T cells would become leukemic. To address this, the ability of CASTAT5-transduced T cells to become immortal was examined. It was found that CASTAT5 CD4[+] T cells died out when cultured in the absence of antigenic stimulation or growth factors, though in a delayed pace compared to control CD4[+] T cells, (FIG. 8D). The leukemic potential of CASTAT5-transduced T cells in vivo was examined next. Splenocytes were isolated from mice that became tumor-free after receiving CASTAT5 CD4 T cells. These splenocytes, in which up to 30% were CASTAT5-transduced CD4 T cells, were adoptively transferred into naïve mice. None of the recipient mice developed leukemia in a 6-month timeframe (data not shown). Together, these data suggest that CASTAT5 transduction by itself does not make primary T cells immortal or leukemic.

Example 4. CASTAT5 Drives Genome-Wide Transcriptional and Epigenetic Remodeling in Cd4[+] T Cells Materials and Methods Cell preparations for next-generation sequencing: 10 days after T cell transfer, mice spleens and tumors were collected and processed into single cell suspensions. Cells were stained with anti-CD4 and anti-Thy1.1 Abs and subjected to cell sorting on a FACSAria sorter. For samples with low donor T cell frequencies (<1%), cells were pre-enriched for CD4[+] T cells using a negative CD4[+] T cell isolation kit (Stemcell technology) before FACS-sorting. The purity of sorted donor CD4[+] T cells was normally greater than 98%. For bulk RNAseq and ATACseq analyses using spleen samples, donor CD4[+] T cells derived from three individual mice under each treatment condition were used as biological replicates. For single-cell RNAseq. 1.7×10^5 CD4[+] T cells sorted from three individual mice were admixed as pooled sample for each treatment condition. Pooled samples were also used for ATACseq analysis designed to compare the chromatin accessibility status in donor CD4[+] T cells collected before adoptive transfer versus those recovered from the spleen and tumor 10 days post transfer.

RNAseq library preparation and sequencing: Total RNA was isolated from FACS-sorted donor CD4[+] T cells using TRIzol reagent (Thermo Fisher). 100 ng of total RNA was used for RNAseq library preparation by following the Illumina TruSeq stranded mRNA sample preparation guide. The RNA-seq libraries were subjected to quantification process, pooled for cBot amplification and subsequently sequenced on a HiSeq3000 (Illumina) sequencer with 50 bp single-end cycling. Demultiplexing with Bcl2fastq2 were employed to generate the fastq file for each sample. 23-32 million single-end reads were obtained for each sample, respectively.

RNAseq analysis: The RNAseq analysis was performed on Galaxy main server. The raw reads were mapped to mouse genome mm[10] using HISTAT2 (Galaxy Version 2.1.0) with default settings. Reads mapped to annotated features were counted using featureCounts (Galaxy v1.6.3). The DEseq2 package v1.24.0 was used to normalize the raw accounts and identify differentially expressed genes. Genes with less than 10 reads total were filtered out before perform DESeq2 analysis. Log transformation was performed using rlog function and PCA plot was generated using plotPCA function within DESeq2 package. Volcano plots and heatmaps were generated using EnhancedVolcano v1.2.0 and ComplexHeatmap v2.0.0 in R3.6.0, respectively.

ATACseq profiling: The ATACseq libraries were prepared based on the Omni-ATACseq protocols with some minor modification (Corces, et al., *Nat Methods*, 14:959-962 (2017)). Briefly, 60,000 FACS-sorted CD4[+] T cells were suspended in 60 μl ATAC resuspension buffer (RSB, 10 mM Tris-HCl pH 7.4, 10 mM NaCl, 3 mM MgCl$^2$, 0.1% NP40, 0.1% Tween-20, and 0.01% Digitonin), incubated on ice for 3 minutes, and then washed with 1 ml RSB buffer without NP40 and Digitonin. The resulted nuclei were pelleted at 500 RCF for 10 minutes at 4° C. in a fixed angle centrifuge and resuspended in 30 μl of Tagmentation DNA (TD) buffer. 5 μl of the nuclei was removed, mixed with Trypan Blue solution at (1:1) ratio and examined under microscope to confirm a successful nuclei preparation. The remaining 25 μl of nuclei was incubated with 2.5 μl of Nextera Tn5 transposase (Illumina) in a total volume of 50 μl 1× TD buffer containing 0.01% Digitonin and 0.1% Tween-20. The transposition reaction was performed at 37° C. for Ihr in a PCR machine. The transposition mixture was purified using a Zymo DNA Clean and Concentrator kit. The ATAC libraries were amplified for 11-13 cycles using NEBNext 2× MasterMix and Nextera Index primers. The amplified libraries were size-selected using AMPure breads (0.5×) to remove the large fragment of DNA and then purified using Zymo DNA Clean and Concentrator kit. Six ATAC libraries were pooled and sequenced on a NextSeq500 instrument in a pair-end 75 cycle run. 60-100 million read pairs were obtained for each sample.

ATACseq analysis: The ATACseq analysis was performed on Galaxy server. Adaptor and quality trimming were performed using Trim Glore! Modules (Galaxy v0.4.3.1). Trimmed reads were mapped to mouse genome mm[10] using Bowtie2 (Galaxy v2.3.4.3) using default settings. Reads mapped to mitochondria genome were removed using Filter SAM or BAM function under samtools module (Galaxy v1.8) and PCR duplicates were removed using MarkDuplicates from Picard tool v2.20.2. ATAC-seq peak calling was performed using MACS2 v2.1.2 with following command "-p 0.01 --nomodel --shift --100 --extsize 200 -B --SPMR --keep-dup all --call -summits". BigWig files were generated by bedGraphtoBigwig and visualized in Integrated genome viewer (IGV) v2.5.2. The Bed file contains common peaks among three biological replicates were generated using bedTools Multiple Intersect function for CASTAT5 and control samples, respectively. The two bed files were combined using bedtools MergeBED function (Galaxy v1.2.0) to generate a single bed file that contains all peaks identified in both CASTA5 and control samples. Finally, the number of paired fragments overlaps with the intervals identified in the merged peak file was counted using bedtools MultiCovBed function (Galaxy v2.27.1) for each of six ATAC-seq samples, respectively. DEseq2 package v1.24.0 was used to call differential peaks (80) and ChIPseeker v1.20.0. was used to annotate the differential peaks (81). DiffBind (Galaxy v. 2.6.6.4) (82) was used to identify differential peaks with fixed window length of 400 bp (summit±200 bp), which were used for motif analysis by MEME-ChIP v5.05 and HOMER v4.9.

Weighted gene expression network analysis: Weighted gene coexpression network analysis (WGCNA) was performed using R package WGCNA v1.67 (Langfelder, P. and S. Horvath, *BMC Bioinformatics,* 9:559 (2008)) to identify highly correlated gene modules and establish regulatory network in the scRNAseq data. The power parameter was determined by the pickSoftThreshold function to allow scale-free topology. The adjacency matrix was calculated to measure the single cell correlation network connectivity. Hierarchical clustering was used to group genes with similar expression profile into modules based on the dissimilarity of topological overlap matrix (TOM) with a minimum number of 30 genes included in each module. Gene correlation network was visualized using R package igraph v 1.2.4.1.

Gene regulatory network: The *Mus musculus* transcription factor motifs were downloaded from *HOmo sapiens* COmprehensive MOdel Collection (HOCOMOCO) v11. For each transcription factor, we mapped its position weight matrix to the promoter region (−3000 to +3000) around the transcriptional start site of the gene in the mouse genome (version mm10) using the Find Individual Motif Occurrences program in the MEME Suite (Grant, C. E., et al., *Bioinformatics,* 27:1017-1018 (2011)). This map was intersected with the RNAseq data, ATACseq data and ChIP-seq data (GSE79518), resulting in a set of regulatory interactions from 45 transcription factors to 888 genes. Then this data was used to construct the regulatory network models in Cytoscape 3.7.

Transcription factor footprinting analysis: ATACseq footprinting analysis was performed using Rgt-HINT package (Li, Z., et al., *Genome Biol,* 20:45 (2019)). The BAM files from the six ATACseq experiments (three biological replicates each from the CASTAT5 and control CD4$^+$ T cells) were merged. The merged two BAM files were used to call peaks with MACS2 as described above (Zhang, Y., et al., *Genome Biol,* 9: R137 (2008)). The narrowpeak and BAM files were then analyzed using rgt-footprinting, followed by rgt-hint differential modules. The transcription factor footprinting line plots were generated by the analysis.

Pathway analysis: Ingenuity pathway analysis (IPA) were performed using Ingenuity pathway analysis suite spring 2019 release (Qiagen). Go-term analysis, Wikipathway and KEGG pathway enrichment and gene-set enrichment analysis (GSEA) were performed using R package clusterProfiler v3.12.0 (Yu, G., et al., *OMICS,* 16:284-287 (2012)).

Statistical analysis: Data were shown as mean+s.d. unless otherwise indicated. Data were analyzed using Prism 7.0 (GraphPad Software, Inc.). The statistical significance of the results was determined using unpaired two-tailed Student's t test. Differences in tumor sizes among different treatment groups were analyzed using the Mann-Whitney U test. p values less than 0.05 were considered statistically significant.

Results

Figure 3A:
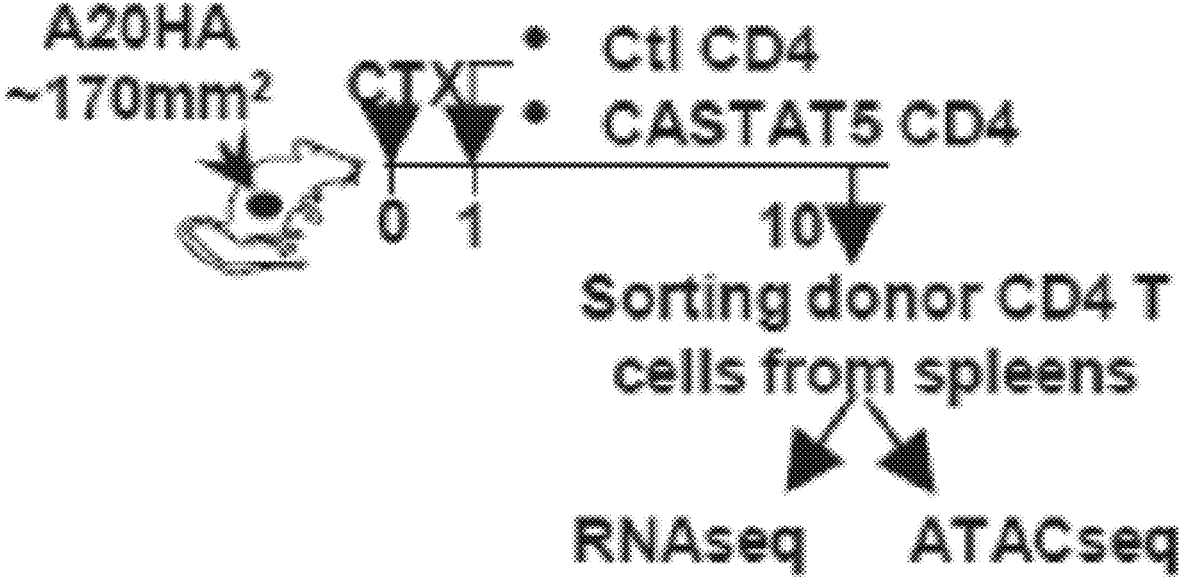
FIG. 3A is a schematic illustration of the experimental procedures followed for FIGS. 3B-3R.

To understand at the molecular level the biological impact of CASTAT5 on CD4$^+$ T cells, bulk RNA sequencing (RNAseq) and assay for transposase-accessible chromatin was performed using sequencing (ATACseq) on FACS-sorted donor CD4+ T cells (FIG. 3A).

Figure 3B:
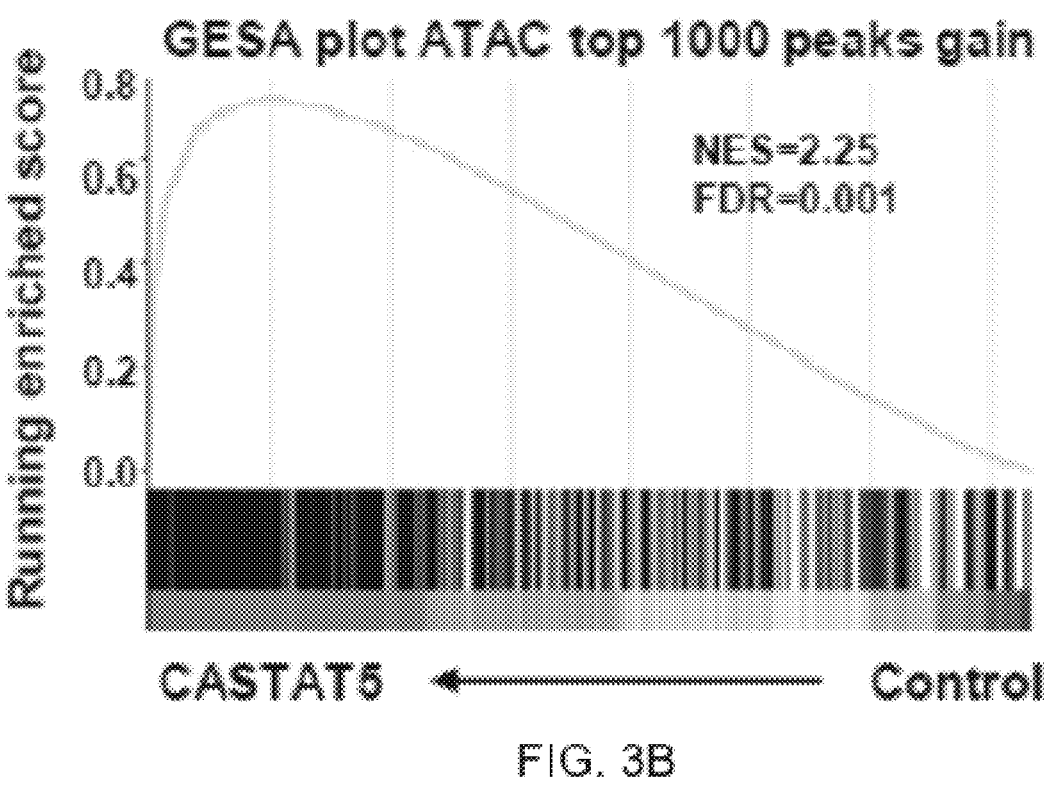
FIGS. 3B-3C show the results of gene-set enrichment analysis demonstrating the correlation between chromatin states and transcription activities. Genes associated with top 1000 ATAC peaks gained (FIG. 3B) and top 500 peaks lost (FIG. 3C) in CASTA5 CD4+ T cells were used as separate gene sets and compared with rank sorted gene expression from matched samples.
Figure 3C:
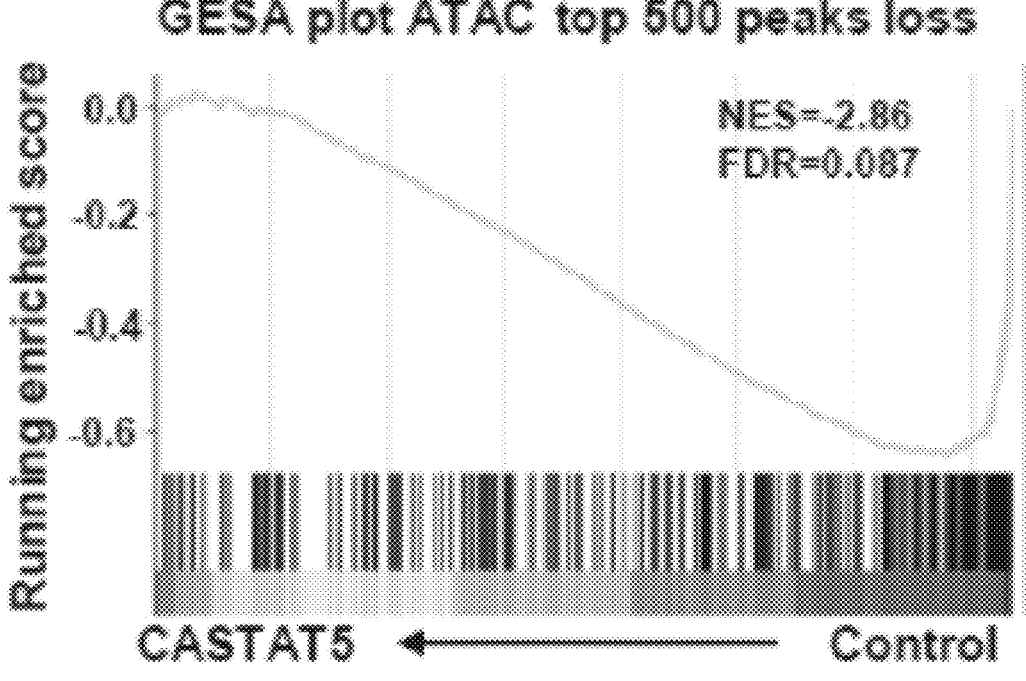
Figures 3D, 3E, 3F:
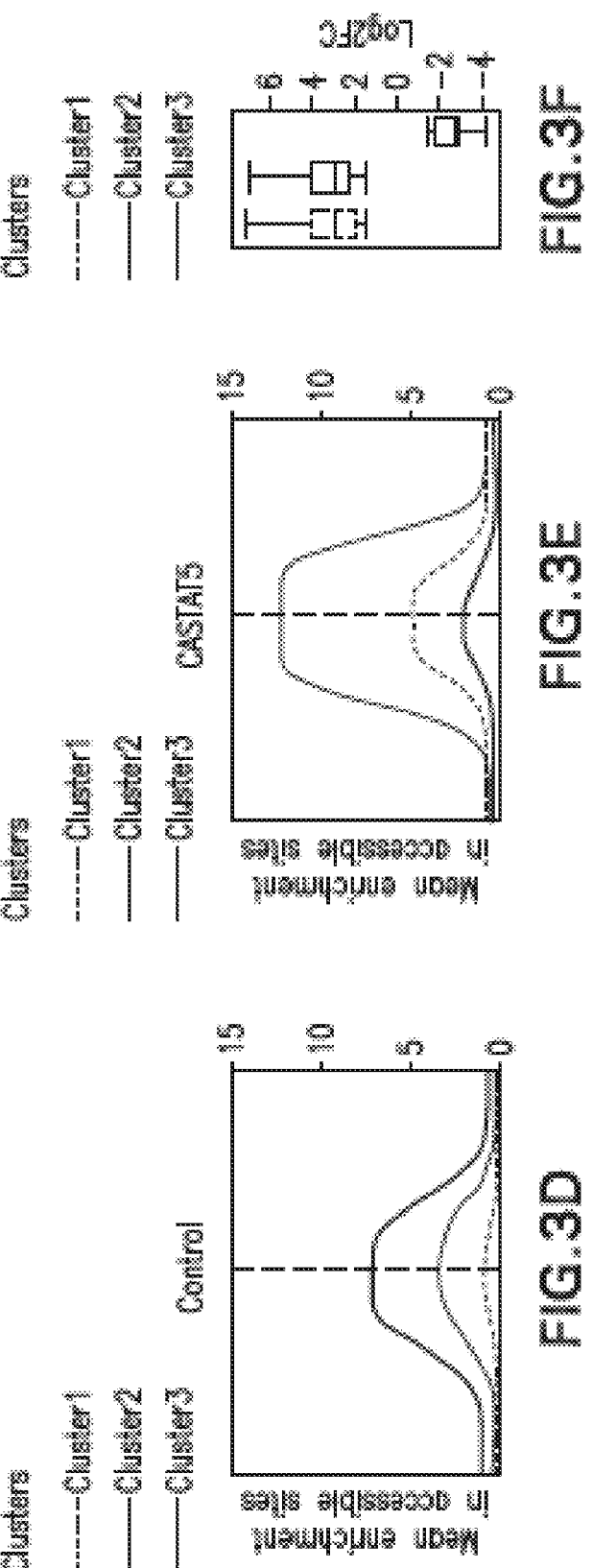
FIGS. 3D-3E are lines graphs demonstrating the average accessibility profiles of each cluster, respectively.
FIG. 3F is a box plot that summarizes the expression profile shown as log 2FC of each cluster. Representative genes with significant changes in both chromatin accessibility and gene expression are listed beside the heatmap.
Figure 3G:
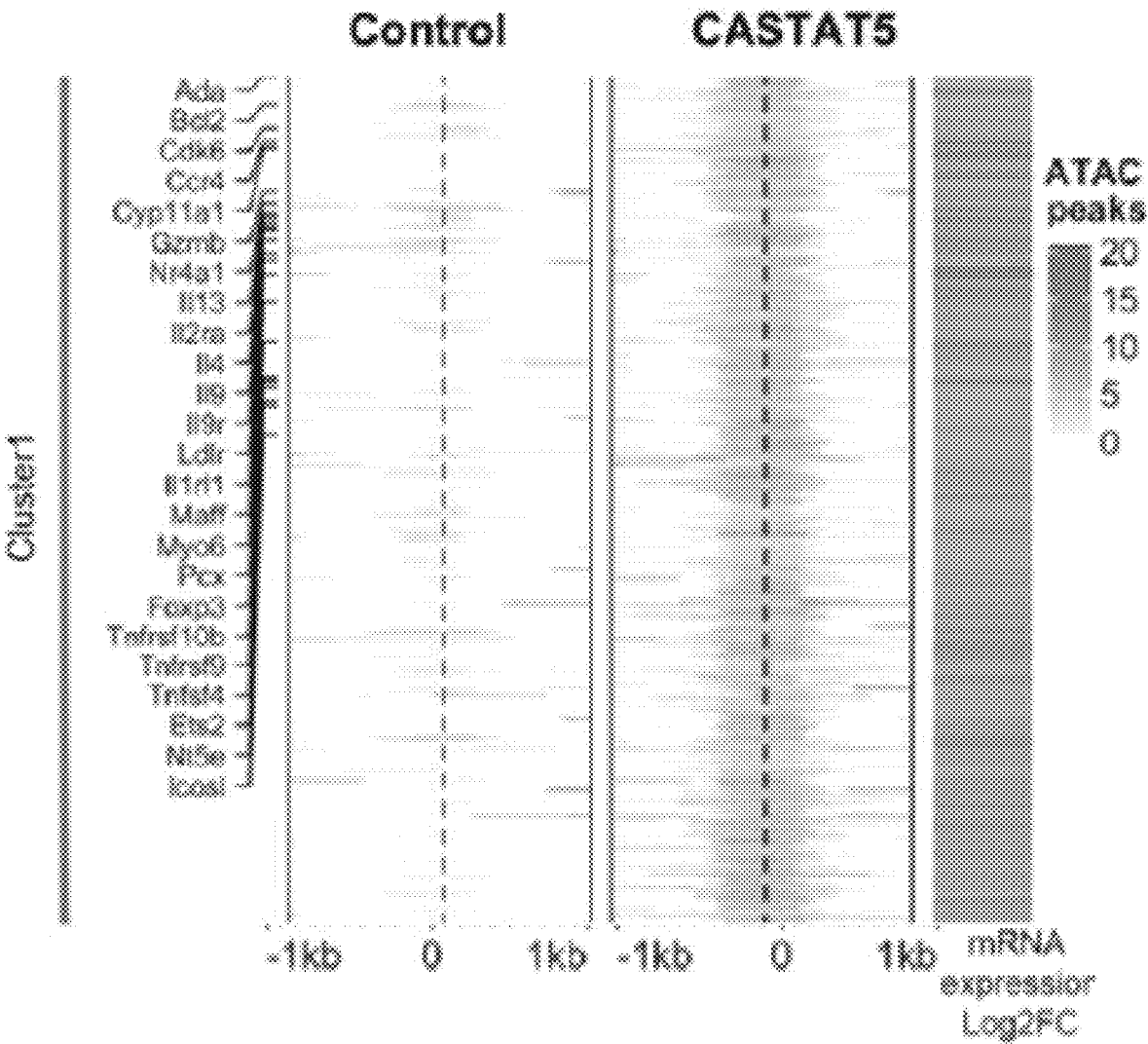
FIGS. 3G-3H are heatmaps illustrating differential chromatin accessibility at 2 kb windows centered at the summit of the ATAC peaks identified. Clusters 1 and 2 show peaks with increased accessibility, while cluster 3 shows peaks with decreased accessibility in CASTAT5 CD4+ T cells.
Figure 3H:
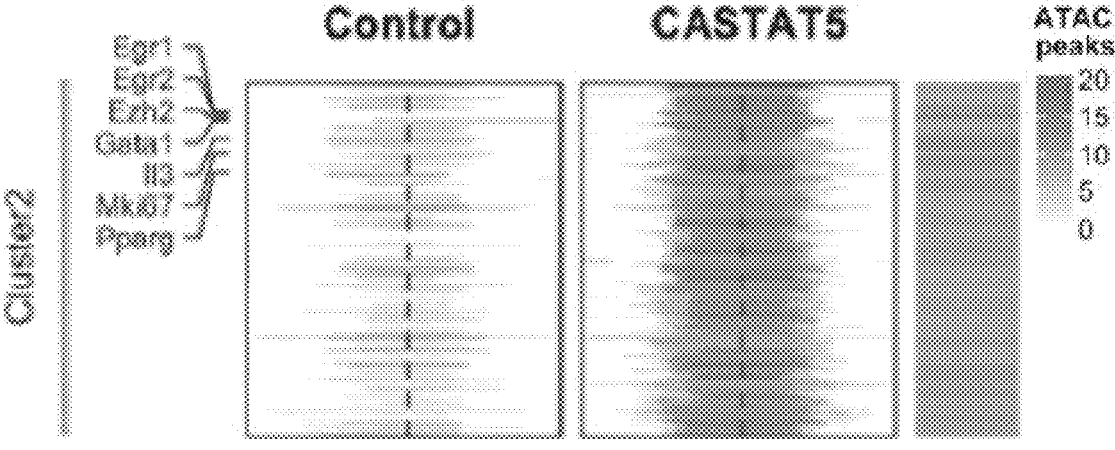
Figure 3I:
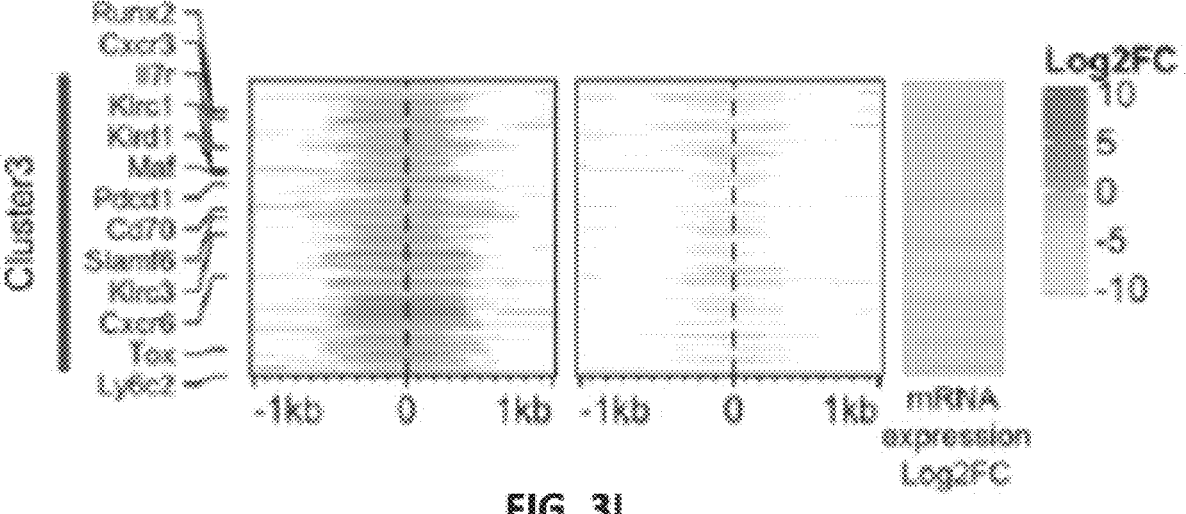
FIG. 3I shows matched expression log 2 fold changes (log 2FC), which correlate well with the chromatin accessibility profiles.
Figure 3J:
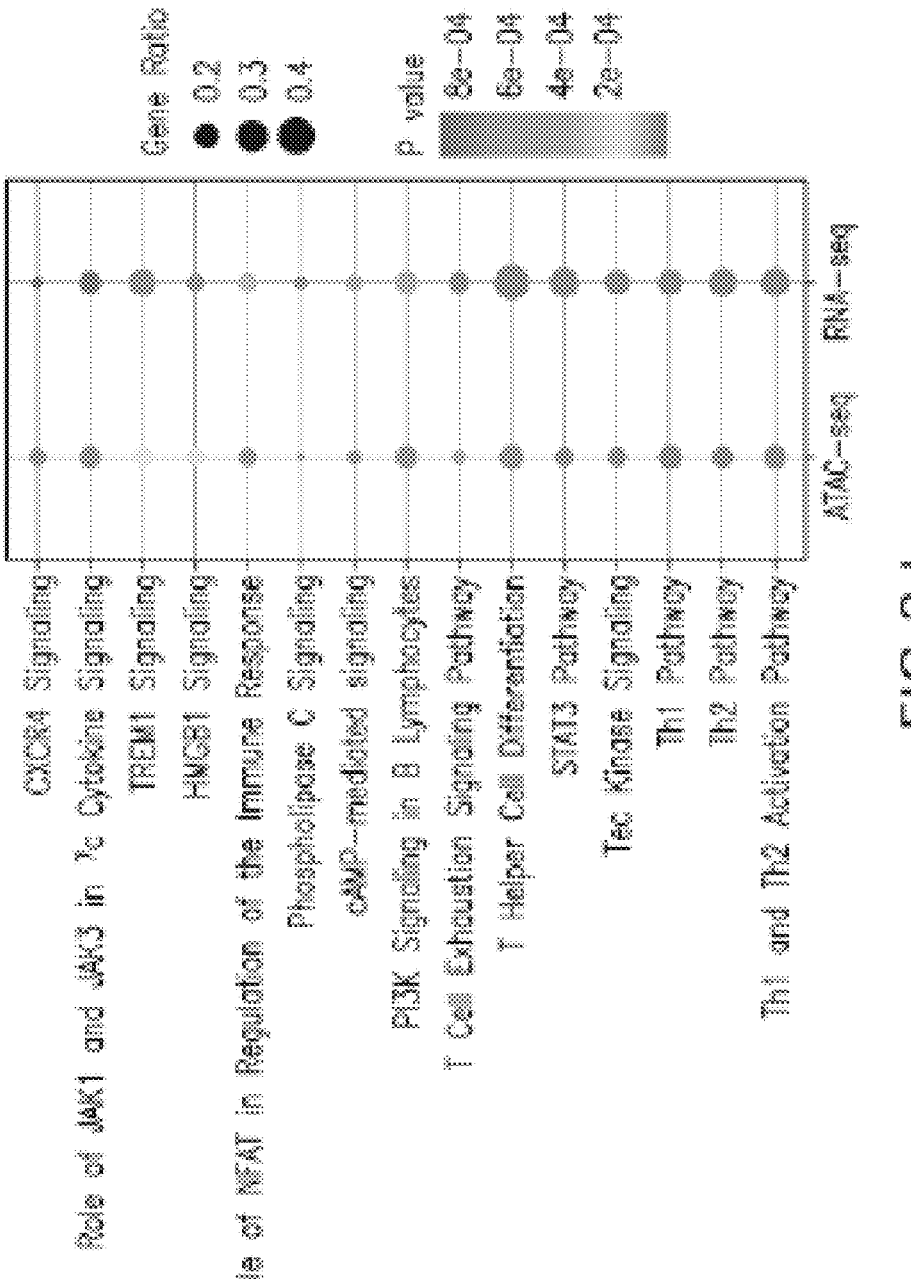
FIG. 3J is a dot plot showing the IPA results from both ATACseq and matched RNAseq results. The genes associated with differential ATACseq peaks (log 2FC>1, adjusted p-value <0.05) and differentially expressed genes (log 2FC>1, adjusted p-value <0.05) are used in the IPA analysis.
Figure 3S:
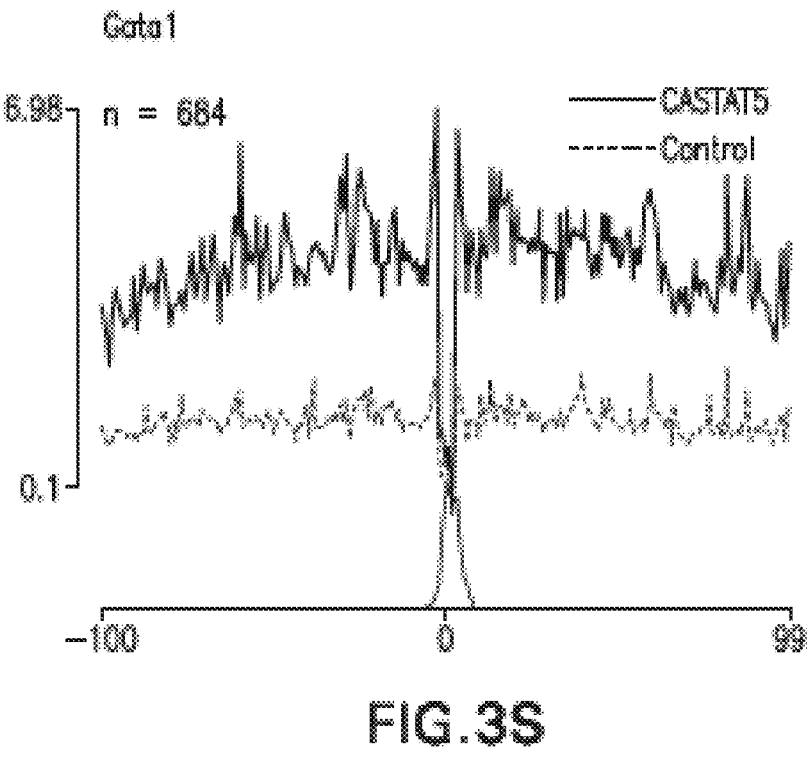
FIGS. 3S-3V are line plots showing normalized chromatin accessibility signals centered at the 200 bp window flanking the indicated transcription factor binding sites from the transcription factor footprinting analysis using the ATACseq data.
Figure 3T:
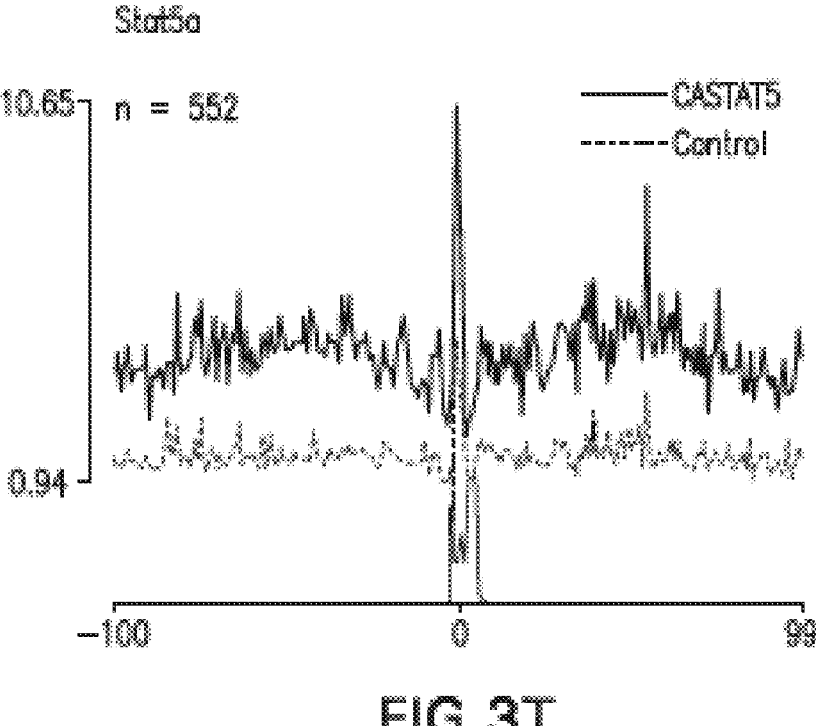
Figure 3U:
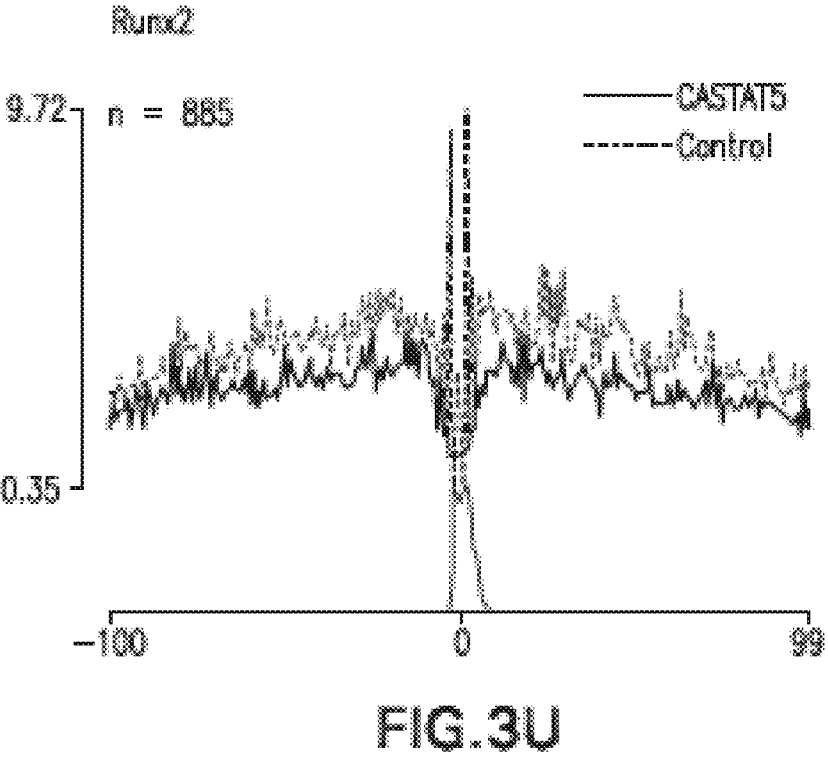
Figure 3V:
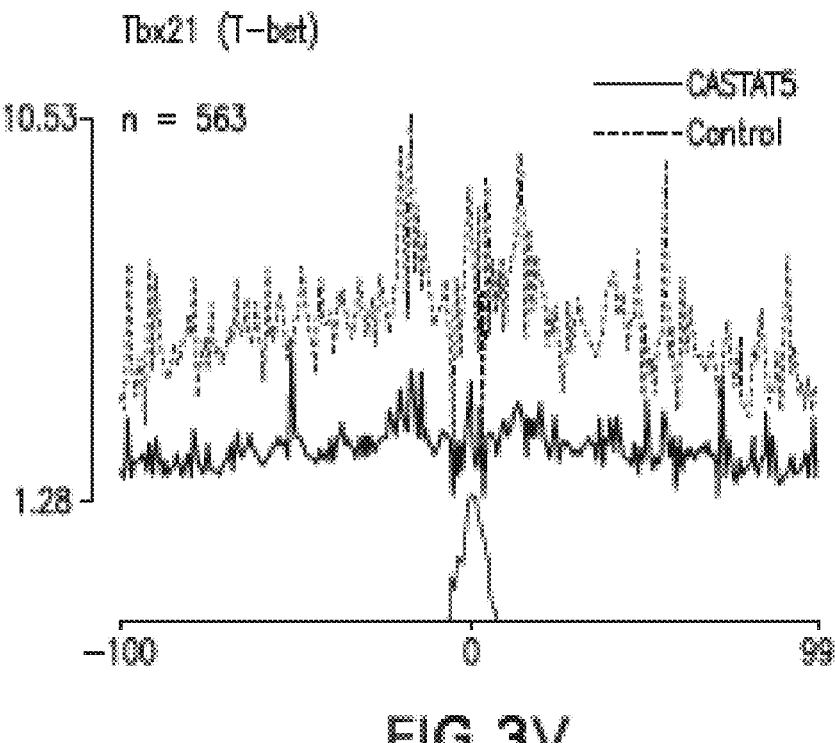
Figure 9F:
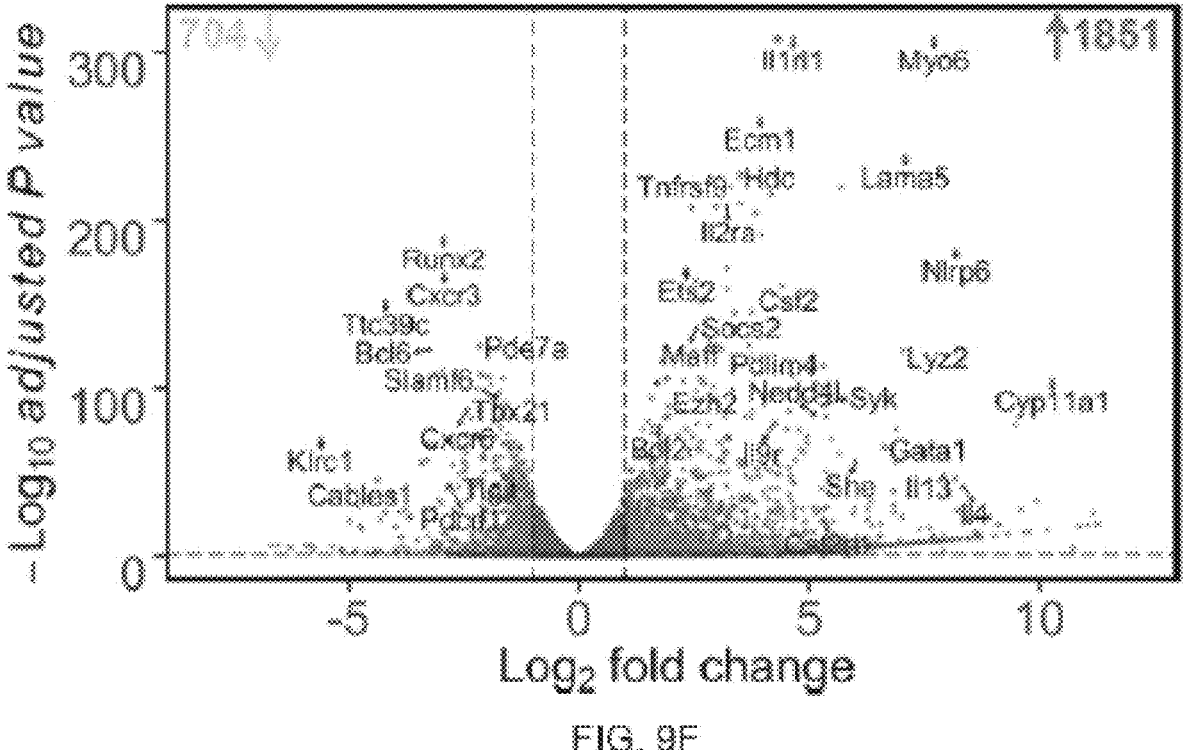
FIG. 9F is a volcano plot showing differentially expressed genes. The numbers at the left and right corners indicate the number of down (closed circle with line) and up (closed circle) regulated genes, respectively (log FC>1, and adjusted p value <0.05).
Figure 9G:
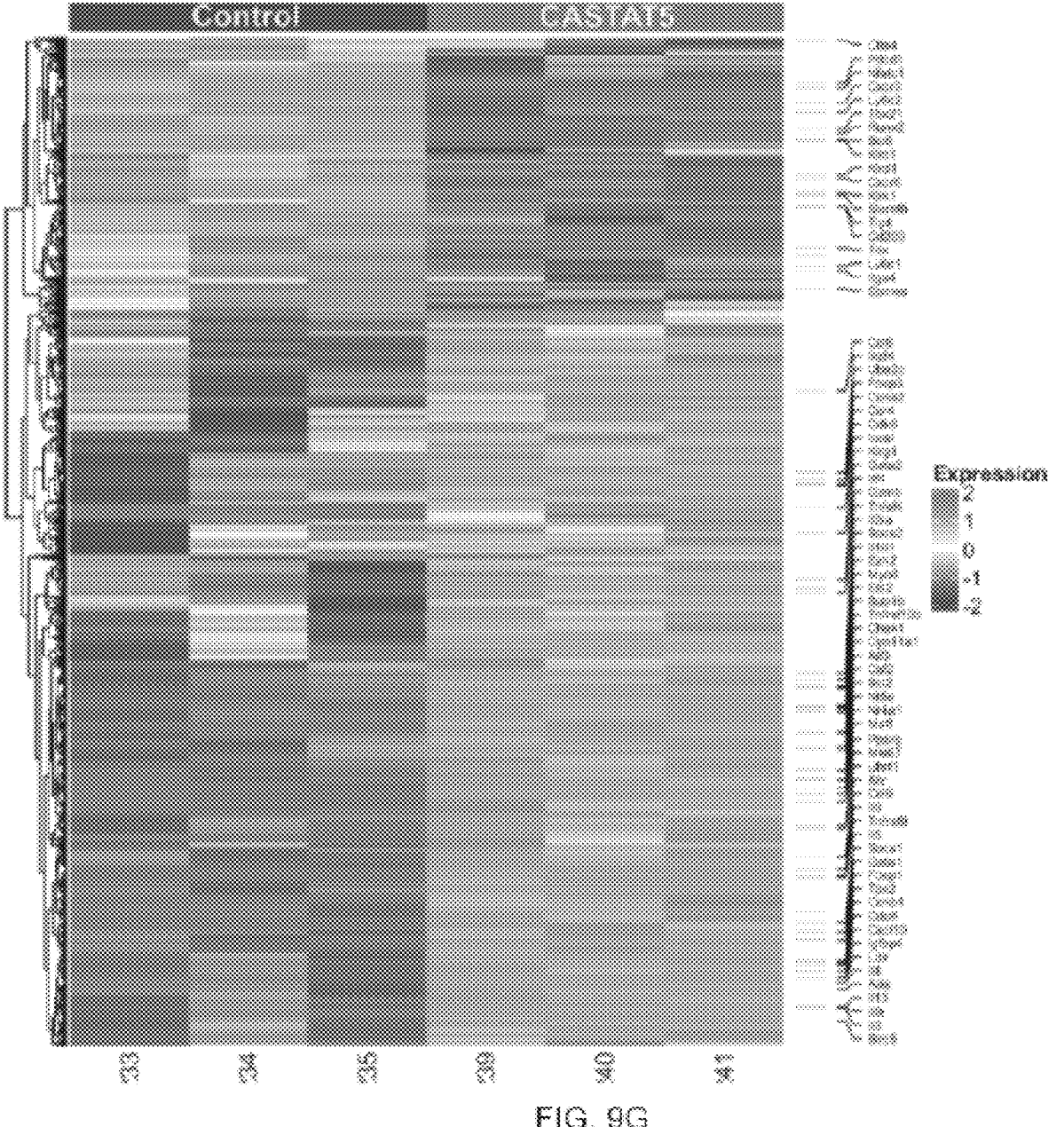
FIG. 9G is a heatmap of differentially expressed genes between CASTAT5 and control CD4+ T cells. The columns represent cells and the rows present genes.
Figure 10A:
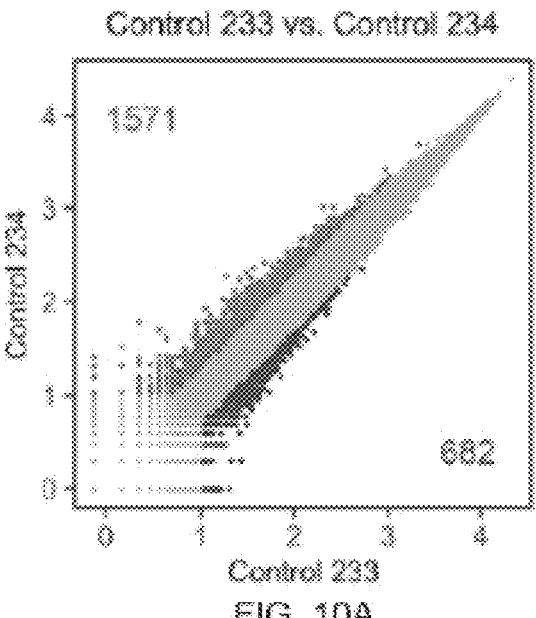
FIGS. 10A-10D are scatter plots showing pair-wise comparison between the biological replicates of the specified T cell samples as well as between CASTAT5 and control CD4+ T cell samples. The x and y-axis represent normalized and log 10 transformed ATACseq read counts for each sample.
Figure 10B:
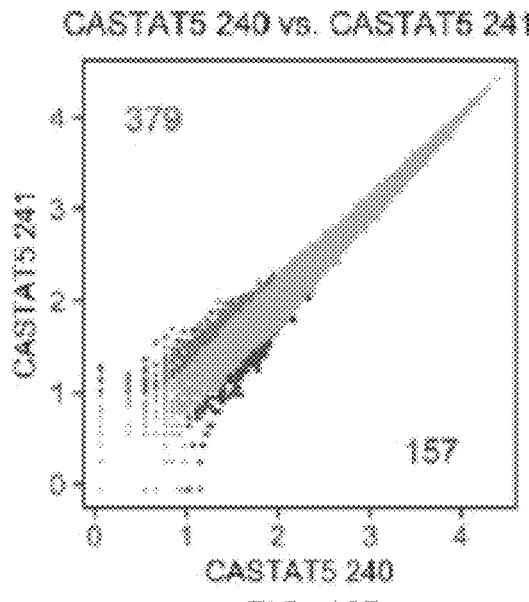
Figure 10C:
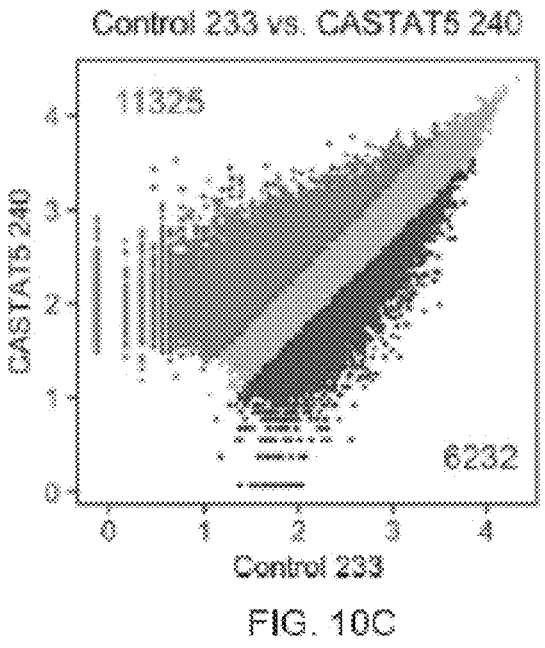
Figure 10D:
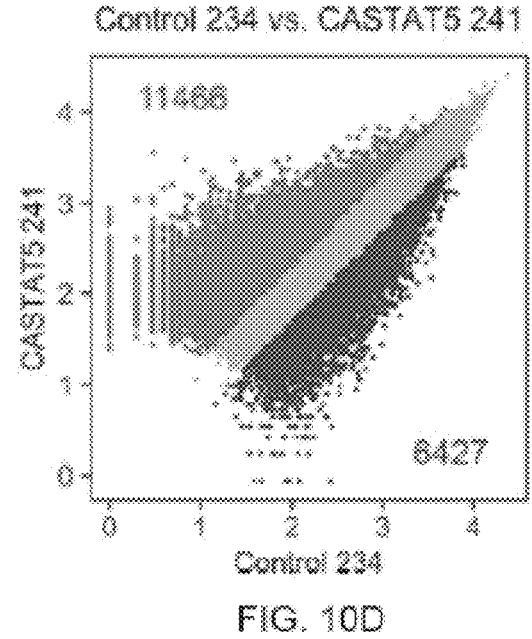
Figure 10E:
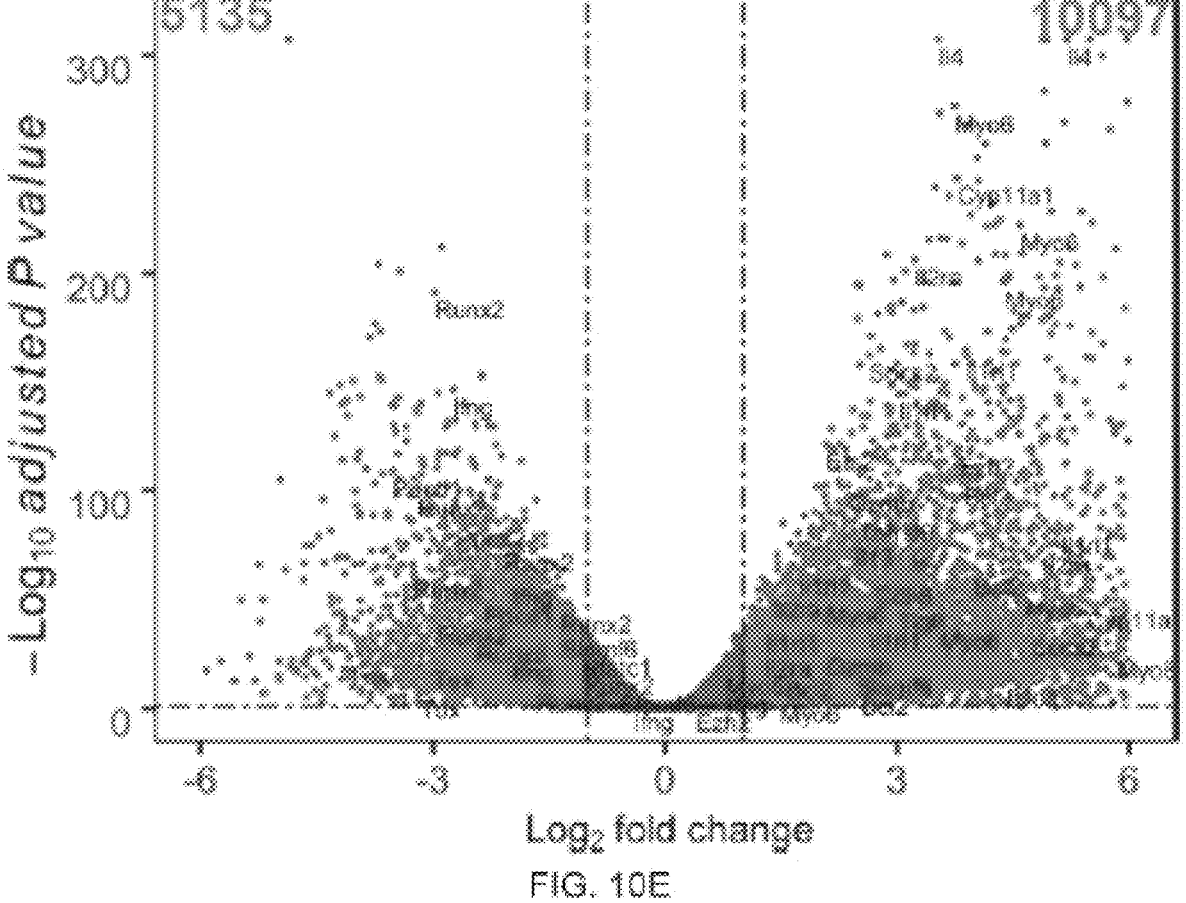
FIG. 10E is a volcano plot showing the identification of peaks with differential chromatin accessibility. The numbers at the left and right corners indicate the number of loci with loss (left panel) or gain (right panel) of chromatin accessibility, respectively (log FC>1, and adjusted p value <0.05).
Figure 10F:
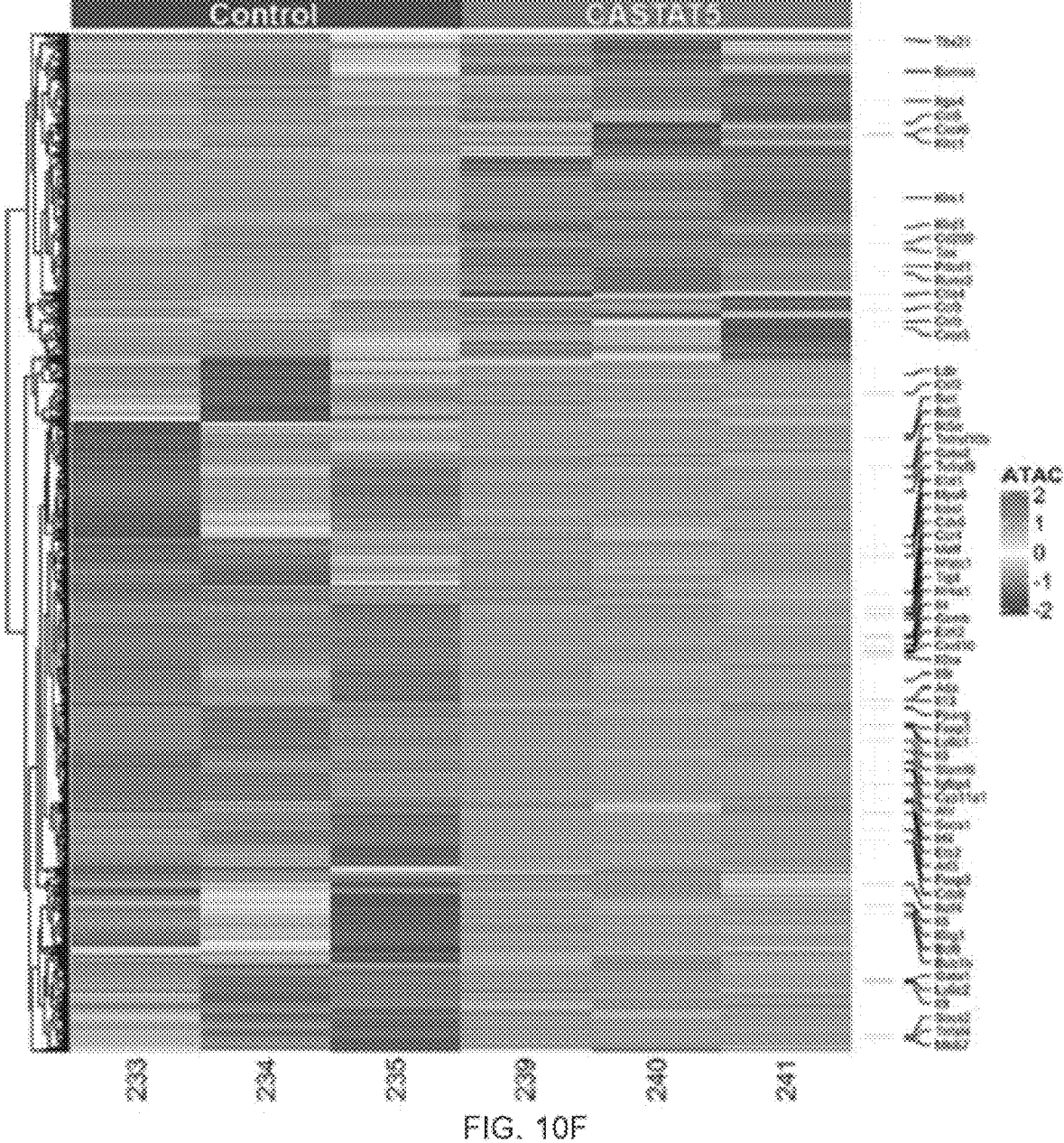
FIG. 10F is a heatmap of differential ATACseq peaks between CASTAT5 and control CD4+ T cells. The columns represent cells and the rows present ATACseq peaks.
Figure 10G:
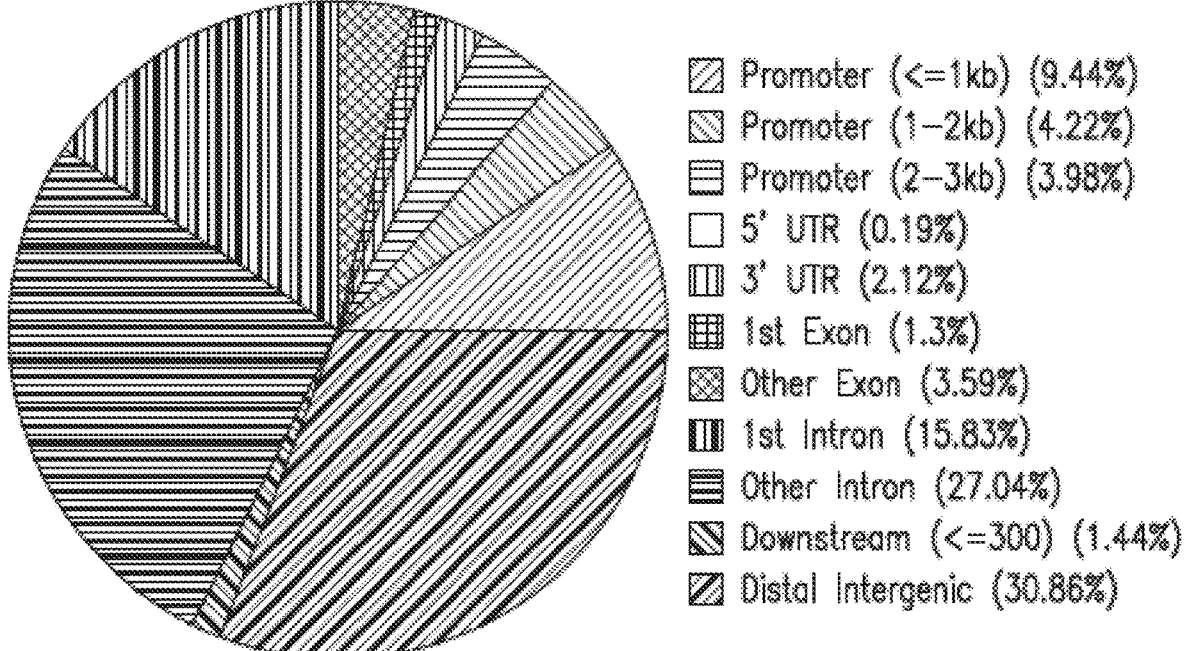
FIG. 10G is a pie chart showing the distribution of differential ATACseq peaks among several major categories of genomic features including promoter, 5-UTR, 3-UTR, exons, introns, and intergenic regions.

RNAseq analysis demonstrates a clear separation of CASTAT5 CD4$^+$ T cells from control CD4$^+$ T cells (FIGS. 9A-9E). Using fold change ≥2 and adjusted p-value <0.05 as cutoff values, 1851 up-regulated and 704 down-regulated genes were identified in CASTAT5 CD4$^+$ T cells as compared to control CD4$^+$ T cells, respectively (FIG. 9F). Heatmap indicates the markedly different gene expression patterns between control CD4$^+$ and CASTAT5 CD4$^+$ T cells (FIG. 9G). Similarly, ATACseq analysis identified 10097 and 5135 peaks with increased or decreased chromatin accessibility in CASTAT5 CD4$^+$ T cells as compared to control CD4$^+$ T cells (fold change ≥2 and adjusted p-value <0.05), respectively (FIG. 10A-10E) and reveals clear epigenetic differences as shown in the heatmap (FIG. 10F). A majority (about 60%) of the differential ATACseq peaks are located in the non-coding regions of the genome (FIG. 10G). Gene set enrichment analysis (GSEA) plots show that genes associated with more accessible chromatin had more overlaps with up-regulated genes than down-regulated genes, and vice versa (FIGS. 3B-3c), suggesting that gene expression changes are highly correlated with chromatin changes. The genome-wide alterations in chromatin accessibility landscape were compared with the corresponding gene expression changes. As illustrated in FIGS. 3D-3I, the increases in read densities seen in CASTAT5 as compared to control CD4$^+$ T cells are positively correlated with increases in gene expression and vice versa. Furthermore, ingenuity pathway analysis (IPA) of RNAseq data and ATACseq data results in highly consistent pathway identification (FIG. 3J).

The chromatin accessibility of genes related to T cell polyfunctionality was examined. Notably, cytokines that showed significantly increased productions in CASTAT5 CD4$^+$ T cells, including I14, I113, I19, Csf2 and GzmB, all had markedly increased chromatin accessibility in the corresponding gene loci (FIGS. 3K-3N). The Ifng gene locus showed reduced chromatin accessibility in CASTAT5 CD4$^+$ T cells, in line with the slight reduction in Ifng expression in these cells detected by ICS. No obvious chromatin structure changes were observed in the Tnf gene locus, although modest gain in TNFα expression was detected by ICS in CASTAT5 CD4$^+$ T cells. In contrast, genes associated with T cell dysfunction, such as Pdcd1 and Ctla4, showed reduced chromatin accessibility in CASTAT5 CD4+ T cells, indicating a widespread yet selective remodeling of the epigenetic landscape by CASTAT5.

Figure 3W:
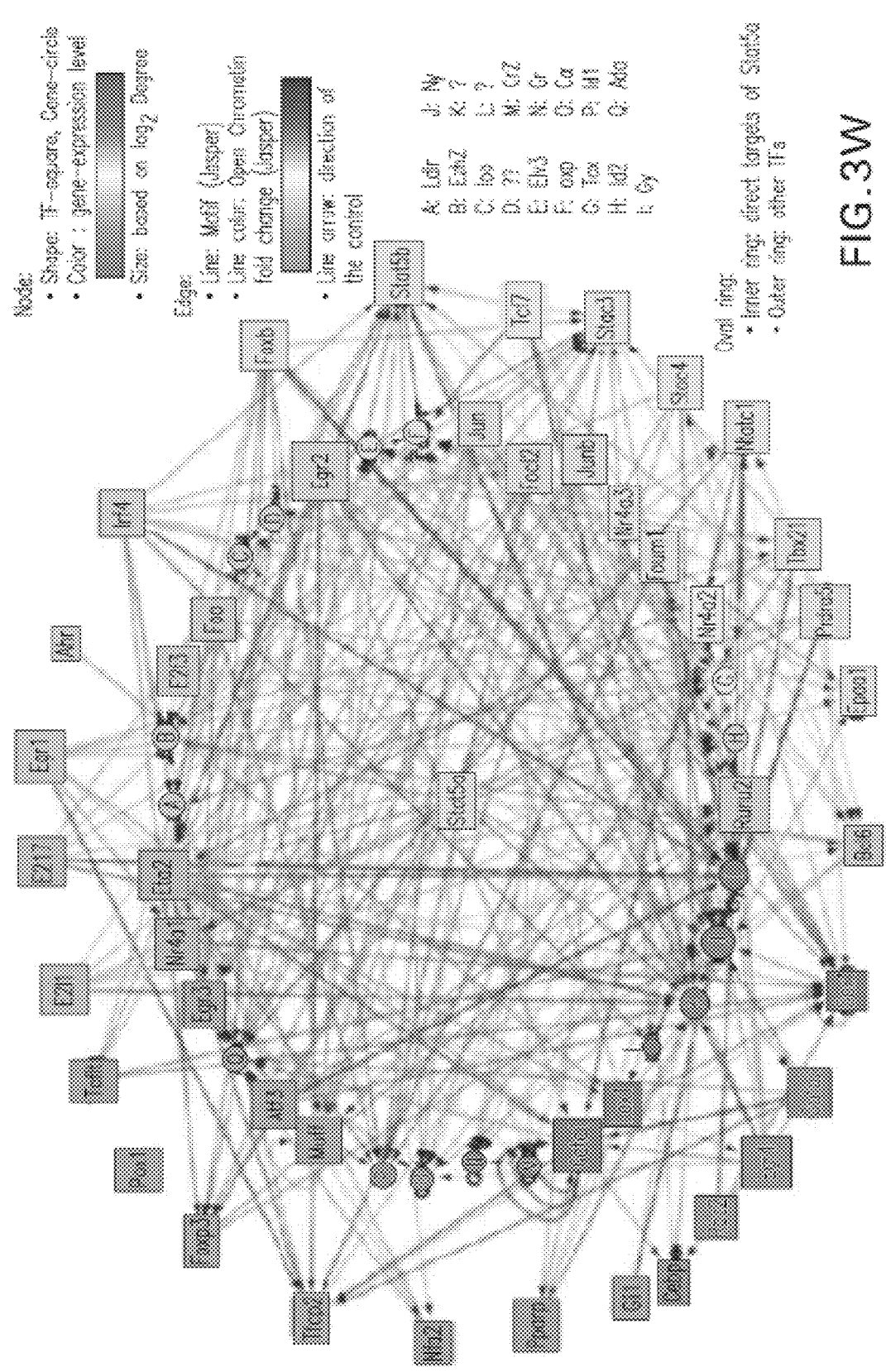
FIG. 3W shows a transcription regulatory network built on the ATACseq and RNAseq data from this study, as well as a published Stat5a ChIP-seq data (GSE79518).
Figure 11A:
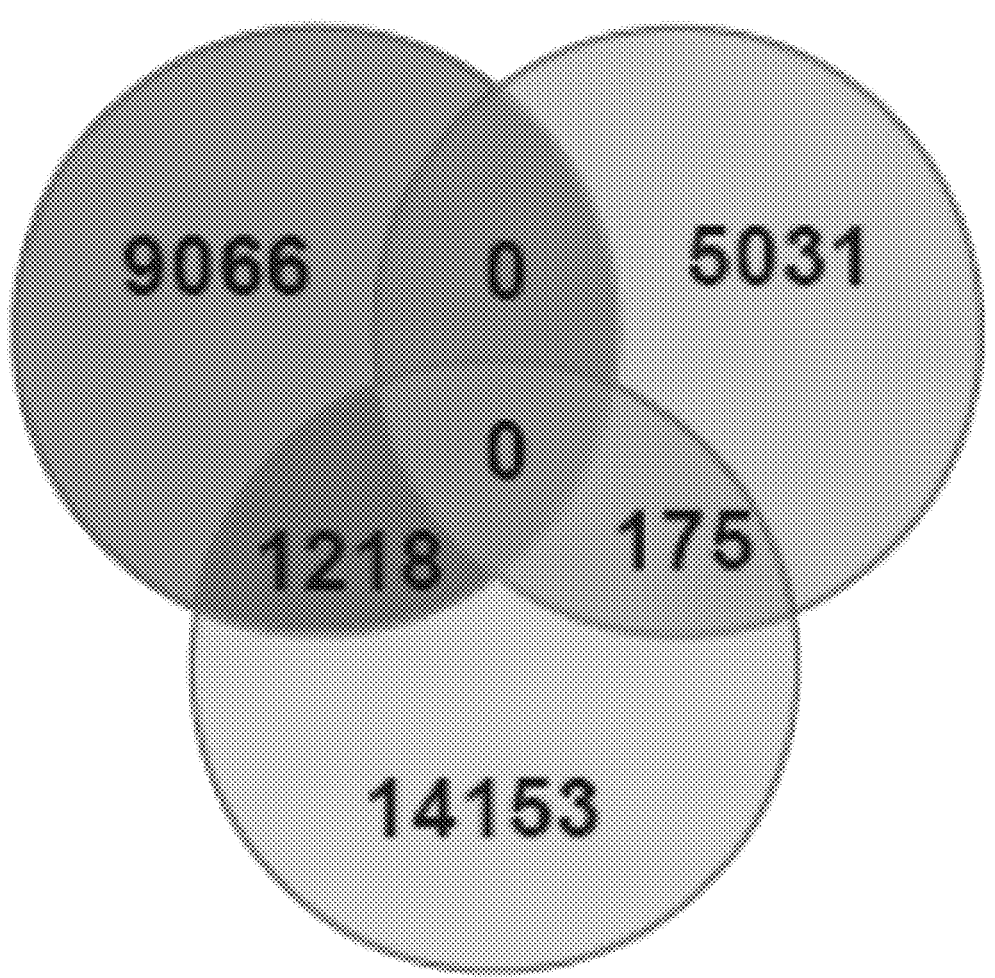
FIGS. 11A-11B are Venn diagrams showing the overlaps between Stat5a target genes identified in a previous Stat5a ChIP-seq study (GSE79518) and genes with significant chromatin accessibility changes in CASTAT5 CD4 T cells identified by ATACseq (FIG. 11A), or genes with significant expression changes (fold change >4) in CASTAT5 CD4+ T cells identified by RNAseq (FIG. 11B).
Figure 11B:
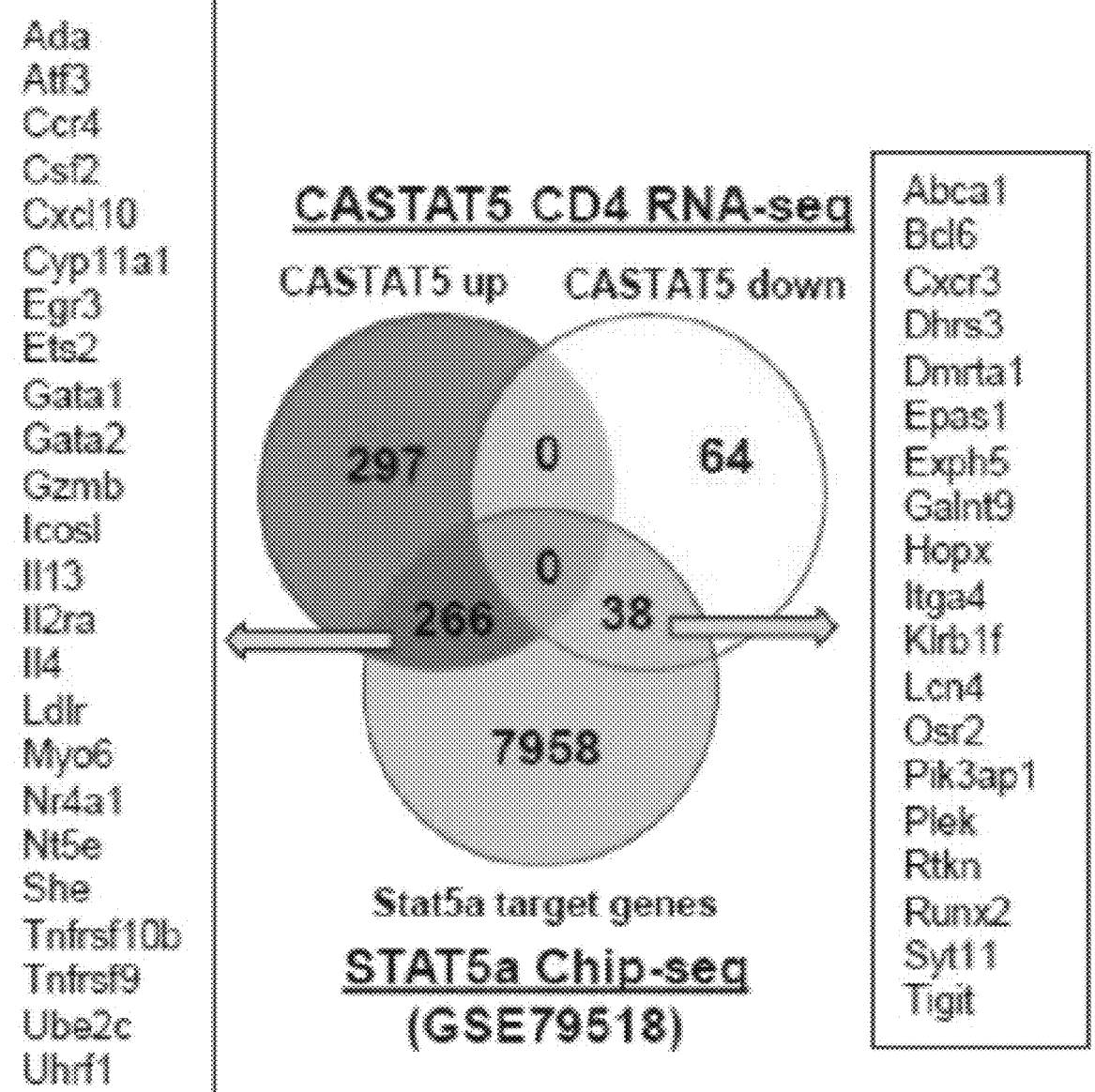
Figure 11C:
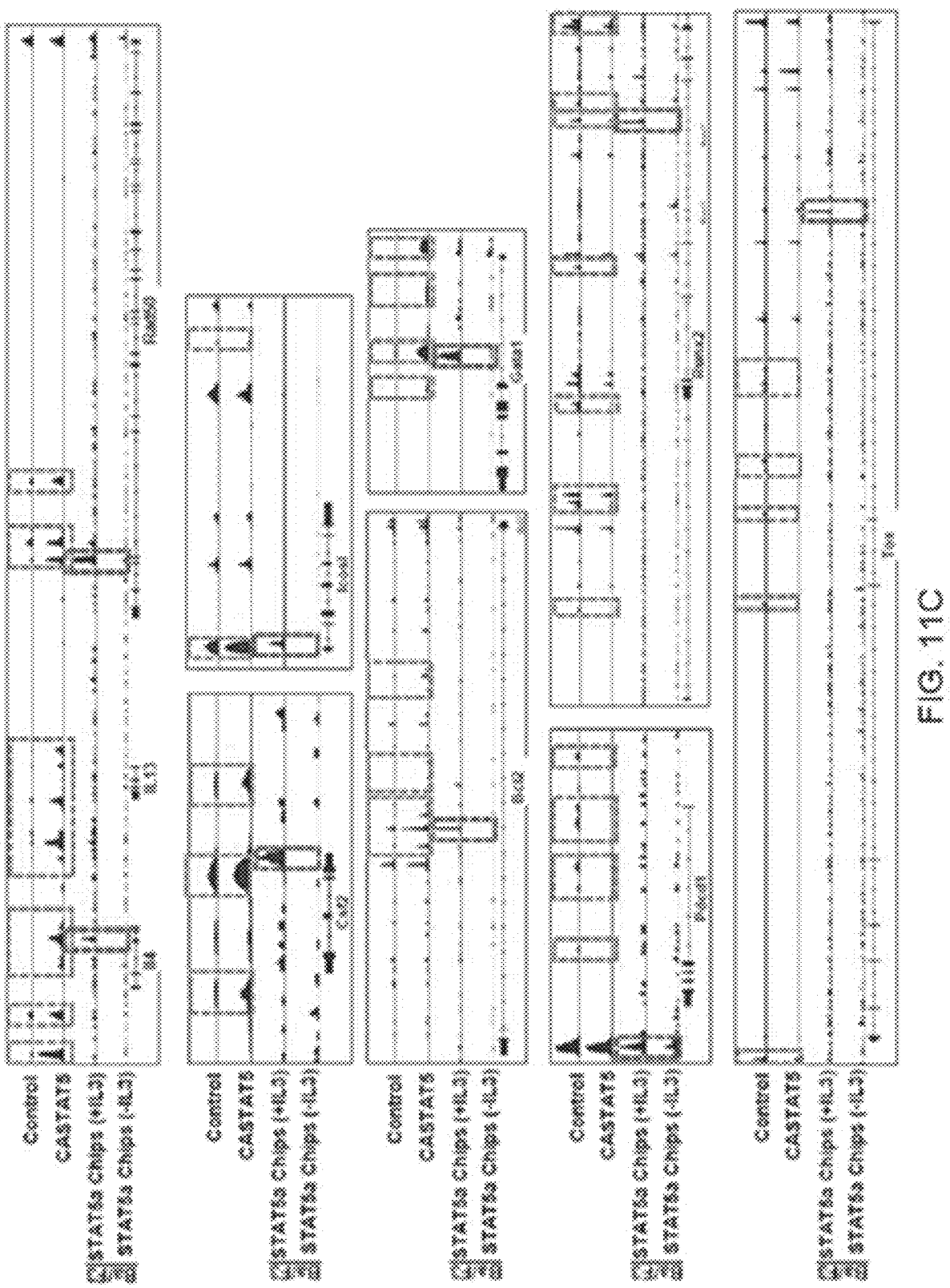
FIG. 11C shows examples of overlaps between ATACseq and Stat5a ChIP-seq peaks showing in IGV browser. The top rectangles mark differential ATACseq peaks between CASTAT5 and control CD4+ T cells. The bottom rectangles mark Stat5a ChIP-seq peaks detected in the relevant gene loci in IL3-treated Ba/F3 cells but not in untreated Ba/F3 cells.
Figure 12A:
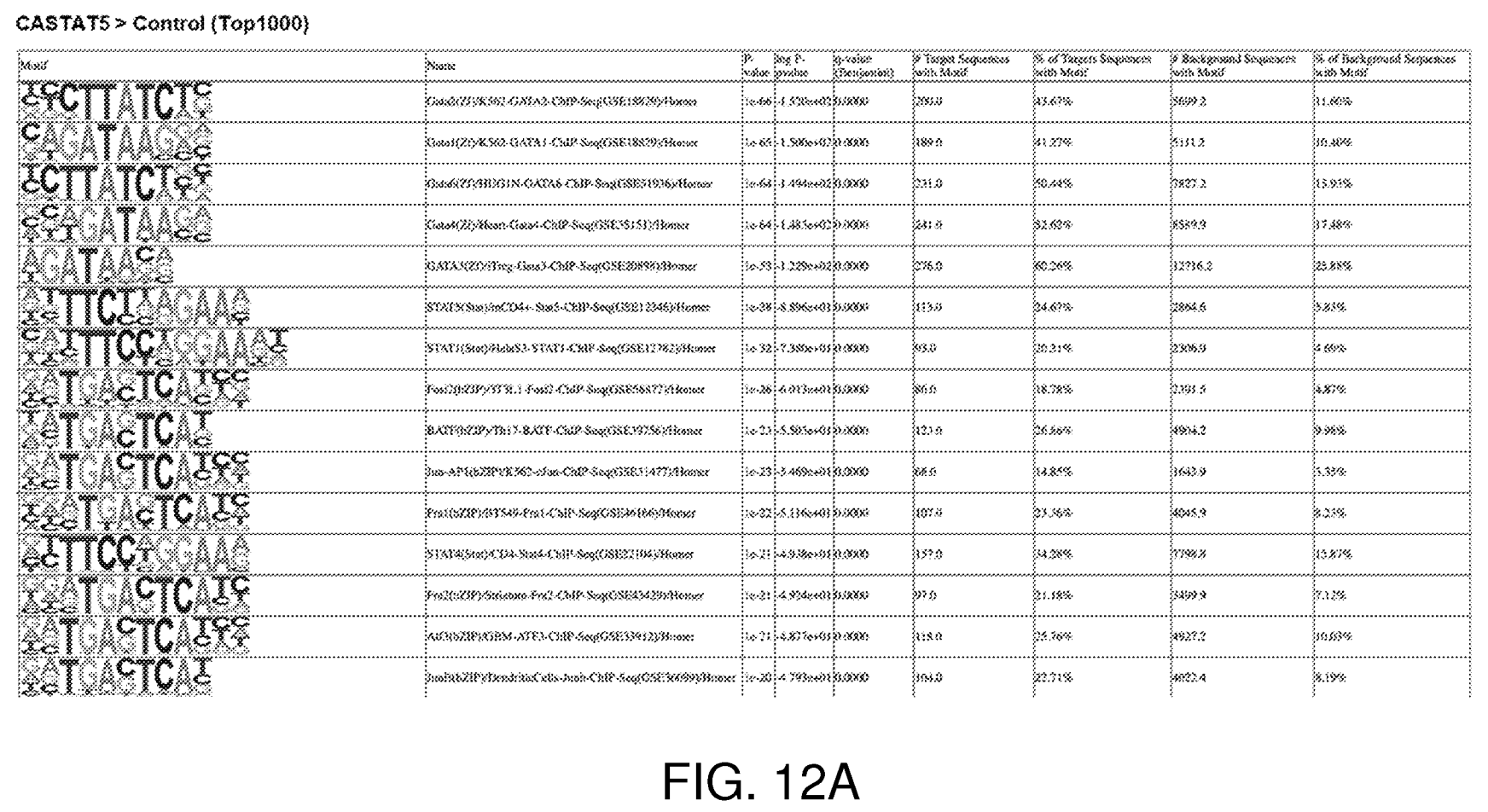
Figure 12B:
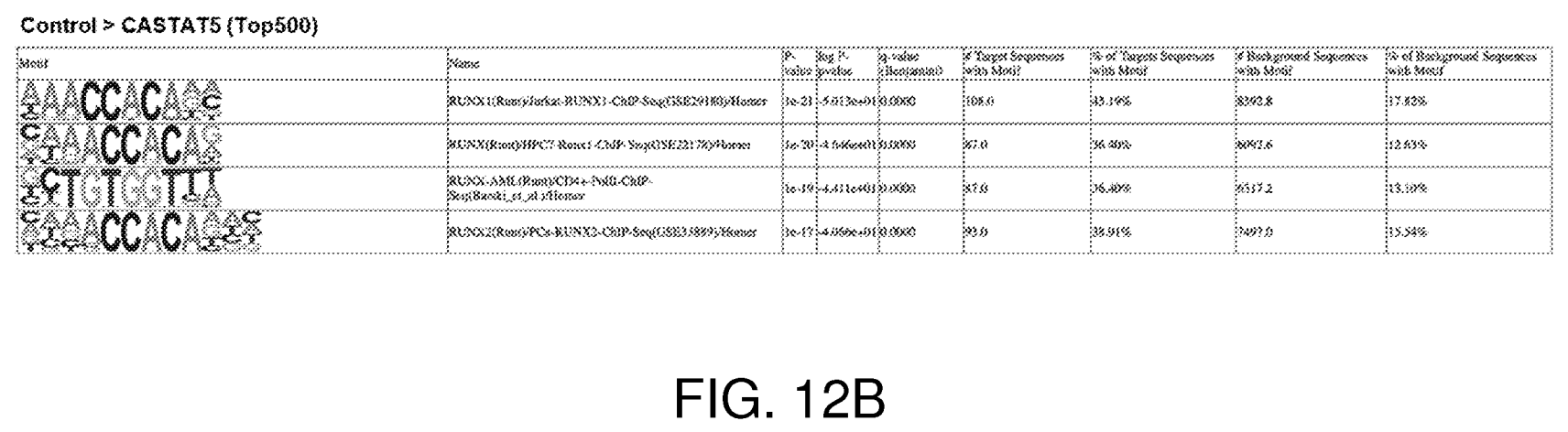
Figure 13A:
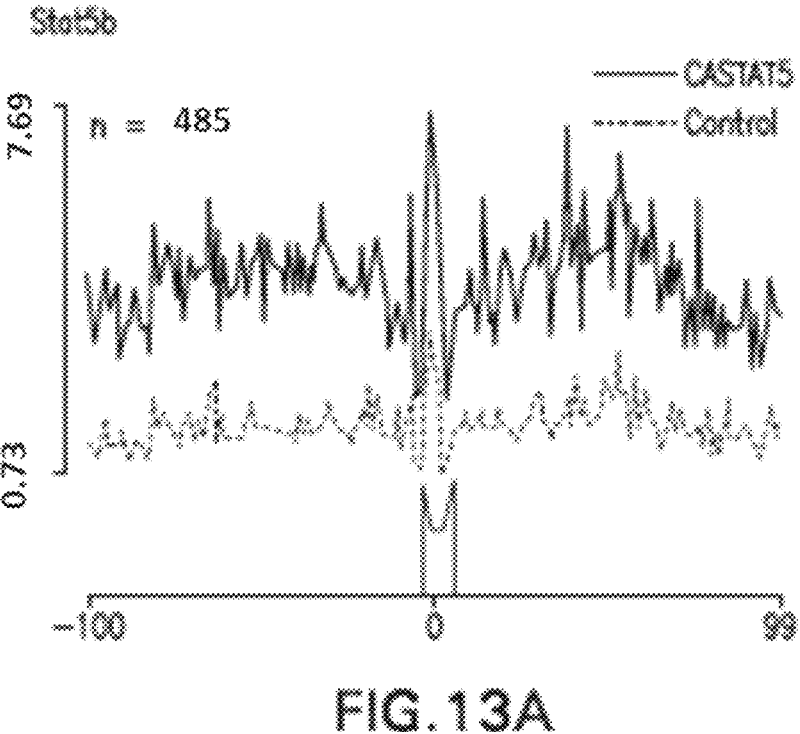
FIGS. 13A-13T are graphical plots of transcription factor footprinting. In each plot, lines represent average signals of the normalized counts of Tn5 transposase cutting sites which were plotted within a 200 bp window centered at each transcription factor consensus binding site. The solid and hatched lines indicate CASTAT5 and control CD4+ T cells, respectively.
Figure 13B:
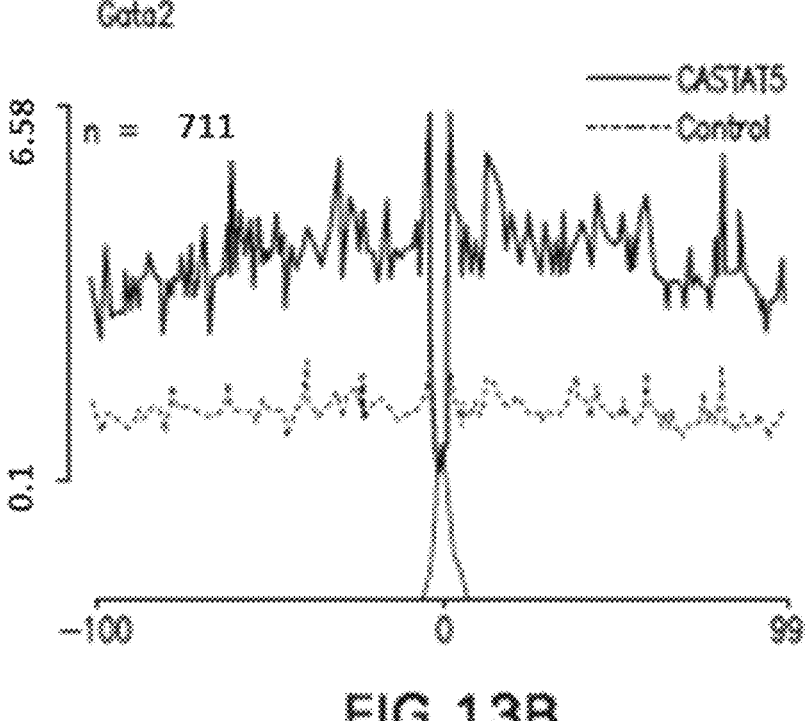
Figure 13C:
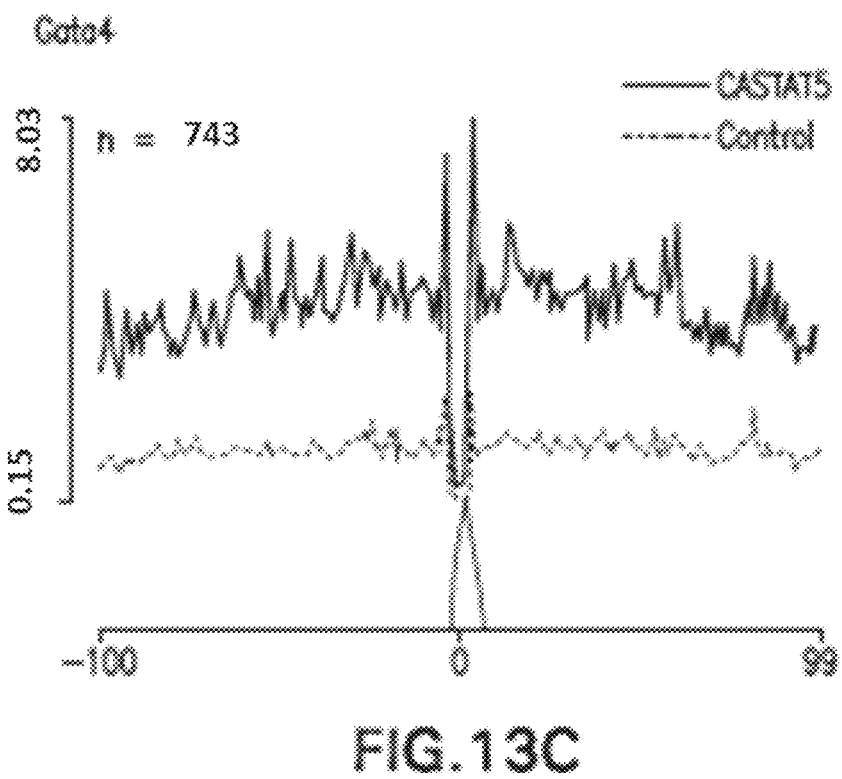
Figure 13D:
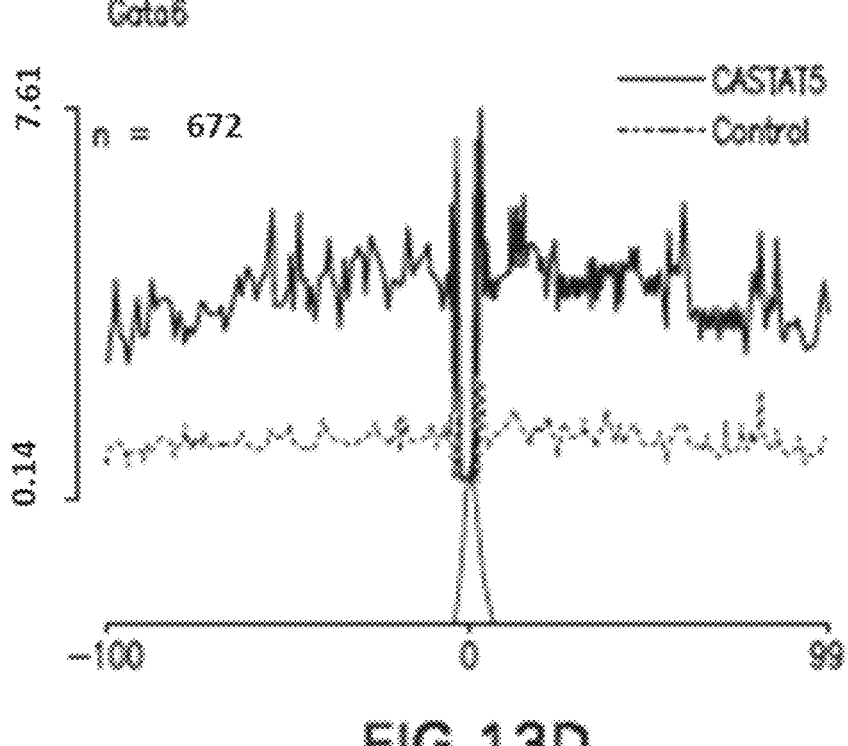
Figure 13E:
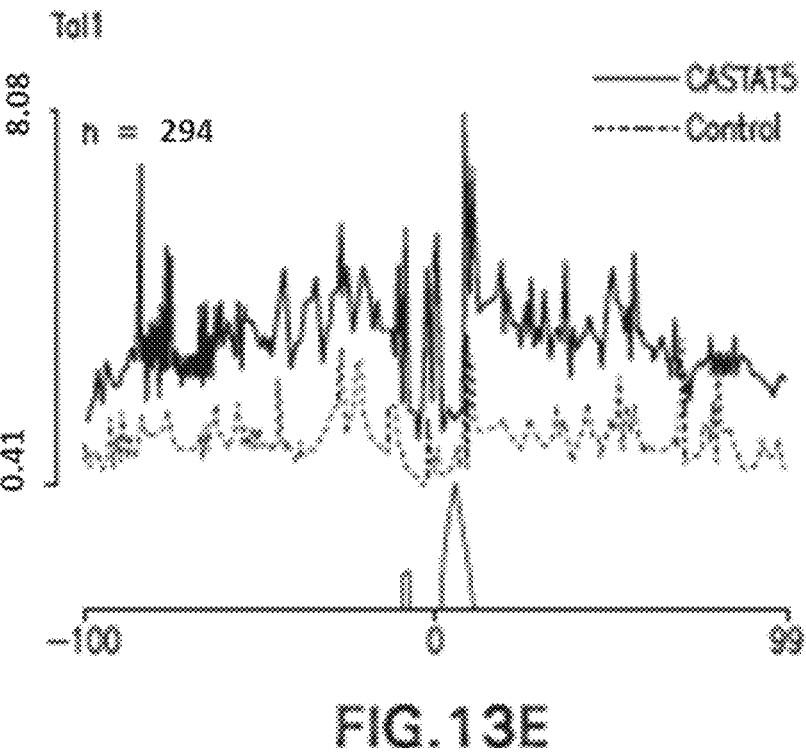
Figure 13F:
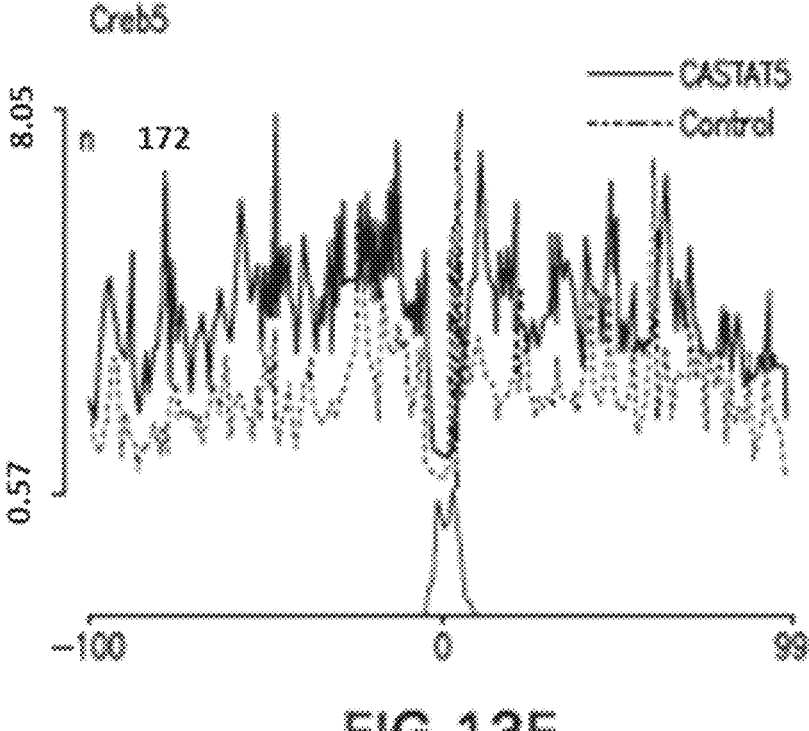
Figure 13G:
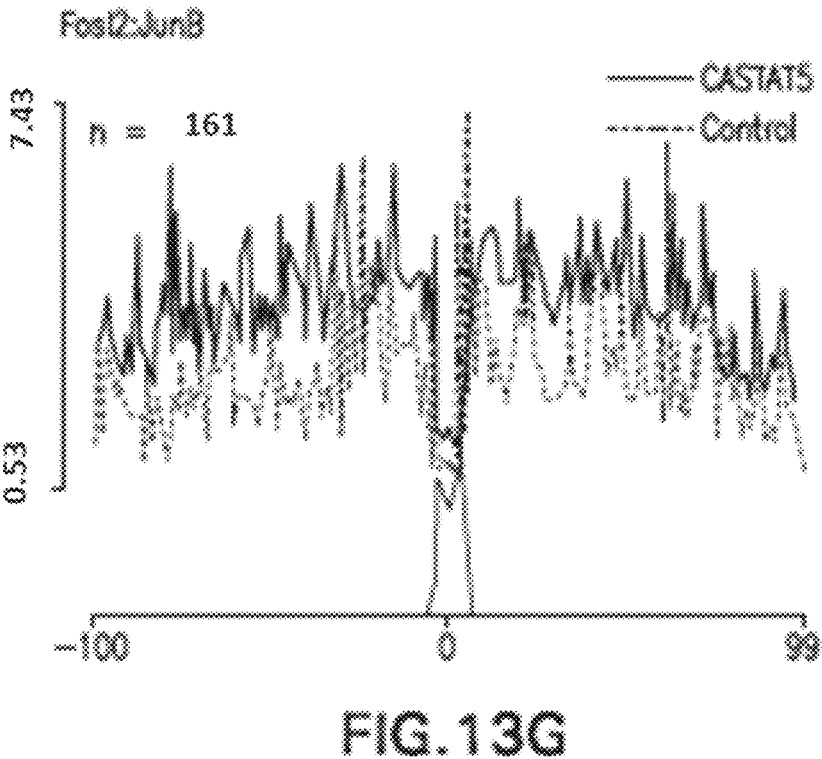
Figure 13H:
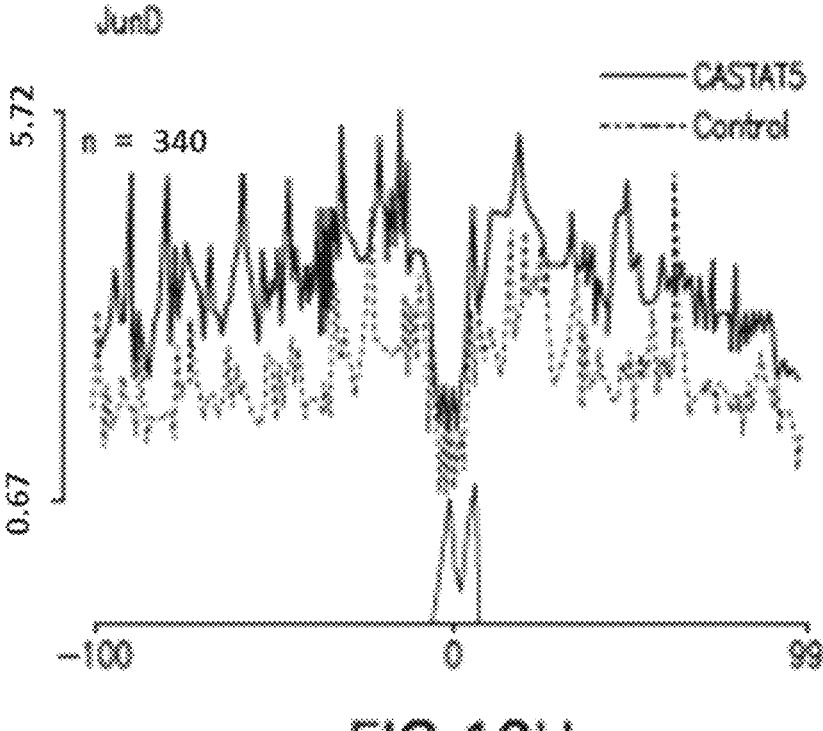
Figure 13I:
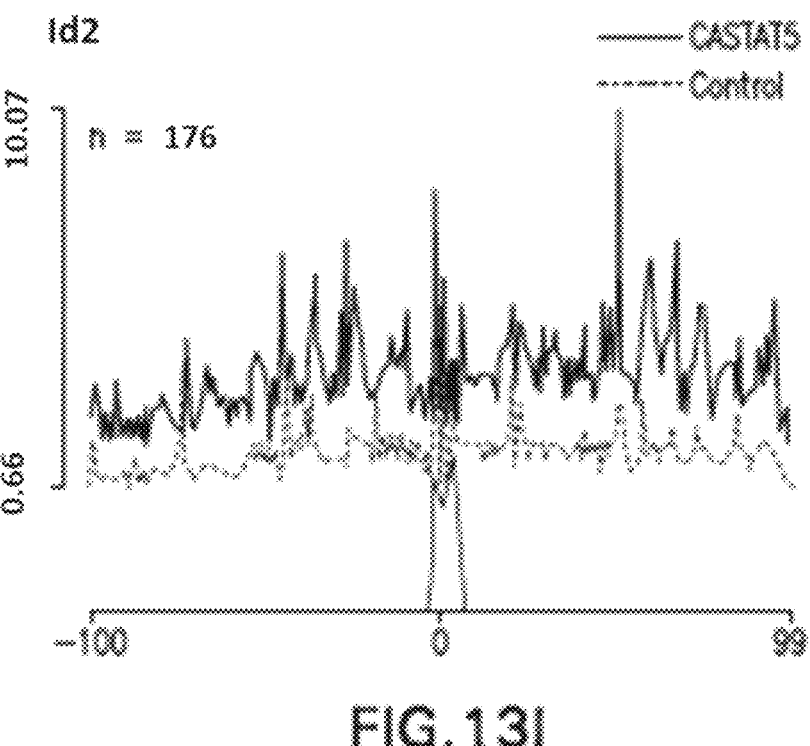
Figure 13J:
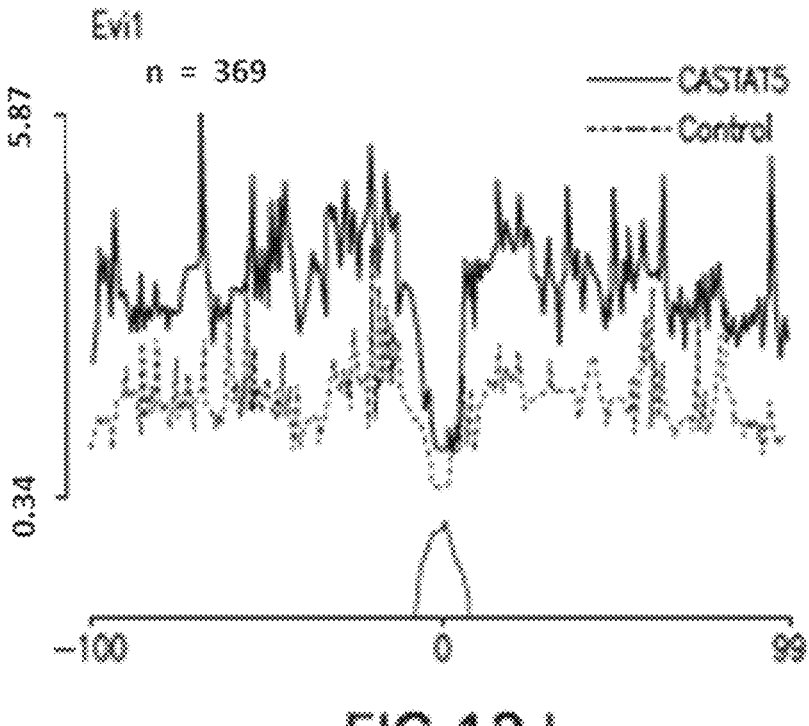
Figure 13K:
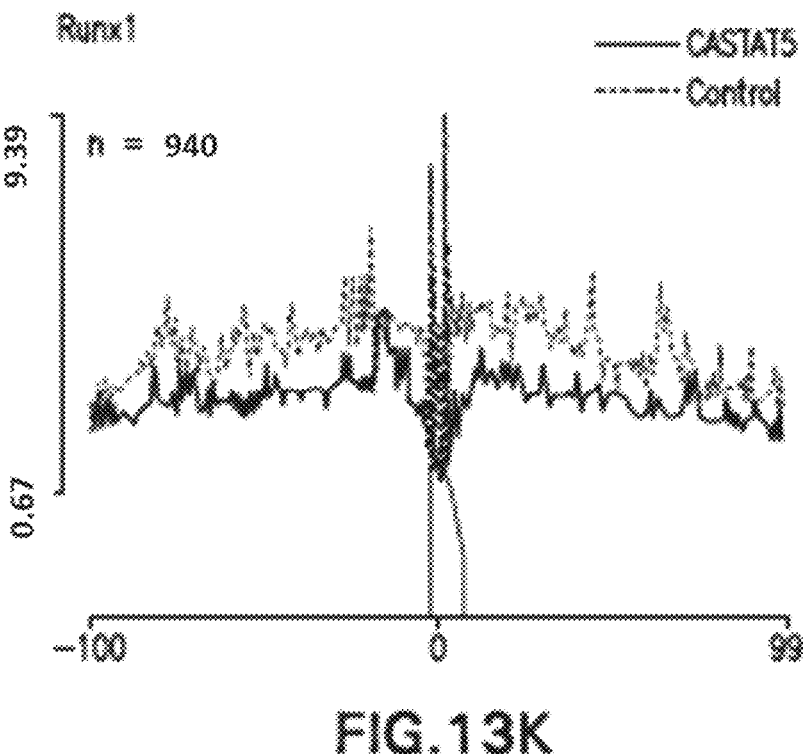
Figure 13L:
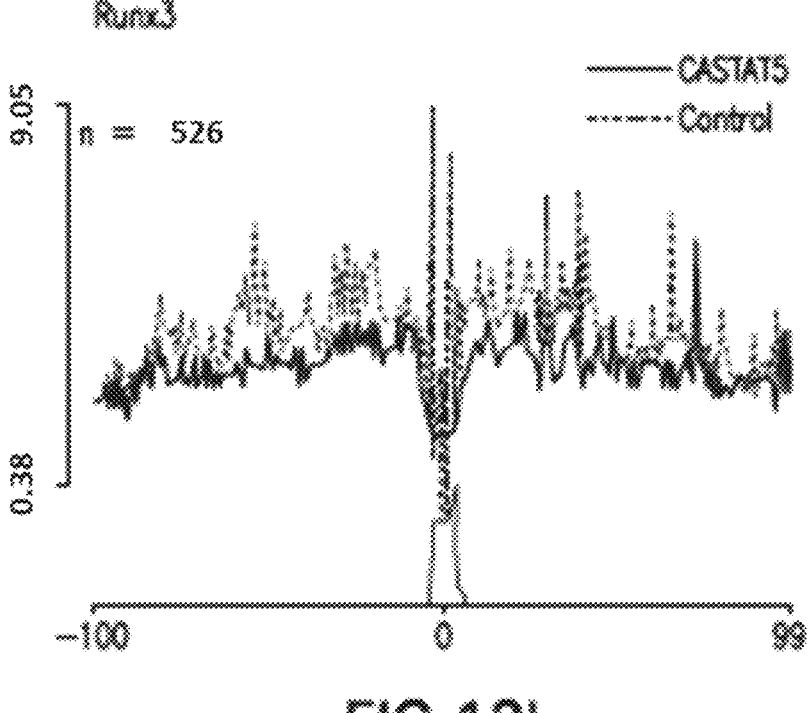
Figure 13M:
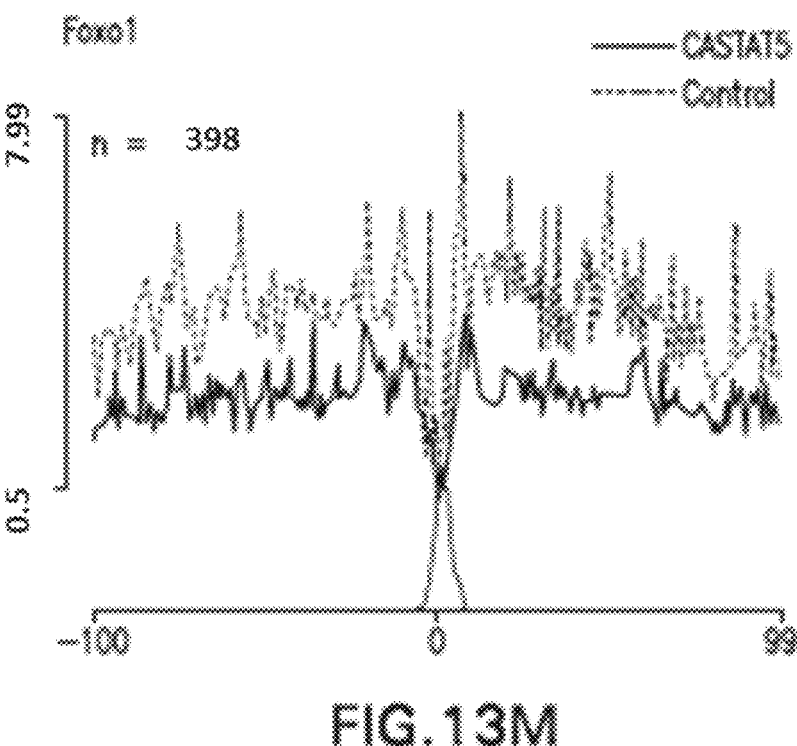
Figure 13N:
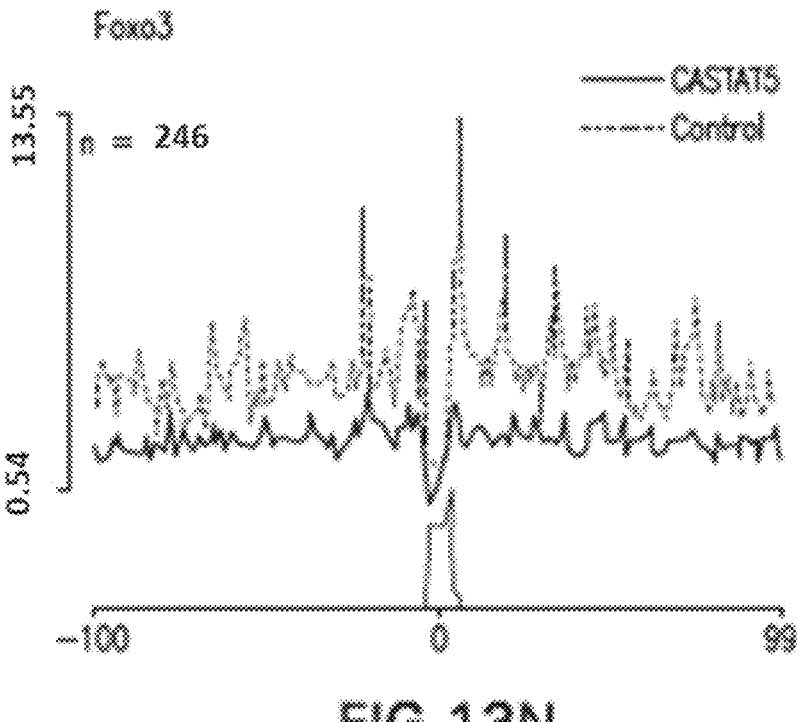
Figure 13O:
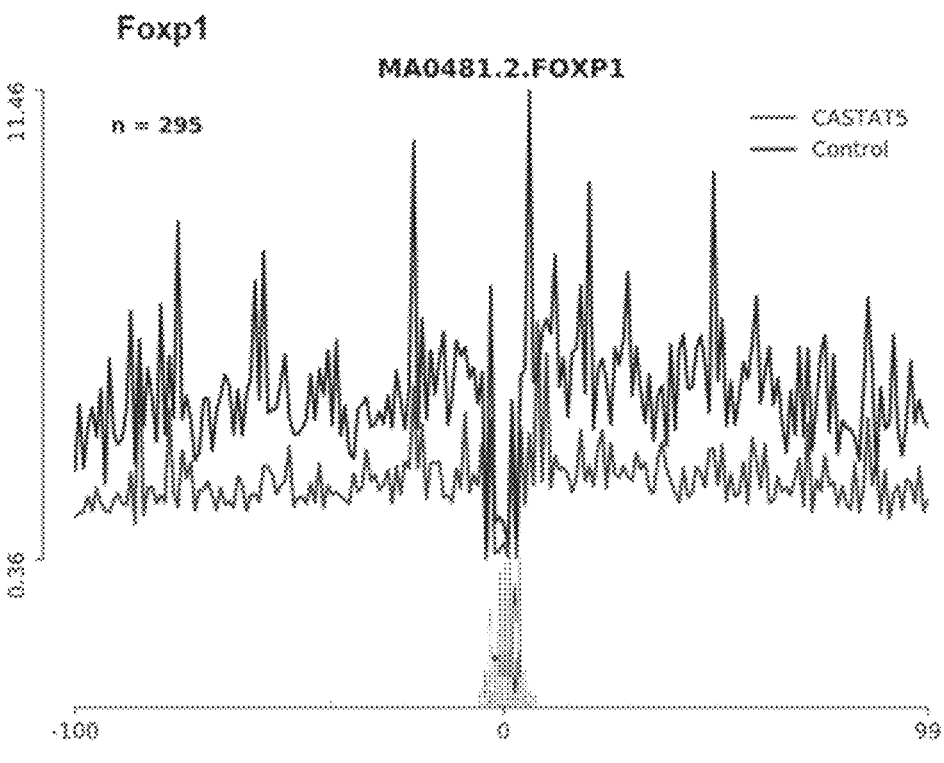
Figure 13P:
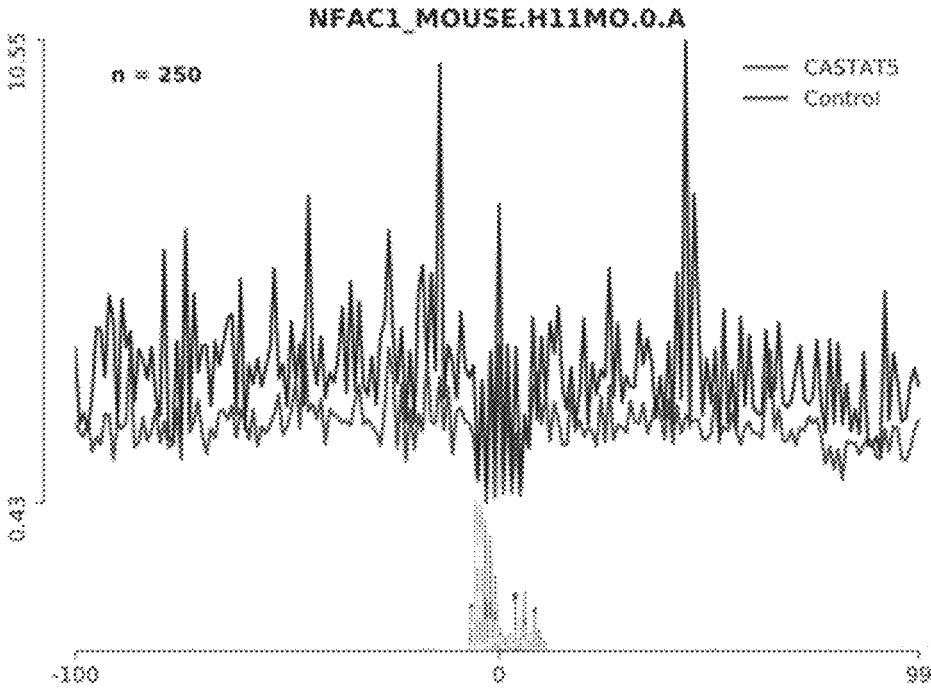
Figure 13Q:
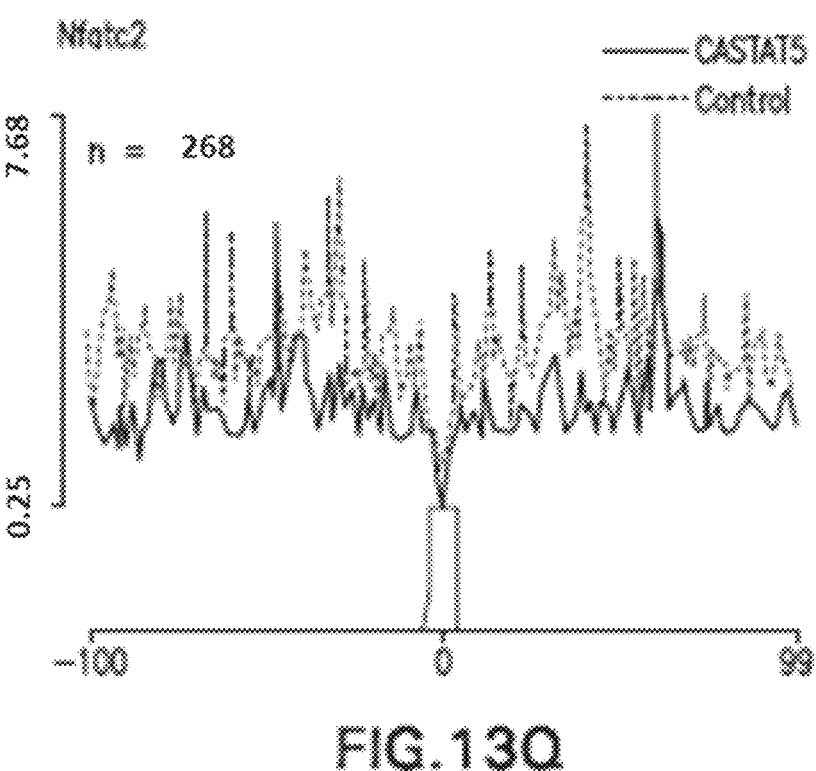
Figure 13R:
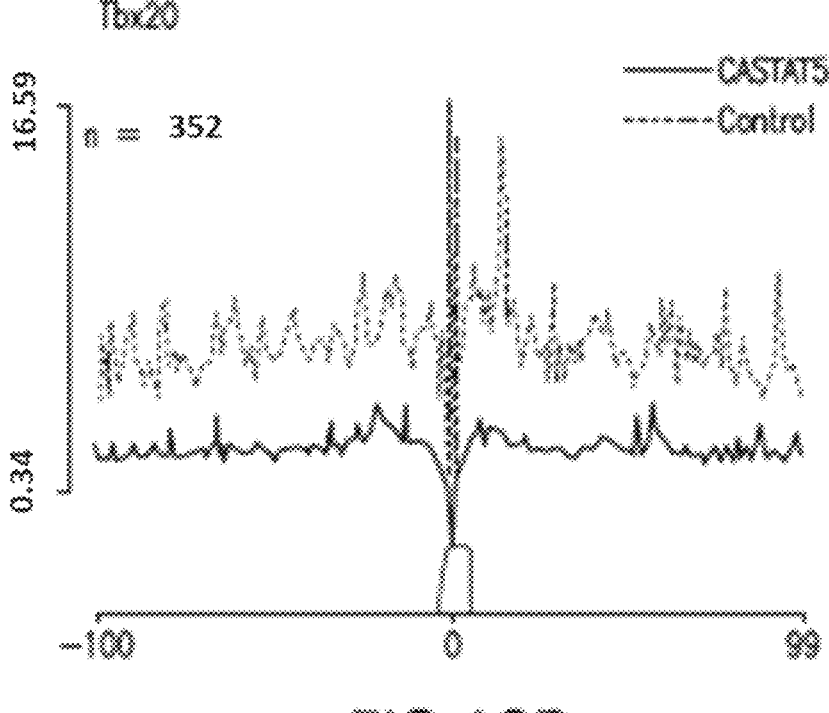
Figure 13S:
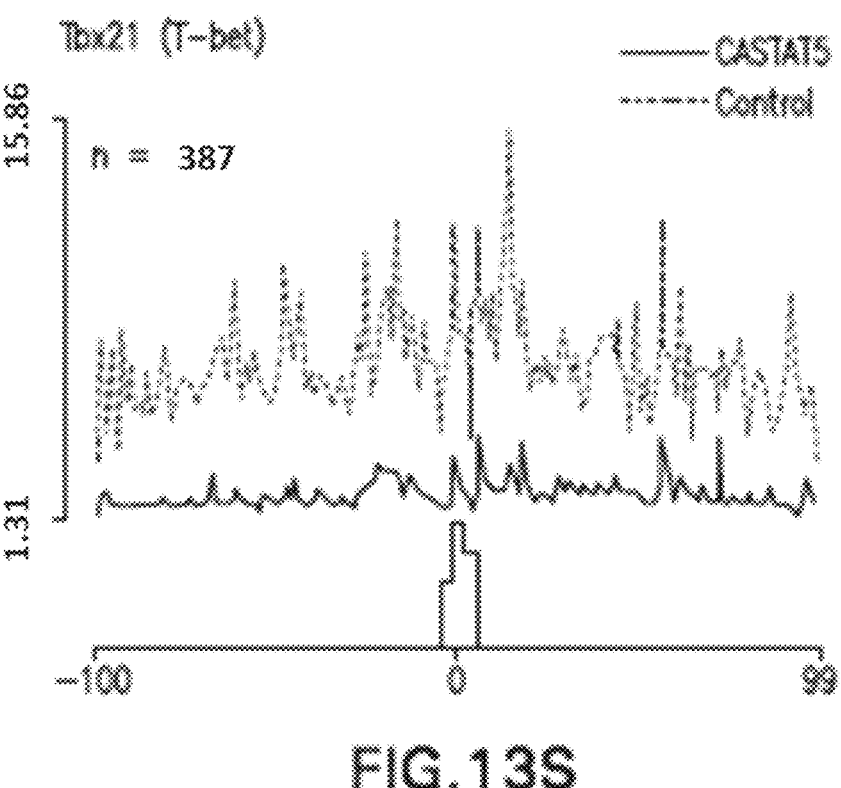
Figure 13T:
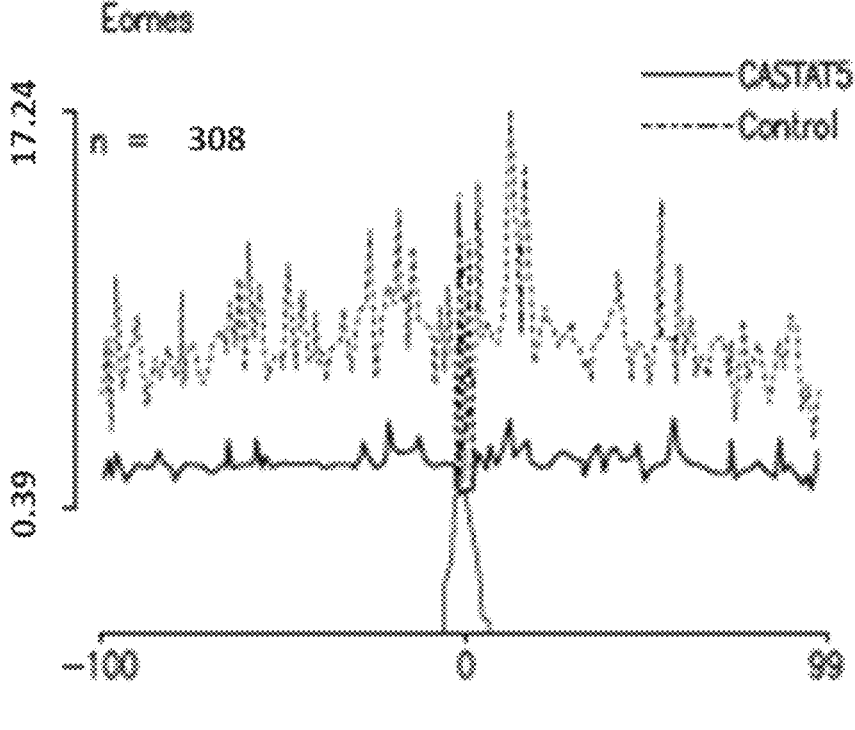

It is known that STAT5 can bind directly to gene regulatory regions to mediate gene expression (Owen, D. L. and M. A. Farrar, *F1000Res,* 6:32 (2017); Wingelhofer, B., et al., *Leukemia,* 32:1713-1726 (2018)). By comparing with a published STAT5A ChIP-seq dataset in murine pro-B cell line Ba/F3 stimulated with or without STAT5 inducer IL3 (Nanou, A., et al., *Nucleic Acid Res,* 45:142-145 (2017)), it was observed that about 9% of ATACseq peaks (fold change >2) in this study directly overlap with STAT5A ChIP-seq peaks and most of them (1218 out of 1393) are associated with gain of chromatin accessibility in CASTAT5 CD4$^+$ T cells (FIG. 11A). More importantly, by aligning our RNAseq dataset with the same STAT5A ChIP-seq dataset, it was found that 266 out of 563 (47%) highly up-regulated genes (fold change >4) and also 38 out of 102 (37%) most down-regulated genes in CASTAT5 CD4⁺ T cells, are potential direct targets of STAT5A (FIG. 11B). For example, in CASTAT5 CD4⁺ T cells, Stat5 binding sites are not only found in genes with increased chromatin accessibility such as the Il4/Il13/Rad50, Csf2, Icosl, Bcl2 and Gata1 locus, but also in genes with reduced chromatin accessibility such as Runx2 (FIG. 11C). The locations of these Stat5 binding sites can be found in the promoter, intron, exon or 3'UTR regions, and in many cases overlap with or fall close to the ATACseq peaks, consistent with the role of Stat5 as an epigenetic regulator. Interestingly, although STAT5A ChIP-seq peaks do not directly overlap with the loci associated with differential ATACseq peaks in Pdcd1 and Tox, it was found that STAT5A binds to downstream of Pdcd1 and the first intron of Tox in Ba/F3 cells, suggesting previously unknown epigenetic regulation of Pdcd1 and Tox by STAT5A. To test if other transcription factors are also involved in epigenetic reprogramming, we performed transcription factor motif analysis using two most-used MEME-Chip and HOMER software packages. Analysis of the top 1000 ATACseq peaks with increased chromatin accessibility in CASTAT5 CD4+ T cells using MEME-Chip revealed enrichment for GATA family transcription factors and STAT5A/B consensus binding motifs, while analysis of the top 500 less accessible ATACseq peaks revealed enrichment for Runx2 and Tbx21 (T-bet) binding motifs (FIGS. 30-3R). Similar results were obtained using HOMER (FIGS. 12A-12B). Interestingly, in addition to Stat5a, Gata and Runx family transcription factor consensus motifs are among the most consistently enriched in peaks with gain or loss of chromatin accessibilities, respectively. One of the advantages of ATACseq is that it allows for performance of transcription factor (TF) footprinting analysis. As shown in FIGS. 3S-3V, differential TF footprinting analysis using Rgt-HINT software package demonstrates significant higher Tn5 cutting site signals at the TF binding site of STAT5A/B and Gata1, and reduced signals at Runx2 and Tbx21 consensus sites. Additional TF footprinting analysis shows that TFs with increased activity include Gata and API family transcription factors, while TFs with decreased activity include Runx, FoxO, Nfat and Tbx family transcription factors (FIGS. 13A-13T). By integrating the predicted TF binding map and expression changes of these TFs, an integrated regulatory network was constructed to explore the transcriptional circuitry in CASTAT5 CD4⁺ T cells (FIG. 3W). This network identifies augmented activities of Stat5, Gata1, Apl and decreased activities of Nfat, Runx and Tbx21. STAT5A appears to directly activate Gata1, Jun, Junb, Fos, Fos12 and Ezh2, while repressing Runx2, Id2, Nr4a2 and Tox. In sum, this study provides comprehensive information on how persistent STAT5 activation reprograms CD4⁺ T cell epigenetic and transcriptomic landscapes, leading to the formation of polyfunctional CD4⁺ T cells.

Example 5. CASTAT5 CD4⁺ T Cells Acquire an Epigenetic Landscape that is in Concordance with Gene Transcription and Protein Expression Profiles Materials and Methods See examples above for descriptions of materials and methods used herein.

Results

RNAseq and ATACseq datasets were further analyzed to establish the concordance between gene transcription profile and chromatin accessibility status. As illustrated in FIGS.

4A-4B, a selection of genes (n=94) distributed across multiple important functional categories demonstrate highly correlative RNAseq and ATACseq data. CASTAT5 CD4⁺ T cells had increased expression and chromatin accessibility for receptors associated with Th2 and Th9 cytokines, including Ccr4, Il1rl1 (Il33r) and Il9r. Of note, gene expression and ATACseq peaks were both increased in CASTAT5 CD4 T cells for Mki67 and genes involved in regulating cell cycle (Myo6, Conb2, Ccna2, Conb1, Cdk6 and Chek1), indicating enhanced proliferative potential compared to control CD4⁺ T cells. Interestingly, CASTAT5 CD4⁺ T cells exhibited higher expression and more open chromatin structure in multiple co-stimulatory molecule genes, including Tnfrsf9 (4-1bb), Tnfsf4 (Ox401), Icosl and Icos, while the opposites (lower expression and reduced chromatin accessibility) were observed in many inhibitory molecule genes associated with T cell dysfunction/exhaustion, including Tigit, Lag3, Haver2 (Tim3), Slamf6 in addition to Pdcd1 and Ctla4. CASTAT5 CD4⁺ T cells had increased levels of expression and chromatin accessibility for pro-survival gene Bcl2 and genes associated with T cell memory or stemness, including Sell, Fas, Kit and Il2rb. Moreover, CASTAT5 CD4⁺ T cells had upregulated expression and more open chromatin structure in genes involved in regulating the metabolism of cholesterol (Cyp11a1 and Ldlr), adenosine (Nt5e, Entpd1 and Ada) and pyruvate (P$_{CX}$), suggesting a unique metabolic demand of these cells. Furthermore, CASTAT5 altered the transcription and chromatin accessibility of many TFs, including Nr4a1, Nr4a2, Nr4a3, Cblb, Nfatc1 and Nfatc2, genes known to regulate CD8⁺ T cell exhaustion. Finally, CASTAT5 CD4⁺ T cells showed significant changes in transcription and chromatin accessibility in genes encoding epigenetic modifiers, including the nuclear DNA binding molecule Tox, histone lysine methyltransferases (Ezh2, Dot11), histone deacetylase Hdac 6 and acetyltransferase Kat2a, and molecules involved in DNA methylation (Uhrf1, Dnmt1 and Dnmt3a), supporting the notion that CASTAT5 shapes CD4⁺ T cell transcriptome through epigenetic regulations.

Figures 4C, 4D, 4E, 4F, 4G, 4H:
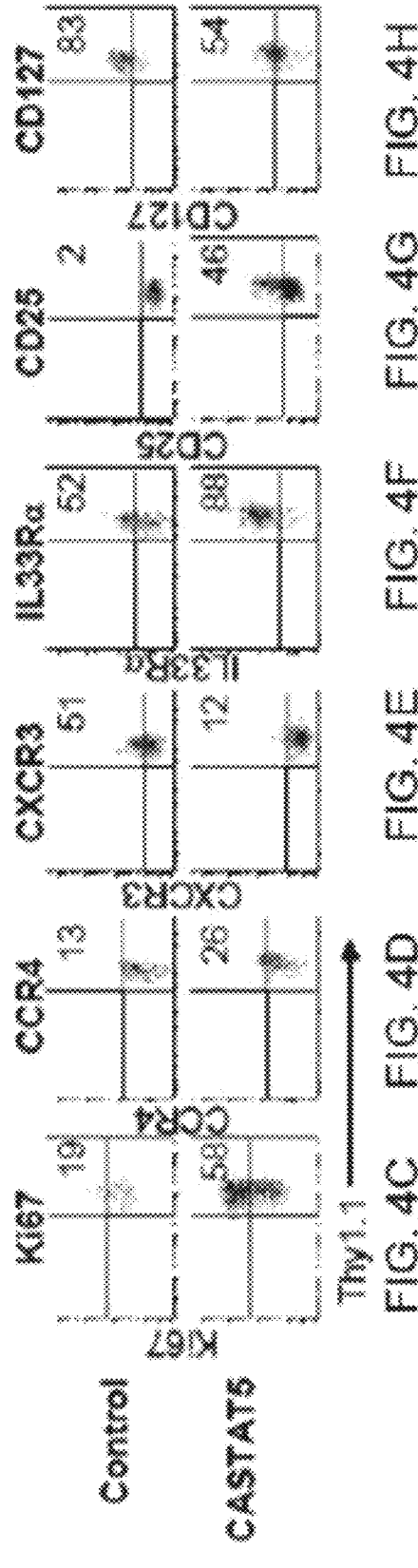
FIGS. 4C-4S are representative dot plots confirming the differential expressions of a panel of molecules in CASTAT5 and control CD4+ T cells. The dot plots shown are gated on Thy1.1+ donor CD4+ T cells.
Figures 4N, 4O, 4P, 4Q, 4R, 4S:
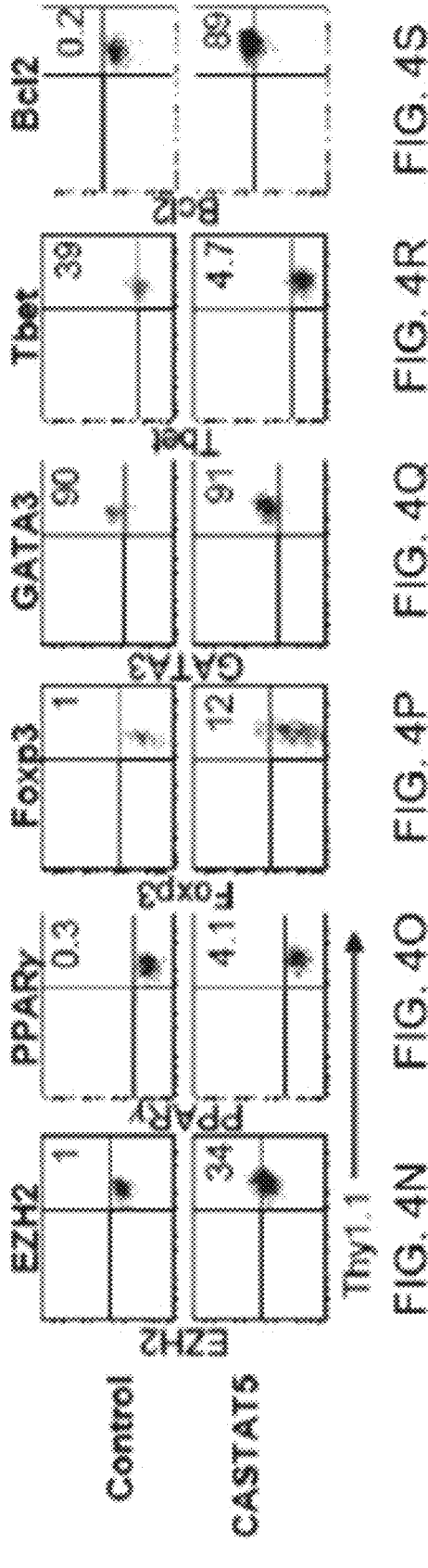
Figure 4T:
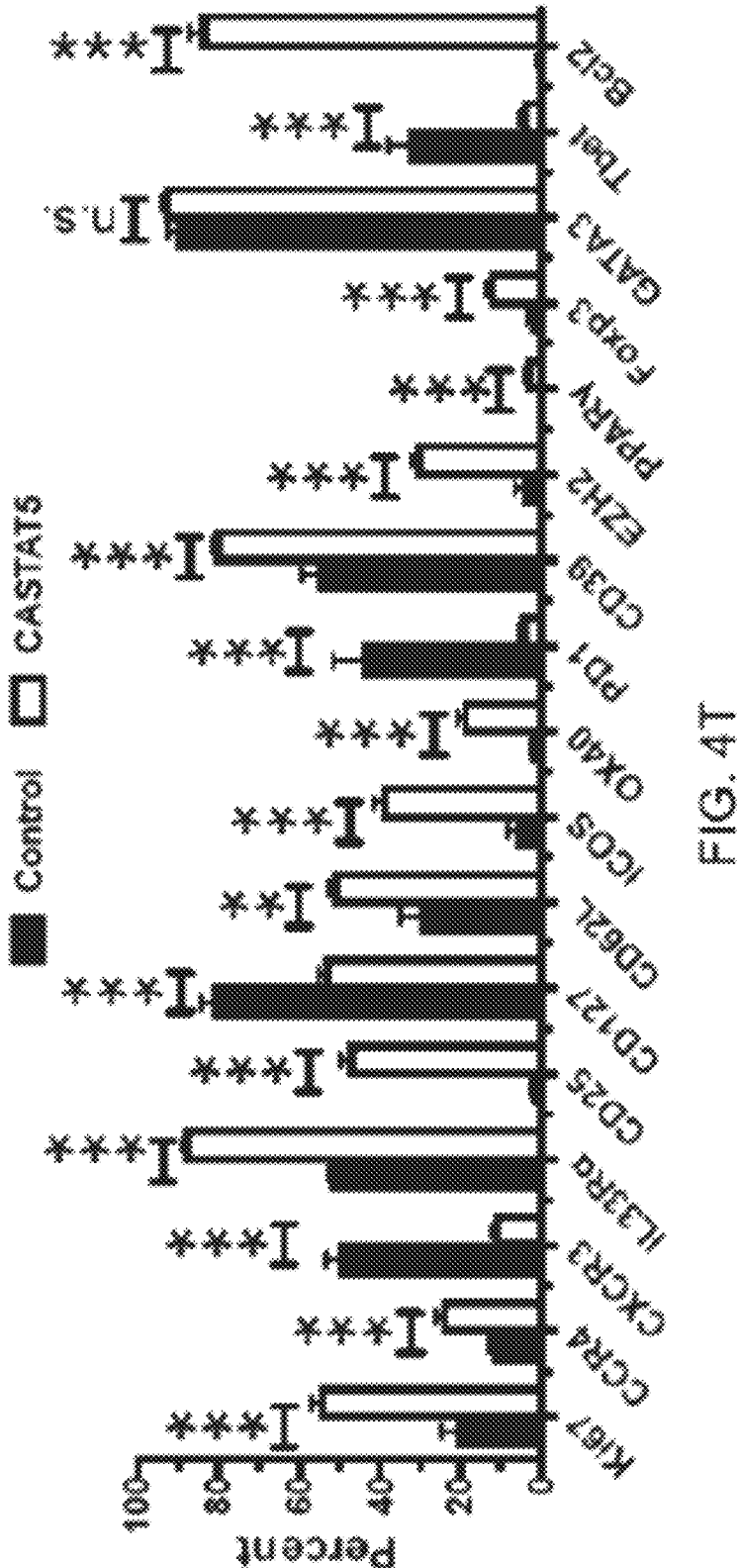
FIG. 4T is a bar graph showing a summary of the results of FACS analysis. The percentages of donor CD4+ T cells positive for the indicated markers are shown as mean+/−s.d.

Additional FACS analysis was performed for CASTAT5 and control CD4⁺ T cells to confirm the differential expressions, as predicted by ATACseq and RNAseq data, of a panel of molecules at the protein level (FIGS. 4C-4T). CASTAT5 CD4⁺ T cells expressed higher levels of Ki67 and BCL2, indicating proliferative and survival advantages over control CD4⁺ T cells. In addition, CASTAT5 CD4⁺ T cells had markedly reduced expression of PD1 but increased expression of ICOS, suggesting that CASTAT5 may suppress exhaustion induction. In terms of TFs associated with T helper lineage differentiation, CASTAT5 CD4⁺ T cells expressed significantly higher levels of Treg-specific FOXP3 and Th9-promoting PPARg, but lower level of Th1 cell-specific TBX21 (Tbet); interestingly, both CASTAT5 CD4⁺ T cells and control CD4 T cells expressed comparable high-level of Th2 lineage-defining factor GATA3. The expression status (at protein level) of these lineage specific TFs in CASTAT5 CD4⁺ T cells was consistent with these cells' cytokine profile, and in line with published studies showing that STAT5 promotes the differentiation of Th2, Th9, ThGM and Treg (Owen, D. L. and M. A. Farrar, *F1000Res,* 6:32 (2017)). As predicted, CASTAT5 CD4⁺ T cells expressed higher levels of CCR4 and IL33R, receptors associated with Th2 and Th9 cells, but reduced CXCR3, a receptor preferentially expressed by Th1 cells. Of note, EZH2, a histone methyltransferase previously shown to regulate T cell polyfunctionality (Zhao, E., et al., *Nat Immunol,* 17:95-103 (2016)), was significantly induced in CASTAT5 CD4$^+$ T cells. Altogether, the data disclosed herein indicate that CASTAT5 CD4$^+$ T cells have acquired a distinct epigenetic landscape that is in concordance with gene transcription and protein expression profiles.

Example 6. CASTAT5 CD4$^+$ T Cells Exhibit Similar Epigenetic Features in Spleen and Tumor Materials and Methods See examples above for materials and methods descriptions.

Results

Figures 14A, 14B, 14C:
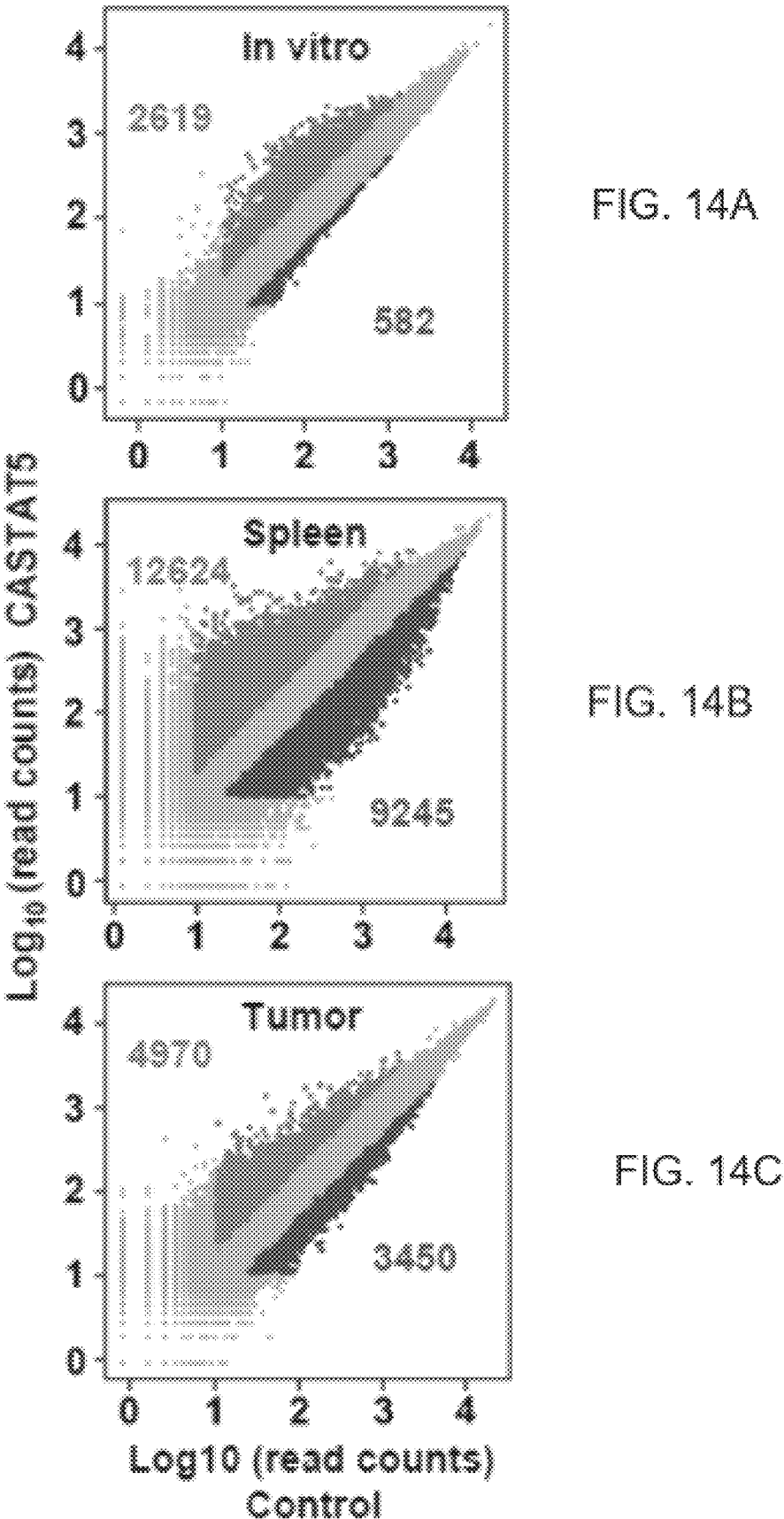
FIGS. 14A-14C are scatter plots comparing the ATACseq peak signals between paired CASTAT5 and control samples isolated in vitro and from spleen and tumor samples. The numbers in each panel indicate the number of peaks with gain (top) or loss (bottom) of chromatin accessibility, respectively.
Figures 14D, 14E, 14F:
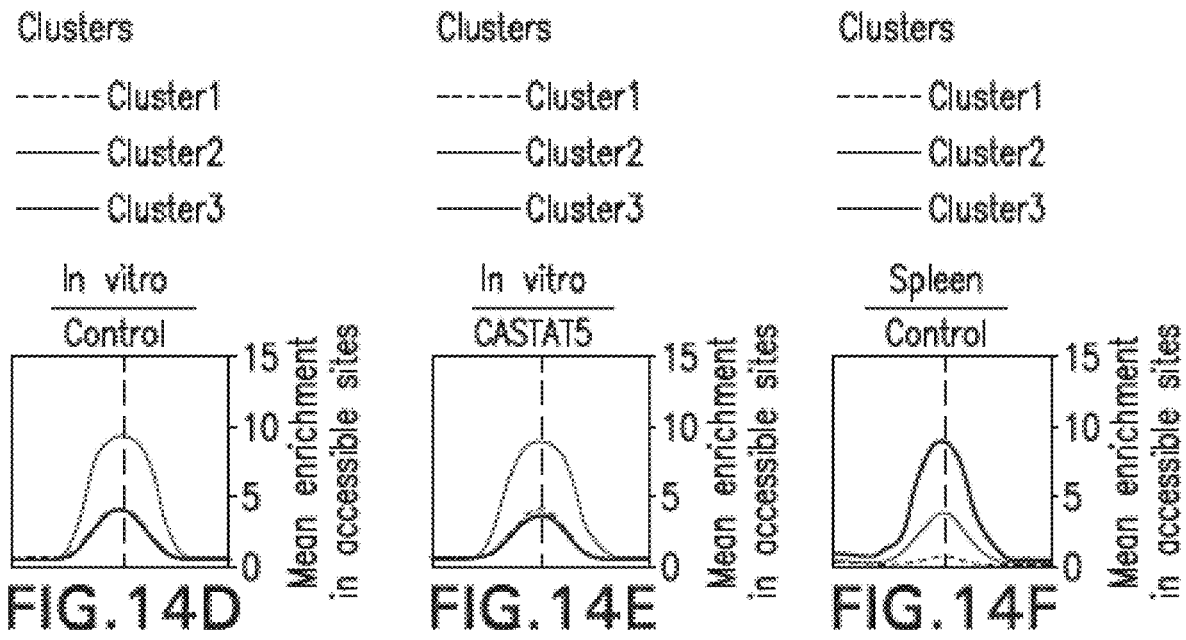
FIGS. 14D-14I are line graphs that show the average accessibility profiles of clusters 1-3, respectively.
Figures 14G, 14H, 14I:
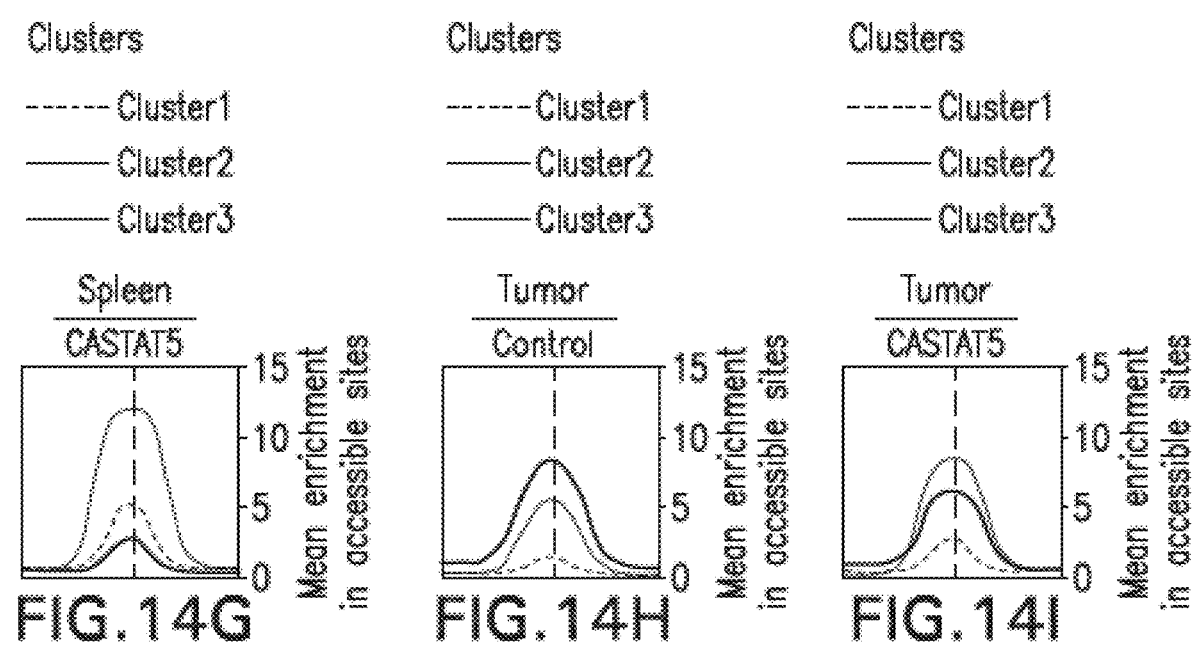
Figure 14L:
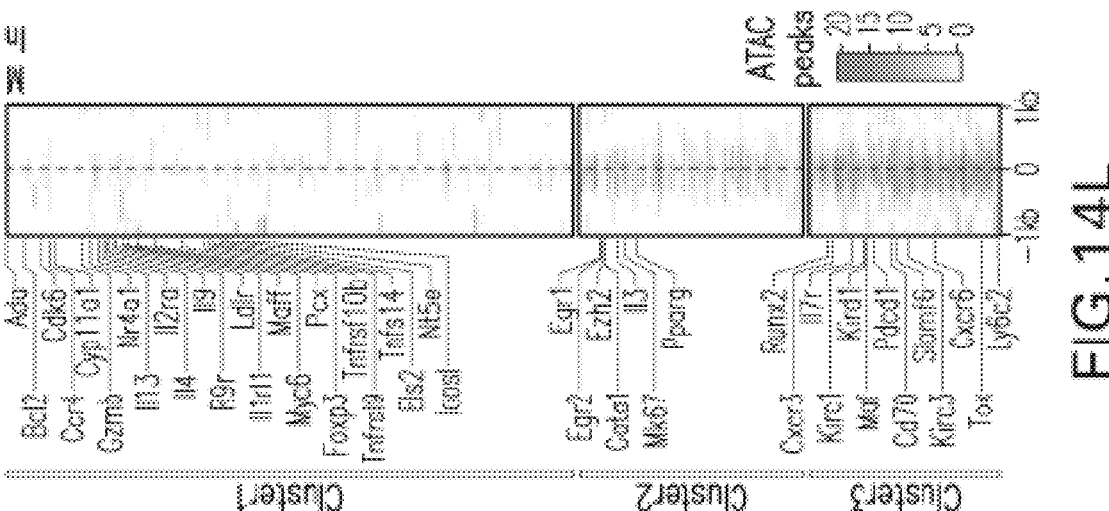
FIGS. 14J-14O are heatmaps that illustrate differential chromatin accessibility at 2 kb windows centered at the summit of the ATACseq peaks identified between different samples. The heatmaps were generated using the same ATACseq peak regions from FIGS. 3D-3I and plotted in the same orders as in FIG. 3D-3I.
Figure 14K:
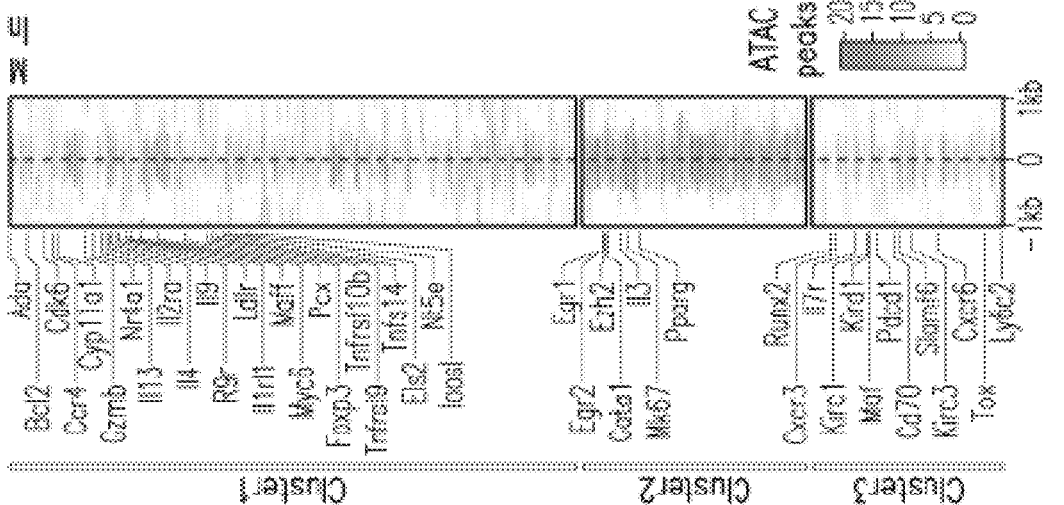
Figure 14J:
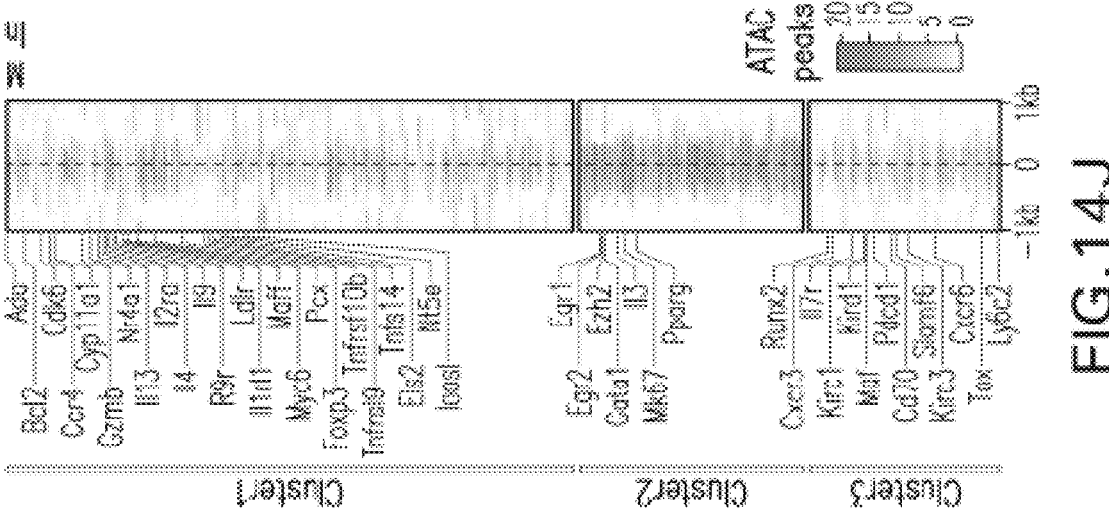
Figure 14O:
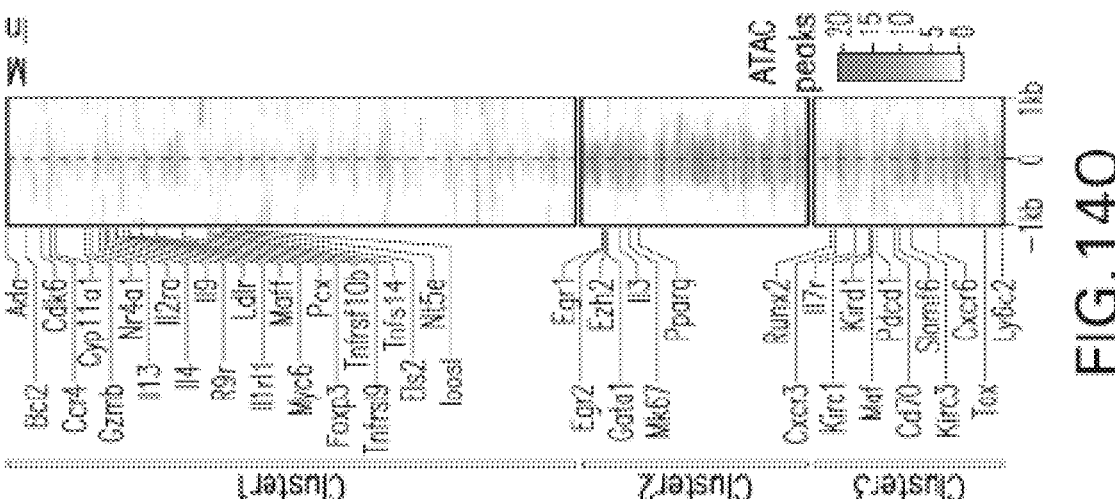
Figure 14N:
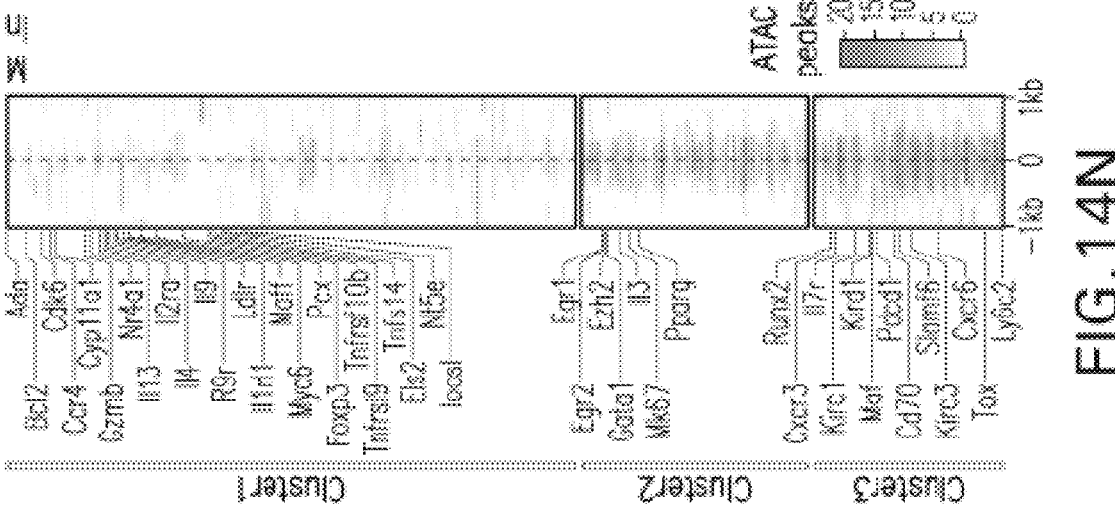
Figure 14M:
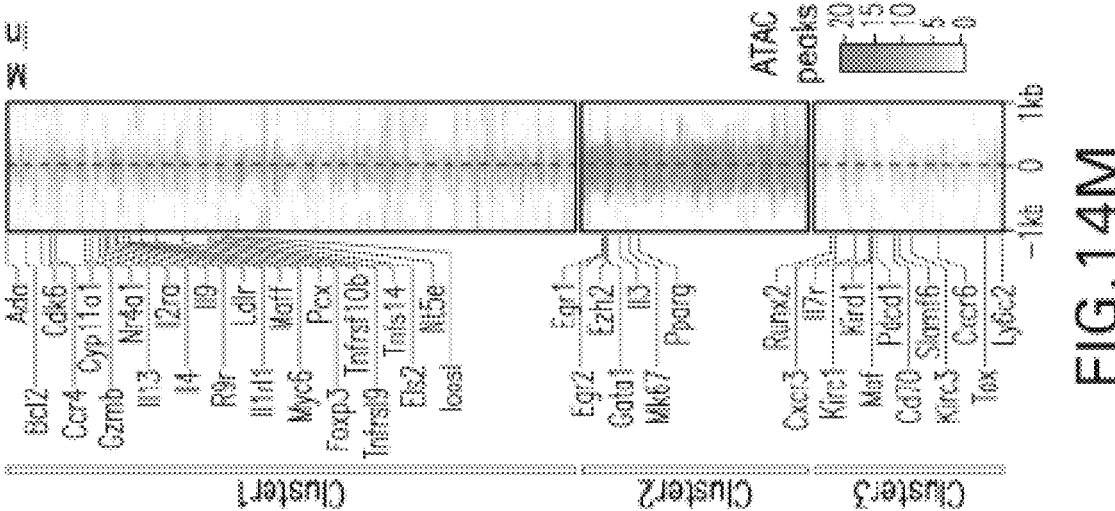
Figure 14P:
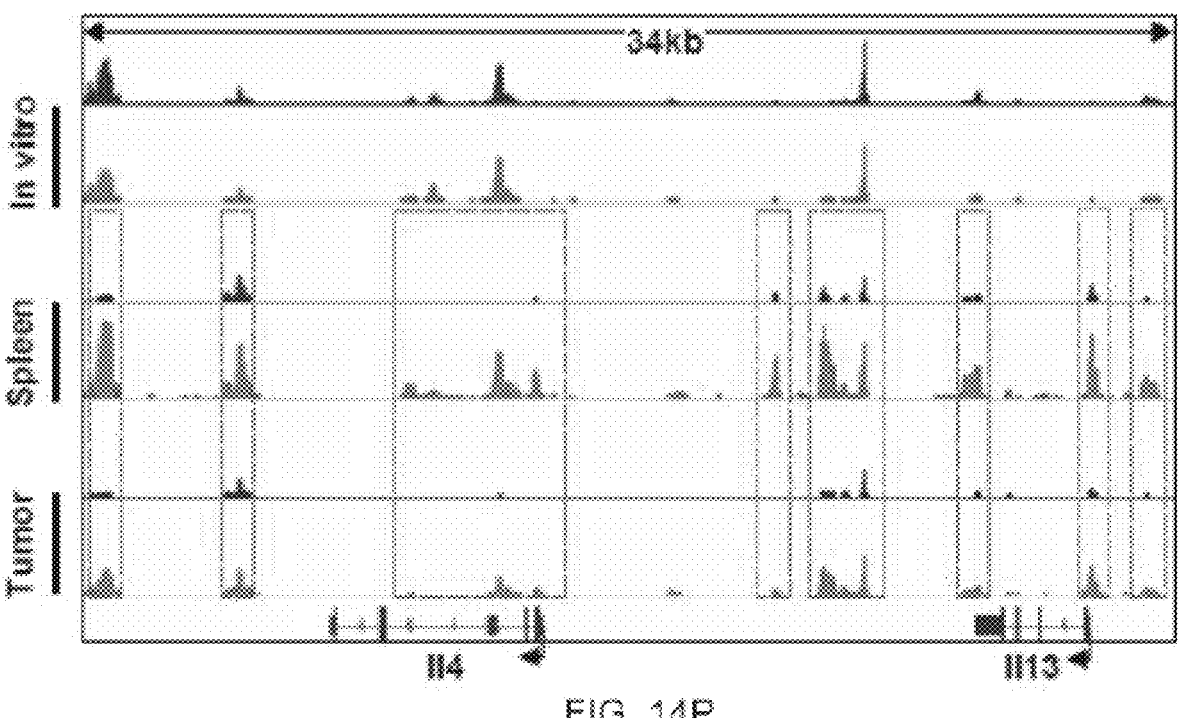
FIGS. 14P-14Q are chromatin accessibility tracks of representative genes. Bottom and top tracks correspond to CASTAT5 and control CD4+ T cells, respectively. The rectangles on spleen and tumor-derived samples mark ATACseq peaks showing increased signal intensity in CASTAT5 CD4+ T cells compared to control CD4+ T cells (FIG. 14P). The rectangles on spleen and tumor-derived samples mark ATACseq peaks that disappeared or reduced in intensity in CASTAT5 CD4+ T cells compared to control CD4+ T cells (FIG. 14Q). These differential ATACseq peak profiles between CASTAT5 and control CD4+ T cells are not observed in in vitro samples.
Figure 14Q:
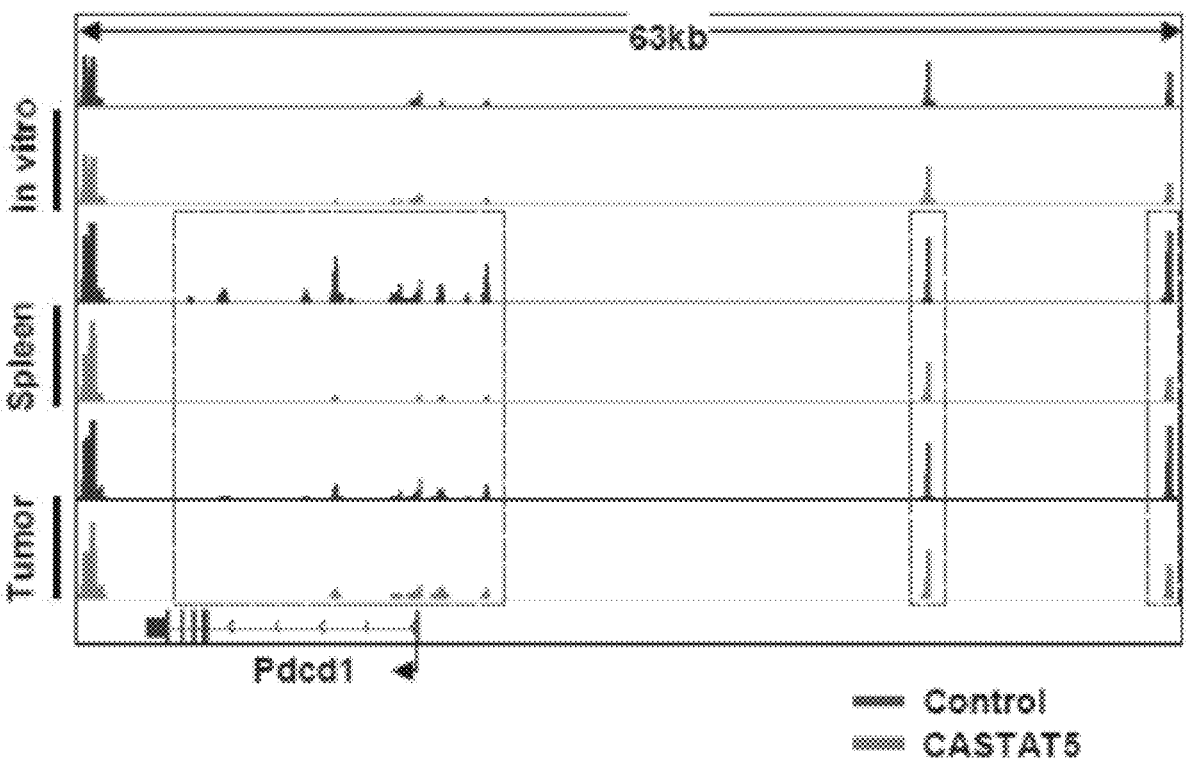

It should be mentioned that for the above analyses donor T cells from mice spleens were used to ensure collection of sufficient number of donor T cells for downstream experimental procedures. It is known that T cells residing in different organs can have different properties. It was asked whether the epigenetic changes seen in spleen-derived donor T cells can be found in tumor-infiltrating donor T cells. To address this, ATACseq analyses were performed for CASTAT5 and control CD4 T cells which were either collected right before adoptive transfer, or were FACS-sorted from mice spleens or tumors 10 days after T cell transfer. A pair-wise comparison between CASTAT5 and control CD4$^+$ T cells revealed that CASTAT5 induced overt changes in chromatin accessibility in both spleen and tumor samples, although the changes in tumor-infiltrating T cells were less profound (FIGS. 14A-14C), suggesting that the epigenetic landscape of T cells is subjected to regulation by the microenvironment where the T cells reside. To identify the epigenetic changes unique to each cell population, a data matrix was generated containing ATACseq peaks identified from all samples and the top 5% peaks with largest variation among them were selected. Then the genes of interest identified by bulk RNAseq as shown in FIGS. 3D-3I were selected to re-plot the heatmap (FIGS. 14D-14O). Notably, the majority of the epigenetic differences between CASTAT5 versus control CD4$^+$ T cells recovered from the spleen were also found in donor T cells recovered from the tumor, although to a lesser extent in tumor-infiltrating T cells. In contrast, the in vitro cultured CASTAT5 and control CD4$^+$ T cells did not differ in epigenome. FIGS. 14P-14Q illustrates the typical pattern of epigenetic changes in donor T cells recovered from the spleen versus tumor for 3 representative genes.

Example 7. Single Cell RNAseq Reveals the Heterogeneity of CASTAT5-Induced Polufunctional CD4$^+$ T Cells Materials and Methods Single cell RNA sequencing (scRNAseq): FACS-sorted donor CD4$^+$ T cells were processed for scRNAseq libraries using the Chromium Controller (10× Genomics). scRNAseq libraries were generated for approximately 2,000 cells per sample using 10× 3' single cell mRNAseq V3 reagents. The scRNAseq libraries were sequenced using Illumina Next-Seq500 sequencer to collect approximately 80k reads per cell. Each cell was tagged with a 16 bp barcode sequence, which represents the identity of each single cell throughput the analysis pipeline.

scRNAseq analysis: The raw reads in fastq format was processed using 10× genomics cellranger analysis package. CASTAT5 and control samples will be pooled using cellranger aggr pipeline. The cellranger pipeline outputs containing gene-by-cell expression data from the aggregated libraries were imported into R package Seurat 3.0. to create a Seurat object (Butler, A., et al., *Nat Biotechnol,* 36:411-420 (2018)). Quality control measures were implemented in Seurat to filter out cells expressing >6000 genes. Cells with a higher percentage of mitochondrial genes (percent of mt >0.3) were also excluded from the subsequent analysis. Normalization and scaling were performed within Seurat before subsequent analysis such as PCA, umap, tSNE, and clustering analyses. Visualization of the scRNA data were performed using Seurat tSNEplot, Vinplot, Featureplot, Dotplot and DoHeatmap functions. Cell cycle analysis was performed using Seurat cell cycle scoring function. A cell cycle gene signature containing 97 cell cycle related genes (Tirosh, I., et al., *Science,* 352:189-196 (2016)) were used to derive the G1/S and G2/M scores. The Seurat 3 dataset with cluster ID was imported into monocle 2.0 (Trapnell, C., et al., *Nat Biotechnol,* 32:381-386 (2014)) using a custom script and then analyzed for pseudotime trajectory using cells in clusters 4-6 which mainly consist of CASTAT5 CD4$^+$ T cells.

Results

Figure 5B:
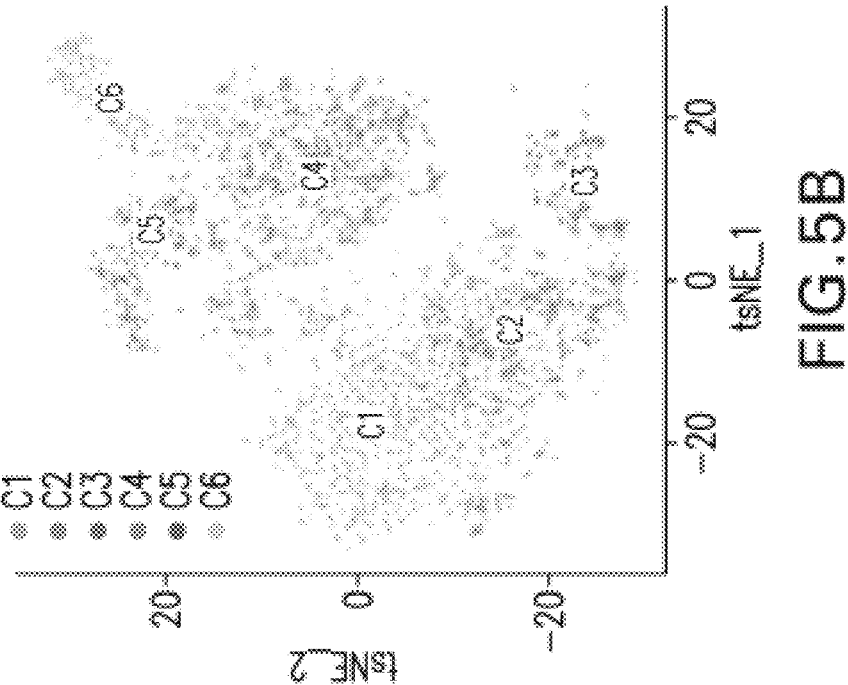
FIGS. 5A-5B are t-SNE plots generated using scRNAseq data show clear separation of CASTAT5 and control CD4+ T cells (FIG. 5A), and each of them can be further projected into three sub-clusters based on gene expression profiles (FIG. 5B).
Figure 5A:
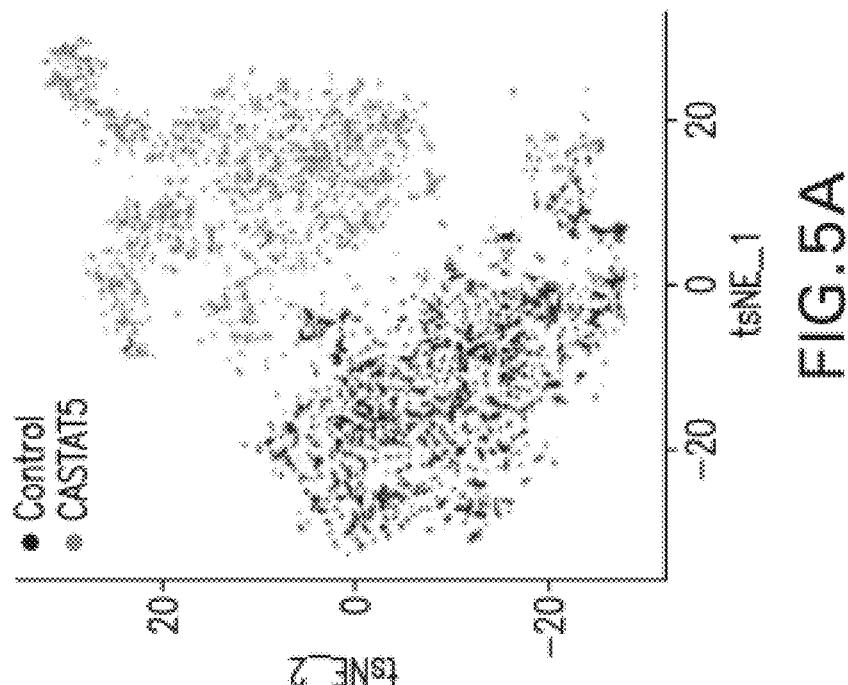
Figures 5C, 5D, 5E, 5F:
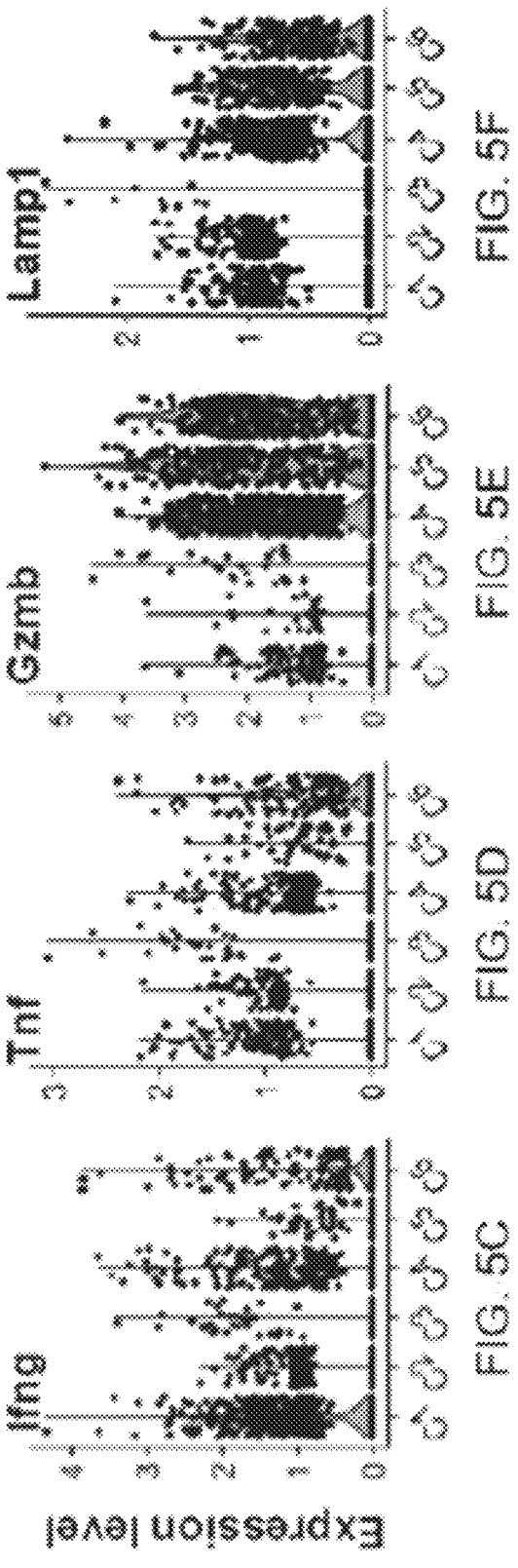
Figure 5K:
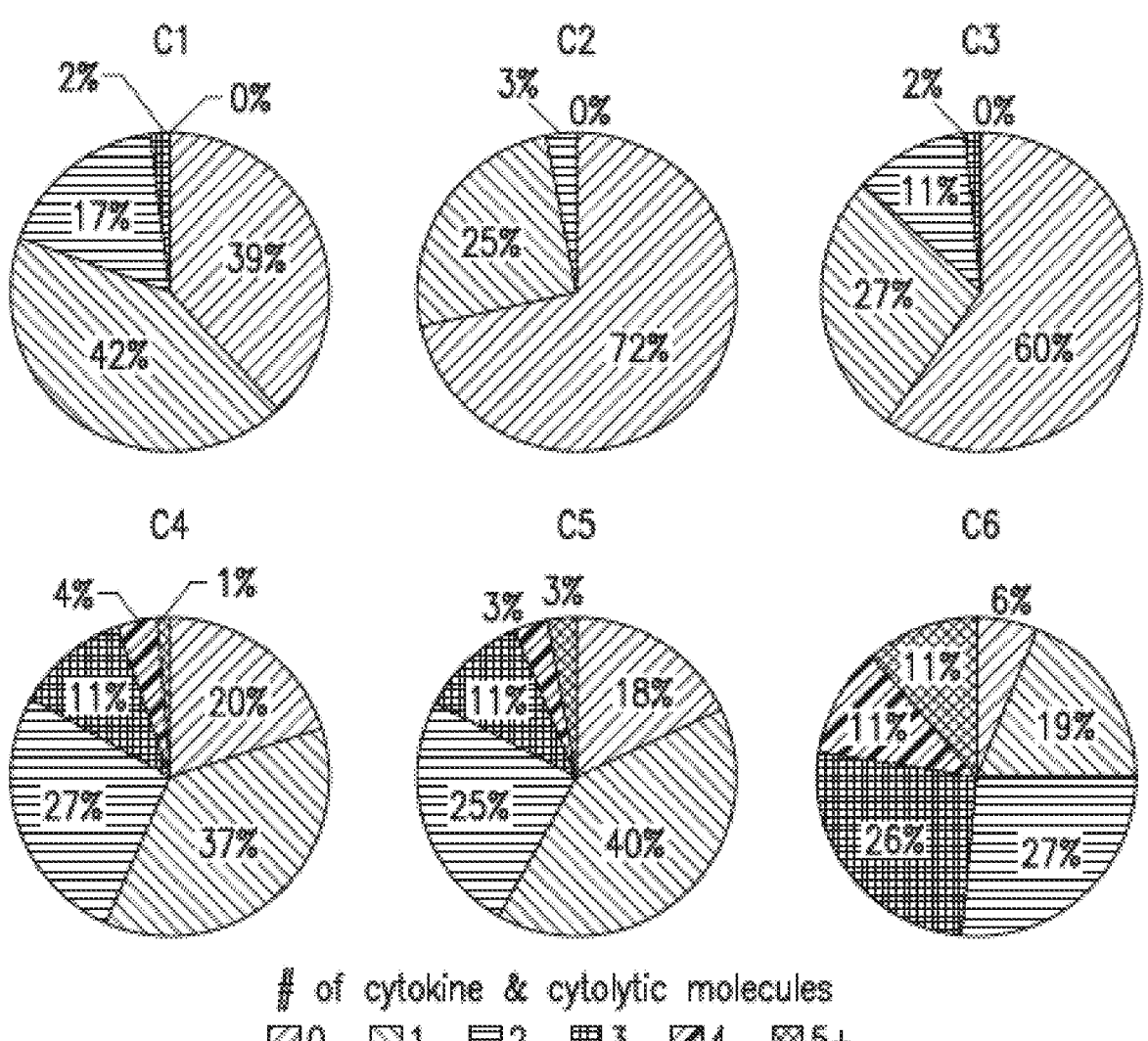
FIG. 5K is pie charts showing the percent of CD4+ T cells expressing varied number (0 to >5) of effector molecules in each cluster of cells. The number of cells with positive expression of each effector molecule was counted based on the presence or absence of raw sequencing reads mapped to the mRNA sequences of each relevant gene. Cells with at least 1 read mapped to the relevant gene were called as positive for the corresponding gene.
Figure 5L:
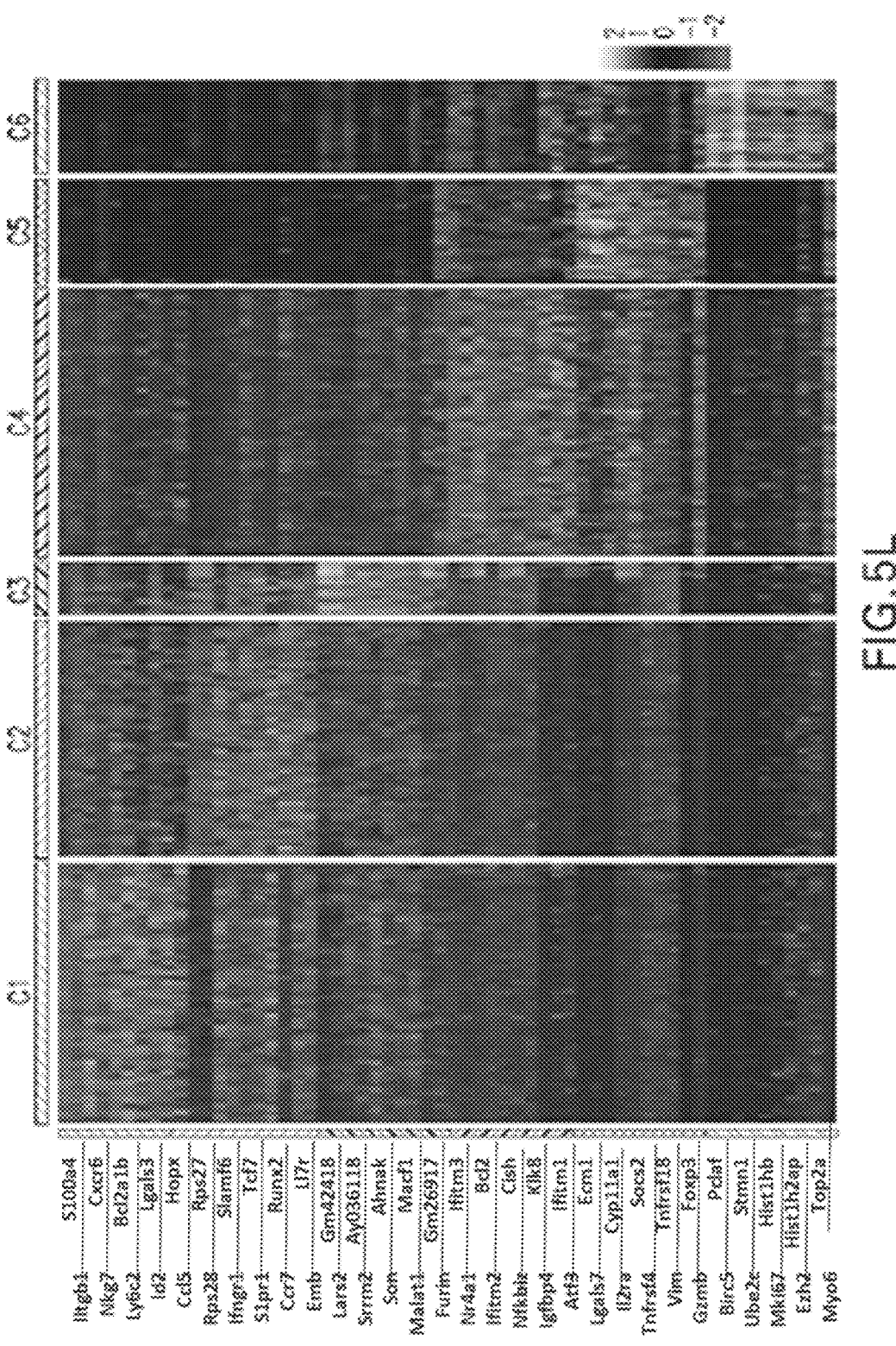
FIG. 5L is a heatmap of top 10 genes expressed in each cluster. The columns represent cells and the rows present genes. Cells are grouped by clusters and top 10 most significant markers are shown.
Figure 5O:
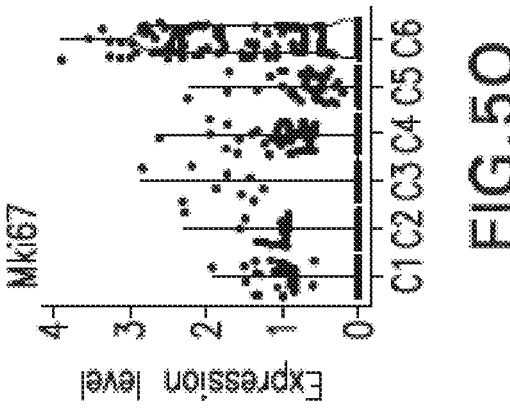
FIGS. 5M-5R are violin plots of six unique marker genes representing cluster 6. Each dot represents one cell and the violin shows the distribution of probability density at each value.
Figure 5R:
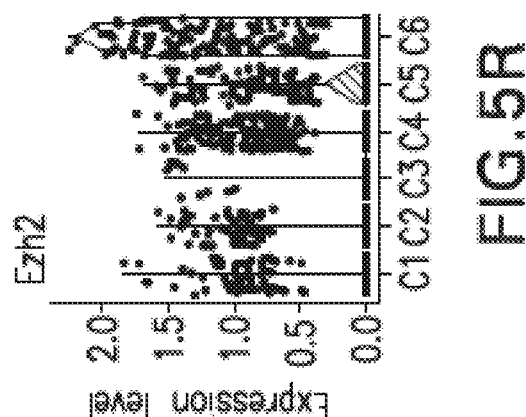
Figure 5N:
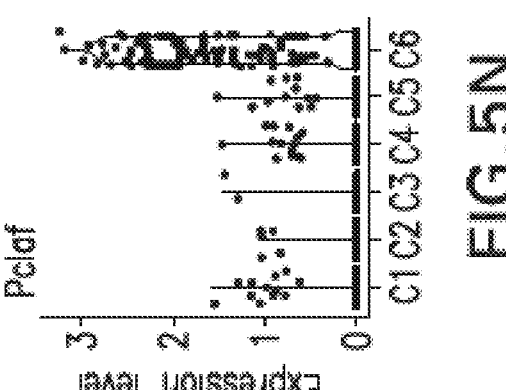
Figure 5Q:
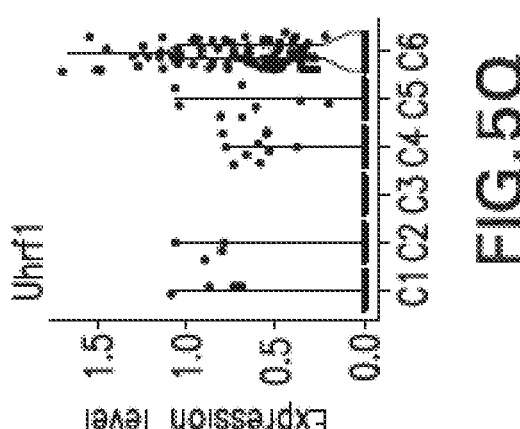
Figure 5M:
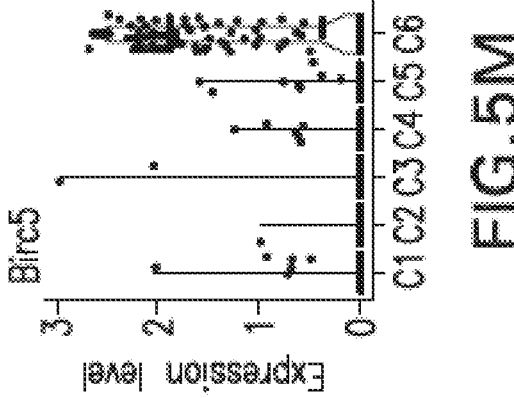
Figure 5P:
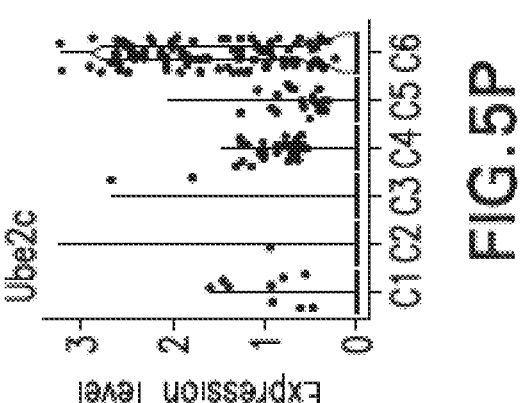
Figure 5S:
FIG. 5S is a gene co-expression network specific to cells of cluster 6 is identified using WGCNA.
Figure 15A:
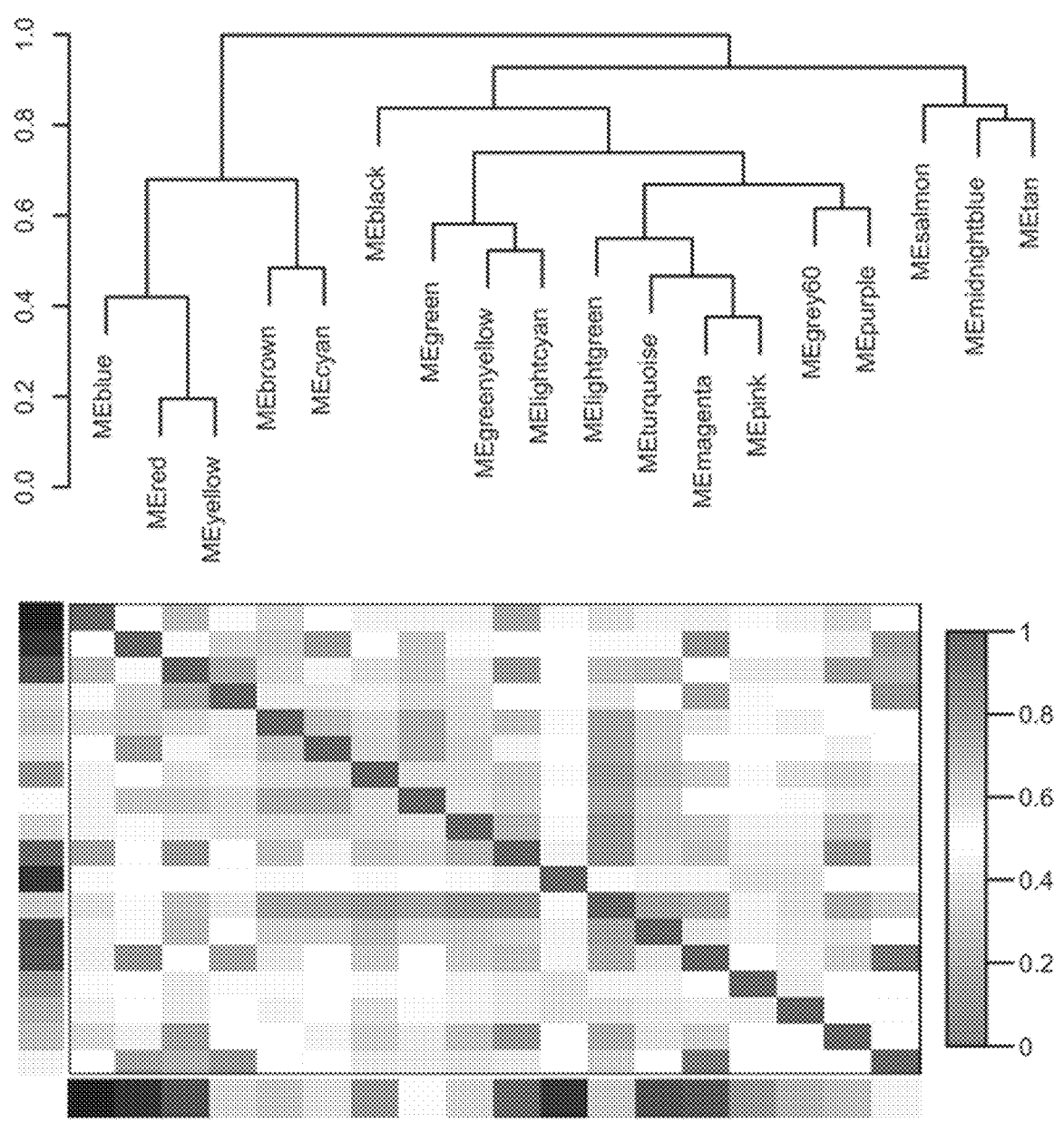
FIG. 15A is an eigengene network showing the unsupervised hierarchical clustering heatmap (bottom) and dendogram (top) with dissimilarity based on topological overlap and intercorrelation of each module identified by WGCNA. The gradient indicates modules. Gradient key indicates the correlation value.
Figure 15B:
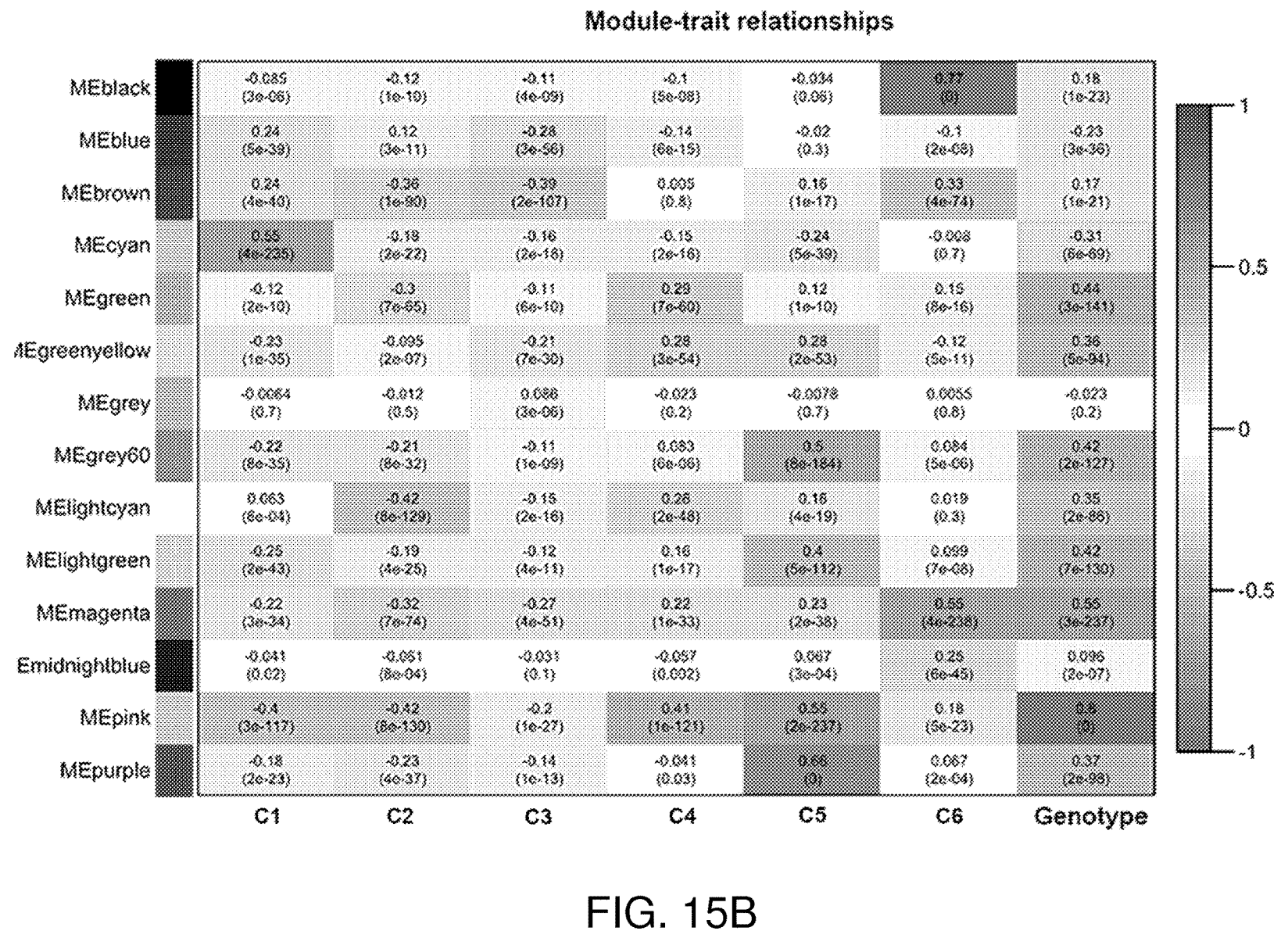
Figure 15C:
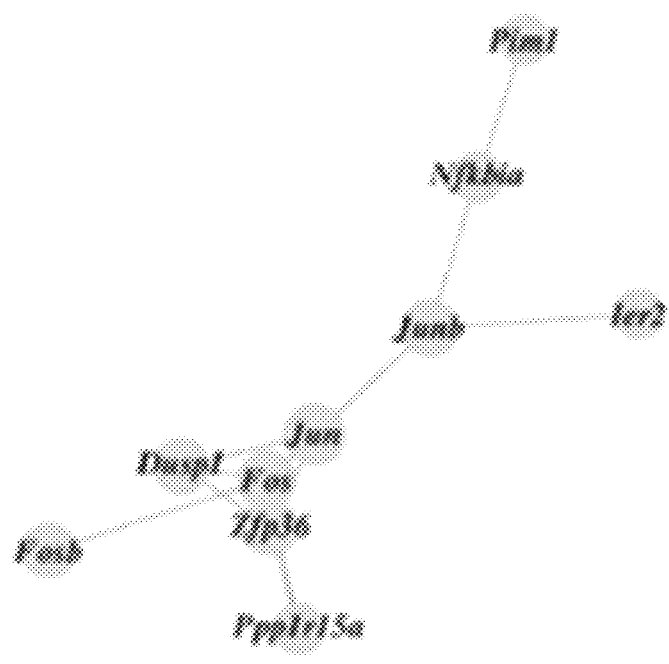
FIGS. 15C-15D are gene co-expression networks identified specific to cluster 4 and cluster 5.
Figure 15D:
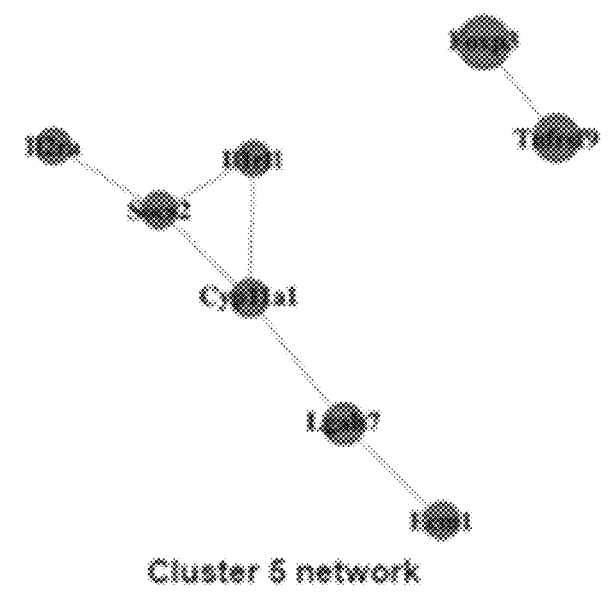
Figure 16A:
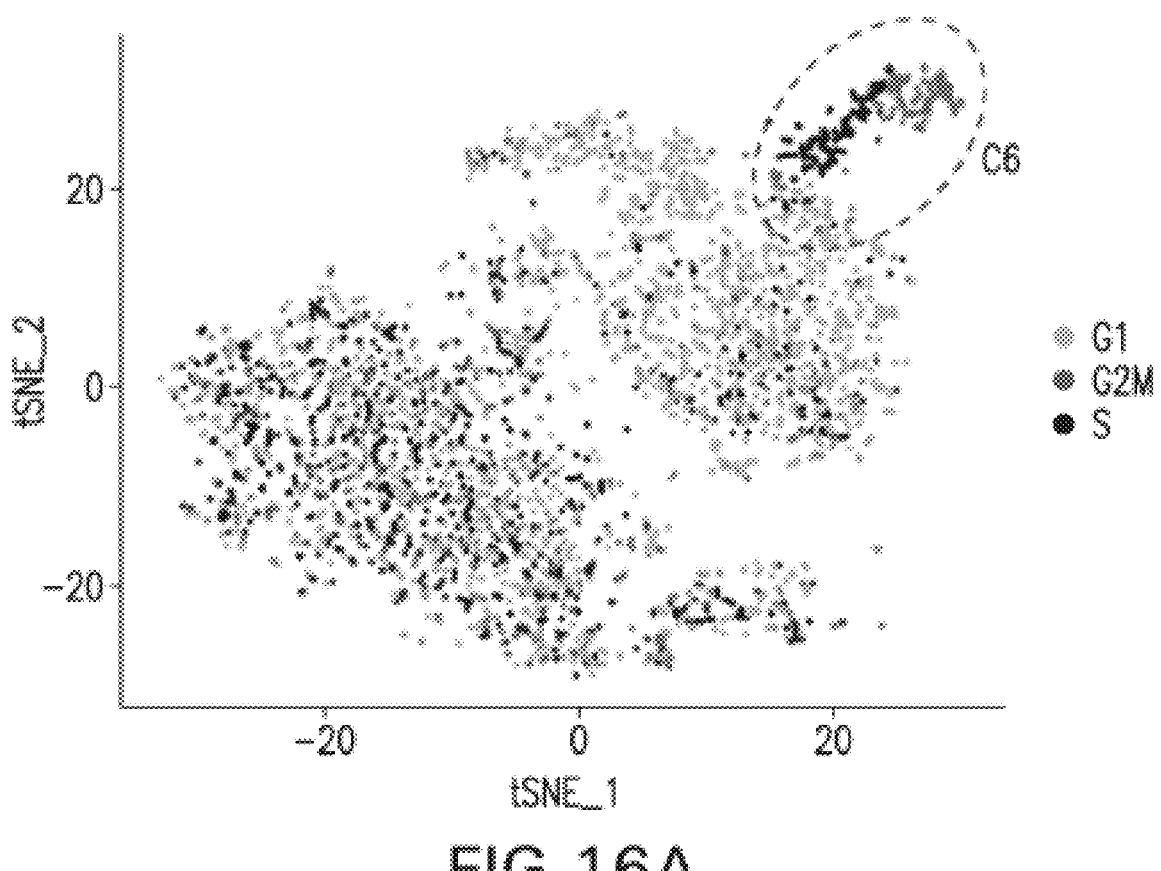
FIG. 16A is a SNE plot of CASTAT5 and control CD4+ T cells constructed with cell cycle scores calculated using Seurat 3.0 based on a group of 97 cell cycle genes. The gradient key indicates the cell cycle phase.
Figure 16B:
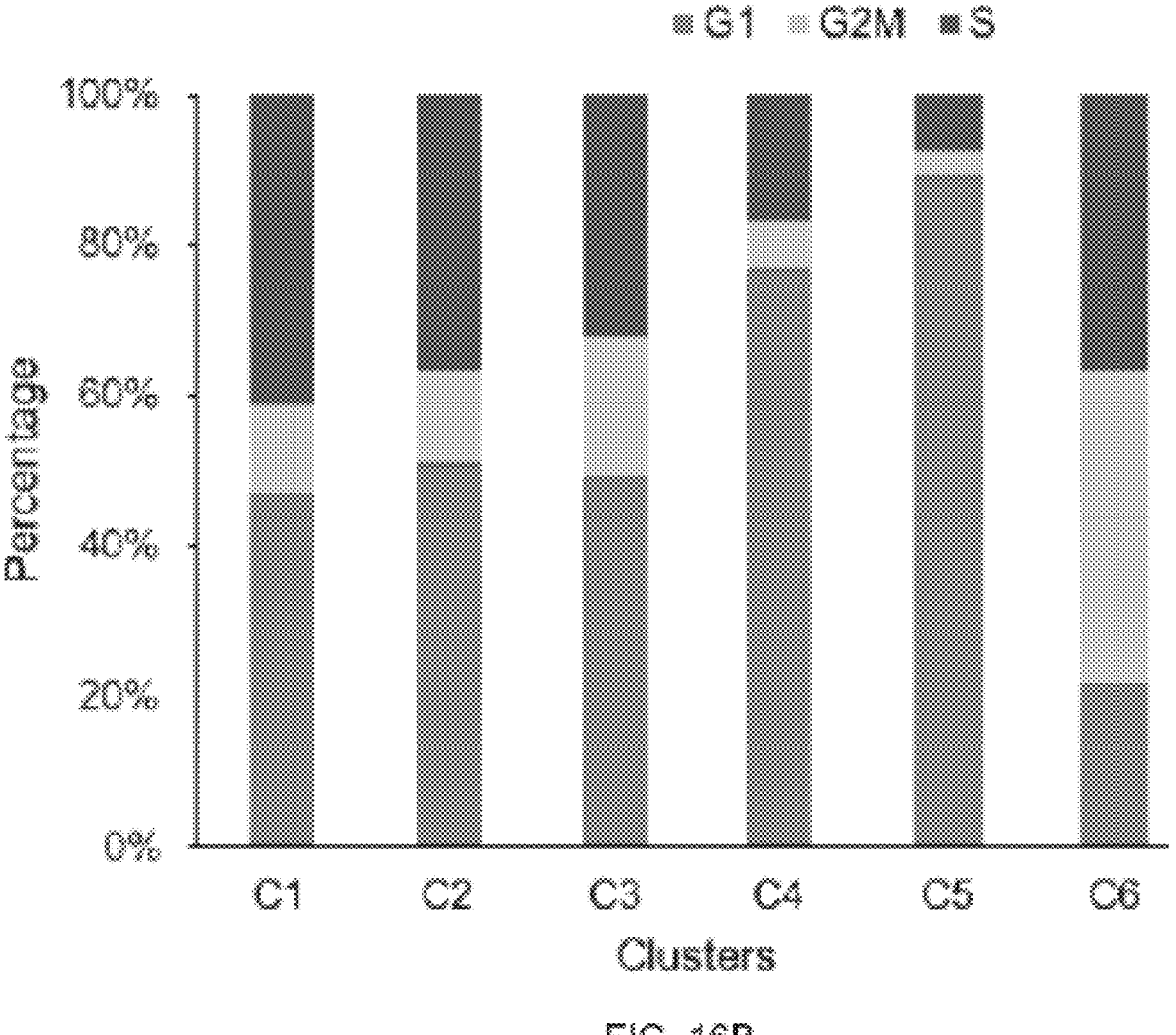
FIG. 16B is a bar graph showing the percent of cells in G1. G2/M and S phase according the cell cycle scores in each cluster as defined in FIGS. 5A-5B.

To further understand the heterogeneity of the T cell population and the transcriptome associated with polyfunctionality, single-cell RNA sequencing analysis (scRNAseq) was conducted for CASTAT5 and control CD4$^+$ T cells using the 10× Genomics platform. As shown in FIGS. 5A-5B, 1,531 CASTAT5 and 1,632 control CD4$^+$ T cells from pooled samples can be clearly separated apart on the t-distributed stochastic neighbor embedding (t-SNE) plot. Using unsupervised cluster analysis, the 3163 single cells can be further partitioned into 6 clusters based on their transcriptomes. Cells in clusters 1-3 belonged to control CD4 T cells, whereas cells in clusters 4-6 were mostly CASTAT5 CD4$^+$ T cells. Consistent with the bulk RNAseq data and ICS results, 114, 1113, 119, Csf2, Gzmb and Lamp1 (CD107a) transcripts were predominantly detected in CASTAT5 CD4+ T cells (clusters 4-6) while Ifng and Tnf transcripts were present in all clusters (FIGS. 5C-5J). Based on scRNAseq data, the frequency of cells expressing one or more of the effector molecules was computed, including the aforementioned 6 cytokines plus granzyme B and Lamp1 (CD107a) as displayed in FIGS. 5C-5J. A significant increase in the number of cells expressing 2 or more effector molecules was observed in CASTAT5 CD4$^+$ T cells compared to control CD4$^+$ T cells. Particularly, nearly 70% of cells in cluster 6 expressed at least 2 and about 48% of them expressed 3 or more effector molecules simultaneously (FIG. 5K). Thus cluster 6 represented a unique population highly enriched for polyfunctional CD4$^+$ T cells. The scRNAseq analysis identified the gene signatures associated with each cluster (FIG. 5L). Notably, the signature genes defining cluster 6 include genes regulating cell survival (Birc5), proliferation (Mki67, Pclaf), and chromatin modification (Uhrf1, Ezh2) (FIGS. 5M-5R). To further identify modules of co-expressed genes in each cluster, the scRNAseq data were subjected to co-expression network analysis and a total of 18 modules were identified and color-coded (FIGS. 15A-15B). The gene co-expression network associated with cluster 6 features multiple genes involved in regulating cell cycle progression, chromosome segregation and spindle checkpoint activity (FIG. 5S), which is consistent with cell cycle analysis based on the expression patterns of 97 genes involved in regulating cell cycle. Cluster 6 displayed a unique cell cycle status with most cells in G2/M and S phases (FIGS. 16A-16B). The co-expression networks associated with other clusters are similarly identified (Supplementary FIG. 15C). For instance, cluster 5 is associated with a module containing Foxp3.

Figure 5T:
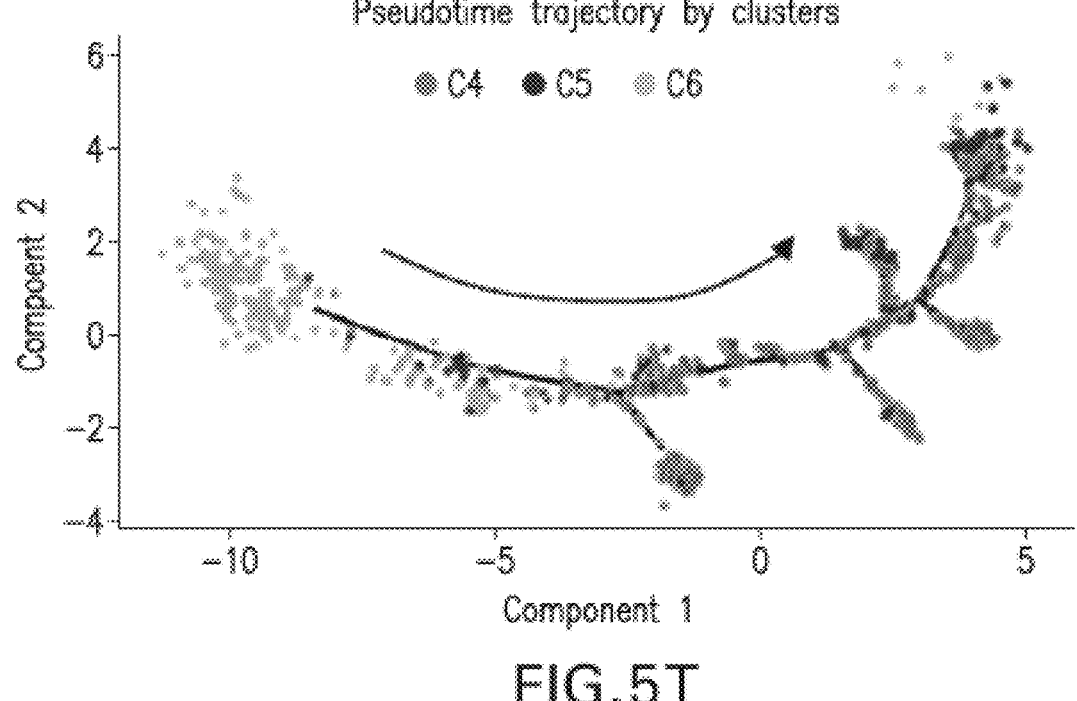
FIG. 5T is a pseudotime trajectory determined by Monocle v. 2 showing the order of CASTAT5 CD4+ T cells from 3 different clusters. Each dot represents one cell. The grey gradient indicates the clusters to which the cells belong, as defined in FIG. 5A-5B.
Figure 17A:
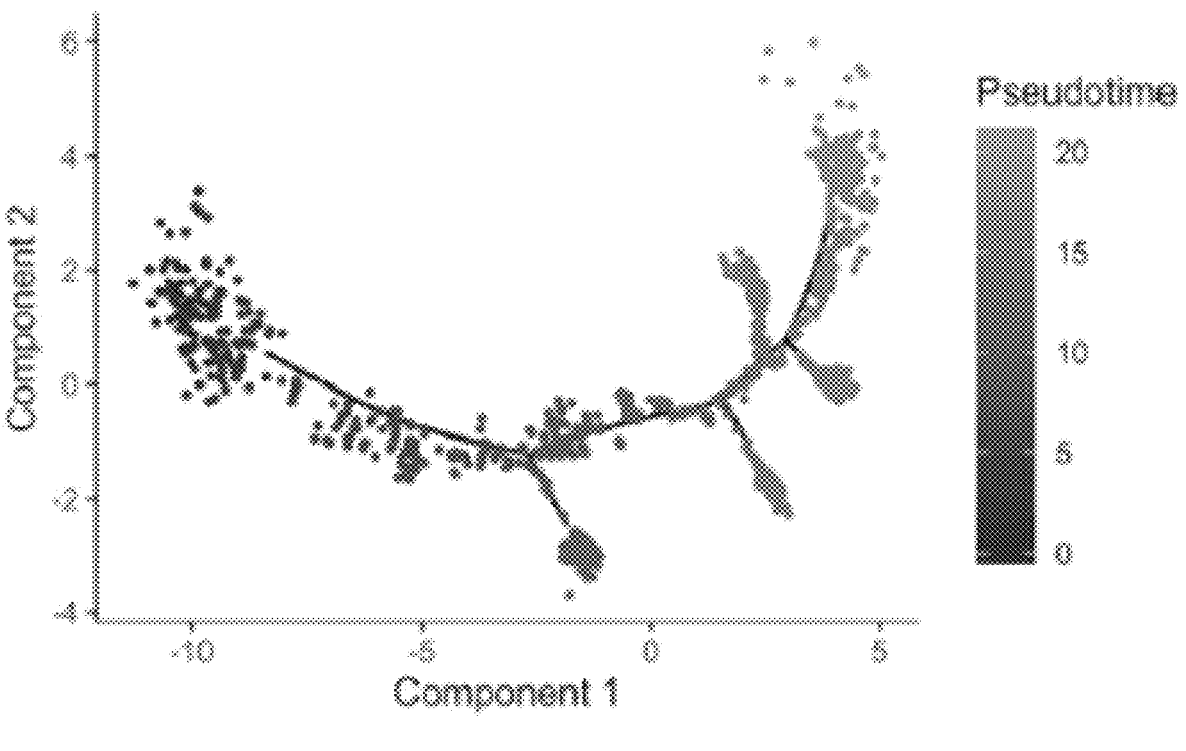
FIG. 17A is pseudo differentiation time plot showing trajectory of CASTAT5 CD4+ T cells.
Figure 17B:
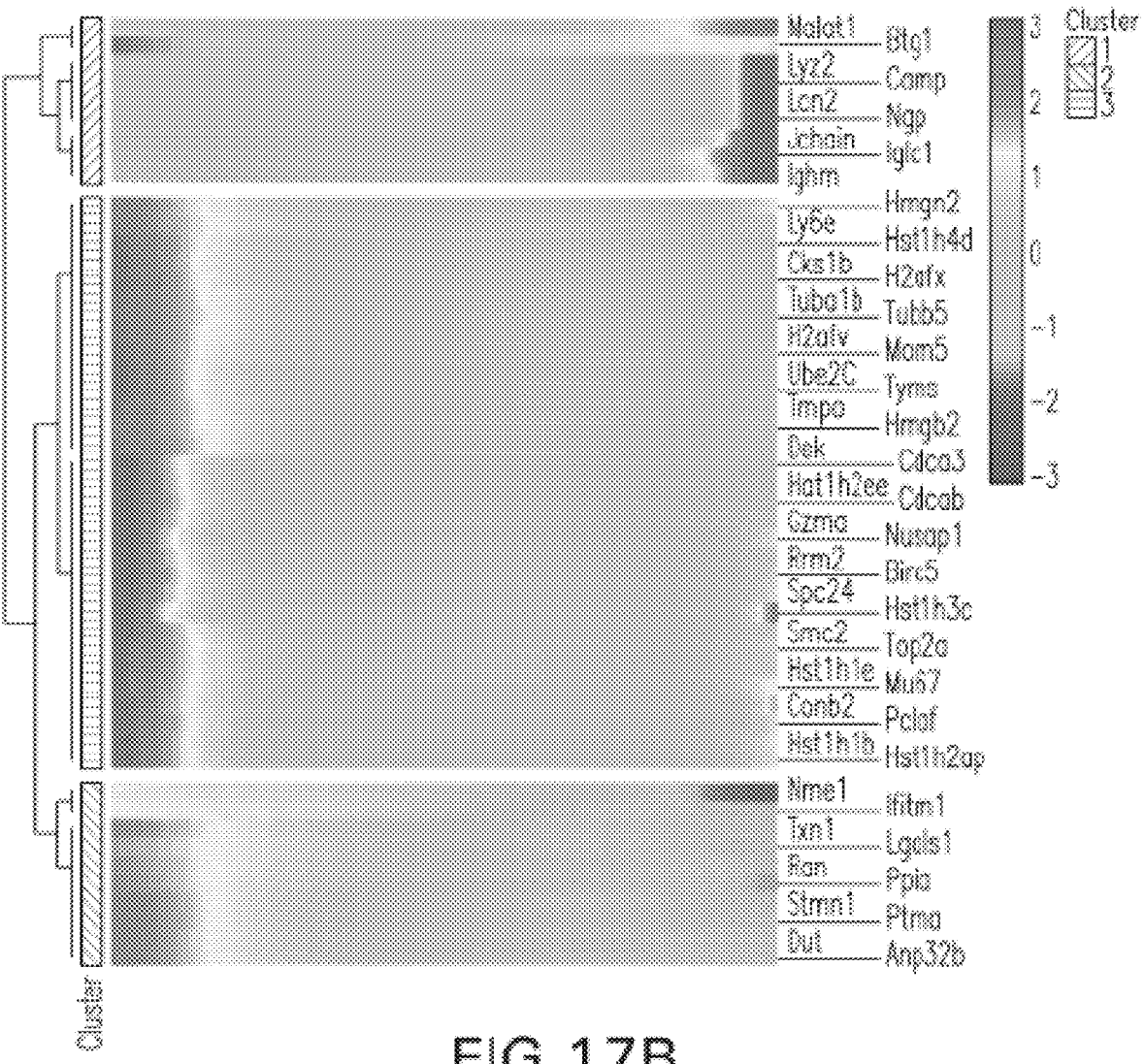
FIG. 17B is a heatmap of the top 50 significantly changed genes (p<0.01) identified by Monocle showing a trend of gradual changes of expression along the Pseudo time trajectory.
Figure 17C:
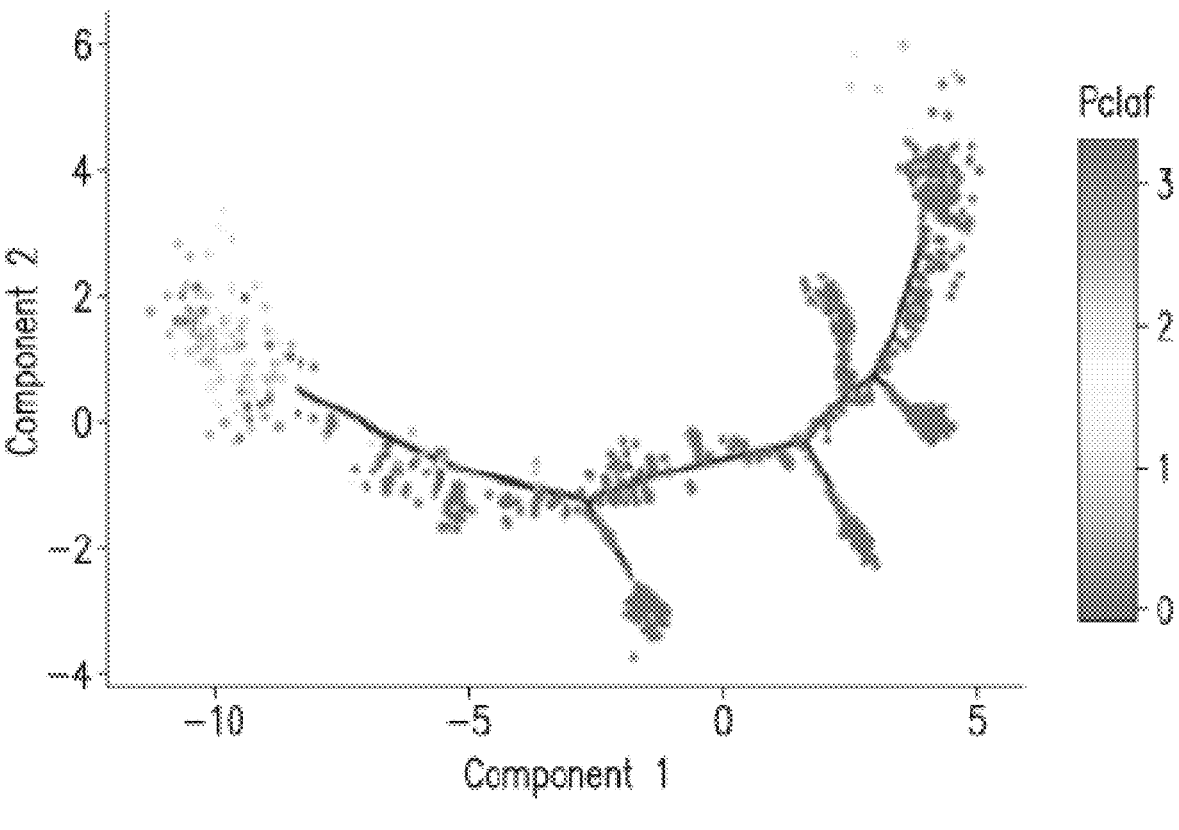
FIG. 17C is a plot showing the expression level of Pclaf, a cluster 6 maker gene, along the Pseudo time trajectory.

To explore the transcriptional dynamics of CASTST5 CD4$^+$ T cells, the scRNAseq data was also used to create pseudotime trajectory for each cluster. Based on the predicted pseudotime trajectory (FIG. 17A), CASTAT5A CD4$^+$ T cells were ordered along a trajectory with cluster 6 cells having the shortest peudo-differentiation time (FIG. 5T). Expression levels of markers for differential clusters further confirm the cluster distribution along the pseudotime differentiation trajectory (FIG. 17B-17C). Thus, cluster 6 cells are positioned as the progenitors of cells in other clusters based on the pseudo-time trajectory projection. The result supports the notion that cluster 6 cells represent a resource population, or progenitor-like cells, which may give rise to more polarized but less polyfunctional effector CD4$^+$ T cells. Following the same categorization schema used for bulk RNAseq and ATACseq, the expression patterns of additional genes were examined at the single-cell level (FIGS. 18A-18H). In general, the scRNAseq results are in congruence with the bulk RNAseq data and ATACseq data. scRNAseq analyses not only validate the transcriptional changes detected by bulk RNAseq and ATACseq, but also provide additional information on the activity of gene transcription within in each cell cluster.

It should be noted that not all CD4$^+$ T cells would express CASTAT5 after retroviral transduction. It was possible that the donor CD4$^+$ T cells sorted for NGS contained both transduced (CASTAT5 positive) and untransduced (CASTAT5 negative) T cells, raising the question to what extent our data reflected the effects of CASTAT5 on CD4$^+$ T cells. To address this issue, both the bulk and single cell RNAseq data were examined to check if the specific STAT5A mutations (H299R and S711F), which were introduced during mutagenesis to create CASTAT5 (Onishi, et al., *Mol Cell Biol,* 18:3871-3879 (1998)), can be detected in the bulk and single cell RNAseq reads. As expected, the presence of these mutant alleles was prevalent (mutant allele frequency ≥89%) for both mutations in sequencing reads generated from CASTAT5 CD4$^+$ samples (FIGS. 19A-19D). In contrast, these mutations were not detected in control CD4$^+$ samples. The results indicate that at the time of analysis, the sorted CASTAT5 CD4$^+$ samples contained predominantly transduced T cells, likely due to better expansion and survival of CASTAT5-transduced T cells.

Example 8. CASTAT5 Potentiates the Efficacy of CD19CAR T Cell Therapy

Materials and Methods

Mouse T cell retroviral transduction: The murine stem cell virus (MSCV) retroviral vector containing CASTAT5 and Thy1.1 marker interspaced by IRES was a gift from Dr. Susan Kacch. The retroviral vector MSGV-1D3-28Z.1-3 containing CD19CAR was provided by Dr. James N. Kochenderfer at National Cancer Institute. Retroviral vector MSCV-luciferase-IRES-Thy1.1 was generated as described previously (Ding, Z. C., et al., *Oncoimmunology,* 5, c1171445 (2016)). To produce retroviral supernatant, 293 FT cells were infected with retroviral vector and pcLEco packaging plasmid using Lipofectamine 2000 (Thermo Fisher Scientific) according to manufacturer's instruction. Mouse T cell retroviral transduction was done as described previously (Ding, Z. C., et al., *Oncoimmunology,* 5, e1171445 (2016)). Briefly, T cells were purified from mouse splenocytes and stimulated with mouse CD3/CD28 activation Dynabeads (Thermo Fisher Scientific) in the presence of 30 U/ml hIL2 overnight. Cells were harvested and transduced twice in two consecutive days with retroviral supernatant using retronectin. 24 hours after the second transduction, anti-CD3/CD28 magnetic beads were removed, and cells were washed twice with PBS before infusion to mice via tail vein.

Detect CD19CAR by PCR: Genomic DNA was isolated from bone marrow aspirates with Qiagen Blood and Tissue Kit according to manufacturer's protocol and used as template. PCR was carried out on an Eppendorf cycler with the primers specific to CD19CAR (forward primer: 5'-ATC-CATGGAGATCTATGAAGTGGCC-3' (SEQ ID NO: 3), and reverse primer: 5'-ATGTCGACGTTAACT-CATCTGGGG-3', (SEQ ID NO: 4)).

Results

Figure 6A:
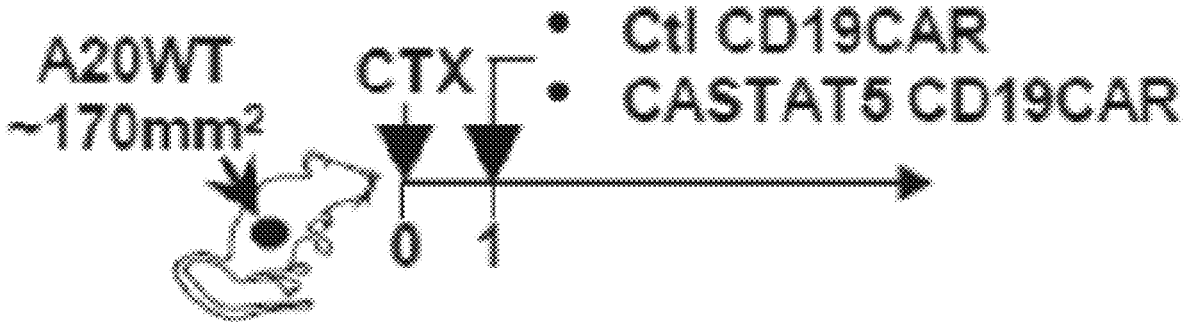
FIG. 6A is a schematic illustration showing the timeline of the experimental procedures followed for FIGS. 6B-6K. Briefly, A20WT tumor cells were subcutaneously inoculated to mice. When tumor sizes reached 170 $mm^2$, mice were randomly grouped and received either no treatment (No Tx), CTX only, CTX+control CD19CAR T cells, or CTX+ CASTAT5 CD19CAR T cells.
Figures 6B, 6C, 6D:
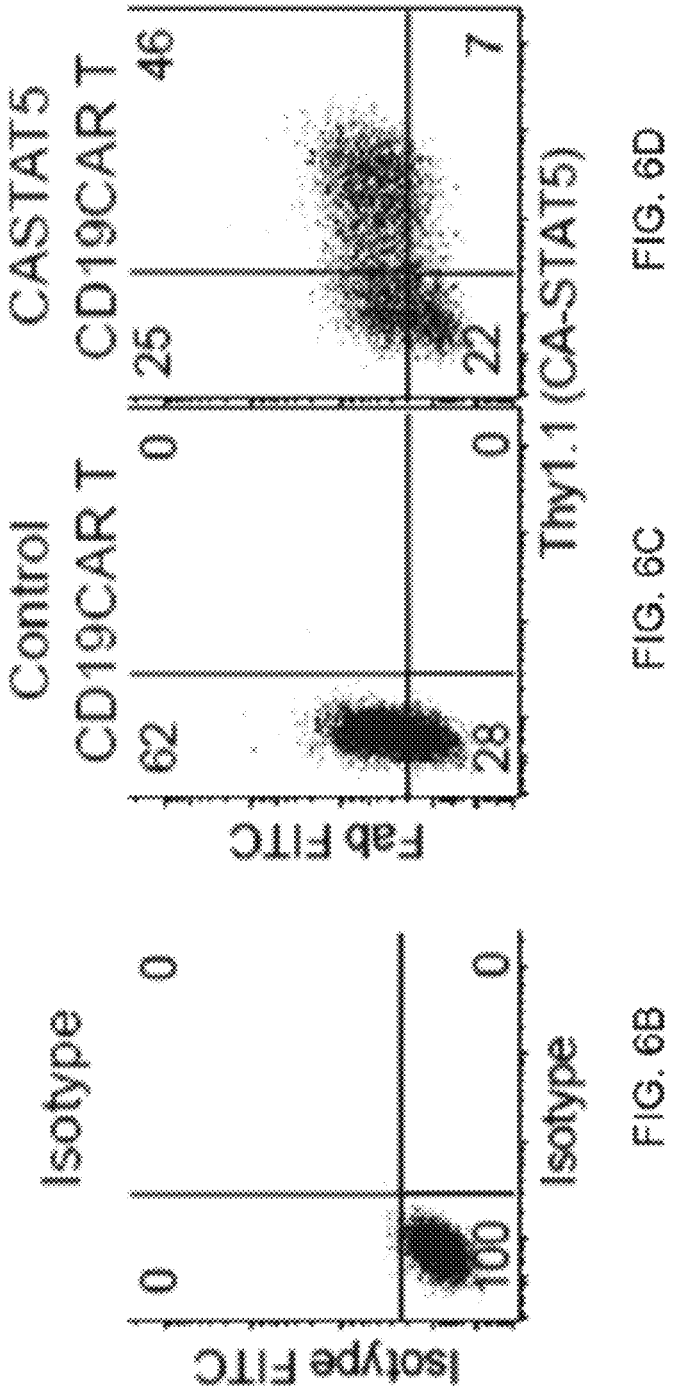
FIGS. 6B-6D are flow cytometry plots showing the levels of CD19CAR and CASTAT5 in T cells transduced to express CD19CAR alone or co-express CD19CAR and CASTAT5.
Figures 6E, 6F, 6G, 6H:
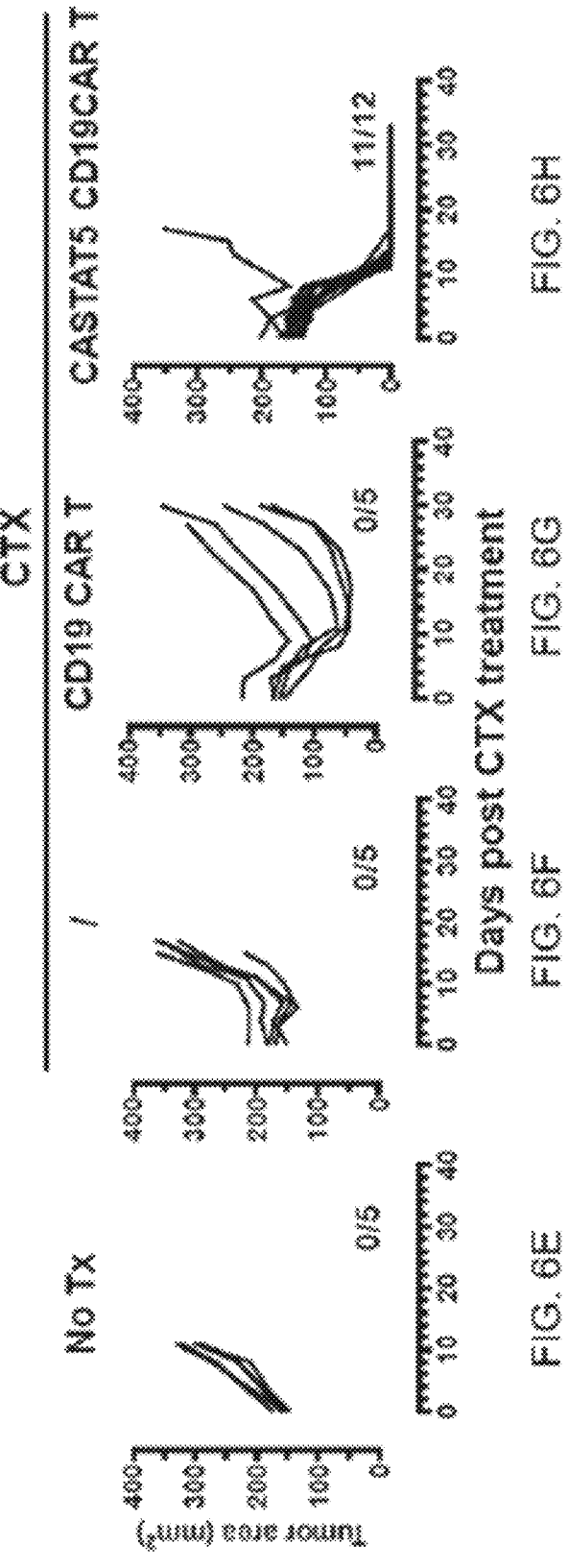
FIGS. 6E-6H are tumor growth curves of each mouse under each condition. The numbers indicate the number of tumor-free mice among treated mice at the end point.
Figure 61:
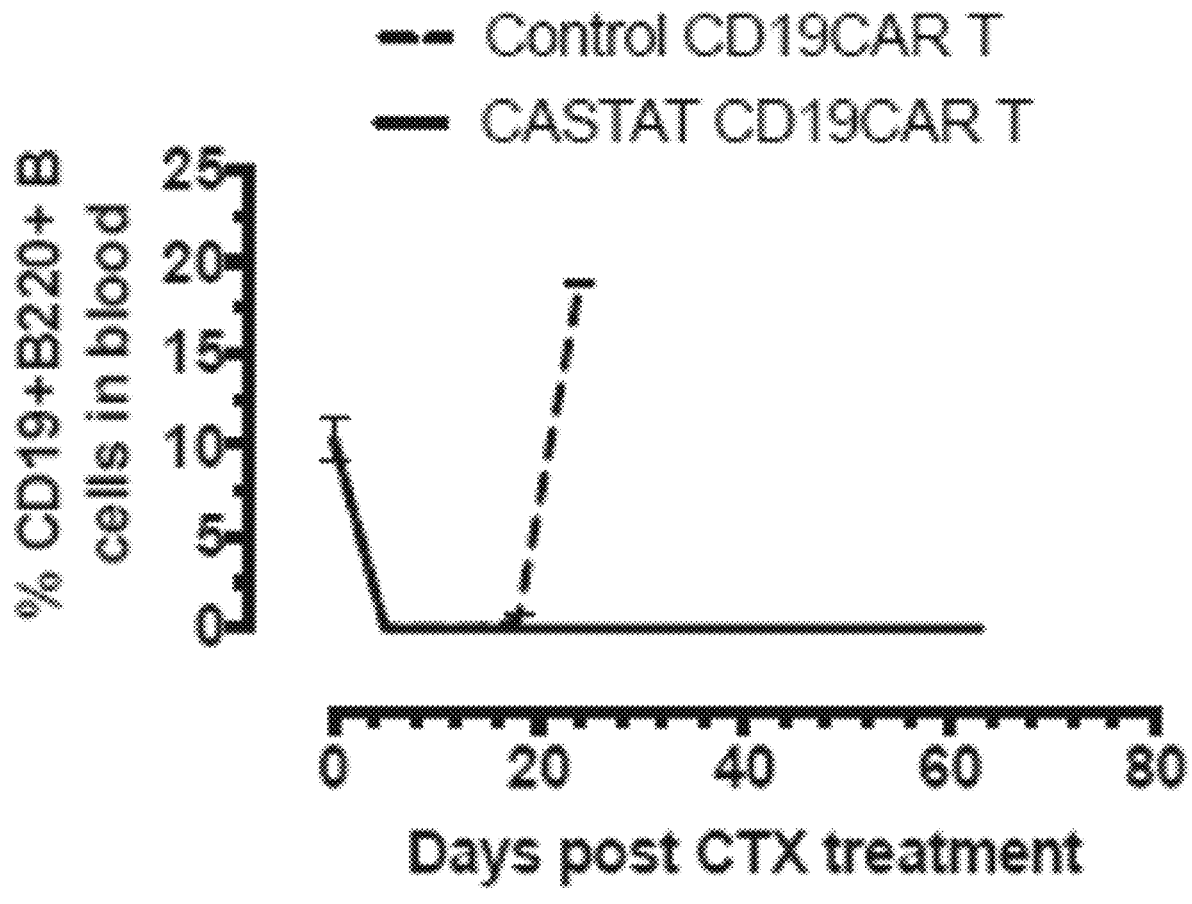
Figure 6J:
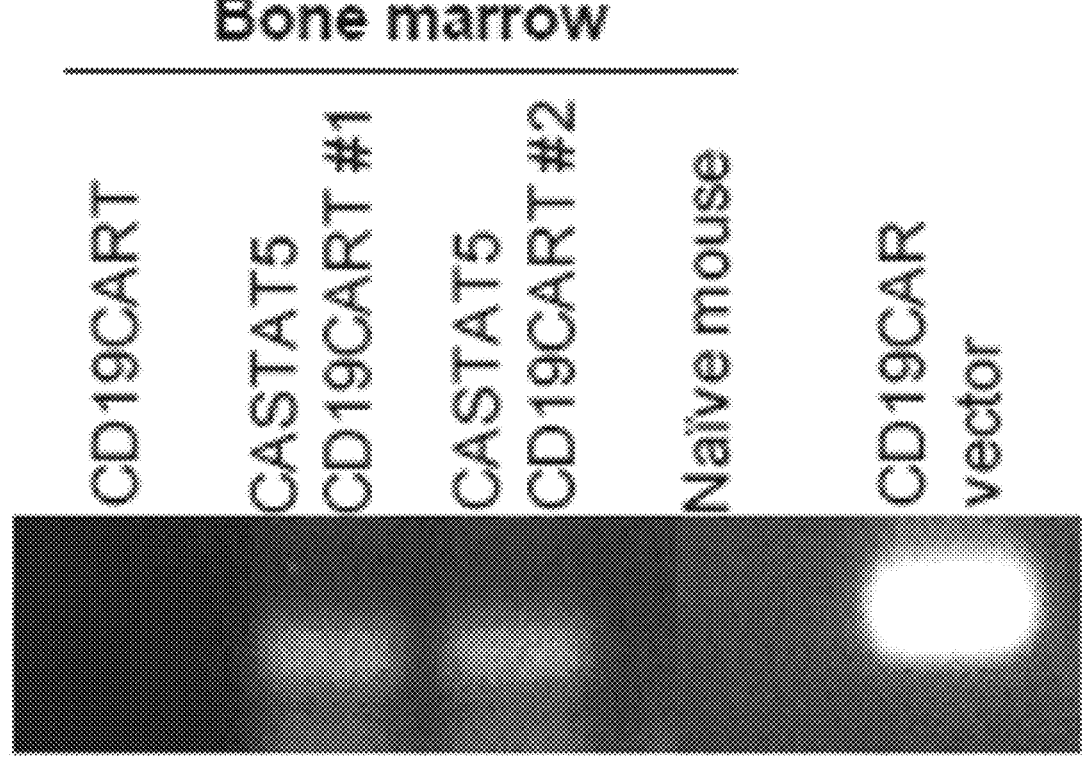
FIG. 6J is a representative PCR gel showing the presence of CD19CAR T cells evaluated by PCR detection of the CD19CAR viral vector.
Figure 6K:
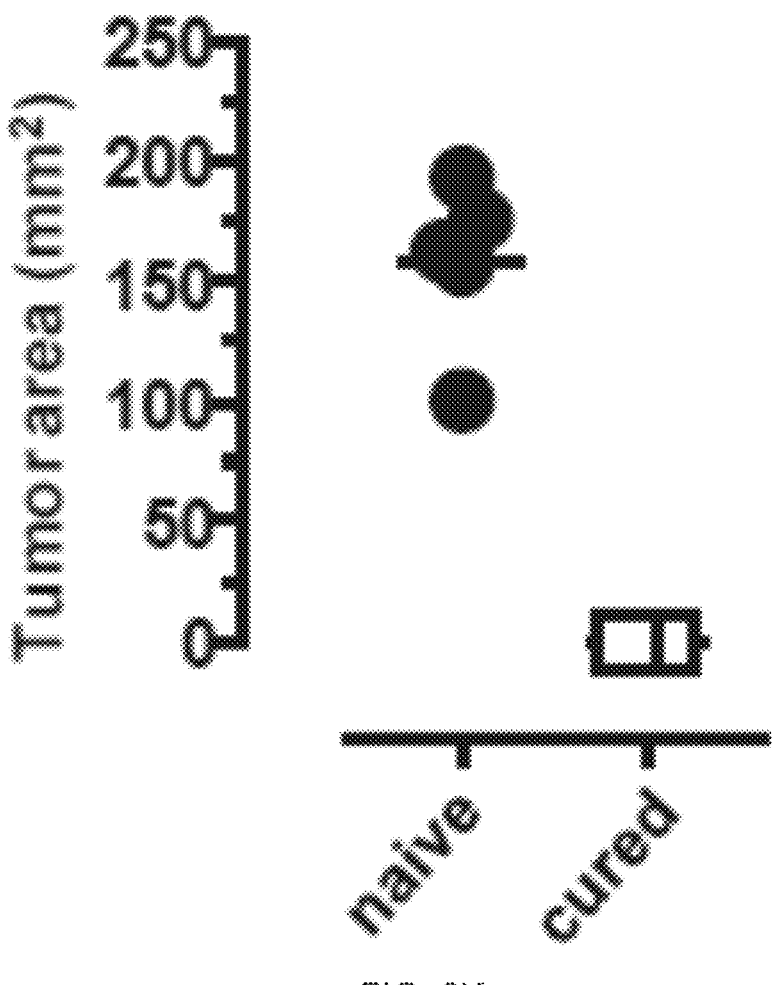
FIG. 6K is a dot plot showing tumor size in CTX+CASTAT5 CD19CAR T cell cured mice and control mice 3 weeks after re-inoculation with A20WT tumor cells.
Figures 20A, 20B:
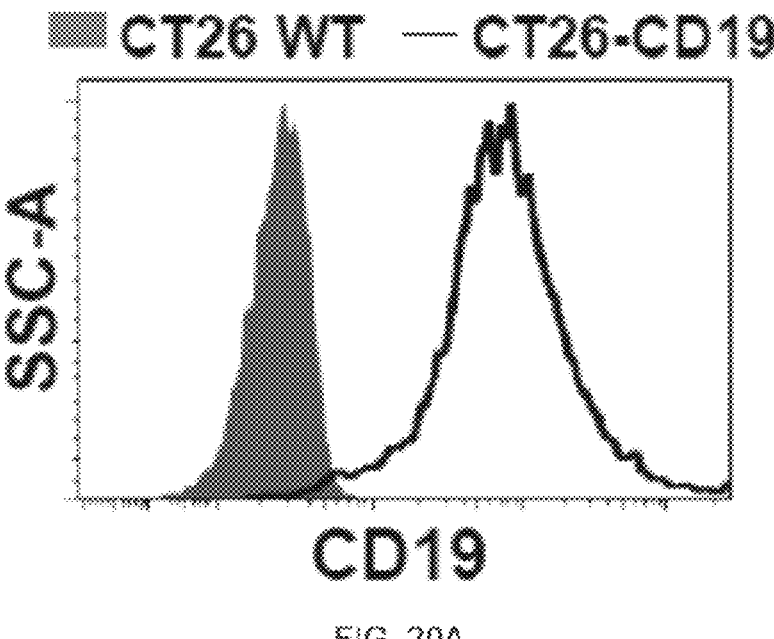
FIG. 20A-20B are flow cytometry data showing the frequencies of donor T cells plotted against time in tumor-bearing mice adoptively transferred with either control CD19CAR T cells or CASTAT5 CD19CAR T cells.
Figure 20C:
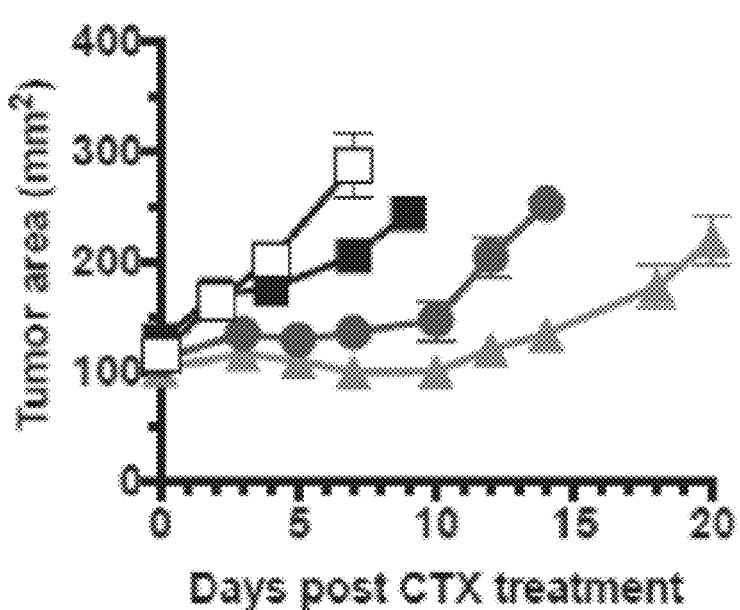
FIG. 20C is a tumor growth curve for tumor-bearing mice receiving either no treatment, CTX treatment alone, or CTX treatment with adoptive transfer of either control CD19CAR T cells or CASTAT5 CD19CAR T cells. The number of mice in each group is provided.
Figures 20D, 20E, 20F, 20G:
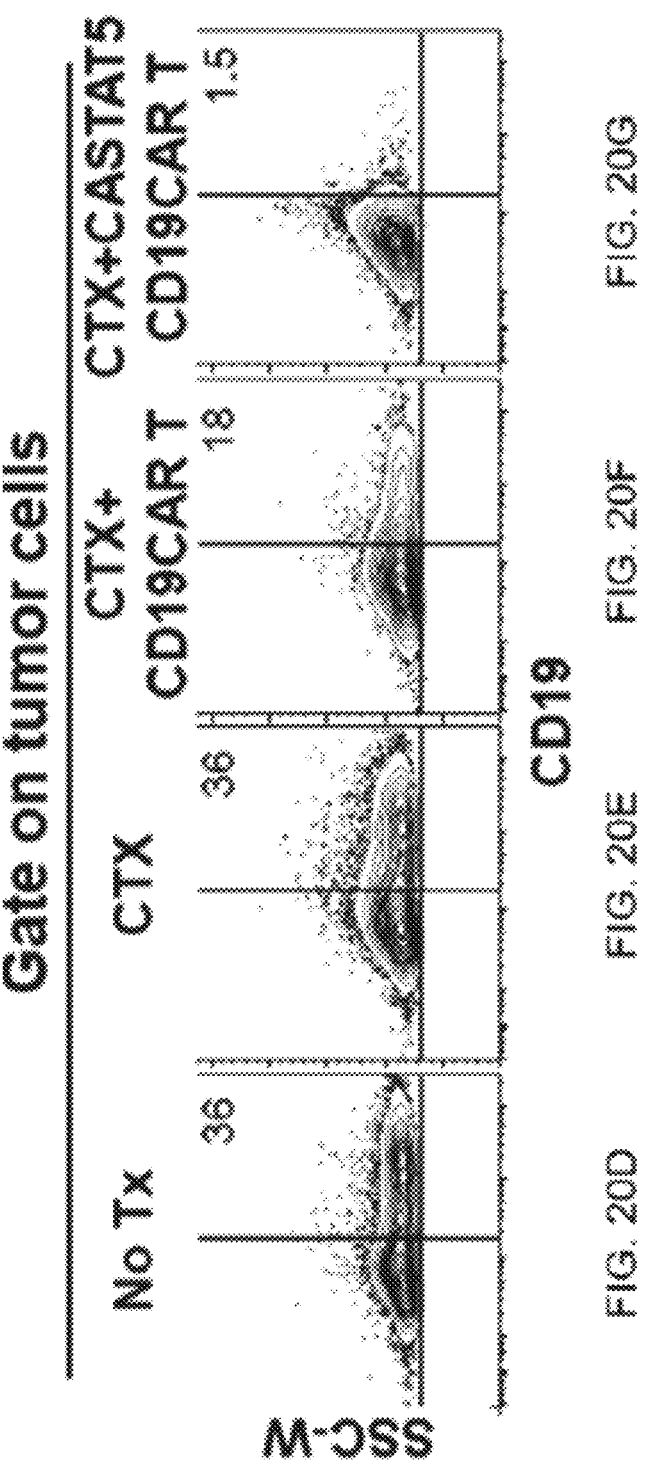
FIGS. 20D-20G are representative dot plots showing the percentage of CD19$^+$ cells in tumor cells resected from mice receiving the different treatments outlined in FIG. 20C.
Figure 20H:
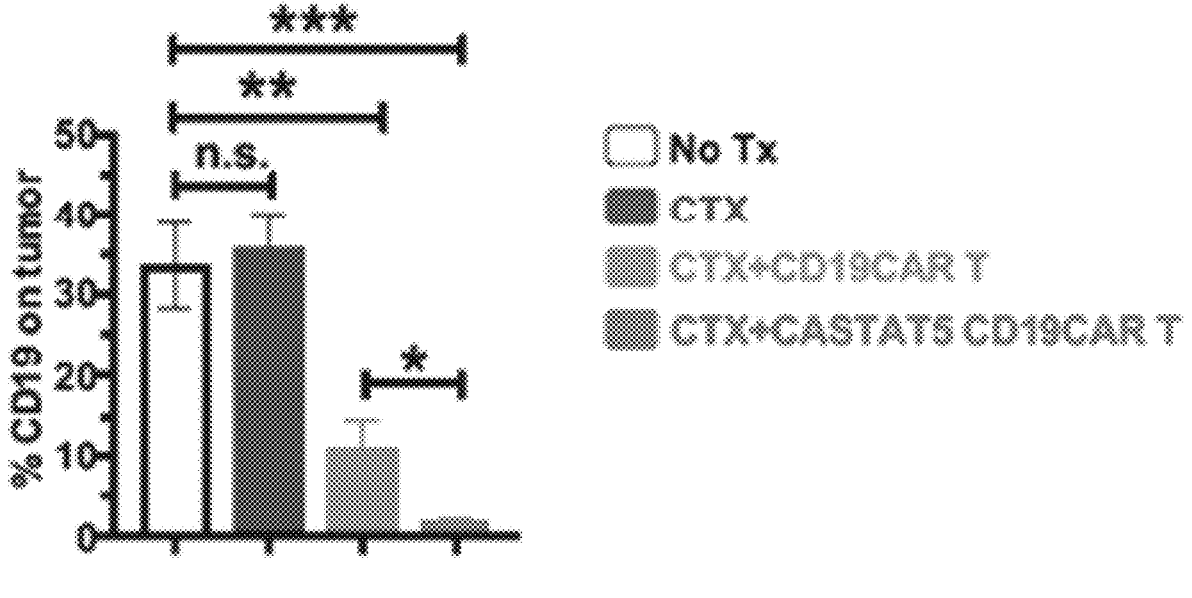
FIG. 20H is a bar graph showing the averaged results of the flow cytometry plots.

CD4$^+$ T cell polyfunctionality was found to correlate with the clinical outcomes of CD19CART therapy (Rossi, J., et al., *Blood,* 132:804-814 (2018)). It was postulated that CASTAT5 can be used to enhance the efficacy of CD19CAR T cells. This was tested using a mouse model of CD19CART therapy for B-cell lymphoma (Habtetsion, T., et al., *Cell Metab,* 28:228-242 c226 (2018); Kuczma, M. P., et al., *Oncotarget,* 8:111931-111942 (2017)). As shown in FIGS. 6A-6C, mice with established subcutaneous A20 tumors were conditioned with CTX, followed by infusion of T cells transduced to express CD19CAR alone or co-transduced to express both CD19CAR and CASTAT5. FIGS. 6E-6H shows that adoptive transfer of CD19CAR T cells resulted in only transient tumor regression, simulating an ineffective treatment scenario frequently observed in the clinic. In contrast, adoptive transfer of CASTAT5 CD19CAR T cells was curative to nearly all mice. Since normal B cells express CD19 and can be targeted by CD19CAR T cells, the level of B cells in peripheral blood can serve as an indicator of the presence of functional CD19CAR T cells. FIG. 6I shows that CASTAT5 CD19CAR T cells caused long-term B cell aplasia, whereas B cells in mice receiving control CD19CAR T cells began to increase when these mice started to have tumor relapse (>day 20). To examine the persistence of CD19CAR T cells, bone marrow aspirates were collected from mice 30 days after T cell infusion and analyzed by a sensitive PCR-based approach. CD19CAR vector DNA was detected in the bone marrows recovered from mice that had received CASTAT5 CD19CAR T cells, but not in the bone marrows from untreated naïve mice or mice that had received the control CD19CAR T cells (FIG. 6J). Furthermore, mice cured by CASTAT5 CD19CAR T cells were resistant to tumor re-challenge (FIG. 6K), indicating the formation of immune memory. The usefulness of CASTAT5-modified CAR in a typical solid tumor model in which CD19-expressing CT26 colon cancer cells were used for tumor inoculation was tested (FIG. 20A). Enhanced donor T cell expansion and persistence were observed for CASTAT5-transduced CD19CAR T cells compared to control CD19CAR T cells (FIG. 20B). CASTAT5-transduced CD19CAR T cells also led to significantly improved anti-tumor effects (FIG. 20C), although curative outcome was not achieved due to the outgrowth of CT26 tumors that lost CD19 expression (FIGS. 20D-20G).

Example 9. Concurrent Expression of CASTAT5 in CD4+ and CD8+ CD19CAR T Cells Leads to Optimal Therapeutic Outcomes Materials and Methods See examples above for material and methods descriptions for methods used herein.

Results

Figure 7A:
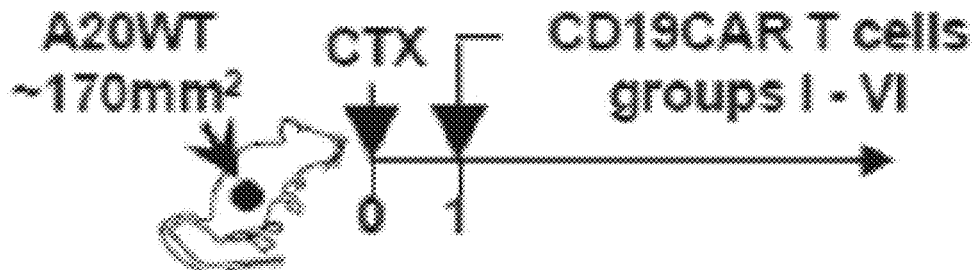
FIG. 7A is a schematic illustration showing the experimental setup and treatment conditions for FIGS. 7B-7EE. $CD4^+$ T cells and $CD8^+$ T cells, which were separately purified from the splenocytes of CD45.1 mice, were transduced to express CD19CAR only, or co-express CD19CAR and CASTAT5. A20WT-bearing mice were conditioned by CTX followed by adoptive transfer of control or CASTAT5 CD8+ CD19CAR T cells, in the presence or absence of equal numbers of control or CASTAT5 CD4+ CD19CAR T cells. The different combinations of engineered CD4+ and CD8+ CD19CAR T cells are outlined in the chart.
Figures 7H, 7I, 7J, 7K, 7L, 7M:
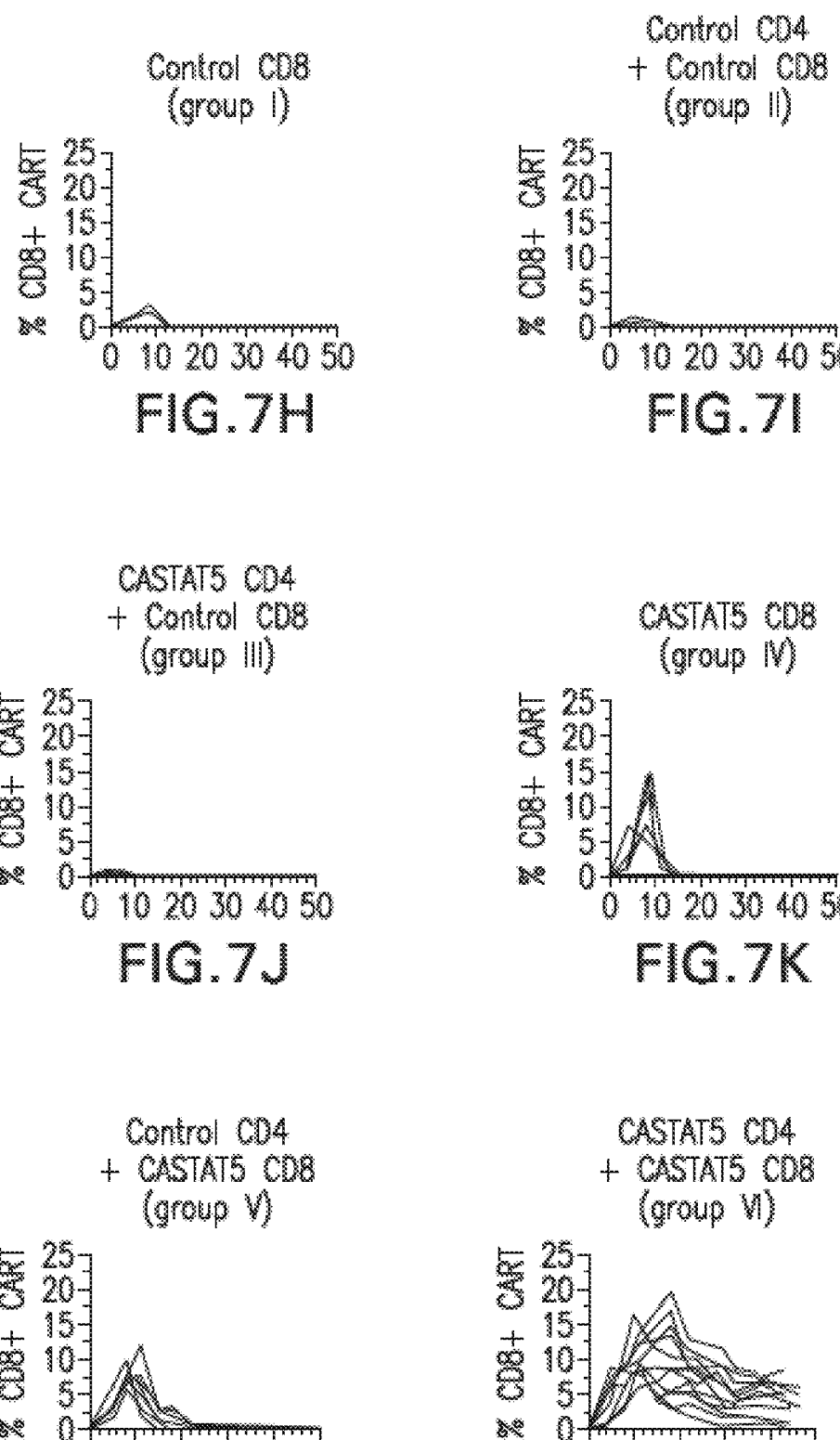
FIGS. 7H-7M show the frequencies of donor CD8+ T cells in recipient mice during the course of CD19CAR T cell therapy. At the indicated time points, tail blood was collected from mice and subjected to FACS to detect the donor CD8+ T cells (CD45.1+CD8+). The frequencies of donor $CD8^+$ T cells were plotted against time.
Figure 7N:
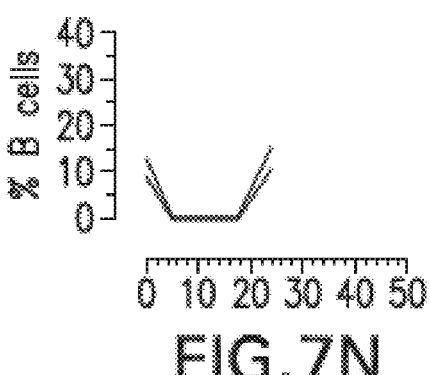
FIGS. 7N-7S show the frequencies of host B cells (CD19+ B220+) in blood evaluated by FACS.
Figure 7O:
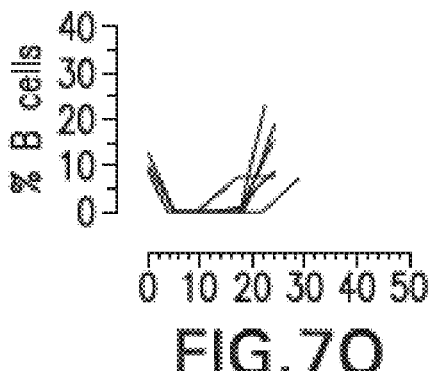
Figure 7P:
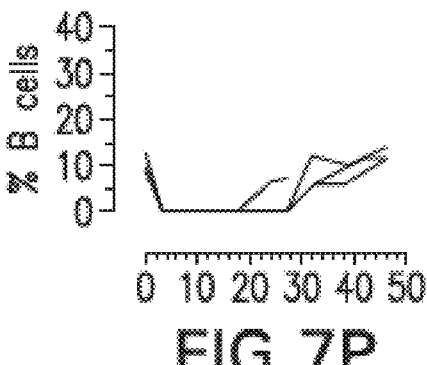
Figure 7Q:
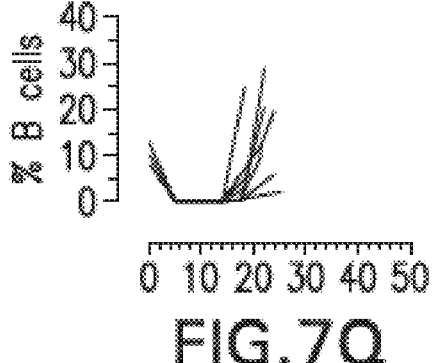
Figure 7R:
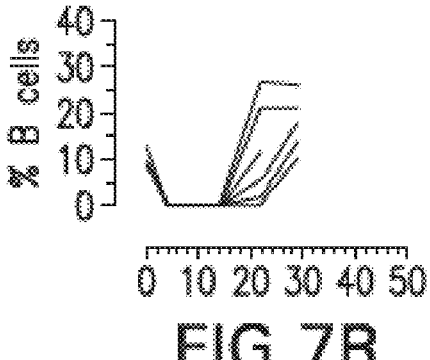
Figure 7S:
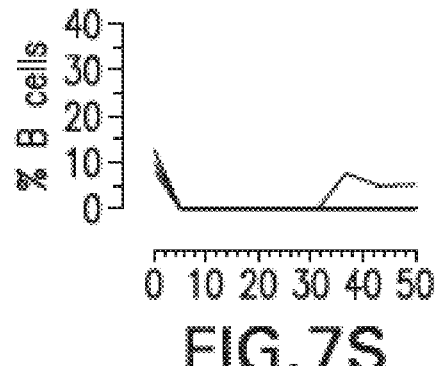
Figure 7T:
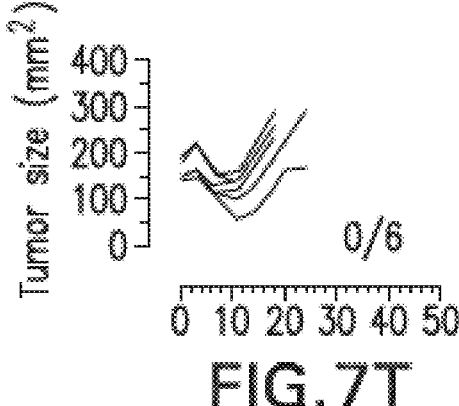
FIGS. 7T-7Y are tumor growth curves of mice in each group. The numbers indicate the number of tumor-free mice among treated mice at the end point of experiment.
Figure 7U:
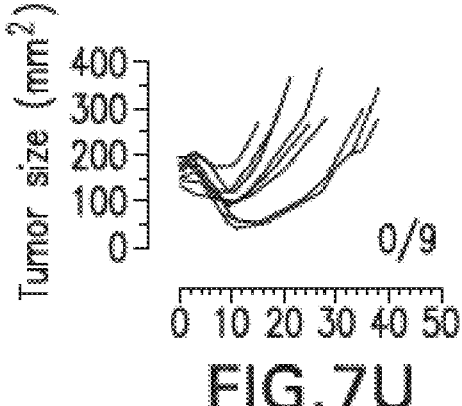
Figure 7V:
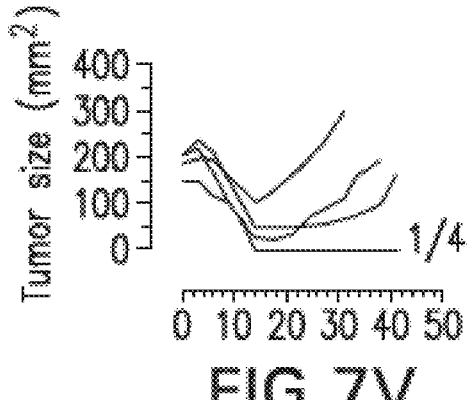
Figure 7W:
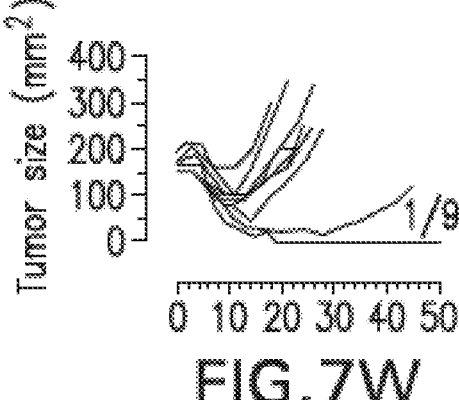
Figure 7X:
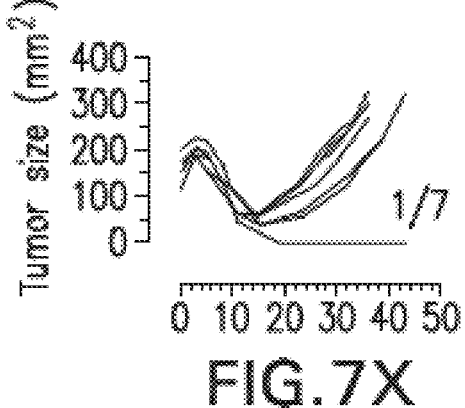
Figure 7Y:
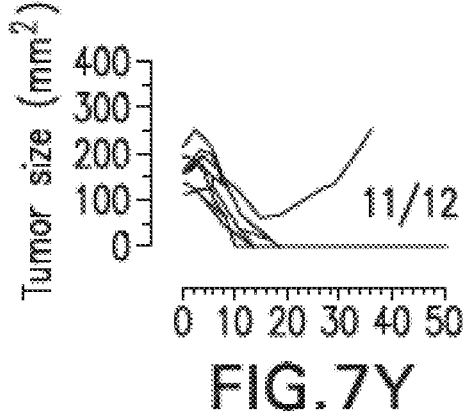

Since the CD19CAR T cell infusion products contained both CD4$^+$ and CD8$^+$ T cells, how expression of CASTAT5 in each subset affected CD19CAR T cell expansion, persistence and efficacy was determined. To this end, splenic CD4$^+$ and CD8$^+$ T cells, separately isolated from normal mice, were transduced with CD19CAR only, or co-transduced with CD19CAR and CASTAT5 (FIGS. 7A-7F). As depicted in FIG. 7G, mice with established A20 tumors were grouped and conditioned with CTX, followed by infusion of CD8+ CD19CAR T cells, either CASTAT5-null (Control CD8) or CASTAT5-positive (CASTAT5 CD8), in the absence or presence of equal numbers of CD4$^+$CD19CAR T cells that were either CASTAT5-null (Control CD4) or CASTAT5-positive (CASTAT5 CD4). Longitudinal tail blood FACS staining analysis revealed that CASTAT5-null CD8$^+$CD19CAR T cells (control CD8) transferred alone had minimal expansion in recipient mice (FIG. 7H), and that this poor expansion cannot be rescued by co-transfer of CASTAT5-null or CASTAT5-positive CD4$^+$CD19CAR T cells (FIGS. 7I-7J). When transferred alone, CASTAT5-positive CD8$^+$CD19CAR T cells (CASTAT5 CD8) expanded initially, reaching the peak (~10% in blood) around day 8, but underwent a rapid contraction and returned to the baseline by day 14 (FIG. 7K). Co-transfer of CASTAT5-null CD4$^+$CD19CAR T cells did not enhance the expansion but slightly slowed down the contraction of CASTAT5 CD8$^+$ CD19CAR T cells (FIG. 7L). Notably, in the presence of CASTAT5-positive CD4$^+$ CD19CAR T cells, CASTAT5 CD8$^+$ CD19CAR T cells underwent more robust expansion (up to 20% in blood), and remained readily detectable (~5% in blood) 40 days after infusion (FIG. 7M). B cell aplasia, an on-target off-tumor effect of CD19CAR T cells, occurred rapidly (~5 days after T cell infusion) in all groups, but persisted only in group VI in which mice received a mixture of CASTAT5 CD4$^+$ and CASTAT5 CD8$^+$ CD19CAR T cells (FIGS. 7N-7S). Corresponding to the robust expansion and persistence of donor T cells, mice in group VI had the best therapeutic outcome, measured by percentage of tumor-free mice on day 40 (FIGS. 7T-7Y). Importantly, cytokine profile analysis revealed that CASTAT5 CD19CAR CD4$^+$ T cells acquired polyfunctionality as evidenced by simultaneous productions of IFNγ, IL4, IL13 and GM-CSF (FIGS. 7Z-7EE), a phenotype similar to CASTAT5-transduced HA-specific CD4$^+$ T cells (FIGS. 1P-1R). Altogether, the results indicate that CASTAT5 expression is required in both CD4$^+$ and CD8$^+$ CD19CAR T cells to achieve optimal synergistic therapeutic effects.

Example 10. CASTAT5 is Functional in Transduced Primary Human CD4$^+$ T Cells

Materials and Methods

Human T cell transduction: Phoenix Amphotropic (Phoenix-AMPHO) cell line expressing amphotropic envelope protein was used to prepare CASTAT5 retroviral supernatant for human T cell transduction. Briefly, Phoenix-AMPHO were transfected with CASTAT5 retroviral vector using Lipofectamine 2000 (Thermo Fisher Scientific) according to manufacturer's instruction. 6 h after transfection, medium was replaced with fresh DMEM supplemented with 10% fetal bovine serum albumin (FBS), 1% non-essential amino acids and 1% glutamine. Supernatant containing CASTAT5 retrovirus was collected 24, 48 and 72 hours after transfection, pooled and stored at −80° C. Human T cells were isolated from the buffy coat of healthy donors using EasySep human T cells isolation kit (Stemcell Technology). Purified T cells were activated by human CD3/CD28 activation Dynabeads (Thermo Fisher Scientific) in the presence of 30 U/ml hIL2 for 48 h. Activated T cells were spin-infected twice in two consecutive days with CASTAT5 retroviral supernatant using retronectin. Anti-CD3/CD28 beads were removed 24 h after the 2nd transduction, and T cells were further expanded for 7 days in the presence of 100 U/ml hIL2 before adoptive transfer.

Results

The constitutively active STAT5A mutant used in this study was created by random mutagenesis in murine STAT5A (Onishi, et al., *Mol Cell Biol*, 18:3871-3879 (1998)). Although naturally occurring equivalent mutations in human STAT5A have not been reported, it has been shown that the murine origin CASTAT5 was functional in CASTAT5-transduced human hematopoietic stem cells and erythroid progenitors (Garcon, L., et al., *Blood*, 108:1551-1554 (2006); Schuringa, J. J., et al., *J Exp Med*, 200:623-635 (2004); Schuringa, J. J., et al., Stem Cells, 22:1191-1204 (2004)). To examine the activity of CASTAT5 in primary human T cells, total T cells isolated from the peripheral blood mononuclear cells (PBMC) of a healthy donor were mock-transduced (control) or CASTAT5-transduced (CASTAT5), and adoptively transferred to immunodeficient NOD-Scid IL2Rgamma-null mice (NSG). Two weeks later, the mutant murine STAT5A, reflected by Thy1.1, was still detectable in a fraction of CASTAT5-transduced human CD4$^+$ T cells recovered from mice spleens (FIG. 7G). Interestingly, the level of human BCL2, a known downstream target of STAT5A, was significantly higher in the fraction of human CD4$^+$ T cells expressing murine CASTAT5 (Thy1.1$^+$) compared to the CASTAT5-fraction or mock-transduced T cells (FIGS. 7FF-7HH). In addition, CASTAT5-transduced human CD4$^+$ T cells exhibited a polyfunctional cytokine profile compared to mock-transduced cells (FIGS. 7KK-7MM). The results suggest the potential of using CASTAT5 to engineer polyfunctional human CD4$^+$ T cells.

Figure 18A:
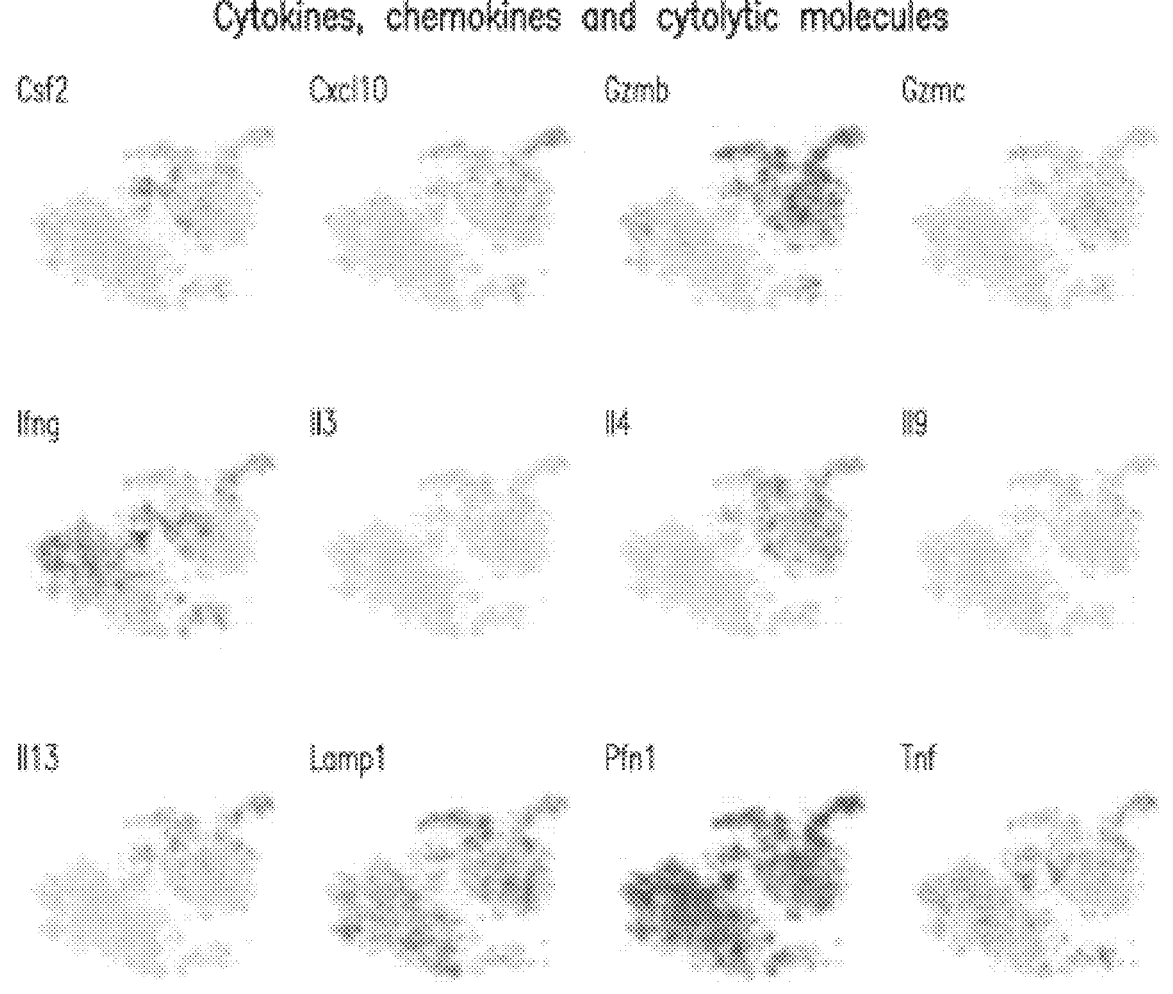
FIGS. 18A-18H are dot plots of selected genes which have been grouped into several functional categories. In each plot, each dot represents one cell. Cells with positive gene expression are shown in dark grey. Genes are listed in alphabetical order.
Figure 18B:
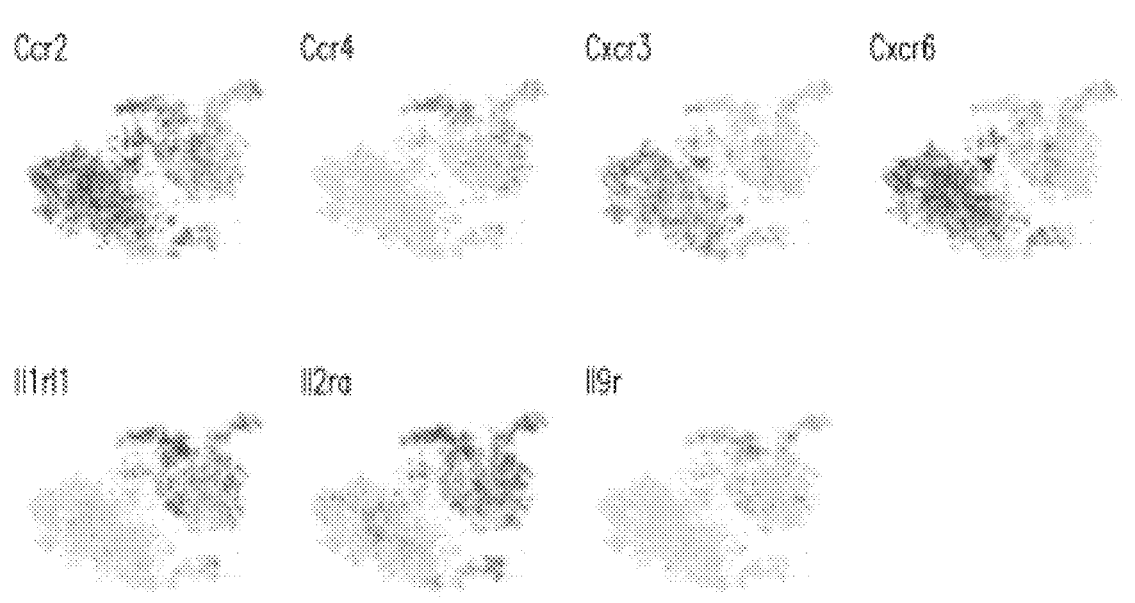
Figure 18C:
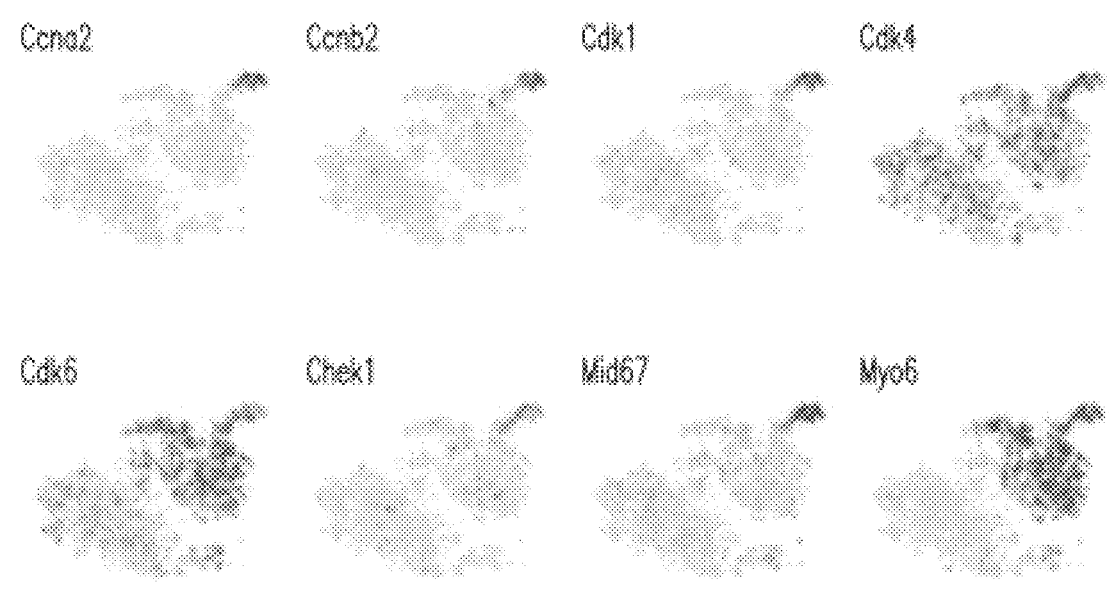
Figure 18D:
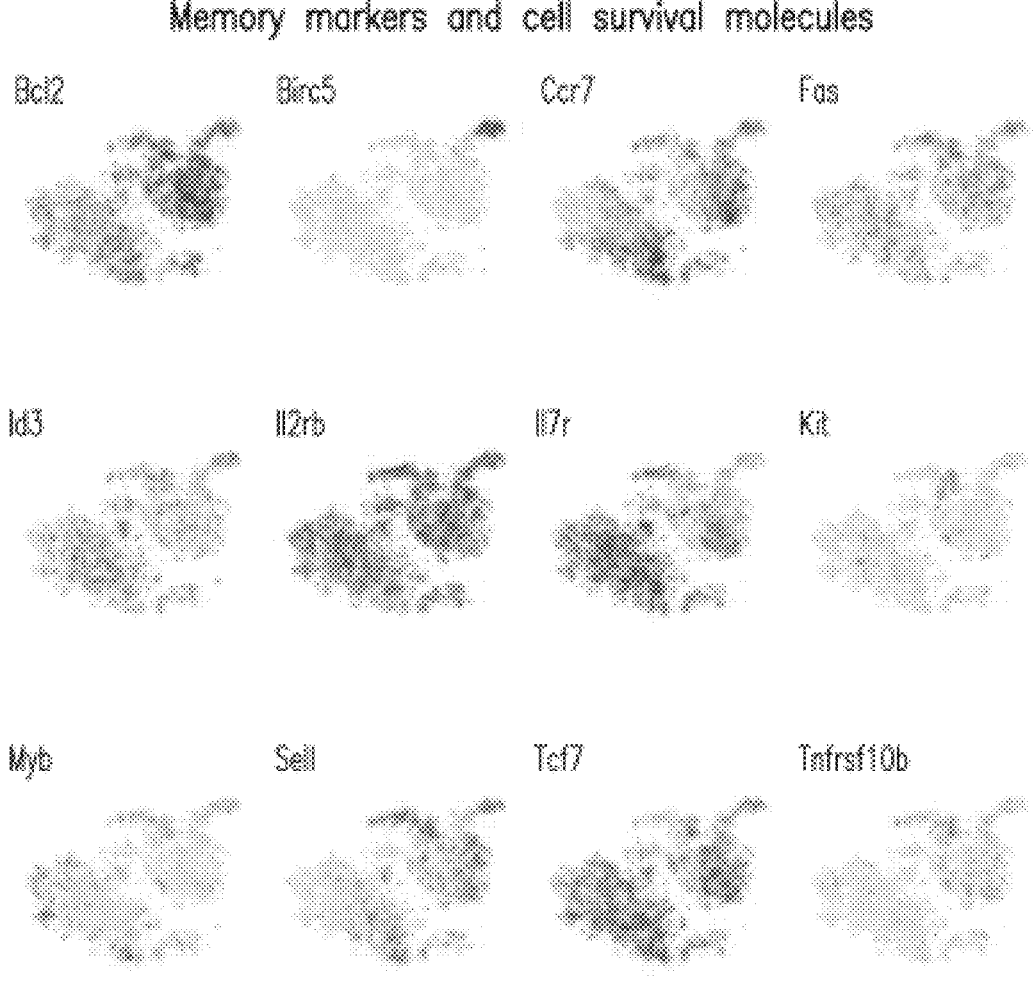
Figure 18E:
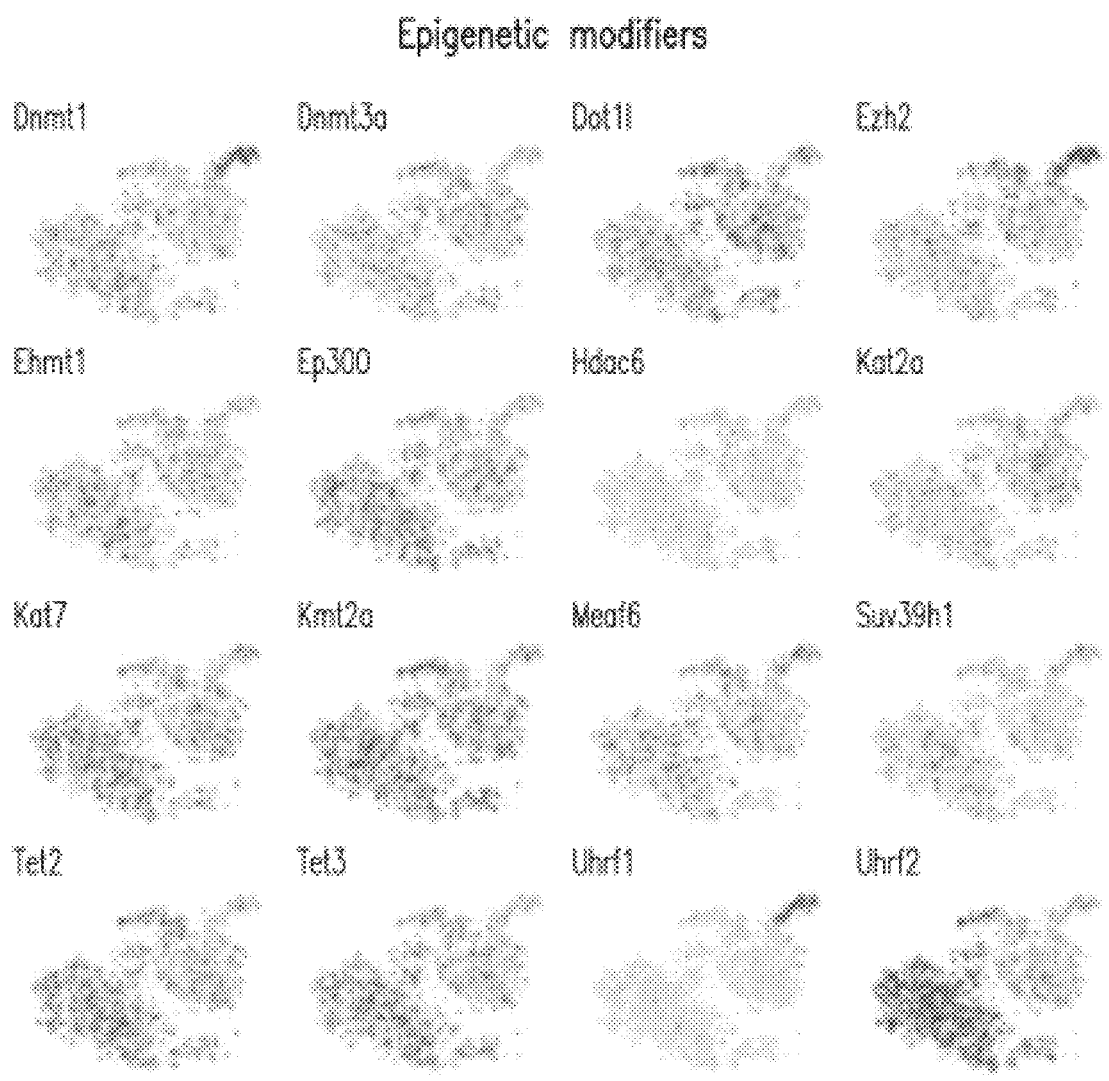
Figure 18F:
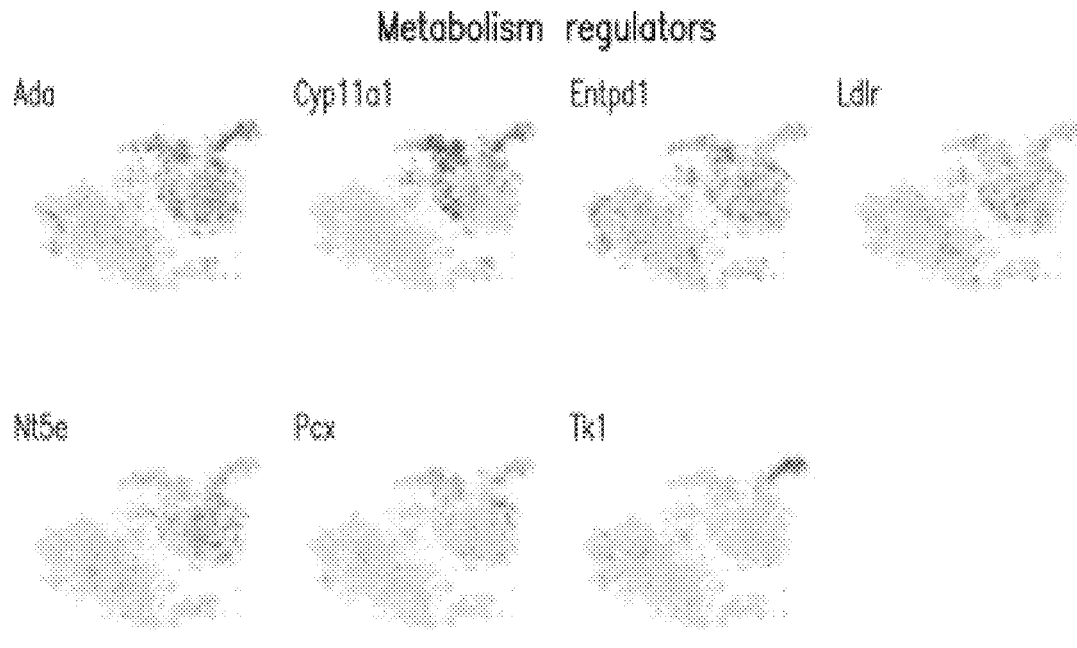
Figure 18G:
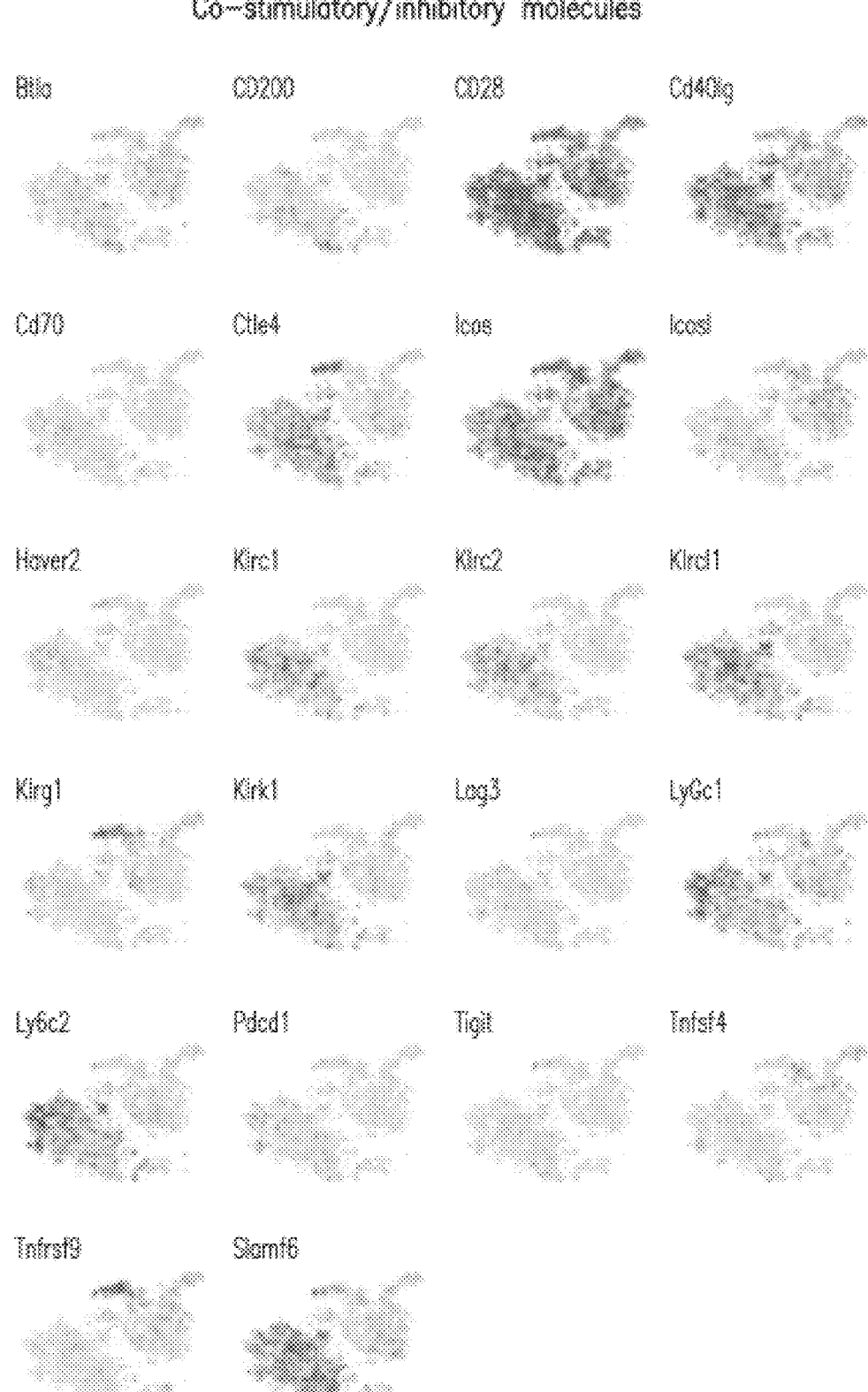
Figure 18H:
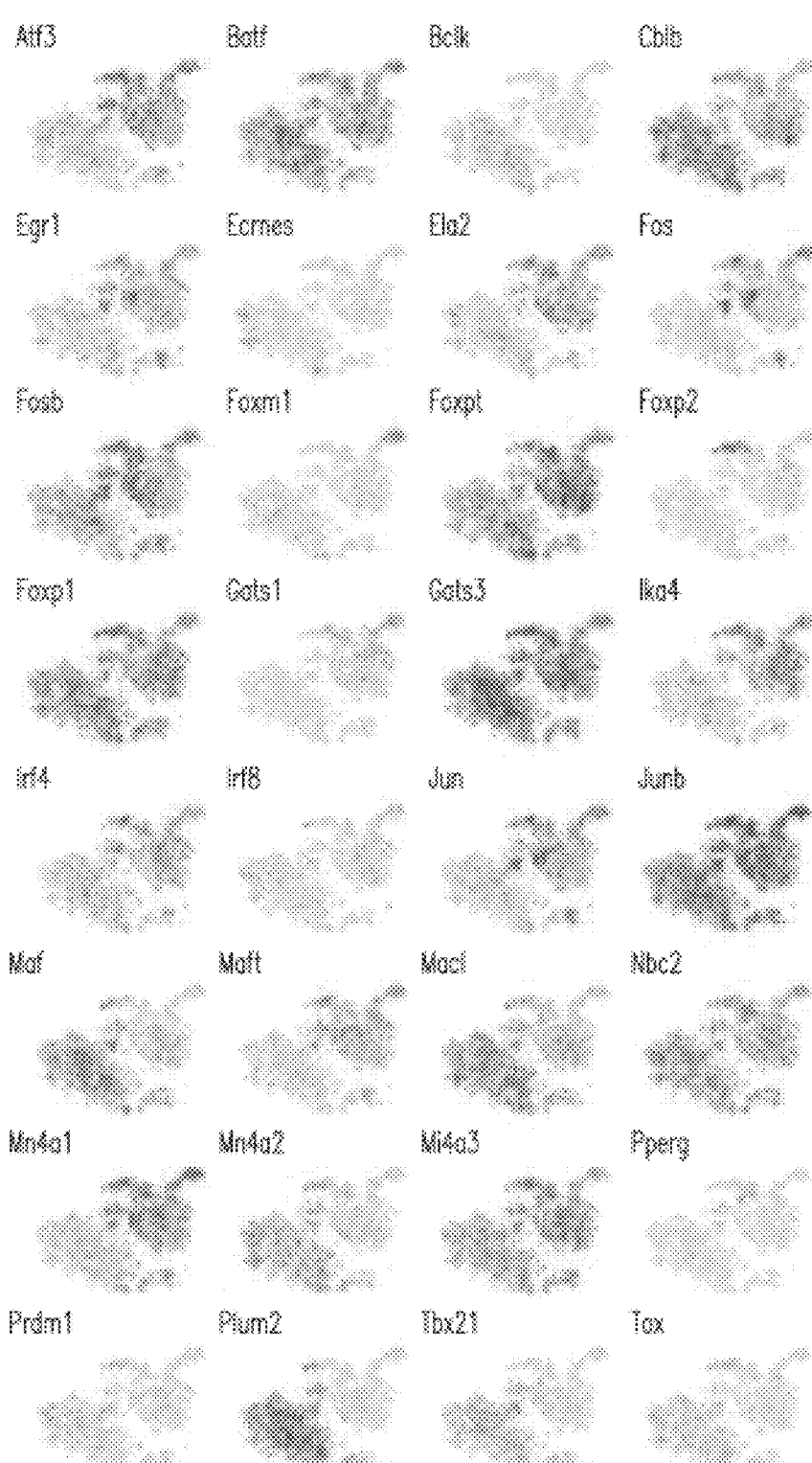
Figure 19A:
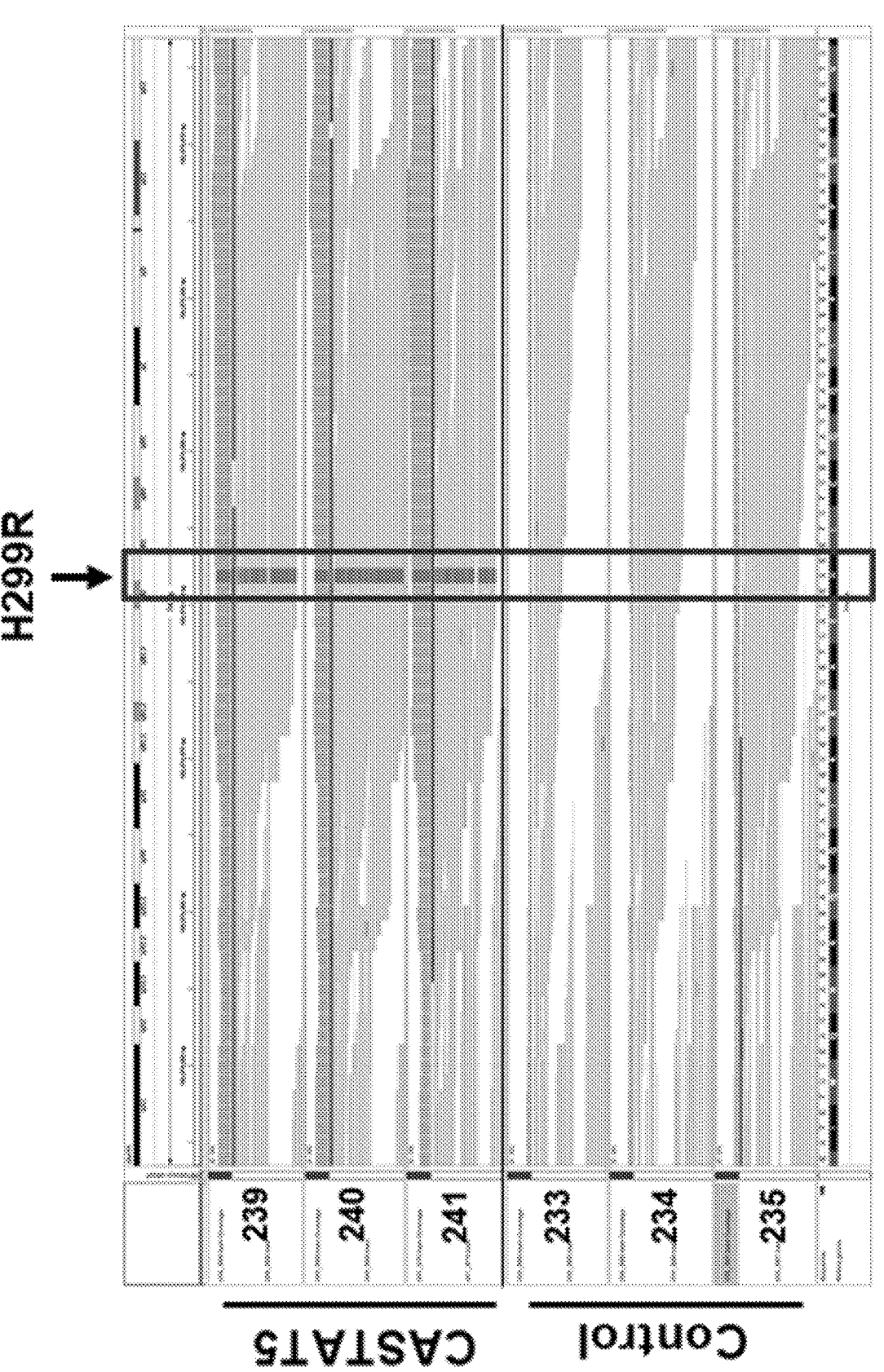
FIGS. 19A-19D are screenshots of IGV browser view of BAM file track at a 75 bp window which shows the presence of H299R (FIGS. 19A, 19C) and S711F (FIGS. 19B, 19D) mutations in CASTAT5 CD4+ T cell bulk RNAseq data (3 biological replicates) but not in control CD4+ T cell data (3 biological replicates).
Figure 19B:
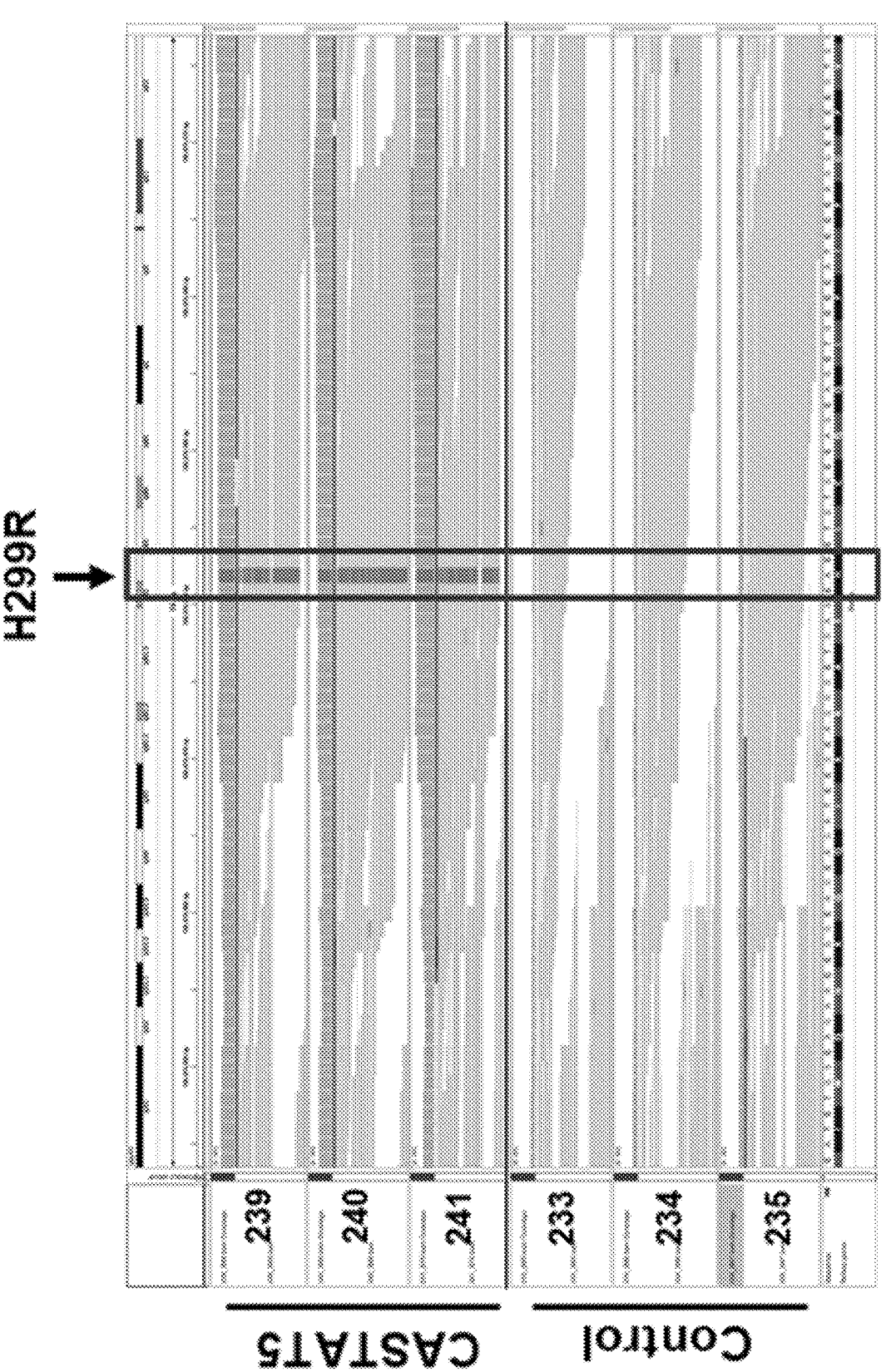
Figure 19C:
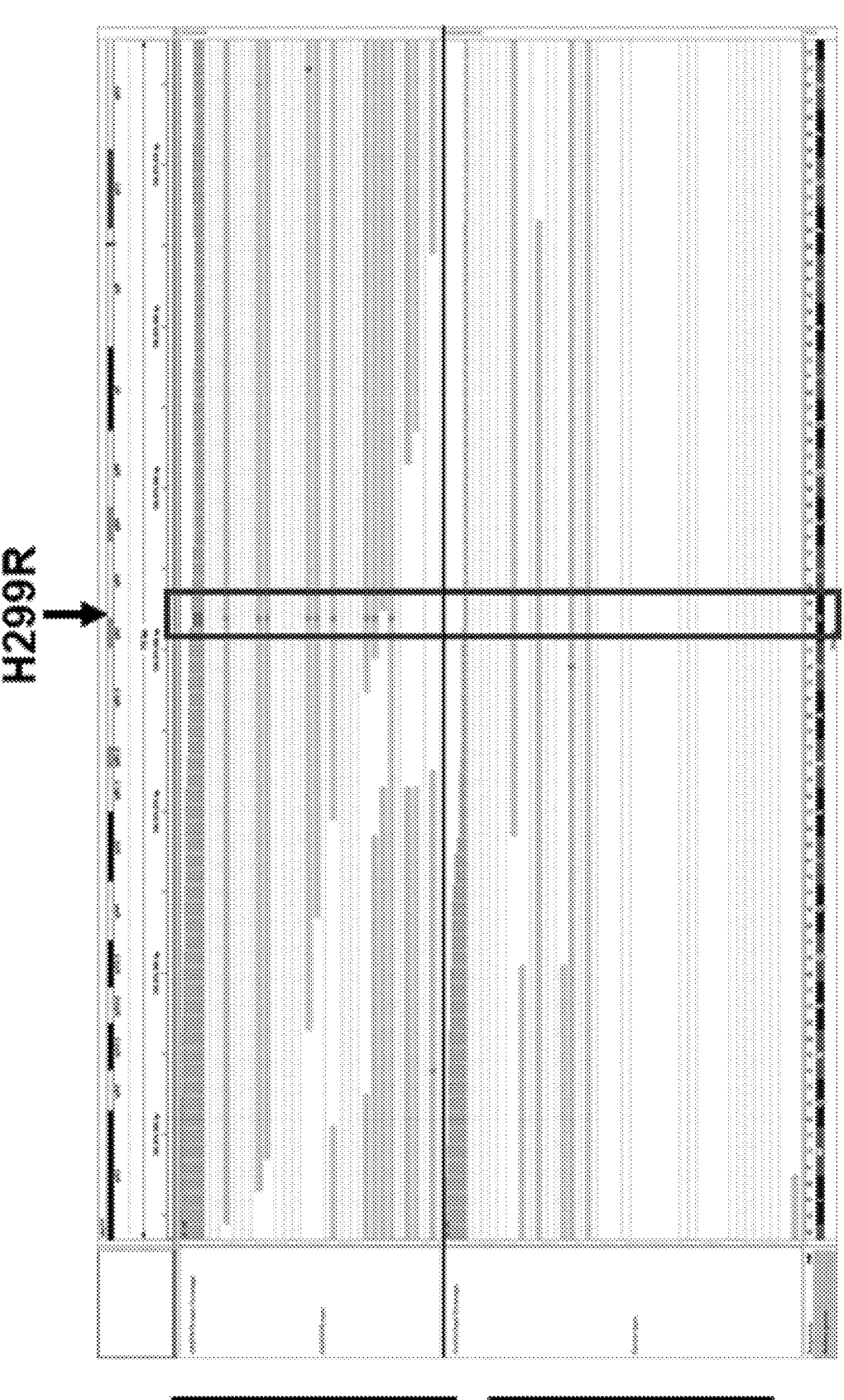
Figure 19D:
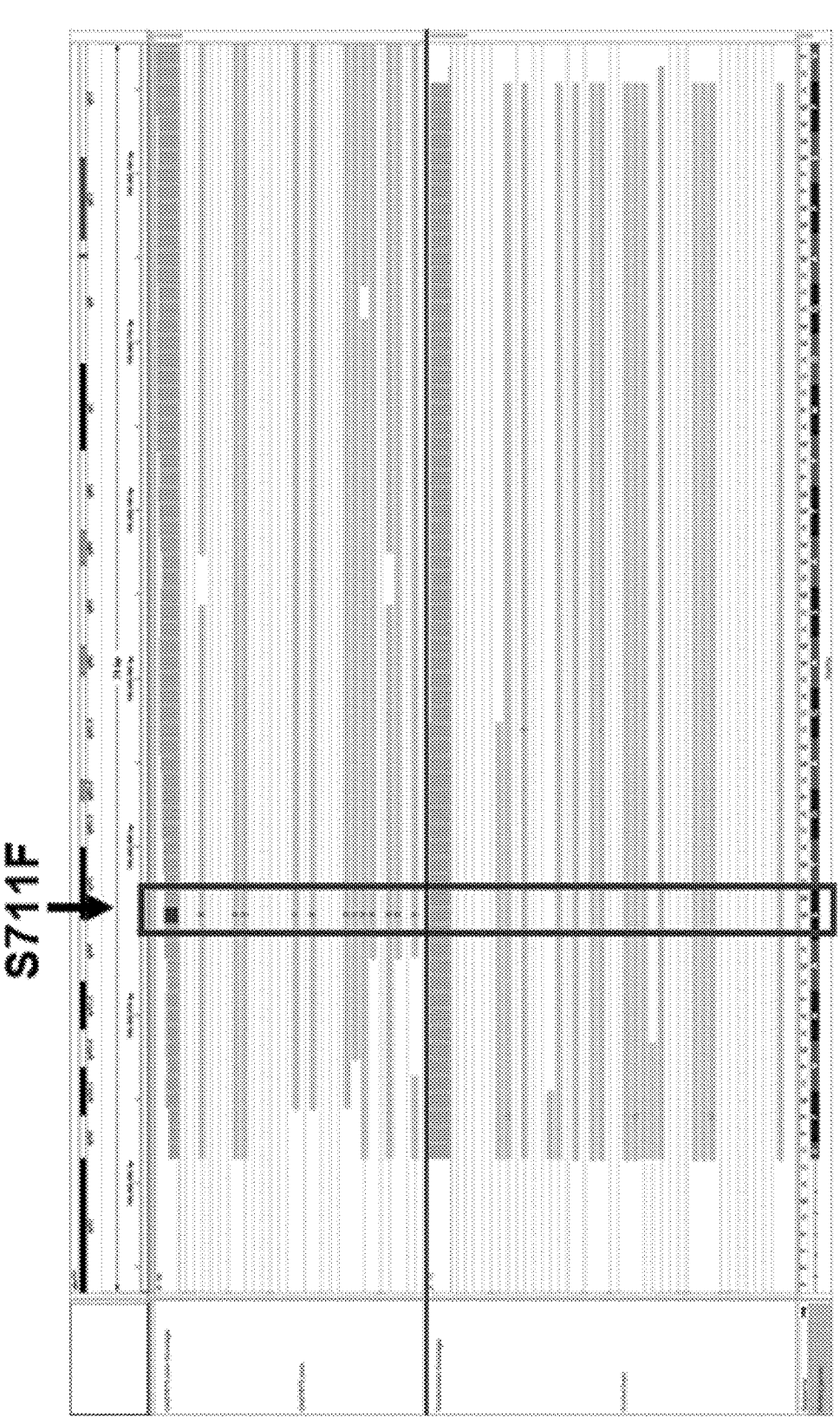

Reported herein is a genome-wide epigenetic reprogramming in CD4$^+$ T cells induced by persistent STAT5 activation. The data provide evidence that the unique polyfunctional status of CD4$^+$ T cells is driven by CASTAT5-induced transcriptional and epigenetic remodeling. Similar to STAT5-induced epigenetic remodeling in hematological cancer cells (Wingelhofer, B., et al., *Leukemia*, 32:1713-1726 (2018)), the epigenetic landscape of CASTAT5 CD4$^+$ T cells is likely shaped by coordinated actions of STAT5 and multiple epigenetic modifiers. Indeed, as revealed by scRNAseq, there were noticeable presence of multiple epigenetic modifiers in CASTAT5 CD4$^+$ T cells, particularly in cluster 6 (FIG. 18E). These molecules are involved in regulating DNA methylation, histone methylation, and histone acetylation. It is important to point out that Kmt2a, which catalyzes trimethylation of H3K4 (H3K4me3), and Ezh2, which catalyzes trimethylation of H3K27 (H3K27me3), were both present in cluster 6. Chromatin bivalency, i.e., the co-presence of activating H3K4me3 and repressive H3K27me3 modifications at gene promoters, has been found in pluripotent stem cells (Bernstein, B. E., et al., *Cell*, 125:315-326 (2006)), and considered as a mechanism contributing to CD4$^+$ T cell lineage plasticity (Wei, G., et al., *Immunity*, 30:155-167 (2009); Tripathi, S. K., et al., *Immunol Rev*, 261:62-83 (2014); Schmidl, C., et al., *J Allergy Clin Immunol*, 142:728-743 (2018)). It is plausible that bivalent histone modifications at the relevant target genes may underlie CASTAT5-driven CD4 polyfunctionality, which essentially denotes a progenitor cellular state.

Numerous studies have shown that CD4 help to CD8 T cells is essential to the success of cancer immunotherapy (Pardoll, D. M., et al., *Curr Opin Immunol*, 10:588-594 (1998); Bevan, M. J., *Nat Rev Immunol*, 4:595-602 (2004); Ding, Z. C., and G. Zhou, *Clin Dev Immunol*, 890178 (2012); Borst, J., et al., *Nat Rev Immunol*, 18:635-647 (2018)). Emerging evidence indicates that the efficacy of CD19CART therapy benefits from the co-presence of CD4 and CD8 T cells in the infusion products (Turtle, C. J., et al., *J Clin Invest* (2016); Sommermeyer, D., et al., *Leukemia* (2015)). A recent study reported that in patients with non-Hodgkin lymphoma (NHL) treated with CD19CAR infusion products, the clinical outcomes were associated with CD19CAR T-cell polyfunctionality, and that the correlation was greater with the polyfunctionality of CD4 CAR T cells compared to that of CD8 CAR T cells (Rossi, J., et al., *Blood*, 132:804-814 (2018); Davila, M. L., *Blood*, 132:769-770 (2018)).

It has been reported that CAR T cells made to secret IL7, or respond to exogenous IL7, exhibited improved expansion, persistence and antitumor activities in preclinical models (Perna, S. K., et al., *Clin Cancer Res*, 20:131-139 (2014); Adachi, K., et al., *Nat Biotechnol*, 36:346-351 (2018); Shum, T., et al., *Cancer Discov*, 7:1238-1247 (2017); Bajgain, P., et al., *J Immunother Cancer*, 6:34 (2018)). Shum et al recently reported that CAR T cells engineered to express a constitutively active IL7Ra, which subsequently activated STAT5, exhibited enhanced antitumor efficacy in preclinical models. The disclosed study further underscores the importance of the STAT5 signaling pathway in generating and maintaining T cells with the desirable functional features, and provides an additional strategy to manipulate this pathway in T cells for therapeutic benefits. Importantly, the data not only demonstrate the critical contribution of polyfunctional CD4+ T cells to effective antitumor immunity, but also reveal the gene regulatory network induced by CASTAT5 to drive CD4 polyfunctionality. The results may lead to better utilization of tumor-reactive CD4+ T cells in cancer immunotherapy. One safety concern associated with persistent STAT5 activation is the leukemic potential of CASTAT5-transduced T cells (Chai, S. K., et al., *J Immunol*, 159:4720-4728 (1997); Spickermann, K., et al., *Clin Cancer Res*, 9:2140-2150 (2003); Birkenkamp, K. U., et al., *Leukemia*, 15:1923-1931 (2001); Shuai, K., et al., *Oncogene*, 13:247-254 (1996); Ribicro, D., et al., *Blood Adv*, 2:2199-2213 (2018); Pham, H. T. T., et al., *J Clin Invest*, 128:387-401 (2018))). Development of leukemia in mice cured long after (3 months) receiving CASTAT5-transduced CD19CAR T cells was not observed (data not shown). It should be noted that leukemogenesis is often driven by mutations in signaling pathways acting upstream of STAT5, such as Janus Kinases, FLT3 and BCR/ABL, which result in abnormal STAT5 activation in hematopoietic precursor cells (Sillaber, C., et al., *Blood*, 95:2118-2125 (2000); Kralovics, R., et al., *N Engl J Med*, 352:1779-1790 (2005); Choudhary, C., et al., *Blood*, 110:370-374 (2007)). Moreover, mutations in STAT5B, but not STAT5A, have been frequently found in human leukemia (Kontro, M., et al., *Leukemia*, 28:1738-1742 (2014); Bandapalli, O. R., et al., *Haematologica*, 99:0188-192 (2014); Kollman, S., et al., *Leukemia*, 33:1583-1597 (2019)). Therefore, it is speculated that persistent STAT5A activation (CASTAT5) per se is insufficient to drive T cells into leukemic cells. For adoptive T cell therapy using the CASTAT5 strategy, the safety concern can be further addressed by incorporating additional safety measures such as inducible CAR T cell suicide system (Hoyos, V., et al., *Leukemia*, 24:1160-1170 (2010)).

In summary, the disclosed study sheds light on the heterogeneity of polyfunctional CD4+ T cells, and reveals the transcriptomic and epigenomic programs that dictate CD4+ T cell polyfunctionality. The results imply that persistent activation of STAT5 in CD4+ T cells represents a promising strategy to potentiate the efficacy of ACT including CAR T cell therapy.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

I claim:

1. A method of adoptive transfer comprising:
   a) isolating CD4$^+$ and CD8$^+$ T cells from a subject,
   b) expanding the CD4$^+$ and CD8$^+$ T cells ex vivo,
   c) genetically engineering the CD4$^+$ and CD8$^+$ T cells to produce polyfunctional CD4$^+$ and CD8$^+$ T cells which express a cluster of differentiation 19 protein chimeric antigen receptor (CD 19CAR) and constitutively express signal transducer and activator of transcription 5 (Stat5a) by transducing the CD4$^+$ and CD8$^+$ T cells with SEQ ID NO: 1 or 2, and
   d) administering the polyfunctional CD4$^+$ and CD8$^+$ T cells expressing CD19CAR and constitutively expressing Stat5a to the subject in an amount effective to induce an immune response to cancer,
   wherein the subject has a hematological cancer,
   wherein the polyfunctional CD4$^+$ and CD8$^+$ T cells expressing CD19CAR reverse exhaustion in tumor-specific CD4$^+$ and CD8$^+$ T cells and the constitutive STAT5a activity induces epigenetic changes and changes in expression in comparison to control CD4$^+$ and CD8$^+$ T cells in hematological cancer, and wherein the polyfunctional CD4$^+$ and CD8$^+$ T cells expressing CD19CAR and constitutively expressing Stat5a, when administered in combination, synergistically enhances tumor infiltration and retention of CD4$^+$ and CD8$^+$ T cells compared to control CD4$^+$ and CD8$^+$ T cells in hematological cancer.

2. The method of claim 1, wherein the immune response is production and release of cytokines from the polyfunctional CD4$^+$ and CD8$^+$ T cells, wherein the cytokines are selected from the group consisting of IFNγ, IL4, IL13, and GMCSF.

3. The method of claim 1, wherein the polyfunctional CD4$^+$ and CD8$^+$ T cells are administered to the subject in an aqueous solution by parenteral administration or infusion.

4. The method of claim 1, wherein the polyfunctional CD4$^+$ and CD8$^+$ T cells are autologous.

5. The method of claim 1, wherein the immune response reduces or prevents tumor growth or progression, or a combination thereof, compared to untreated tumors, in the subject in need thereof.

6. The method of claim 1, wherein the hematologic cancer is B cell lymphoma.

*    *    *    *    *